(12) United States Patent
Nakayama et al.

(10) Patent No.: US 7,056,917 B2
(45) Date of Patent: Jun. 6, 2006

(54) DRUG EFFLUX PUMP INHIBITOR

(75) Inventors: Kiyoshi Nakayama, Funabashi (JP); Masami Ohtsuka, Tokyo (JP); Haruko Kawato, Tokyo (JP); William Watkins, Sunnyvale, CA (US); Jason Zhang, Foster City, CA (US); Monica Palme, San Jose, CA (US); Aesop Cho, Mountain View, CA (US)

(73) Assignees: Daiichi Pharmaceutical Co., Ltd., Tokyo (JP); Trine Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 09/842,234

(22) Filed: Apr. 26, 2001

(65) Prior Publication Data

US 2003/0092720 A1 May 15, 2003

(51) Int. Cl.
 *C07D 417/06* (2006.01)
 *C07D 417/12* (2006.01)
 *A61K 31/427* (2006.01)

(52) U.S. Cl. ............... 514/233.2; 514/248; 514/258; 514/300; 514/312; 544/116; 544/235; 544/236; 544/282; 546/122; 546/153; 546/155; 546/156

(58) Field of Classification Search .......... 514/233.2, 514/258, 248, 300, 312; 544/116, 282, 235, 544/236; 546/122, 153, 155, 156
See application file for complete search history.

(56) References Cited

U.S. PATENT DOCUMENTS

| | | | |
|---|---|---|---|
| 3,753,993 A | | 8/1973 | Lesher et al. |
| 3,870,712 A | * | 3/1975 | Holmes |
| 3,907,808 A | | 9/1975 | Lesher et al. |
| 4,013,647 A | | 3/1977 | Sellstedt et al. |
| 4,057,632 A | | 11/1977 | Sellstedt et al. |
| 4,116,960 A | | 9/1978 | Sellstedt et al. |
| 4,123,432 A | | 10/1978 | Sellstedt et al. |
| 4,129,735 A | | 12/1978 | Sellstedt et al. |
| 4,404,207 A | | 9/1983 | Stern |
| 4,638,067 A | | 1/1987 | Culbertson et al. |
| 4,665,079 A | | 5/1987 | Culbertson et al. |
| 4,771,054 A | | 9/1988 | Damagala et al. |
| 4,777,175 A | | 10/1988 | Culbertson et al. |
| 4,777,252 A | * | 10/1988 | Slusarchyk et al. |
| 4,891,428 A | * | 1/1990 | Nordhoff et al. |
| 4,902,700 A | * | 2/1990 | Hayasi et al. |
| 4,992,434 A | | 2/1991 | Töpfl et al. |
| 5,135,927 A | | 8/1992 | Töpfl et al. |
| 5,206,235 A | | 4/1993 | Fisher et al. |
| 5,273,986 A | * | 12/1993 | Holland et al. |
| 5,281,612 A | | 1/1994 | Domagala et al. |
| 5,310,737 A | | 5/1994 | Fisher et al. |
| 5,368,771 A | | 11/1994 | Namekawa et al. |
| 5,443,755 A | | 8/1995 | Namekawa et al. |
| 5,508,408 A | * | 4/1996 | Sprecher et al. |
| 5,512,581 A | * | 4/1996 | Brooks et al. |
| 5,643,932 A | | 7/1997 | Chihiro et al. |
| 5,677,319 A | | 10/1997 | Chihiro et al. |
| 5,935,977 A | * | 8/1999 | Yamazaki et al. |
| 5,981,559 A | * | 11/1999 | Nagaoka et al. |
| 6,080,764 A | | 6/2000 | Chihiro et al. |
| 6,114,310 A | | 9/2000 | Chamberland et al. |
| 6,204,279 B1 | * | 3/2001 | Leger et al. |
| 6,245,746 B1 | | 6/2001 | Chamberland et al. |
| 6,255,321 B1 | * | 7/2001 | Ichikawa et al. |
| RE37,556 E | | 2/2002 | Chihiro et al. |
| 6,376,671 B1 | * | 4/2002 | Ichikawa et al. |
| 6,436,980 B1 | | 8/2002 | Leger et al. |
| 2002/0049235 A1 | | 4/2002 | Kawai et al. |

FOREIGN PATENT DOCUMENTS

DE          3417840       * 11/1984

(Continued)

OTHER PUBLICATIONS

Nishigaki et al., Synthetic Antibacterials. v. 7–substituted 1–ethyl–1,4–dihydro–4–oxo–1, 8–naphthyridine–3–carboxylic acids, Chem. Pharm. Bull., 23(12), pp. 3170–3177, 1975.*
Nishigaki et al., Chem. Abstract 84:74139h, 1976.*

(Continued)

*Primary Examiner*—Deepak Rao
(74) *Attorney, Agent, or Firm*—Greenblum & Bernstein, P.L.C.

(57) ABSTRACT

A medicament for preventive and/or therapeutic treatment of a microbial infection which comprises as an active ingredient a compound represented by the following general formula (I):

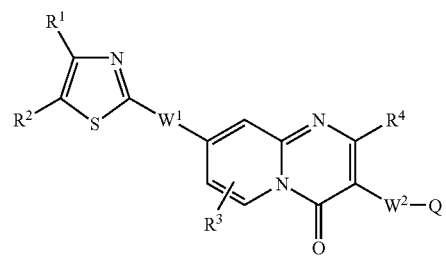

wherein, $R^1$ and $R^2$ represent hydrogen atom, a halogen atom, hydroxyl group or the like, $W^1$ represents —CH=CH—, —CH$_2$O—, —CH$_2$CH$_2$— or the like; $R^3$ represents hydrogen atom, a halogen atom, hydroxyl group or an amino group; $R^4$ represents hydrogen atom, a group of —OZ$_{0-4}$R$^5$ (Z$_{0-4}$ represents an alkylene group, a fluorine-substituted alkylene group or a single bond, and $R^5$ represents a cyclic alkyl group, an aryl group or the like); $W^2$ represents a single bond or —C(R$^8$)=C(R$^9$)— (R$^8$ and R$^9$ represent hydrogen atom, a halogen atom, a lower alkyl group or the like, Q represents an acidic group, but $W^2$ and Q may together form vinylidenethiazolidinedione or an equivalent heterocyclic ring; m and n represent an integer of 0 to 2, and q represents an integer of 0 to 3.

22 Claims, No Drawings

FOREIGN PATENT DOCUMENTS

| | | | |
|---|---|---|---|
| EP | 0279239 | * | 8/1988 |
| EP | 0330353 | | 8/1989 |
| EP | 0513387 | * | 11/1992 |
| EP | 0513974 | * | 11/1992 |
| EP | 0594861 | * | 5/1994 |
| EP | 0786457 | | 7/1997 |
| EP | 1227084 | | 7/2002 |
| EP | 1-227084 | * | 7/2002 |
| FR | 1458066 | | 11/1966 |
| GB | 1305820 | | 2/1973 |
| JP | 44-2219 | | 1/1969 |
| JP | 44-13952 | | 9/1969 |
| JP | 54144397 | * | 11/1979 |
| JP | 57144264 | | 9/1982 |
| JP | 60197686 | | 10/1985 |
| JP | 61092597 | * | 5/1986 |
| JP | 61246188 | | 11/1986 |
| JP | 62-12760 | | 1/1987 |
| JP | 62142168 | | 6/1987 |
| JP | 2-219892 | * | 9/1990 |
| JP | 3-207789 | * | 9/1991 |
| JP | 5-43878 | * | 2/1993 |
| JP | 6-80654 | | 3/1994 |
| JP | 7-179426 | | 7/1995 |
| JP | 10195063 | | 7/1998 |
| JP | 10310578 | * | 11/1998 |
| JP | 2000-224998 | * | 8/2000 |
| JP | 2002-128768 | * | 5/2002 |
| WO | 93/07141 | | 4/1993 |
| WO | 93/22312 | | 11/1993 |
| WO | 93/22315 | | 11/1993 |
| WO | 96/02507 | | 2/1996 |
| WO | 96/33181 | | 10/1996 |
| WO | 96/33285 | * | 10/1996 |
| WO | 97/03967 | | 2/1997 |
| WO | 98/02430 | * | 1/1998 |
| WO | 98/04913 | | 2/1998 |
| WO | 98/17625 | * | 4/1998 |
| WO | 98/57935 | | 12/1998 |
| WO | 98/57957 | | 12/1998 |
| WO | 99/36422 | | 7/1999 |
| WO | 99/37667 | * | 7/1999 |
| WO | 99/54304 | | 10/1999 |
| WO | 01/30757 | | 5/2001 |
| WO | 02087589 | * | 11/2002 |

OTHER PUBLICATIONS

English Language Abstract of JP 57–144264, 1982.

English Language Abstract of JP 60–197686, 1985.

Laura McMurry et al., "Active Efflux of Tetracycline Encoded by Four Genetically Different Tetracycline Resistance Determinants in *Escherichia coli*", Proc. Natl. Acad. Sci. USA, vol. 77, No. 7, pp. 3974–3977, (1990).

Keith Poole et al., "Multiple Antibiotic Resistance in *Pseudomans aeruginosa*: Evidence for Involvement of an Efflux Operon", Journal of Bacteriology, vol. 175, No. 22, pp. 7363–7372 (1993).

Keith Poole et al., "Overexpression of the mexC–mex-D–oprJ Efflux Operon in nfxB–type Multidrug–Resistant Strains of *Pseudomans aeruginosa*", Molecular Microbiology, vol. 21, No. 4, pp. 713–724 (1996).

Thilo Köhler et al., "Characterization of MexE–MexF–OprN, a Positively Regulated Multidrug Efflux System of *Pseudomans aeruginosa*", Molecular Microbiology, vol. 23, No. 2, pp. 345–354 (1997).

Tomoyuki Mine et al., "Expression in *Exherichia coli* of a New Multidrug Efflux Pump, MexXY, from *Pseudomonas aeruginosa*", Antimicrobial Agents and Chemotherapy, vol. 43, No. 2, pp. 415–417 (1999).

Daniel T.W. Chu, "Syntheses of 6–Fluoro–7–piperazin–1–yl–9–cyclopropyl–2,3,4,9–tetrahydroisothiazolo[5,4–b]quinoline–3,4–dione and 6–Fluoro–7–piperazin–1–yl–9–p–fluorophenyl–2,3,4,9–tetrahydroisothiazolo[5,4–b]quinoline–3,4–dione [1]", J. Heterocyclic Chem., vol. 27, pp. 839–843 (1990).

English Language Abstract of JP 2002–128768, 2002.*

Sadao Nishgaki et al., Chemical Pharm. Bulletin, 1975, vol. 23, pp. 3170–3177.*

English Language Abstract of JP 2002–224998, 2000.*

English Language Abstract of JP 61–092597, 1986.*

Biseibutsugaku Handbook Henshu linkai Hen, Biseibutsugaki Handbook, Kabushiki Kaisha Gihodo, Dec. 25, 1957, pp. 1230–1233.*

English Language Abstract of JP 3–207789, 1991.

English Language Abstract of JP 2–219892, 1990.

English Language Abstract of JP 5–43878, 1993.

English Language Abstract of JP 10–310578, 1998.

English Language Abstract of JP 62–142168, 1987.

English Language Abstract of JP 10–195063, 1998.

English Language Abstract of JP 61–246188, 1986.

English Langauge Abstract of JP 62–12760, 1987.

English Language Abstract of JP 60–197686, 1985.

S. Nishigaki et al., Chem. Parm. Bull. 1969, vol. 17, No. 9, pp. 1827–1831.

X. –A. Li et al., Antimicrob. Agents Chemother., 1994, vol. 38, No. 8, pp. 1732–1741.

J. Greene et al., J. Chem. Inf. Comput. Sci., 1994, No. 34, pp. 1297–1308.

J.–P. Chupp et al., J. Heterocycl. Chem., 1989, vol. 26, No. 6, pp. 1771–1780.

D. DeJohn et al., J. Heterocycl. Chem., 1983, vol. 20, pp. 1295–1302.

Chemical Abstracts, vol. 115, 1991, abstract No. 105447 of Khim–Farm. Zh., 25(5), pp. 55–58, 1991.

Chemical Abstracts, vol. 92, 1980, abstract No. 157718 of Vsec. Nauchn. Konf. Khim. Tekhnol. Furanovykh Soedin., [Tezisky Dokl.], $3^{rd}$ pp. 97–98, 1978.

Chemical Abstracts, vol. 72, 1970, abstract No. 111193 of Khim.–Farm. Zh., 4(1), pp. 24–26, 1970.

Chemical Abstracts, vol. 66, 1967, abstract No. 75885 of Yakugaku Zasshi, 86(11), pp. 1014–21, 1996.

Chemical Abstracts, vol. 108, 1988, abstract No. 142146 of Inorg. Chem., 27(7), pp. 1167–73, 1988.

Chemical Abstracts, vol. 106, 1987, Abstract No. 196227 of Tap Chi Hoa Hoc, 23(5), pp. 9–11, 1985.

Chemical Abstracts, vol. 103, 1985, abstract No. 87754 of Yiyao Gongye, 16(2), pp. 66–8, 91, 1985.

Chemical Abstracts, vol. 100, 1984, abstract No. 138915 of Khim. Geterotsikl. Soedin. (11), pp. 1521–3, 1983.

Chemical Abstracts, vol. 92, 1980, abstract No. 128023 of Khim. Geterosikl. Soedin. (9), pp. 1194–200, 1979.

Chemical Abstracts, vol. 89, 1978, abstract No. 109013 of Tezisy Dokl. –Resp. Konf. Molodykh Uch.–Khim., 2nd, vol. 1, pp. 14–15, 1977.

Chemical Abstracts, vol. 78, 1973, abstract No. 97460 of J. Heterocycl. Chem., 9(6), pp. 1203–7, 1972.

Y.C. Martin et al., J. Comp. Aided Mol. Design, 1993, vol. 7, pp. 83–102.

R.D. Cramer, J. Am. Chem. Soc., 1988, vol. 110, pp. 5959–5967.

Chem. Pharm. Bull., 39(5), pp. 1099–1105, 1991.

J. Org. Chem., 1996, vol. 61, pp. 4810–4811.

* cited by examiner

DRUG EFFLUX PUMP INHIBITOR

TECHNICAL FIELD

The present invention relates to a medicament useful for preventive and therapeutic treatment of microbial infectious diseases.

BACKGROUND ART

For preventive or therapeutic treatment of infectious diseases caused by microorganisms, various antibacterial agents have so far been developed, and drugs such as β-lactam antibiotics (penicillins, cephems, monobactams, carbapenems, and penems), aminoglycosides, quinolones, macrolides, tetracyclines, rifamycins, chloramphenicols, and phosphomycins have been practically used. However, with the increase of clinically used amount of antibacterial agents, remarkable numbers of resistant bacterial strains to these antibacterial agents have emerged, which becomes a serious problem in the treatment of infectious diseases.

Examples of problematic bacteria, which cause particularly intractable or serious infectious diseases among those caused by resistant bacteria, include *Pseudomonas aeruginosa* and methicillin-resistant *Staphylococcus aureus* (MRSA). Antibacterial agents effective against these bacteria have been limited so far, and it is not certain whether or not therapeutic efficacy of the currently available drugs will be expected in the future. In particular, no drug is available at present by which specifically high efficacy against resistant *Pseudomonas aeruginosa* can be achieved. With the increase of aged population and the popularization of sophisticated medical technologies including human organ transplantation and anti-cancer treatments, infections frequently occurring particularly in patients with reduced immunity, i.e., so-called opportunistic infections, have become an extremely serious problem in the clinical field, and under the circumstances, early developments of measures against the resistant bacteria are desired.

Recently, the presence of drug efflux pumps has recognized as a bacterial excretion mechanism of drugs through researches on resistance acquiring mechanisms of resistant bacteria. In earlier researches, a pump that specifically excretes a tetracycline antibacterial agent from bacterial cells was identified in 1980 by the group of Levy, and the discovery was noted as a major factor of the resistance to tetracycline (L. McMurry, Proc. Natl. Acad. Sci. U.S.A., 77, 3974, 1980). Furthermore, based on recent researches, the presence of multidrug-excreting drug efflux pumps was reported in *Escherichia coli*, *Pseudomonas aeruginosa*, *Bacillus subtilis*, Staphylococcus bacteria, *Diplococcus pneumoniae*, and *Neisseria gonorrhoeae*. Four multidrug efflux pumps have so far been reported as homological drug efflux pumps deriving from *Pseudomonas aeruginosa*, and they have been considered as a cause of low drug sensitivity inherent to *Pseudomonas aeruginosa* (K. Poole et al., J. Bacteriol., 175, 7363, 1993; K. Poole et al., M. Microbiol., 21, 713, 1996; T. Kohler et al., M. Microbiol., 23, 345, 1997; T. Mine et al., Antimicrob. Agents Chemother., 43, 415, 1999).

The drug efflux pumps of *Pseudomonas aeruginosa* excrete various drugs including β-lactams, tetracyclines, chloramphenicols, and quinolones, to which the drug resistance of *Pseudomonas aeruginosa* is attributable.

In order to overcome the problem, it will be effective to invent an antibacterial agent that has a novel structure, by which resistance acquisition due to a drug efflux pump, one of factors of resistance acquisition, can be avoided, or develop an agent for a combinational use with currently available antibacterial agents that can restore their efficacy by inhibiting functions of drug efflux pumps.

DISCLOSURE OF THE INVENTION

Therefore, an object of the present invention is to provide a novel medicament for the treatment of infectious diseases that improves therapeutic efficacy of an agent against pathogenic microorganisms, in particular, a medicament that acts on a microorganism with acquired resistance to an antimicrobial agent, and eliminates the resistance of the bacteria by inhibiting a drug efflux pump so as to improve preventive and/or therapeutic effect of the antimicrobial agent.

In order to achieve the aforementioned object, the inventors of the present invention conducted various researches to search for compounds that eliminate resistance to an antimicrobial drug of *Pseudomonas aeruginosa* that has acquired the resistance. As a result, they found that the compounds represented by the following general formula (I) or (II) had the desired activity, and thus achieved the present invention.

The present invention thus provides a medicament for preventive and/or therapeutic treatment of microbial infections, which comprises as an active ingredient a compound represented by the following general formula (I) or a physiologically acceptable salt thereof, or a hydrate thereof:

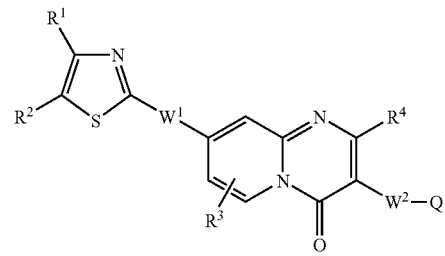

wherein, $R^1$ and $R^2$ each independently represent hydrogen atom, a halogen atom, hydroxyl group, a group of $OZ_{1-6}$ (the group of $OZ_{1-6}$ represents an alkyl group having 1–6 carbon atoms or a fluoroalkyl group having 1–6 carbon atoms, which bonds via the oxygen atom), a group of $S(O)_n Z_{1-4}$ ($Z_{1-4}$ represents an alkyl group having 1–4 carbon atoms or a fluoroalkyl group having 1–4 carbon atoms or an alkylene group derived therefrom), a group of $N(R^{12})(R^{13})$ ($R^{12}$ and $R^{13}$ each independently represent hydrogen atom, an alkyl group having 1–4 carbon atoms or a fluoroalkyl group having 1–4 carbon atoms), a group of $Z_{1-8}$ which may be substituted ($Z_{1-8}$ represents an alkyl group having 1–8 carbon atoms or a fluoroalkyl group having 1–8 carbon atoms), a 5- to 7-membered cyclic alkyl group, an aryl group, a heteroaryl group, or a 4- to 7-membered saturated or partially saturated heterocyclic group (the cyclic alkyl group, aryl group, heteroaryl group and heterocyclic group may have one to three substituents selected from the group consisting of a halogen atom, hydroxyl group, a group of $OZ_{1-4}$, a group of $S(O)_n Z_{1-4}$, a group of $N(R^{12})(R^{13})$, a group of $Z_{1-4}$, carboxyl group, a group of $CO_2 Z_{1-4}$, group of $CONH_2$, a group of $CONH(Z_{1-4})$ and a group of $CON(Z_{1-4})(Z_{1-4})$);

$W^1$ represents a group selected from the group consisting of —CH=CH—, —N($R^{12}$)CO—, —CON($R^{12}$)—, —CH₂O— and —CH₂CH₂— (each of the aforementioned groups binds to the thiazole ring at the left end);

$R^3$ represents hydrogen atom, a halogen atom, hydroxyl group or an amino group; $R^4$ represents a group selected from the group consisting of hydrogen atom, a group of —$OZ_{0-4}R^5$ ($Z_{0-4}$ represents an alkylene group having 1–4 carbon atoms, a fluorine-substituted alkylene group having 1–4 carbon atoms or a single bond, and $R^5$ represents a 5- to 7-membered cyclic alkyl group, an aryl group, a heteroaryl group or a 4- to 7-membered saturated or partially saturated heterocyclic group (the cyclic alkyl group, aryl group, heteroaryl group and heterocyclic group may have one to three substituents selected from the group consisting of a halogen atom, hydroxyl group, a group of $OZ_{1-4}$, a group of $S(O)_nZ_{1-4}$, a group of $N(R^{12})(R^{13})$, a group of $Z_{1-4}$, carboxyl group, a group of $CO_2Z_{1-4}$, group of $CONH_2$, a group of $CONH(Z_{1-4})$ and a group of $CON(Z_{1-4})(Z_{1-4})$), a group of —$S(O)_nZ_{0-4}R^5$, a group of —$N(R^6)(R^7)$ {$R^6$ and $R^7$ each independently represent hydrogen atom or $Z_{1-4}$, or they may bind to each other to form a saturated or unsaturated 5- to 7-membered ring (the ring may contain one or two hetero atoms as ring constituting atoms), and $R^6$ and $R^7$ may have one to three substituents selected from the group consisting of a halogen atom, hydroxyl group, a group of $OCON(R^{12})(R^{13})$, a group of $CON(R^{12})(R^{13})$, a group of $N(R^{12})CON(R^{12})(R^{13})$, a group of $Z_{1-4}$, a group of $OZ_{1-4}$, a group $S(O)_nZ_{1-4}$, group of $CH_2OH$, a group of $(CH_2)_mN(R^{12})(R^{13})$, carboxyl group, cyano group, a group of $CO$—$Z_{1-4}(R^{10})$—$N(R^{12})(R^{13})$ ($R^{10}$ is a substituent corresponding to a side chain on an amino acid carbon or a group of —$Z_{1-4}$—$R^{11}$ ($R^{11}$ represents a substituent which forms a quaternary salt) and a group of:

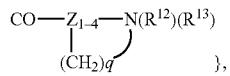

}, a 5- or 6-membered aryl group which may be substituted and a 5- or 6-membered unsaturated heterocyclic group which may be substituted;

$W^2$ represents a single bond or —$C(R^8)$=$C(R^9)$— ($R^8$ and $R^9$ each independently represent hydrogen atom, a halogen atom, a lower alkyl group, an alkoxy group, cyano group, carboxyl group, hydroxymethyl group, cyanomethyl group, vinyl group or a group of $N(R^{12})(R^{13})$), Q represents an acidic group, and $W^2$ and Q may bind together to form vinylidenethiazolidinedione in E- or Z-configuration or an equivalent heterocyclic ring; m and n each independently represent an integer of 0 to 2, and q represents an integer of 0 to 3.

As other aspects of the present invention, provided are a medicament for eliminating resistance of a microorganism with acquired drug resistance, which comprises a compound represented by the aforementioned general formula (I) or a physiologically acceptable salt thereof as an active ingredient; and a medicament for enhancing effect of an antimicrobial agent, which comprises a compound represented by the aforementioned general formula (I) or a physiologically acceptable salt thereof as an active ingredient. The aforementioned medicaments wherein the microorganism is *Pseudomonas aeruginosa* are preferred embodiments of the present invention. The present invention also provides a pharmaceutical composition for preventive and/or therapeutic treatment of microbial infections, which comprises a compound represented by the aforementioned general formula (I) or a physiologically acceptable salt thereof together with an antimicrobial agent.

As further aspects of the present invention, provided are a method for preventive and/or therapeutic treatment of microbial infections, which comprises the step of administering to a mammal including human a preventively and/or therapeutically effective amount of a compound represented by the aforementioned general formula (I) or a physiologically acceptable salt thereof; a method for eliminating resistance of a microorganism with acquired resistance to an antimicrobial agent, which comprises the step of contacting with the microorganism an effective amount of a compound represented by the aforementioned general formula (I) or a physiologically acceptable salt thereof; a method for inhibiting acquisition of resistance to an antimicrobial agent by a microorganism, which comprises the step of contacting with a microorganism an effective amount of a compound represented by the aforementioned general formula (I) or a physiologically acceptable salt thereof; a method for enhancing sensitivity of a microorganism to an antimicrobial agent, which comprises the step of contacting with a microorganism an effective amount of a compound represented by the aforementioned general formula (I) or a physiologically acceptable salt thereof; and a method for improving effect of an antimicrobial agent, which comprises the step of administering to a mammal including human an effective amount of a compound represented by the aforementioned general formula (I) or a physiologically acceptable salt thereof. The compounds represented by the aforementioned general formula (I) or physiologically acceptable salts thereof are usually administered with one or more of antimicrobial agents simultaneously or separately, or successively. The present invention also provides a use of the compounds represented by the aforementioned general formula (I) or physiologically acceptable salts thereof for the manufacture of the aforementioned medicaments.

In addition to the aforementioned inventions, the present invention also provides a medicament for preventive and/or therapeutic treatment of microbial infections, which comprises as an active ingredient a compound represented by the following general formula (I), a physiologically acceptable salt thereof, or hydrates thereof:

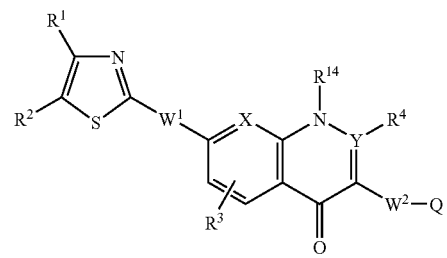

In the formula, $R^1$, $R^2$, $R^3$, $R^4$, $W^1$, $W^2$ and Q have the same meanings as those defined above; $R^{14}$ represents hydrogen atom, $Z_{1-4}$, $Z_{1-4}R^5$ or $Z_{1-4}OR^5$; and X and Y each independently represent C—H or nitrogen atom.

BEST MODE FOR CARRYING OUT THE INVENTION

In the specification, the "alkyl group" means a linear, branched or cyclic alkyl group or an alkyl group consisting of a combination thereof. The same is applied to an alkyl moiety of a substituent having the alkyl moiety (for example, fluoroalkyl group).

In the general formula (I), $R^1$ is preferably an alkyl group. Examples of the alkyl group include a linear or branched alkyl group having 1–8 carbon atoms (for example, methyl group, ethyl group, n-propyl group, isopropyl group, n-butyl group, isobutyl group, sec-butyl group, tert-butyl group, n-pentyl group and the like), and a cyclic alkyl group having 3–8 carbon atoms, preferably 3–6 carbon atoms (for example, cyclopropyl group, cyclobutyl group, cyclopentyl group, cyclohexyl group and the like). The cyclic alkyl group may have another alkyl group or a halogen atom, hydroxyl group or the like on the ring. $R^1$ is also preferably an aryl group, a heteroaryl group or a heterocyclic group. The aryl group may preferably has a 5- or 6-membered ring. As the heterocyclic group, a heterocyclic group having 3–8, preferably 3–6, of ring constituting atoms can be used, and the ring may be saturated or partially saturated. As a substituent that binds to the heterocyclic group, for example, an alkyl group or a halogen atom is preferred.

$R^2$ is preferably hydrogen atom or a halogen atom.

$W^1$ is preferably a linking group having a length of two atoms, and —CH=CH—, —N($R^{12}$)CO—, —CON($R^{12}$)—, —CH$_2$O— and —CH$_2$CH$_2$— are more preferred.

$R^3$ is preferably hydrogen atom, a halogen atom, amino group or hydroxyl group.

$R^4$ is preferably hydrogen atom, —OZ$_{0-4}R^5$ or —N($R^6$)($R^7$).

$R^5$ is preferably a 5- or 6-membered aryl group, 5- to 7-membered alicyclic group, 4- to 7-membered saturated heterocyclic group, or 5- or 6-membered unsaturated heterocyclic group, which may be substituted, and more preferably a 4- to 7-membered saturated heterocyclic group or a 5- or 6-membered unsaturated heterocyclic group.

$R^6$ and $R^7$ represent hydrogen atom, an alkyl group having 1–4 carbon atoms or a fluoroalkyl group having 1–4 carbon atoms, or they bind to each other to form a saturated or unsaturated 5- to 7-membered ring. The ring may contain one or two hetero atoms as atoms constituting the ring. $R^6$ and $R^7$ may have one to three substituents selected from the group shown as follows: a halogen atom, hydroxyl group, a group of OCON($R^{12}$)($R^{13}$), a group of CON($R^{12}$)($R^{13}$), a group of N($R^{12}$)CON($R^{12}$)($R^{13}$), a group of Z$_{1-4}$, a group of OZ$_{1-4}$, a group S(O)$_n$Z$_{1-4}$, a group of CH$_2$OH, a group of (CH$_2$)$_m$N($R^{12}$)($R^{13}$), carboxyl group, cyano group, a group of CO—Z$_{1-4}$($R^{10}$)—N($R^{12}$)($R^{13}$) and a group of:

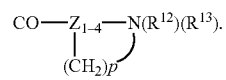

wherein $R^{10}$ is a substituent on α-carbon atom of an amino acid, or a group comprising an alkyl group or a fluoroalkyl group having 1–4 carbon atoms and a quaternary salt such as:

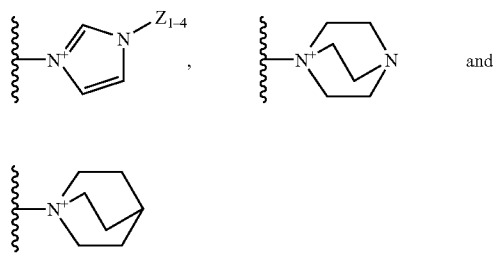

substituted at the terminal of said alkyl or fluoroalkyl group (in the definitions of the aforementioned substituents, $R^{12}$ and $R^{13}$ represent hydrogen atom, an alkyl group or a fluoroalkyl group having 1–4 carbon atoms, n independently represents an integer of 0 to 2, and q represents an integer of 0 to 3).

More preferably, $R^6$ and $R^7$ form a piperidine ring or the like and said ring has a substituent such as fluorine atom, hydroxyl group, a group of OCON($R^{12}$)($R^{13}$) and a group of CON($R^{12}$)($R^{13}$) on the ring. The ring formed by $R^6$ and $R^7$ bound to each other is preferably a piperazine ring, and preferred examples include a piperazine ring of which 4-position (nitrogen atom not bound to the pyridopyrimidine ring) is substituted with an alkyl group or a fluoroalkyl group having 1–4 carbon atoms, or with other substituent such as CO—Z$_{1-4}$($R^{10}$)—N($R^{12}$)($R^{13}$) and

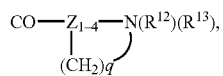

$W^2$ is preferably a single bond or a group represented by —C($R^8$)=C($R^9$)—. $R^8$ and $R^9$ each independently represent hydrogen atom, a halogen atom, a lower alkyl group, an alkoxy group, cyano group, carboxyl group, hydroxymethyl group, cyanomethyl group, vinyl group or a group of N($R^{12}$)($R^{13}$), more preferably hydrogen atom, a halogen atom or a lower alkyl group.

Q represents an acidic group, preferably an acidic group which is carboxyl group, 1,2,3,4-tetrazol-5-yl group or an equivalent thereof. However, type of the acidic group is not particularly limited, and said group may be any one of cyclic or non-cyclic, or a combination thereof. Examples include a lower alkoxy group, hydroxyl group, carboxyl group, N-cyanocarboxamido group, a methanesulfonylamido group having 1–3 fluorine atoms, —CONH-(5-tetrazolyl) group, 5-tetrazolyl group which may be substituted, 1,2,3-triazolyl group which may be substituted, 2,4-dioxothiazolidin-5-ylidenyl group which may be substituted, 4-oxo-2-thioxothiazolidin-5-ylidenyl group which may be substituted, 5-oxo-4-tetrazolyl group which may be substituted, 3-(5-oxo)-[1.2.4]oxadiazolidinyl group which may be substituted, 2-(3,5-dioxo)-[1.2.4]oxadiazolidinyl group which may be substituted, 5-(3-oxo)-[1.2.4]oxadiazolidinyl group which may be substituted, 3-(5-oxo)-[1.2.4]isoxazolidyl group which may be substituted or the like. More preferred examples include carboxyl group, 5-tetrazolyl group which may be substituted, N-cyanocarboxamido group, a methanesulfonylamido group that has 1–3 fluorine atoms, —CONH-(5-tetrazolyl) group or the like.

For $R^1$, $R^2$, $R^3$, $R^4$, $W^1$, $W^2$ and Q of the compounds represented by the general formula (II), those explained as for $R^1$, $R^2$, $R^3$, $R^4$, $W^1$, $W^2$ and Q in the aforementioned general formula (I) can be preferably used, respectively.

$R^{14}$ is preferably an alkyl group having 1–4 carbon atoms or a fluoroalkyl group having 1–4 carbon atoms.

The compounds represented by the aforementioned general formula (I) can be produced by the following methods.

Scheme 1

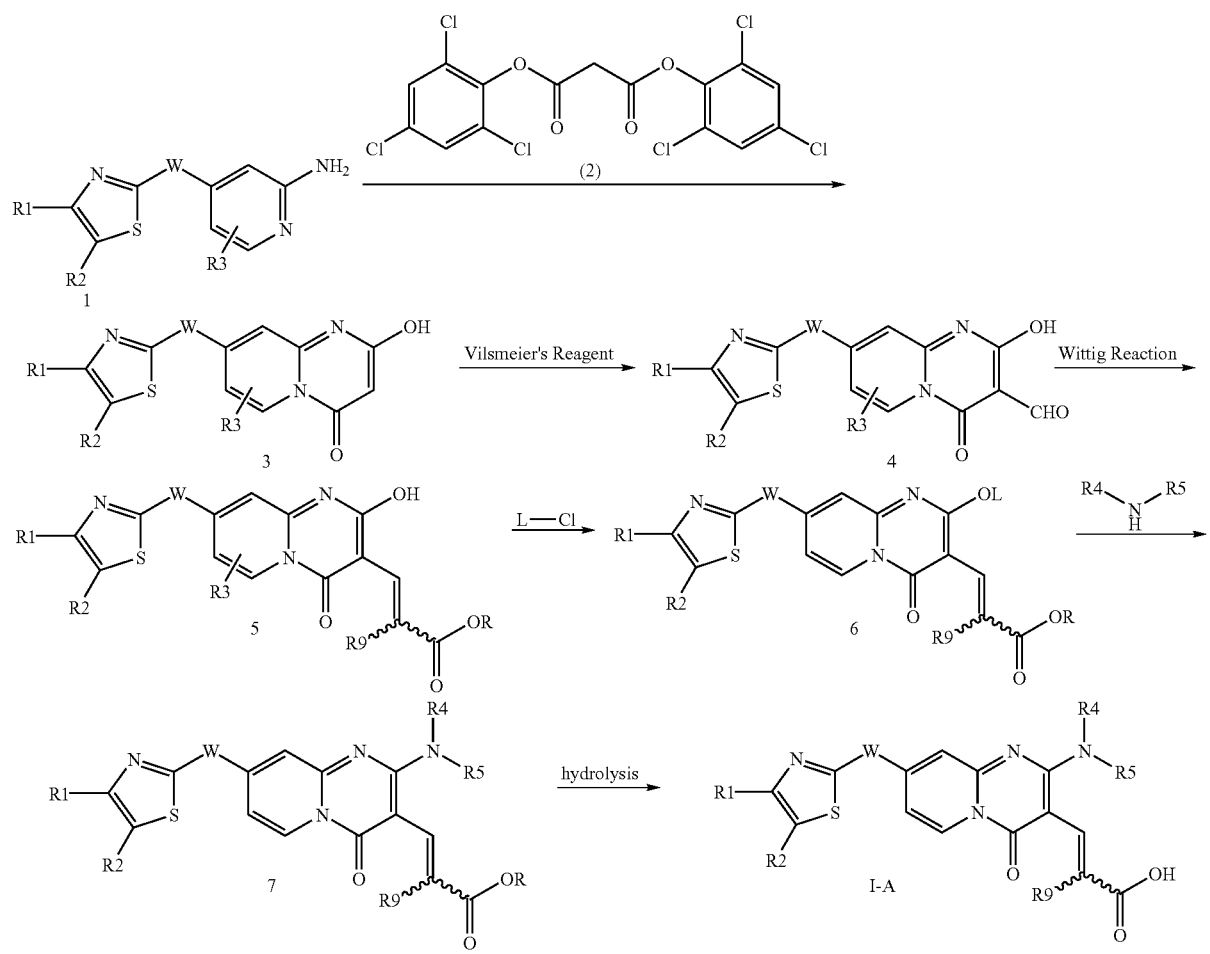

L: Tosyl, Mesyl, Diphenylphosphono group

As shown in Scheme 1, Compound 3 can be obtained by heating Aminopyridine derivative 1 and malonic acid or an ester of malonic acid in a solvent such as toluene and xylene. As the ester of malonic acid, Ester 2 as a phenol ester substituted with an electron-withdrawing group such as a halogen atom can be used. An alkyl ester can also be used. By formylating Compound 3 with Vilsmeier's reagent prepared from phosphorus oxychloride or oxalyl chloride and dimethylformamide (DMF), Aldehyde 4 can be obtained. By subjecting Compound 4 to the Wittig reaction or Horner-Emons reaction, Acrylic acid derivative 5 can be synthesized. Where the Wittig reaction is employed, Compound 5 can be obtained by reacting an alkyloxycarbomethylene-triphenylphosphorane which may be substituted with the aldehyde compound in an inert solvent such as tetrahydrofuran, DMF or methylene chloride. Where the Horner-Emons reaction is employed, the target compound can be synthesized by reacting the aldehyde compound with a dialkylphosphonoacetic acid ester which may be substituted at the 2-position in the presence of a base in an inert solvent such as THF and DMF. Compound 7 having amino group at the 2-position as a linker can be obtained by converting the hydroxyl group at the 2-position of Compound 5 into tosyl group, mesyl group, diphenylphosphoric acid ester or the like, and then replacing the resulting group with an amine. The ester group of the acrylic acid moiety can be hydrolyzed in the final step to obtain Compound I-A. As the ester group, a lower alkyl ester such as those of methyl group and ethyl group, tert-butyl ester, benzyl ester, allyl ester and so forth can be used, and they can be hydrolyzed by hydrolysis under an alkaline or acidic condition, catalytic reduction or a method by using a metal catalyst such as palladium.

Further, Compound I-A can also be synthesized by the method shown in Scheme 2. Compound 9 can be obtained by converting the hydroxyl group at the 2-position of Compound 3 into tosyl group, mesyl group, diphenylphosphoric acid ester or the like and then replacing the resulting group with an amine. The resulting product can be formylated with Vilsmeier's reagent prepared from phosphorus oxychloride or oxalyl chloride and dimethylformamide to obtain Aldehyde 10. By subjecting Compound 10 to the Wittig reaction or Horner-Emons reaction, Acrylic acid derivative 7 can be synthesized. Where the Wittig reaction is employed, Compound 7 can be obtained by reacting an alkyloxycarbomethylenetriphenylphosphorane which may be substituted with the aldehyde compound in an inert solvent such as THF, DMF, toluene or methylene chloride. Where the Horner-Emons reaction is employed, the target compound can be synthesized by reacting the aldehyde compound with a dialkylphosphonoacetic acid ester which may be substituted at the 2-position in the presence of a base in an inert solvent such as THF and DMF.

According to this synthetic scheme, various primary or secondary amines can be reacted with Compound 6 to synthesize variety of 2-substituted derivatives by the multiple parallel synthesis method in a liquid phase.

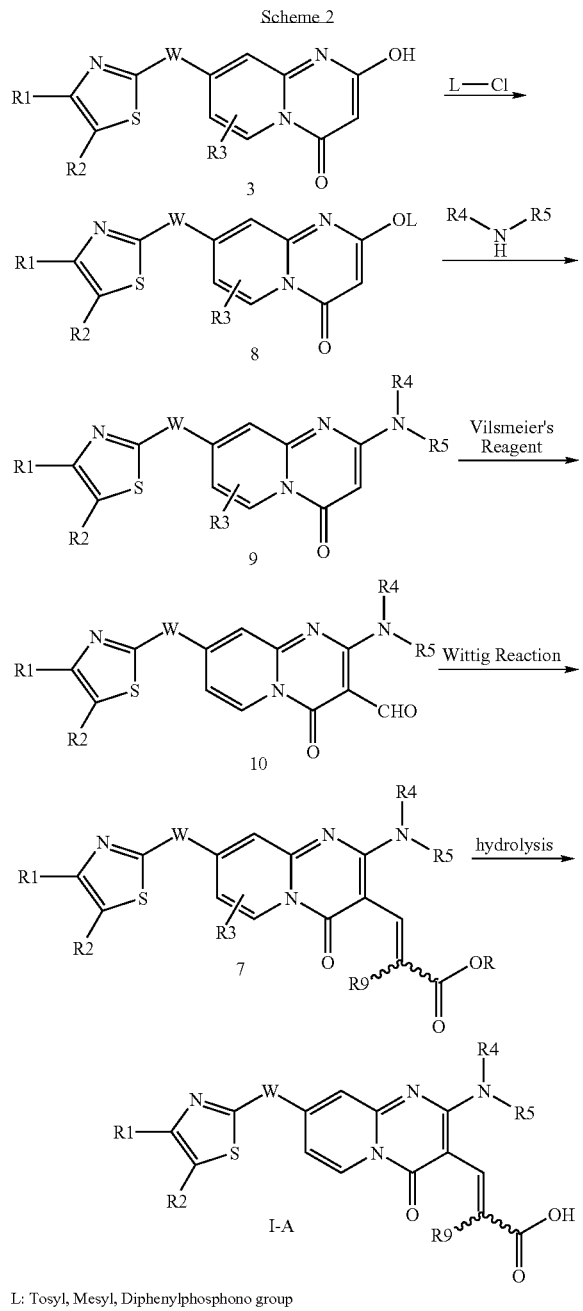

L: Tosyl, Mesyl, Diphenylphosphono group

A compound in which a substituent is introduced at the 2-position of the pyridopyrimidine ring as a linker can be synthesized by the method shown in Scheme 3.

Compound 11 can be synthesized by reacting Compound 5 with an alkylating agent in the presence of a base. The ester portion of the resulting Compound 11 can be hydrolyzed to obtain Compound I-B in a manner similar to that for the aforementioned compound having a nitrogen atom as a linker.

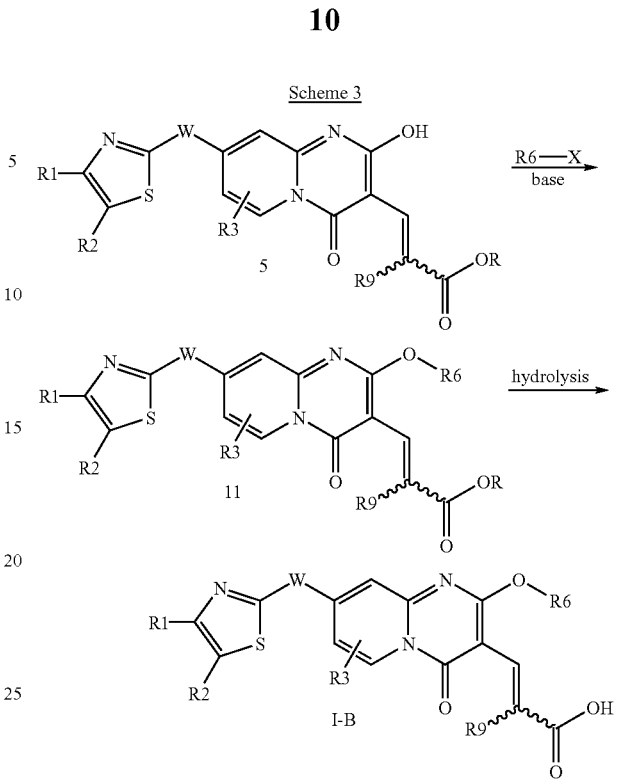

Compound I-B can also be synthesized by the method shown in Scheme 4, i.e., by alkylation of Compound 3 with an alkylating agent and subsequent formylation, olefination and deprotection of the ester portion.

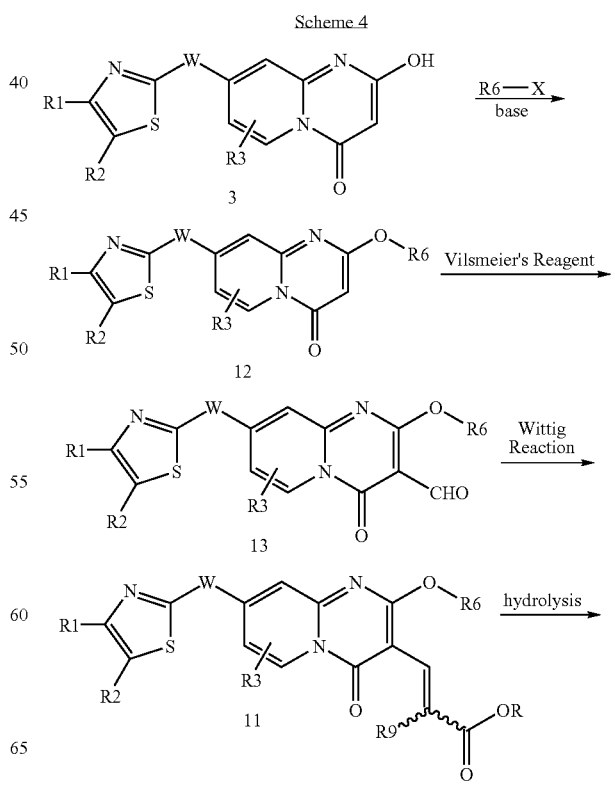

-continued

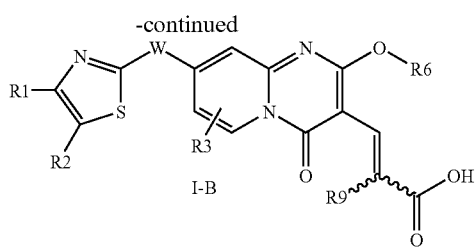

Compound 1 used for the aforementioned synthesis can be synthesized as follows.

For example, Compound 1-A of which W portion is an amide bond can be synthesized by condensing an aminothiazole derivative, which is a known compound or can be synthesized by a known method, and a 2-aminopyridine-4-carboxylic acid derivative of which amino group is protected by a usual method used for a reaction of forming a peptide bond, and deprotecting the protective group of the amino group.

Scheme 5

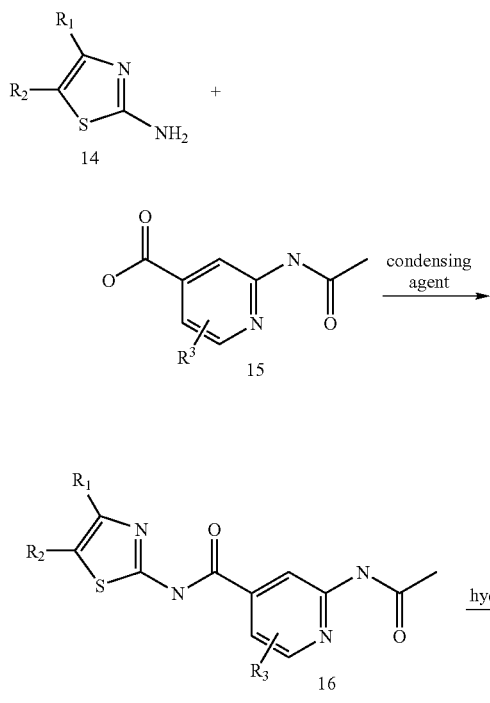

Compound 1-B of which W portion is a double bond can be synthesized by condensing 2-Methylthiazole derivative 17, which is a known compound or can be synthesized by a known method, and 2-Aminopyridine-4-carbaldehyde derivative 18 of which amino group is protected under a condition for the Knoevenagel reaction, and removing the protective group of the amino group. As for the condition of the Knoevenagel reaction, the reaction can also be performed by heating in acetic anhydride or in the presence of a base such as piperidine and piperazine and in the co-presence of an acid such as acetic acid.

Scheme 6

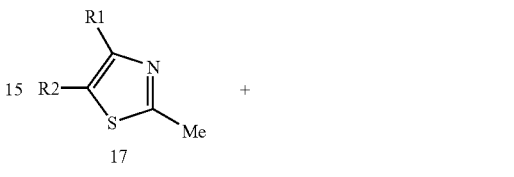

Prot: Protective Group

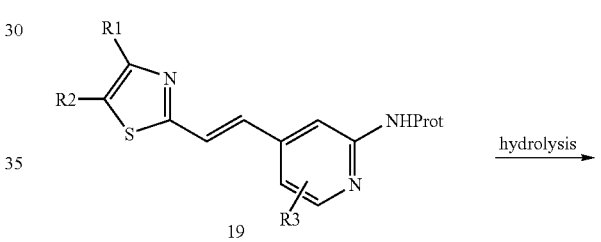

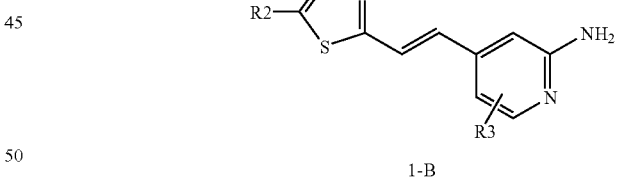

An anion that can be obtained by treating 2-Amino-4-methylpyridine derivative 20 of which amino group is protected with a strong base such as n-BuLi and an aldehyde are reacted, and then the resulting hydroxyl group can be subjected to tosylation, mesylation or the like, or the resulting product is converted into a halogenated compound such as by chlorination or bromination. The resulting product is then subjected to elimination reaction using a base such as DBU to obtain Double bond-containing derivative 23. By removing its amino protective group, Compound 1-C can be synthesized.

the resulting product to a rearrangement reaction and, if required, removing the protective group of the amino group.

Scheme 7

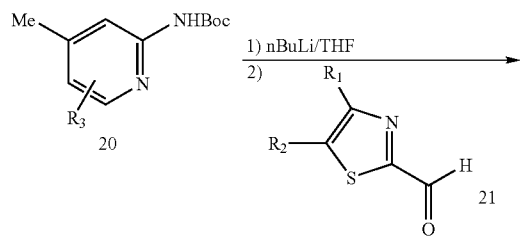

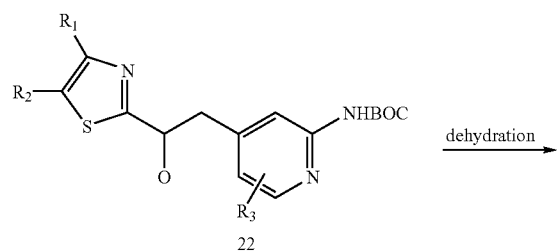

Scheme 8

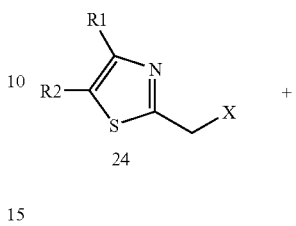

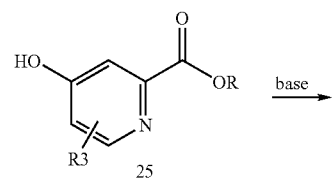

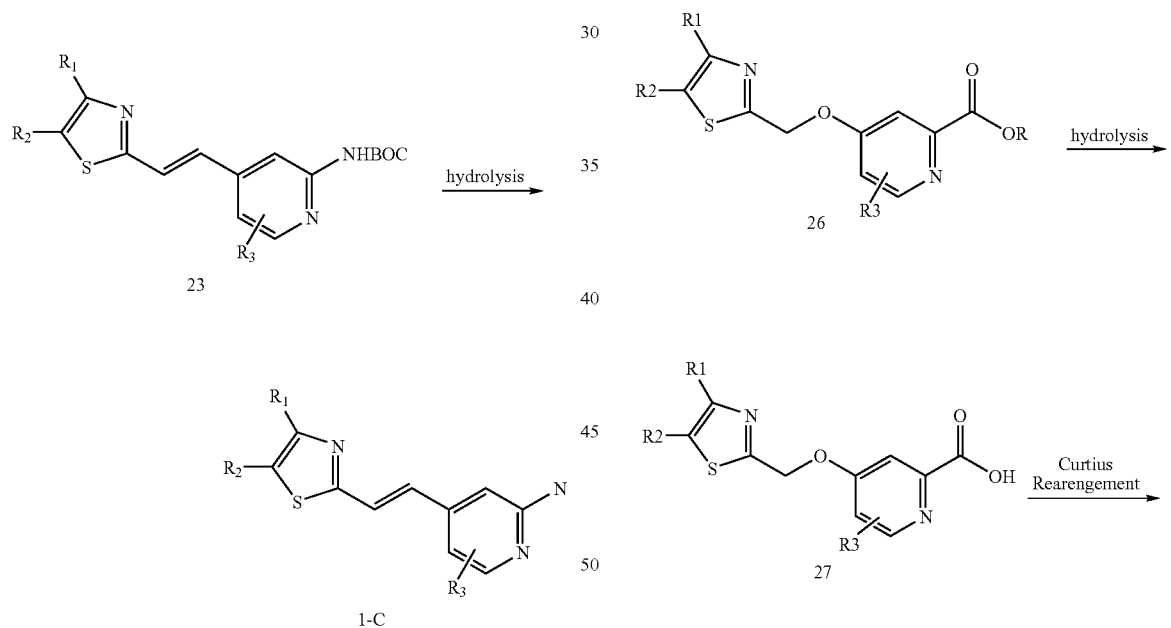

Compound 1-D of which W portion is an ether bond can be synthesized by condensing Thiazolemethyl halide 24, which is a known compound or can be synthesized by a known method, and 4-Hydroxypyridine-2-carboxylic acid ester 25 in the presence of a base, hydrolyzing the ester portion of the resulting Compound 26, and then converting the produced carboxylic acid into Amine derivative 28 by employing the Curtius rearrangement or the like. Amino compound 1-D can also be obtained by first converting the carboxylic acid into a condensation product with hydrazine, then converting the resulting product into an acid azide with a nitrous acid salt or a derivative thereof, further subjecting

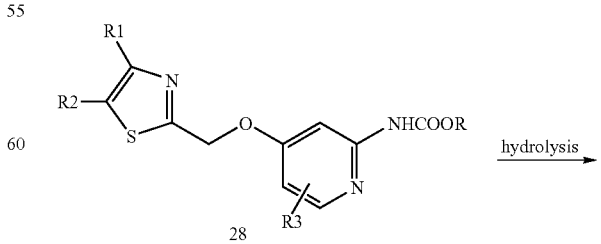

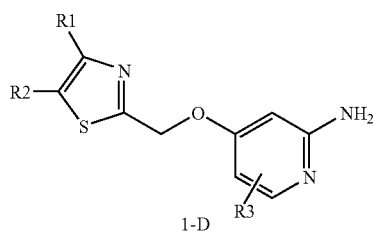

1-D

Compound 1-E, where W portion is ethylene, can be synthesized by reacting an anion, obtained by treating 2-Amino-4-methylpyridine derivative 20 of which amino group is protected with a strong base such as n-BuLi, with Thiazolemethyl halide 24 to obtain a condensation product and then removing the protective group of the amino group.

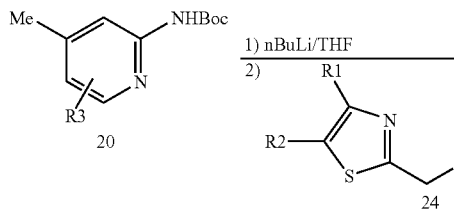

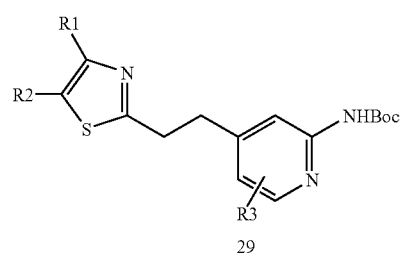

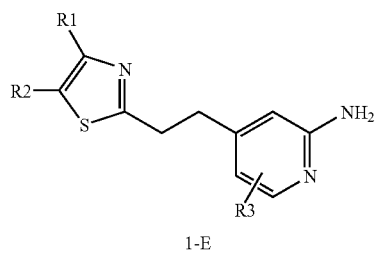

1-E

As shown in Scheme 10, Compound 1-E can also be synthesized by reacting an anion, obtained by treating 2-Amino-4-methylpyridine derivative 20 of which amino group is protected with a strong base such as n-BuLi, with Halogenoacetic acid derivative 30 to obtain a condensation product, converting the ester portion into an amide, then converting the resulting product into a thioamide compound by using Lawesson's reagent, diphosphorous pentasulfide or the like and condensing the product with a haloketone compound.

Scheme 10

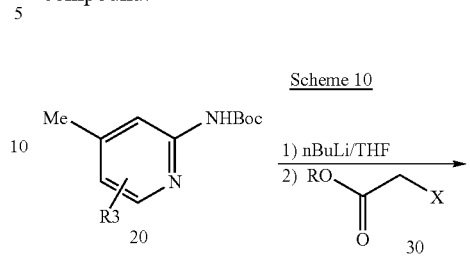

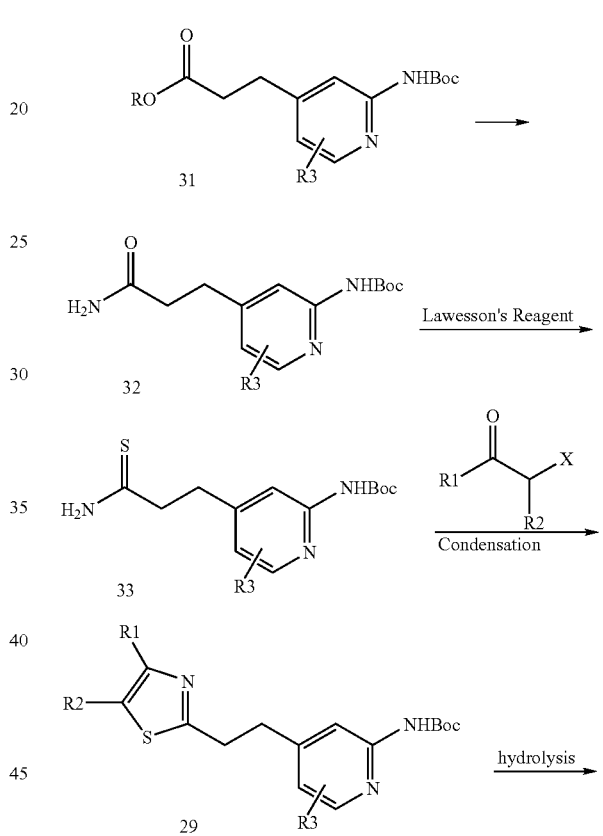

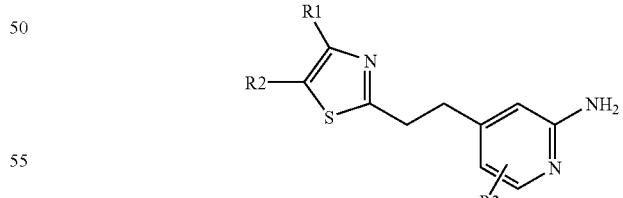

1-E

A compound of which W portion is a triple bond can be synthesized by the synthetic methods described in WO9633181 published Oct. 24, 1996.

The compound represented by the general formula (II) can be synthesized by the method shown in Scheme 11.

Scheme 11

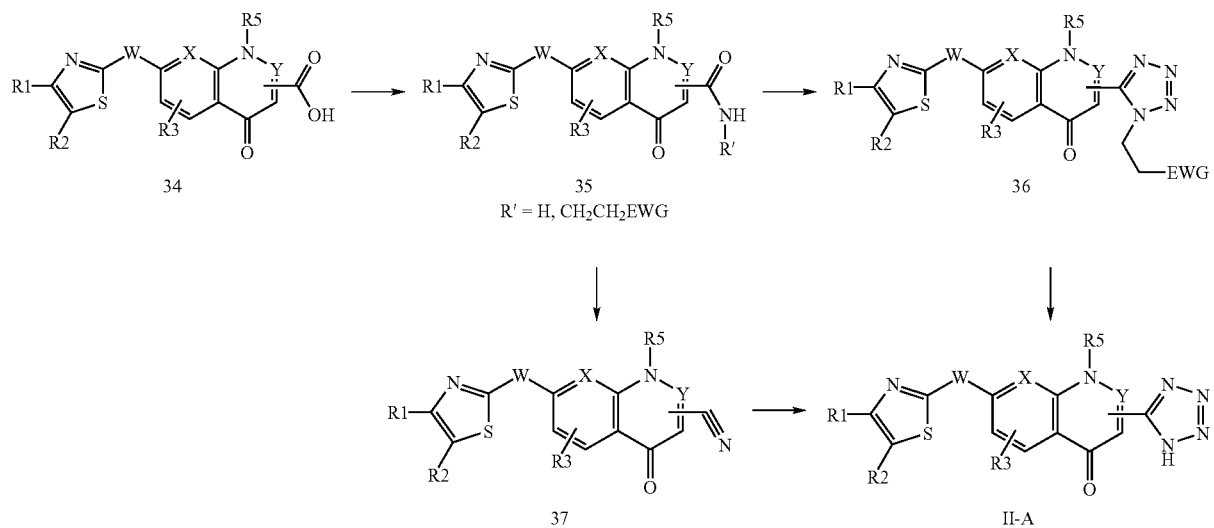

Amide derivative 35 can be obtained by converting N-Alkyl-quinolone-carboxylic acid derivative 34 described in PCT/JP00/07565 into a mixed acid anhydride, and then reacting the resulting product with ammonia or an ethylamine having an electron-withdrawing group (EWG) such as cyanoethylamine and 3-aminopropanoic acid ester. The alkylamide derivative can be converted into Compound 36 by treatment with sodium azide and trifluoromethanesulfonic acid anhydride in an acetonitrile solvent to form a tetrazole ring. Then, the product can be converted into Tetrazole compound II-A by treatment with DUB in an inert solvent such as methylene chloride or treatment with a base such as sodium methoxide in an alcohol.

Further, Tetrazole compound II-A can similarly be obtained by subjecting Carbamoyl derivative 35 to dehydration reaction to obtain Cyano derivative 37 and treating the resulting compound with sodium azide and aluminum chloride in dimethylformamide. Similarly, Tetrazole compound II-A can be produced by subjecting Carboxylic acid 34 having a cinnolin-4-one or naphthylidin-4-one structure to the same treatment.

Scheme 12

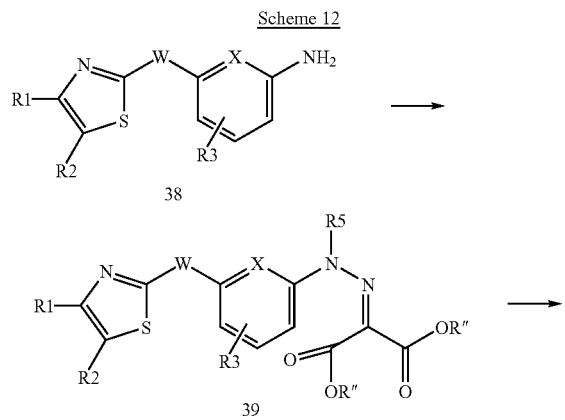

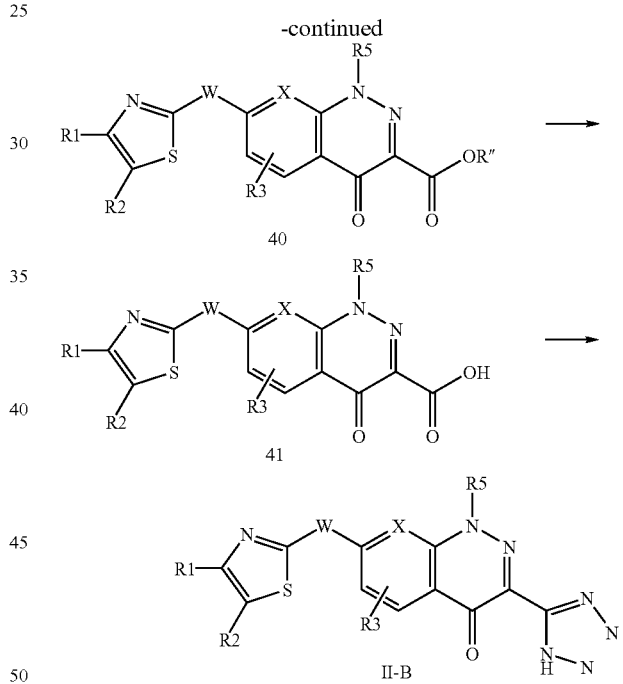

As shown in Scheme 12, where a derivative having a cinnolin-4-one structure is desired, Compound 38, which is a known compound or can be easily derived from a known compound, can be converted into a diazo compound by treating the amino group with sodium nitrite, and the resulting product can be reacted with a malonic acid ester to obtain Compound 39 ($R^5$=H). An electrophilic regent such as an alkyl halide can be reacted with the nitrogen atom of the resulting Compound 39 ($R^5$=H) by using a base such as sodium hydride and potassium carbonate in a solvent such as DMF and THF, and then the product can be heated in a solvent such as Dowtherm A and PPA and treated under an ordinary hydrolysis condition to obtain Carboxylic acid 41. The Carboxylic acid 41 obtained can be subjected to a treatment similar to the aforementioned treatment (Scheme 11) to produce Tetrazole compound II-B.

Scheme 13

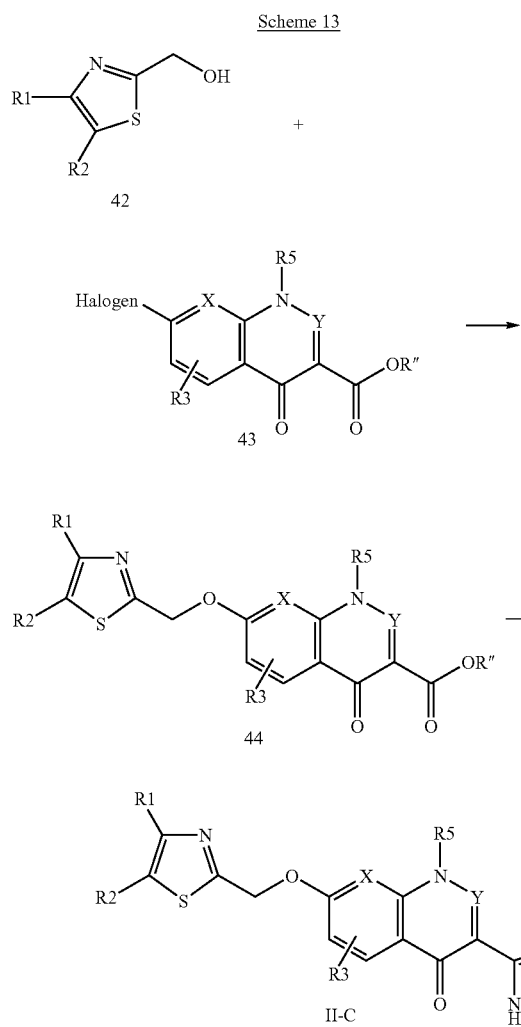

Scheme 14

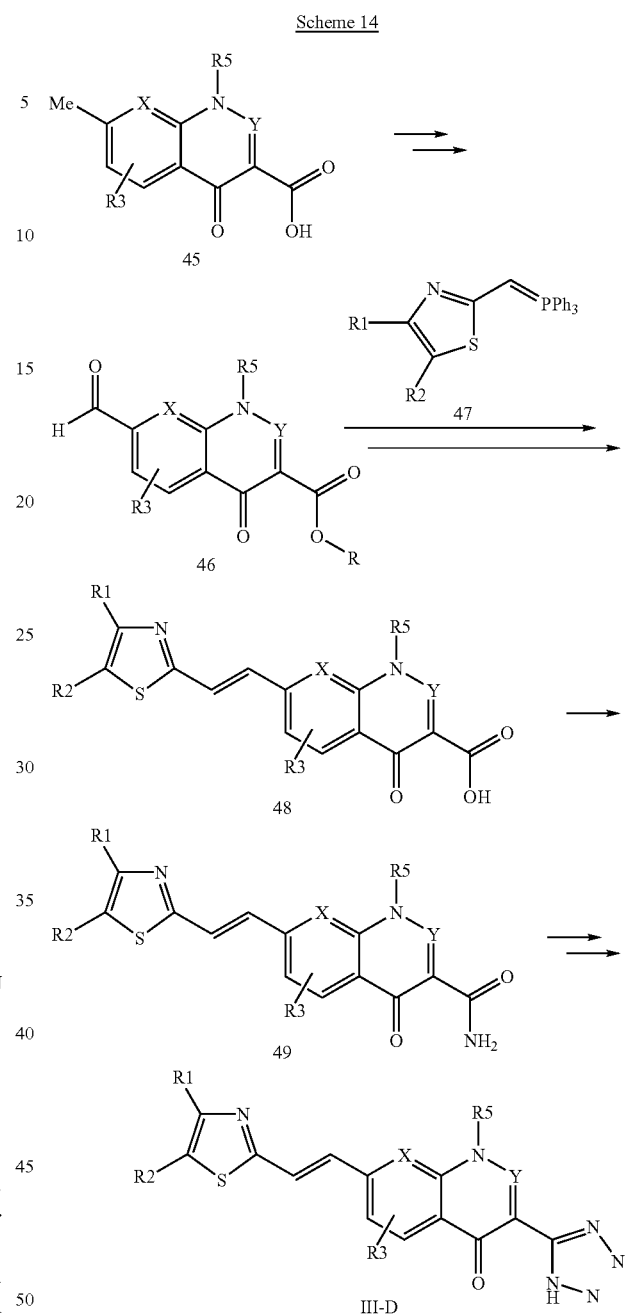

As shown in Scheme 13, when W portion is —CH$_2$O—, Compound 42 can be converted into an alkoxide by treatment with a strong base such as sodium hydride in DMF or THF, and the alkoxide can be reacted with Compound 43, which is a known compound or can be synthesized by a known method (Japanese Patent Un-examined Publication (Kokai) No. 57-144264 or 60-197686), to obtain Compound 44. Subsequently, Compound 44 can be converted into a carboxylic acid by hydrolysis and subjected to a treatment similar to the aforementioned treatment (Scheme 11) to produce Tetrazole compound II-C.

As for the aforementioned production of cinnolin-4-one derivative, a method wherein 3-chloro-4-fluoroaniline is used as a starting material is compared with a method wherein 3,4-difluoroaniline is used, 3,4-difluoroaniline will give much higher yield of cinnolin-4-one-3-carboxylic acid as for the thermal cyclization reaction performed in a solvent such as Dowtherm A and PPA in the production of the known Compound 43 and selectivity of the substitution of the alkoxide shown in Scheme 13.

As shown in Scheme 14, where the compound in which W is an olefin is desired, Compound 45, which is a known compound or can be synthesized by a known method, can be esterified and then subjected to treatment with an oxidizing agent such as selenium dioxide, and the resulting Aldehyde derivative 46 and Compound 47 can be subjected to the Wittig reaction and further subjecting the adduct to addition of ammonia to obtain Carbamoyl compound 49. The resulting Carbamoyl derivative 49 can be converted into Tetrazole compound II-D by using the same method as in Scheme 11.

The synthetic intermediates and the target compounds in the aforementioned preparations can be isolated and purified by using methods for isolation and purification ordinarily used in the field of organic synthetic chemistry, for example, neutralization, filtration, extraction, drying, concentration, recrystallization, various chromatographic techniques and the like. The synthetic intermediates may be used in subsequent reactions without purification. When a salt of compound of the general formula (I) or (II) is desired, a product obtained in the form of a salt may be purified without any treatment. When a product is obtained in a free form, a salt can be formed by dissolving or suspending the product in a suitable organic solvent, and then adding an acid or base. It is also possible to convert a compound represented by the general formula (I) or (II) obtained in the form of a salt into a compound in a free form, and then convert the result into an appropriate salt.

Although it is not intended to be bound by any specific theory, the compounds represented by the general formula (I) have an activity for inhibiting drug efflux pumps of microorganisms. More specifically, the compounds represented by the general formula (I) can act on a microorganism with acquired resistance to an antimicrobial agent to inhibit its drug efflux pump, and eliminate the resistance of the microorganism. In addition, the compounds represented by the general formula (I) can act on a microorganism to inhibit a drug efflux pump, thereby suppress the acquisition of resistance to an antimicrobial agent by a microorganism. Therefore, the medicament of the present invention that comprises a compound represented by the general formula (I) as an active ingredient is useful for preventive and/or therapeutic treatment of microbial infections, generally by a combinational administration with an antimicrobial agent. The medicament of the present invention is extremely useful as a medicament for preventive and/or therapeutic treatment of, in particular, infectious diseases caused by a microorganism with acquired resistance to one or more antimicrobial agents.

Methods for using the medicament of the present invention are not particularly limited. Examples include a method of administering one or more antimicrobial agents, and also administering the medicament of the present invention simultaneously, separately, or successively to enhance the activity of the antimicrobial agent(s); and a method of preparing a pharmaceutical composition comprising one or more antimicrobial agents and the medicament of the present invention (so-called a compound drug) and administering the composition.

Kinds of microbial infections that are applicable by the medicament of the present invention are not particularly limited. Bacteria are suitable as target microorganisms. The medicament of the present invention can be used for various infections by microorganisms including Gram-positive or Gram-negative bacteria, aerobic or anaerobic bacteria and the like. The medicament of the present invention can most suitably be used for infections by *Pseudomonas aeruginosa* with acquired resistance to one or more antimicrobial agents, or infections by *Pseudomonas aeruginosa* with low sensitivity to antimicrobial agents. The medicament of the present invention can be used for microbial infections of mammals including human.

Drugs having variety of structures have been known as antimicrobial agents, and various drugs are clinically used. Kinds of antimicrobial agents that can be administered in combination with the medicament of the present invention are not particularly limited, and examples include, for example, penicillin (penam) antibiotics, cephalosporin (cephem) antibiotics, oxacephem antibiotics, penem antibiotics, carbapenem antibiotics, monobactam antibiotics, aminoglycoside antibiotics, macrolide antibiotics, chloramphenicol antibiotics, tetracycline antibiotics, glycopeptide antibiotics, phosphomycin antibiotics, lincomycin antibiotics, sulfonamide preparations, p-aminosalicylic acid preparations, isonicotinic acid hydrazide preparations, quinolone synthetic antimicrobial agents and the like. However, antimicrobial agents are not limited to these examples. When a pharmaceutical composition comprising one or more antimicrobial agents together with the medicament of the present invention is manufactured, the antimicrobial agents exemplified above can also be used.

As the active ingredient of the medicament of the present invention, a substance selected from the group consisting of the compounds represented by the formula (I) and pharmaceutically acceptable salts thereof, and hydrates thereof and solvates thereof can be used. Two or more of the substances may be used in combination. The aforementioned substance, per se, may be administered as the medicament of the present invention. Generally, however, it is desirable that the substance is administered in the form of a pharmaceutical composition comprising one or more of the aforementioned substances as the active ingredient together with one or more pharmaceutical additives. The pharmaceutical composition may optionally be added with one or more of other pharmaceutically active ingredients such as the aforementioned antimicrobial agents and β-lactamase inhibitors.

A pharmaceutical composition for the use of administration in vivo can be readily prepared by mixing one or more of the aforementioned substances as the active ingredient and one or more pharmaceutically acceptable additives for pharmaceutical preparations according to methods for formulation ordinarily used in the field of manufacturing pharmacy. The route of administration of the medicament of the present invention is not particularly limited; however, it is desirable to appropriately chose the most effective administration route for preventive and/or therapeutic treatment of a target infectious disease. Examples of pharmaceutical compositions suitable for oral administration include, for example, capsules, powders, tablets, granules, subtilized granules, emulsions, syrups, solutions, suspensions and the like. Examples of pharmaceutical compositions suitable for parenteral administration include, for example, inhalants, sprays, intrarectal preparations, injections, drip infusions, ointments, creams, transdermal preparations, transmucosal preparations, eye drops, nasal drops, ear drops, tape preparations, patches and the like. However, the forms of the medicament of the present invention are not limited to these examples.

Among the pharmaceutical compositions suitable for oral administration, liquid preparations such as emulsions and syrups can be prepared by using pharmaceutical additives including water; saccharides such as sucrose, sorbitol, fructose; glycols such as polyethylene glycol and propylene glycol; oils such as sesame oil, olive oil and soybean oil; antiseptics such as p-hydroxybenzoic acid esters; flavors such as strawberry flavor and peppermint and the like. Solid preparations such as capsules, tablets, powders and granules can be prepared by using excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid esters; plasticizers such as glycerin and the like.

Among the pharmaceutical compositions suitable for parenteral administration, liquid preparations such as injections, drip infusions and eye drops can preferably be prepared as sterilized isotonic liquid preparations. For example, injections can be prepared by using an aqueous medium such as a solution of sodium chloride, a solution of glucose, or a mixture of saline and glucose solution. The intrarectal preparations can be prepared generally in the form of suppositories by using carriers such as cacao butter, hydrogenated fat and hydrogenated carboxylic acid. For the preparation of sprays, a non-irritable carrier can be used that enables fine dispersion and enhances absorption of the aforementioned substances as the active ingredient. Examples of such a carrier include lactose, glycerin and the like. Aerosols, dry powders or the like can also be chosen as the form of preparation. However, pharmaceutical additives used for the manufacture of the medicament of the present invention are not limited to those mentioned above, and any additives available for those skilled in the art can be used.

A dose and frequency of administration of the medicament of the present invention are not particularly limited, and a suitable dose can be chosen depending on the type and severity of a microbial infection, the presence or absence of an underlying disease, the age and body weight of a patient and the like.

EXAMPLES

The present invention will be explained more specifically with reference to the examples. However, the scope of the present invention is not limited to the following examples.

Example 1

(E)-3-[8-[2-(4-Cyclobutyl-1,3-thiazol-2-yl)ethyl]-2-(3-hydroxypiperidino)-4-oxo-4H-pyrido[1,2-a]pyrimidin-3-yl]-2-propenoic acid (A) Methyl 3-{2-[(tert-butoxycarbonyl)amino]-4-pyridyl}propanoate tert-Butyl N-(4-methyl-2-pyridyl)carbamate (5 g, 24.0 mmol) was dissolved in tetrahydrofuran (120 ml), cooled to −78° C., and then added dropwise with n-butyl lithium (40 ml, 60 mmol). Then, the reaction solution was warmed and stirred at room temperature. The reaction mixture was stirred for 1 hour, then again cooled to −78° C., and added dropwise with methyl bromoacetate (3.4 ml) dissolved in tetrahydrofuran (10 ml). After the reaction mixture was stirred for 30 minutes, the reaction was stopped with saturated brine and the reaction mixture was extracted with ethyl acetate. The resulting organic layer was dried over sodium sulfate and concentrated under reduced pressure, and the residue was purified by silica gel column chromatography (chloroform:ethyl acetate=3:1→5:1) to obtain 3.95 g (59%) of the title compound as pale yellow crystals.

$^1$H-NMR (CDCl$_3$) δ: 1.53 (9H, s), 2.67 (2H, t, J=7.81 Hz), 2.95 (2H, t, J=7.81 Hz), 3.68 (3H, s), 6.82 (1H, dd, J=1.22, 5.13 Hz), 7.84 (1H, s), 8.13 (1H, d, J=5.13 Hz)

(B) 3-{2-[(tert-Butoxycarbonyl)amino]-4-pyridyl}propanoic acid

Methyl 3-{2-[(tert-butoxycarbonyl)amino]-4-pyridyl}propanoate (30.65 g, 0.11 mol) dissolved in methanol (200 ml) was added with 1 N aqueous sodium hydroxide (164 ml) and stirred at room temperature for 21 hours. After the solvent was evaporated under reduced pressure and the residue was washed with diethyl ether, the resulting aqueous layer was added with concentrated hydrochloric acid until pH of the layer became 1. The solution was washed with ethyl acetate, and the resulting aqueous layer was neutralized by further adding sodium hydroxide. The solution was extracted with chloroform:methanol=10:1, and the resulting organic layer was dried over sodium sulfate and concentrated under reduced pressure to obtain 11.16 g (38%) of the title compound as yellow crystals without purification.

$^1$H-NMR (CD$_3$OD) δ: 1.54 (9H, s), 2.67 (2H, t, J=7.59 Hz), 2.95 (2H, t, J=7.59 Hz), 6.90 (1H, d, J=5.14 Hz), 7.80 (1H, s), 8.08 (1H, d, J=5.14 Hz) EI/MS; m/z: 267 (M$^+$+1)

(C) tert-Butyl N-[4-(3-amino-3-oxopropyl)-2-pyridyl]carbamate

3-{2-[(tert-Butoxycarbonyl)amino]-4-pyridyl}propanoic acid (11.16 g, 41.92 mmol) dissolved in tetrahydrofuran (200 ml) was added with triethylamine (9 ml, 62.89 mmol), cooled with ice, and then added dropwise with ethyl chloroformate (6 ml, 62.89 mmol). The reaction mixture was stirred for 10 minutes, and then added with aqueous ammonia (50 ml) dissolved in tetrahydrofuran (50 ml) at 0° C. The reaction mixture was stirred for 20 minutes under ice cooling, and then the solvent was evaporated under reduced pressure. The resulting residue was washed with water and extracted with chloroform. The resulting organic layer was washed with saturated brine, and the organic layer was dried over sodium sulfate and concentrated under reduced pressure to obtain 11.794 g (100%) of the title compound as brown crystals without purification.

$^1$H-NMR (CD$_3$OD) δ: 1.53 (9H, s), 2.57 (2H, t, J=8.05 Hz), 2.97 (2H, t, J=8.05 Hz), 5.40 (2H, br), 6.84 (1H, dd, J=1.46, 5.13 Hz), 7.83 (1H, s), 8.13 (1H, d, J=5.13 Hz) EI/MS; m/z: 266 (M$^+$+1)

(D) tert-Butyl N-[4-(3-amino-3-thioxopropyl)-2-pyridyl]carbamate

Under argon atmosphere, tert-butyl N-[4-(3-amino-3-oxopropyl)-2-pyridyl]-carbamate (11.79 g, 44.44 mmol) dissolved in tetrahydrofuran (100 ml) was added with Lawesson's reagent (9 g, 22.22 mmol) and stirred at 70–80° C. for 30 minutes. After the reaction mixture was returned to room temperature, the solvent was evaporated under reduced pressure and the resulting residue was purified by silica gel column chromatography (chloroform chloroform:methanol=20:1) to obtain 9.544 g (76%) of the title compound as pale yellow crystals.

$^1$H-NMR (CD$_3$OD) δ: 1.53 (9H, s), 2.89 (2H, t, J=8.30 Hz), 3.09 (2H, t, J=8.30 Hz), 6.94 (1H, d, J=5.13 Hz), 7.75 (1H, s), 8.08 (1H, d, J=5.13 Hz) EI/MS; m/z: 282 (M$^+$+1)

(E) 2-Bromo-1-cyclobutyl-1-ethanone

1-Cyclobutyl-1-ethanone (500 mg, 5.1 mmol) dissolved in methanol (5 ml) was added with bromine (0.3 ml, 5.6 mmol) and stirred at room temperature for 1 hour. The resulting ocher reaction mixture was added with water (3 ml) under ice cooling, and then gradually added with potassium carbonate (350 mg). The mixture was extracted with dichloromethane, and the resulting organic layer was neutralized with saturated aqueous sodium hydrogencarbonate and washed with saturated brine. The resulting organic layer was dried over magnesium sulfate and concentrated under reduced pressure to obtain 867 mg (96%) of the title compound without purification.

$^1$H-NMR (CDCl$_3$) δ:1.88 (1H, m), 2.00 (1H, m), 2.20–2.37 (4H, m), 3.60 (1H, qu, J=8.53 Hz), 3.88 (2H, s)

(F) 8-[2-(4-Cyclobutyl-1,3-thiazol-2-yl)ethyl]-2-hydroxy-4H-pyrido[1,2-a]pyrimidin-4-one tert-Butyl N-[4-(3-amino-3-thioxopropyl)-2-pyridyl]carbamate (1.38 g, 4.9 mmol) dissolved in ethanol was added with 2-bromo-1-cyclobutyl-1-ethanone (867 mg, 4.9 mmol) and refluxed at 100° C. for 1 hour. The resulting reaction solution was cooled to room temperature, then neutralized with saturated aqueous sodium hydrogencarbonate and extracted with chloroform. The resulting organic layer was washed with saturated brine, dried over magnesium sulfate and concentrated under reduced pressure.

The resulting oily compound was added with dichloromethane (50 ml) and slowly added dropwise with trifluoroacetic acid (50 ml) under ice cooling. Then, the reaction solution was warmed to room temperature and stirred 1 hour. The resulting solution was neutralized with saturated sodium hydrogencarbonate and extracted with chloroform. The organic layer was washed with saturated brine, and the resulting organic layer was dried over magnesium sulfate and concentrated under reduced pressure.

The brown oily residue (1.37 g) was added with xylene (7 ml) and trichlorophenyl malonate (2.7 g, 5.83 mmol) and refluxed by heating at 140° C. for 1 hour, and the solvent was evaporated under reduced pressure. The resulting oily compound was purified by silica gel chromatography (ethyl acetate→chloroform:methanol=30:1→10:1→5:1) to obtain 657 mg (41% for the three steps) of the title compound as pale yellow crystals.

$^1$H-NMR (CDCl$_3$) δ: 1.91 (1H,m), 2.01 (1H, qu, J=8.79 Hz), 2.22 (2H, d qu, J=2.44, 8.79 Hz), 2.34 (2H, tq, J=2.44, 8.79 Hz), 3.39 (4H, dd, J=6.84, 20.75 Hz), 3.63 (1H, qu, J=8.79 Hz), 5.33 (1H, s), 6.76 (1H, s), 7.11 (1H, dd, J=1.71, 7.08 Hz), 7.40 (1H, 9.02 (1H, d, J=7.08 Hz)

(G) 8-[2-(4-Cyclobutyl-1,3-thiazol-2-yl)ethyl]-2-(3-hydroxypiperidino)-4H-pyrido-[1,2-a]pyrimidin-4-one 8-[2-(4-Cyclobutyl-1,3-thiazol-2-yl)ethyl]-2-hydroxy-4H-pyrido[1,2-a]pyrimidin-4-one (120 mg, 0.366 mmol) dissolved in tetrahydrofuran (4 ml) and dimethylformamide (1 ml) was added with 4-dimethylaminopyridine (60 mg, 0.475 mmol) and p-tolunenesulfonyl chloride (77 mg, 0.402 mmol) at room temperature and stirred for 30 minutes. The solvent was evaporated under reduced pressure, and the residue was washed with water and extracted with chloroform. The resulting organic layer was dried over magnesium sulfate and concentrated under reduced pressure.

The resulting oily compound was added with dimethylformamide (3 ml) and 3-hydroxypiperidine (45 mg, 0.44 mmol), and stirred at 60° C. for 40 hours. The solvent was evaporated under reduced pressure, and then the residue was purified by silica gel column chromatography (chloroform→chloroform:methanol=20:1) to obtain 103 mg (68% for the two steps) of the title compound as oil.

$^1$H-NMR (CDCl$_3$) δ: 1.56 (1H, m), 1.66 (1H, m), 1.62–2.09 (4H, m), 2.23 (2H, d qu, J=2.20, 9.03 Hz), 2.35 (2H, m), 3.15 (2H, t, J=7.32 Hz), 3.35 (2H, t, J=7.32 Hz), 3.37 (1H, m), 3.48 (1H, m), 3.63 (1H, qu, J=9.03 Hz), 3.68 (1H, m), 3.84 (1H, m), 3.99 (1H, dd, J=2.93, 13.18 Hz), 5.64 (1H, s), 6.71 (1H, dd, J=1.71, 7.32 Hz), 6.76 (1H, s), 7.10 (1H, s), 8.76 (1H, d, J=7.32 Hz) EI/MS; m/z: 411 (M$^+$+1)

(H) 2-(3-{[1-(tert-Butyl)-1,1-dimethylsilyl]oxy}piperidino)-8-[2-(4-cyclobutyl-1,3-thiazol-2-yl)ethyl]-4H-pyrido[1,2-a]pyrimidin-4-one 8-[2-(4-Cyclobutyl-1,3-thiazol-2-yl)ethyl]-2-(3-hydroxypiperidino)-4H-pyrido[1, 2-a]pyrimidin-4-one (103 mg, 0.251 mmol) dissolved in dichloromethane (3 ml) was added with imidazole (51 mg, 0.753 mmol) and tert-butyldimethylsilyl chloride (57 mg, 0.376 mmol) under ice cooling and stirred for 1 hour. Then, as the reaction did not progress, the reaction mixture was warmed to room temperature and further added with imidazole and tert-butyldimethylsilyl chloride so that the reaction was completed. The reaction solution was diluted with chloroform, washed with water, dried over magnesium sulfate and then concentrated under reduced pressure. The resulting residue was purified by silica gel column chromatography (chloroform→chloroform:methanol=20:1) to obtain 128 mg (97%) of the title compound as an orange oily substance.

$^1$H-NMR (CDCl$_3$) δ: 0.87 (9H, s), 0.92 (6H, s), 1.53 (2H, m), 1.80–2.09 (4H, m), 2.23 (2H, m), 2.34 (2H, m), 3.02 (2H, m), 3.14 (2H, t, J=8.04 Hz), 3.35 (2H, t, J=8.04 Hz), 3.64 (2H, m), 4.00 (1H, brd), 4.20 (1H, brd), 5.59 (1H, s), 6.69 (1H, dd, J=1.95, 7.31 Hz), 6.75 (1H, s), 7.06 (1H, s), 8.76 (1H, d, J=7.31 Hz) EI/MS; m/z: 525 (M$^+$+1)

(I) 1-{8-[2-(4-Cyclobutyl-1,3-thiazol-2-yl)ethyl]-3-formyl-4-oxo-4H-pyrido[1,2-a]-pyrimidin-2-yl}-3-piperidyl formate Under ice cooling, dimethylformamide (2 ml) was added with phosphorus oxychloride (34 μl, 0.366 mmol), and then the reaction solution was added dropwise with 2-(3-{[1-(tert-butyl)-1,1-dimethylsilyl]oxy}piperidino)-8-[2-(4-cyclobutyl1,3-thiazol-2-yl)ethyl]-4H-pyrido[1,2-a]pyrimidin-4-one (128 mg, 0.244 mmol) dissolved in dimethylformamide under ice cooling. Then the reaction solution was warmed to room temperature. After 2 hours, the reaction solution was further added with phosphorus oxychloride (34 μl) at room temperature and stirred at room temperature for 20 minutes. The solvent was evaporated under reduced pressure, and the resulting residue was neutralized by adding saturated aqueous sodium hydrogencarbonate and extracted with ethyl acetate and chloroform. The organic layer collected was washed with saturated brine, dried over magnesium sulfate and concentrated under reduced pressure. The residue was purified by silica gel column chromatography (chloroform→chloroform:methanol=20:1) to obtain 69 mg (61%) of the title compound as a yellow oily substance.

$^1$H-NMR (CDCl$_3$) δ: 1.25–2.09 (6H, m), 2.22 (2H, dqu, J=2.45, 9.06 Hz), 2.34 (2H, m), 3.18 (2H, t, J=7.83 Hz), 3.36 (2H, t, J=7.83 Hz), 3.65 (3H, m), 3.82 (1H, dd, J=6.37, 13.47 Hz), 3.91 (1H, dd, J=3.18, 13.47 Hz), 5.07 (1H, m), 6.77 (1H, dd, J=1.71, 7.34 Hz), 6.77 (1H, s), 7.07 (1H, s), 7.98 (1H, s), 8.72 (1H, d, J=7.34 Hz), 10.08 (1H, s) EI/MS; m/z: 467 (M$^+$+1)

(J) tert-Butyl (E)-3-[8-[2-(4-cyclobutyl-1,3-thiazol-2-yl)ethyl]-2-(3-formyloxy-piperidino)-4-oxo-4H-pyrido[1,2-a]pyrimidin-3-yl]-2-propenoate 1-{8-[2-(4-Cyclobutyl-1,3-thiazol-2-yl)ethyl]-3-formyl-4-oxo-4H-pyrido[1,2-a]pyrimidin-2-yl}-3-piperidylformate (69 mg, 0.148 mmol) dissolved in tetrahydrofuran (3 ml) was added with (tert-butoxycarbonylmethylene)triphenylphosphorane (84 mg, 0.222 mmol) and refluxed at 100° C. After 7 hours, the reaction solution was further added with the phosphorane (90 mg) and further refluxed for 11 hours. Then the phosphorane (90 mg) was further added, and after 5 hours, the phosphorane (89 mg) was further added. The reaction solution was refluxed for 10 hours, then added with the phosphorane (90 mg) and refluxed for 5 hours. The reaction solution was returned to room temperature, and the solvent was evaporated under reduced pressure. The residue was purified by thin layer silica gel chromatography (chloroform:methanol=30:1) to obtain 94 mg of the title compound as yellow crystals in a mixture with triphenylphosphine oxide.

$^1$H-NMR (CDCl$_3$) δ: 1.51 (9H, s), 1.89–2.04 (6H, m), 2.22 (2H, m), 2.34 (2H, m), 3.19 (2H, t, J=7.81 Hz), 3.36 (2H, t, J=7.81 Hz), 3.53–3.68 (4H, m), 3.79 (1H, dd, J=3.42, 13.67 Hz), 5.13 (1H, m), 6.76 (1H, s), 6.84 (1H, dd, J=1.95, 7.32 Hz), 7.06 (1H, d, J=15.63 Hz), 7.20 (1H, s), 7.65 (1H, d, J=15.63 Hz), 8.08 (1H, s), 8.85 (1H, d, J=7.32 Hz)

(K) tert-Butyl (E)-3-[8-[2-(4-cyclobutyl-1,3-thiazol-2-yl)ethyl]-2-(3-hydroxypiperidino)-4-oxo-4H-pyrido[1,2-a]pyrimidin-3-yl]-2-propenoate tert-Butyl (E)-3-[8-[2-(4-Cyclobutyl-1,3-thiazol-2-yl)ethyl]-2-(3-formyloxy-piperidino)-4-oxo-4H-pyrido[1,2-a]pyrimidin-3-yl]-2-propenoate (95 mg, 0.168 mmol) dissolved in methanol (4 ml) was added with sodium methoxide (4 mg, 0.074 mmol) under ice cooling and stirred for 45 minutes under ice cooling. Then the reaction solution was further added with sodium methoxide (4 mg), and after 5 minutes, further added with sodium methoxide (10 mg). After the reaction solution was stirred for 15 minutes, the reaction was stopped with saturated brine and added with chloroform for extraction. The organic layer was dried over magnesium sulfate and concentrated under reduced pressure, and the residue was purified by thin layer silica gel chromatography (chloroform:methanol=20:1) to obtain 76 mg (84%) of the title compound as yellow crystals in a mixture with triphenylphosphine oxide.

$^1$H-NMR (CDCl$_3$) δ: 1.51 (9H, s), 1.82–2.08 (6H, m), 2.17–2.25 (2H, m), 2.32–2.36 (2H, m), 3.19 (2H, t, J=7.32 Hz), 3.36 (2H, t, J=7.32 Hz), 3.53–3.65 (4H, m), 3.92 (1H, d, J=13.92 Hz), 4.01 (1H, m), 6.77 (1H, s), 6.86 (1H, dd, J=1.95, 7.32 Hz), 7.03 (1H, d, J=15.63 Hz), 7.19 (1H, s), 7.62 (1H, d, J=15.63 Hz), 8.85 (1H, d, J=7.32 Hz) EI/MS; m/z: 537 (M$^+$+1)

(L) (E)-3-[8-[2-(4-Cyclobutyl-1,3-thiazol-2-yl)ethyl]-2-(3-hydroxypiperidino)-4-oxo-4H-pyrido[1,2-a]pyrimidin-3-yl]-2-propenoic acid tert-Butyl (E)-3-[8-[2-(4-Cyclobutyl-1,3-thiazol-2-yl)ethyl]-2-(3-hydroxy-piperidino)-4-oxo-4H-pyrido[1,2-a]pyrimidin-3-yl]-2-propenoate (76 mg, 0.142 mmol) was added with formic acid (3 ml) and stirred at room temperature for 2 hours and 30 minutes. After the formic acid was evaporated under reduced pressure, the residue was purified by thin layer silica gel chromatography (chloroform:methanol=15:1) to obtain 39 mg (55% for the three steps) of the title compound as yellow crystals.

$^1$H-NMR (CDCl$_3$) δ: 1.25 (1H, m), 1.52 (1H, m), 1.83–2.08 (4H, m), 2.21 (2H, d qu, J=2.44, 8.30 Hz), 2.36 (2H, tq, J=2.93, 8.30 Hz), 3.19 (2H, t, J=7.32 Hz), 3.36 (2H, t, J=7.32 Hz), 3.63 (4H, m), 3.88 (1H, d, J=13.43 Hz), 4.02 (1H, brd), 6.76 (1H, s), 6.86 (1H, dd, J=2.71, 7.32 Hz), 7.06 (1H, d, J=15.63 Hz), 7.19 (1H, s), 7.65 (1H, d, J=15.63 Hz), 8.84 (1H, d, J=7.32 Hz) EI/MS; m/z: 481 (M$^+$+1)

Example 2

(E)-3-{8-[2-(4-Cyclobutyl-1,3-thiazol-2-yl)ethyl]-2-morpholino-4-oxo-4H-pyrido[1,2-a]pyrimidin-3-yl}-2-propenoic acid

(A) 8-[2-(4-Cyclobutyl-1,3-thiazol-2-yl)ethyl]-2-morpholino-4H-pyrido[1,2-a]pyrimidin-4-one 8-[2-(4-Cyclobutyl-1,3-thiazol-2-yl)ethyl]-2-hydroxy-4H-pyrido[1,2-a]-pyrimidin-4-one (302 mg, 0.925 mmol) dissolved in tetrahydrofuran (14 ml) and dimethylformamide (6 ml) was added with 4-dimethylaminopyridine (150 mg, 1.20 mmol) and p-toluenesulfonyl chloride (194 mg, 1.02 mmol) and stirred at room temperature for 20 minutes.

After the solvent was evaporated under reduced pressure, the residue was diluted with chloroform and washed with water. The resulting organic layer was dried over magnesium sulfate and concentrated under reduced pressure.

The residue was dissolved in dimethylformamide (2 ml), added with morpholine (1 ml, 11.5 mmol) and stirred at 70° C. for 3 hours. After the reaction solution was returned to room temperature, the solvent was evaporated under reduced pressure and the residue was purified by silica gel column chromatography (chloroform→chloroform:methanol=20:1) to obtain 351 mg of the title compound as pale yellow crystals as a substance containing dimethylformamide.

$^1$H-NMR (CDCl$_3$) δ: 1.92 (1H, m), 2.02 (1H, m), 2.23 (2H, m), 2.35 (2H, m), 3.16 (2H, t, J=8.32 Hz), 3.35 (2H, t, J=8.32 Hz), 3.66 (4H, t, J=5.38 Hz), 3.70 (1H, m), 3.78 (4H, t, J=5.38 Hz), 5.57 (1H, s), 6.74 (1H, dd, J=2.94, 7.09 Hz), 6.76 (1H, s), 7.13 (1H, s), 8.78 (1H, d, J=7.09 Hz) EI/MS; m/z: 397 (M$^+$+1)

(B) 8-[2-(4-Cyclobutyl-1,3-thiazol-2-yl)ethyl]-2-morpholino-4-oxo-4H-pyrido[1,2-a]-pyrimidine-3-carbaldehyde Reactions were performed in the same manner as in Example 1, (I) by using 8-[2-(4-cyclobutyl-1,3-thiazol-2-yl)ethyl]-2-morpholino-4H-pyrido[1,2-a]pyrimidin-4-one (346 mg, 0.8726 mmol) to obtain 305 mg (82%) of the title compound as ocher solid.

$^1$H-NMR (CDCl$_3$) δ: 1.92–2.96 (6H, m), 3.19 (2H, t, J=7.34 Hz), 3.36 (2H, t, J=7.34 Hz), 3.68 (1H, m)3.73 (4H, t, J=5.14 Hz), 3.82 (4H, t, J=5.14 Hz), 6.77 (1H, s), 6.78 (1H, dd, J=1.96, 7.34 Hz), 7.08 (1H, s), 8.74 (1H, d, J=7.34 Hz), 10.01 (1H, s) EI/MS; m/z: 425 (M$^+$+1)

(C) tert-Butyl (E)-3-{8-[2-(4-cyclobutyl-1,3-thiazol-2-yl)ethyl]-2-morpholino-4-oxo-4H-pyrido[1,2-a]pyrimidin-3-yl}-2-propenoate Reactions were performed in the same manner as in Example 1, (J) by using 8-[2-(4-cyclobutyl-1,3-thiazol-2-yl)ethyl]-2-morpholino-4-oxo-4H-pyrido[1,2-a]-pyrimidin-3-carbaldehyde (100 mg, 0.2356 mmol) to obtain 127 mg (100%) of the title compound as a yellow oily substance in a mixture with triphenylphosphine oxide.

$^1$H-NMR (CDCl$_3$) δ: 2.02 (1H, m), 2.20 (1H, m), 2.23 (2H, m), 2.34 (2H, m), 3.20 (2H, t, J=7.08 Hz), 3.37 (2H, t, J=7.08 Hz), 3.60 (4H, t, J=4.39 Hz), 3.63 (1H, m), 3.83 (4H, t, J=4.39 Hz), 6.76 (1H, s), 6.85 (1H, dd, J=1.71, 7.32 Hz), 7.05 (1H, d, J=15.63 Hz), 7.21 (1H, s), 7.64 (1H, d, J=15.63 Hz), 8.86 (1H, d, J=7.32 Hz) EI/MS; m/z: 523 (M$^+$+1)

(D) (E)-3-{8-[2-(4-Cyclobutyl-1,3-thiazol-2-yl)ethyl]-2-morpholino-4-oxo-4H-pyrido-[1,2-a]pyrimidin-3-yl}-2-propenoic acid Reactions were performed in the same manner as in Example 1, (L) by using tert-butyl (E)-3-{8-[2-(4-cyclobutyl-1,3-thiazol-2-yl)ethyl]-2-morpholino-4-oxo-4H-pyrido[1,2-a]pyrimidin-3-yl}-2-propenoate (127 mg, 0.2430 mmol) to obtain 82.7 mg (73%) of the title compound as yellow crystals.

$^1$H-NMR (CDCl$_3$) δ: 1.92 (1H, m), 2.01 (1H, m), 2.22 (2H, m), 2.34 (2H, m), 3.19 (2H, t, J=8.06 Hz), 3.37 (2H, t,

J=8.06 Hz), 3.61 (4H, s), 3.64 (1H, m), 3.81 (4H, s), 6.86 (1H, dd, J=1.47, 7.32 Hz), 7.08 (1H, d, J=15.63 Hz), 7.19 (1H, s), 7.64 (1H, d, J=15.63 Hz), 8.87 (1H, d, J=7.32 Hz) EI/MS; m/z: 467 (M$^+$+1). IR (cm$^{-1}$): 2962, 2850, 1680, 1647, 1516, 1444

Example 3

(E)-3-{8-[2-(4-Cyclobutyl-1,3-thiazol-2-yl)ethyl]-2-morpholino-4-oxo-4H-pyrido[1,2-a]pyrimidin-3-yl}-2-methyl-2-propenoic acid (A) Ethyl (E)-3-{8-[2-(4-cyclobutyl-1,3-thiazol-2-yl)ethyl]-2-morpholino-4-oxo-4H-pyrido[1,2-a]pyrimidin-3-yl}-2-methyl-2-propenoate 8-[2-(4-Cyclobutyl-1,3-thiazol-2-yl)ethyl]-2-morpholino-4-oxo-4H-pyrido[1,2-a]pyrimidin-3-carbaldehyde (100 mg, 0.236 mmol) dissolved in toluene (2 ml) was added with (carbethoxyethylidene)triphenylphosphorane (102 mg, 0.283 mmol) and refluxed by heating at 130° C. Then the regent was added until the reaction was completed, and 7 equivalents of the regent was finally added. After the reaction mixture was stirred for 4 days, the solvent was evaporated under reduced pressure, and the resulting residue was purified by thin layer silica gel chromatography (chloroform:methanol=40:1) to obtain 443 mg of yellow crystals in a mixture with triphenylphosphine oxide.

$^1$H-NMR (CDCl$_3$) δ: 1.33 (3H, t, J=7.08 Hz), 1.88 (3H, s), 1.90 (1H, m), 2.05 (1H, m), 2.23 (2H, m), 2.35 (2H, m), 3.20 (2H, t, J=7.81 Hz), 3.37 (2H, t, J=7.81 Hz), 3.57 (4H, t, J=4.88 Hz), 3.64 (1H, m), 3.73 (4H, t, J=4.88 Hz), 4.25 (2H, q, J=7.08 Hz), 6.77 (1H, s), 6.82 (1H, d, J=7.33 Hz), 7.21 (1H, s), 7.57 (1H, s), 8.84 (1H, d, J=7.33 Hz)

(B) (E)-3-{8-[2-(4-Cyclobutyl-1,3-thiazol-2-yl)ethyl]-2-morpholino-4-oxo-4H-pyrido-[1,2-a]pyrimidin-3-yl}-2-methyl-2-propenoic acid Ethyl (E)-3-{8-[2-(4-cyclobutyl-1,3-thiazol-2-yl)ethyl]-2-morpholino-4-oxo-4H-pyrido[1,2-a]pyrimidin-3-yl}-2-methyl-2-propenoate (120 mg, 0.236 mmol) dissolved in methanol (5 ml) was added dropwise with 1 N aqueous sodium hydroxide (2 ml) under ice cooling. The reaction solution was stirred for 10 minutes and then warmed to room temperature because the reaction did not progress. The reaction solution was stirred for 45 minutes, then further added with 1 N aqueous sodium hydroxide (2 ml), and after 1 hour, further added with 1 N aqueous sodium hydroxide (2 ml). The solvent was evaporated under reduced pressure, and the resulting sodium salt of the title compound was dissolved in 1,4-dioxane, added with 4 N hydrochloric acid (6 ml) and stirred. Then the reaction solution was concentrated under reduced pressure, and the residue was neutralized with saturated aqueous sodium hydrogencarbonate and extracted with chloroform and methanol. The organic layer was dried over magnesium sulfate and concentrated under reduced pressure. The resulting residue was purified by thin layer silica gel chromatography (chloroform:methanol= 30:1) to obtain 75 mg (66%) of the title compound as yellow crystals.

$^1$H-NMR (CDCl$_3$) δ: 1.84 (3H, s), 1.91 (1H, m), 2.02 (1H, hex, J=9.06 Hz), 2.22 (2H, d, qu, J=2.21, 9.06 Hz), 2.34 (2H, q, J=8.57 Hz), 3.16 (2H, t, J=8.08 Hz), 3.36 (2H, t, J=8.08 Hz), 3.56 (4H, s), 3.64 (1H, qu, J=8.57 Hz), 3.70 (4H, s), 6.76 (1H, s), 6.80 (1H, dd, J=1.22, 7.10 Hz), 7.16 (1H, s), 7.57 (1H, s), 8.83 (1H, d, J=7.10 Hz) EI/MS; m/z: 481 (M$^+$+1) IR (cm$^{-1}$): 2958, 2919, 2850, 1666, 1641, 1440, 1251, 1115

Example 4

(E)-3-{8-[2-(4-Ethyl-1,3-thiazol-2-yl)ethyl]-2-morpholino-4-oxo-4H-pyrido-[1,2-a]pyrimidin-3-yl}-2-propenoic acid (A) 4-[2-(4-Ethyl-1,3-thiazol-2-yl)ethyl]-2-pyridinamine tert-Butyl N-[4-(3-amino-3-thioxopropyl)-2-pyridyl] carbamate (590 mg, 2.10 mmol) dissolved in ethanol (20 ml) was added with 1-bromo-2-butanone (0.23 ml, 2.10 mmol) and refluxed by heating at 100° C. The reaction solution was stirred for 1 hour and then returned to room temperature. The solvent was evaporated under reduced pressure, and the residue was diluted with chloroform. The mixture was washed with saturated aqueous sodium hydrogencarbonate and dried over sodium sulfate, and concentrated under reduced pressure.

The resulting residue was added with dichloromethane (20 ml) and added dropwise with trifluoroacetic acid (20 ml) under ice cooling. Then the reaction solution was warmed to room temperature and stirred for 15 hours. The trifluoroacetic acid was evaporated under reduced pressure, and the residue was neutralized with saturated sodium hydrogencarbonate and extracted with chloroform. The organic layer was washed with saturated brine and the collected organic layer was dried over magnesium sulfate and concentrated under reduced pressure. The resulting residue without purification gave 477 mg (98%) of the title compound as an orange oily substance.

$^1$H-NMR (CDCl$_3$) δ: 1.29 (3H, t, J=7.59 Hz), 2.78 (2H, dq, J=0.98, 7.59 Hz), 2.98 (2H, t, J=8.33 Hz), 3.25 (2H, t, J=8.33 Hz), 6.37 (1H, s), 6.52 (1H, dd, J=1.23, 5.39 Hz), 6.72 (1H, s), 7.93 (1H, d, J=5.39 Hz)

(B) 8-[2-(4-Ethyl-1,3-thiazol-2-yl)ethyl]-2-hydroxy-4H-pyrido[1,2-a]pyrimidin-4-one 4-[2-(4-Ethyl-1,3-thiazol-2-yl)ethyl]-2-pyridinamine (480 mg, 2.044 mmol) dissolved in xylene (10 ml) was added with trichlorophenyl malonate (1 g, 2.160 mmol) and refluxed by heating at 140° C. The reaction solution was stirred for 3 hours and returned to room temperature. The solvent was evaporated under reduced pressure and the resulting residue was purified by silica gel column chromatography (chloroform→chloroform:methanol= 80:1→50:1→5:1) to obtain 135 mg (22%) of orange crystals.

$^1$H-NMR (CDCl$_3$) δ: 1.28 (3H, t, J=7.57 Hz), 2.78 (2H, q, J=7.57 Hz), 3.36 (4H, dd, J=6.35, 17.82 Hz), 5.33 (1H, s), 6.76 (1H, s), 7.09 (1H, d, J=7.08 Hz), 7.39 (1H, s), 9.02 (1H, d, J=7.08 Hz) EI/MS; m/z: 302 (M$^+$+1)

(C) 8-[2-(4-Ethyl-1,3-thiazol-2-yl)ethyl]-2-morpholino-4H-pyrido[1,2-a]pyrimidin-4-one Reactions were performed in the same manner as in Example 2, (A) by using 8-[2-(4-ethyl-1,3-thiazol-2-yl)ethyl]-2-hydroxy-4H-pyrido[1,2-a]pyrimidin-4-one (135 mg, 0.4480 mmol) as a starting material to obtain 120 mg (72%) of the title compound as pale yellow crystals.

$^1$H-NMR(CDCl$_3$) δ: 1.29 (3H, t, J=7.57 Hz), 2.78 (2H, dq, J=0.977, 7.57 Hz), 3.16 (2H, t, J=8.06 Hz), 3.34 (2H, t, J=8.06 Hz), 3.64 (4H, t, J=5.13 Hz), 3.77 (4H, t, J=5.13 Hz), 5.57 (1H, s), 6.74 (1H, d, J=0.977 Hz), 6.74 (1H, dd, J=1.953, 7.08 Hz), 7.12 (1H, d, J=1.953 Hz), 8.79 (1H, d, J=7.08 Hz) EI/MS; m/z: 371 (M$^+$+1)

(D) 8-[2-(4-Ethyl-1,3-thiazol-2-yl)ethyl]-2-morpholino-4-oxo-4H-pyrido[1,2-a]-pyrimidine-3-carbaldehyde Reactions were performed in the same manner as in Example 1, (I) by using 8-[2-(4-ethyl-1,3-thiazol-2-yl)ethyl]-2-morpholino-4H-pyrido[1,2-a]pyrimidin-4-one (120 mg, 0.324 mmol) to obtain 116 mg (90%) of the title compound.

$^1$H-NMR (CDCl$_3$) δ: 1.29 (3H, t, J=7.57 Hz), 2.78 (2H, q, J=7.57 Hz), 3.19 (2H, t J=7.08 Hz), 3.35 (2H, t, J=7.08 Hz), 3.73 (4H, t, J=4.15 Hz), 3.82 (4H, t, J=4.15 Hz), 6.76 (1H, s), 6.78 (1H, dd, J=1.71, 7.32 Hz), 7.07 (1H, d, J=1.71 Hz), 8.74 (1H, d, J=7.32 Hz), 10.11 (1H, s) EI/MS; m/z: 399 (M$^+$+1)

(E) tert-Butyl (E)-3-{8-[2-(4-ethyl-1,3-thiazol-2-yl)ethyl]-2-morpholino-4-oxo-4H-pyrido[1,2-a]pyrimidin-3-yl}-2-propenoate Reactions were performed in the same manner as in Example 1, (J) by using 8-[2-(4-ethyl-1,3-thiazol-2-yl)ethyl]-2-morpholino-4-oxo-4H-pyrido[1,2-a]pyrimidine-3-carbaldehyde (116 mg, 0.2911 mmol)to obtain the title compound as yellow crystals in a mixture with triphenylphosphine oxide.

$^1$H-NMR (CDCl$_3$) δ: 1.28 (3H, t, J=7.57 Hz), 1.51 (9H, s), 2.78 (2H, q, J=7.57 Hz), 3.20 (2H, t, J=7.08 Hz), 3.36 (2H, t, J=7.08 Hz), 3.60 (4H, t, J=4.88 Hz), 3.83 (4H, t, J=4.88 Hz), 6.74 (1H, s), 6.85 (1H, dd, J=1.71, 7.32 Hz), 7.05 (1H, d, J=15.87 Hz), 7.20 (1H, s), 7.68 (1H, d, J=15.87 Hz), 8.87 (1H, d, J=7.32 Hz)

(F) (E)-3-{8-[2-(4-Ethyl-1,3-thiazol-2-yl)ethyl]-2-morpholino-4-oxo-4H-pyrido[1,2-a]-pyrimidin-3-yl}-2-propenoic acid Reactions were performed in the same manner as in Example 1, (L) by using tert-butyl (E)-3-{8-[2-(4-ethyl-1,3-thiazol-2-yl)ethyl]-2-morpholino-4-oxo-4H-pyrido-[1,2-a]pyrimidin-3-yl}-2-propenoate (144 mg, 0.290 mmol) to obtain 93 mg (73%) of the title compound as yellow crystals.

$^1$H-NMR (CDCl$_3$) δ: 1.29 (3H, t, J=7.57 Hz), 2.79 (2H, q, J=7.57 Hz), 3.21 (2H, t, J=7.08 Hz), 3.38 (2H, t, J=7.08 Hz), 3.63 (4H, t, J=6.15 Hz), 3.83 (4H, t, J=6.15 Hz), 6.75 (1H, s), 6.87 (1H, dd, J=1.47, 7.32 Hz), 7.09 (1H, d, J=15.63 Hz), 7.21 (1H, s), 7.68 (1H, d, J=15.63 Hz), 8.87 (1H, d, J=7.32 Hz) EI/MS; m/z: 441 (M$^+$+1) IR (cm$^{-1}$): 2964, 2919, 2850, 1681,1517, 1444

Example 5

(E)-3-{2-(3-Hydroxypiperidino)-8-[(4-isopropyl-1,3-thiazol-2-yl)methoxy]-4-oxo-4H-pyrido[1,2-a]pyrimidin-3-yl}-2-propenoic acid

(A) 4-Methoxy-2-pyridinecarbonitrile

4-Methoxypyridine-N-oxide hydrate (1 g, 6.99 mmol) dissolved in dichloromethane (4 ml) was added with trimethylsilyl cyanide (1 ml, 7.69 mmol) and subsequently added dropwise with N,N-dimethylcarbamoyl chloride (0.8 ml, 9.09 mmol) under ice cooling. The reaction solution was warmed to room temperature, stirred for 1 hour, and then added further with trimethylsilyl cyanide (0.2 ml, 1.40 mmol). The reaction solution was stirred for 19 hours, then added with 10% potassium carbonate (2 ml). The mixture was diluted with ethyl acetate, washed with saturated brine and dried over magnesium sulfate, and then concentrated under reduced pressure. The resulting crystals were washed with hexane to obtain 560 mg (60%) of the title compound as pink crystals without purification.

$^1$H-NMR (CDCl$_3$) δ: 3.92 (3H, s), 7.02 (1H, dd, J=2.44, 5.86 Hz), 7.22 (1H, d, J=2.44 Hz), 8.51 (1H, d, J=5.86 Hz)

(B) 4-Hydroxy-2-pyridinecarbonitrile

4-Methoxy-2-pyridinecarbonitrile (544 mg, 4.055 mmol) was added with 47% hydrobromic acid (6 ml) and refluxed by heating at 130° C. The reaction solution was stirred for 22 hours, returned to room temperature, and then concentrated under reduced pressure. The residue was subjected to azeotropy with toluene and diethyl ether to remove excessive hydrobromic acid. The resulting white crystals were washed with diethyl ether to obtain 1.47 g of the title compound containing hydrogen bromide without purification.

$^1$H-NMR (CD$_3$OD) δ: 7.48 (1H, dd, J=2.44, 6.83 Hz), 7.81 (1H, d, J=2.44 Hz), 8.63 (1H, d, J=6.83 Hz)

(C) Ethyl 4-hydroxy-2-pyridinecarboxylate

4-Hydroxy-2-pyridinecarbonitrile (25.48 g, 0.2121 mol) dissolved in ethanol (400 ml) was added with concentrated hydrochloric acid (40 ml) and refluxed by heating at 110° C. for 6 days. The reaction solution was returned to room temperature, evaporated under reduced pressure and added with chloroform:methanol=20:1. After insoluble crystals were removed by filtration, the resulting filtrate was concentrated under reduced pressure. The resulting residue was purified by silica gel column chromatography (chloroform:methanol=20:1→10:1) to obtain 22.4 g (63% for the two steps) of the title compound as yellow crystals.

$^1$H-NMR (CD$_3$OD) δ: 1.32 (3H, t, J=7.32 Hz), 4.52 (2H, q, J=7.32 Hz), 7.18 (1H, dd, J=2.69, 6.84 Hz), 7.58 (1H, d, J=2.69 Hz), 8.36 (1H, d, J=6.84 Hz) EI/MS; m/z: 168 (M$^+$+1)

(D) 2-(Chloromethyl)-4-isopropyl-1,3-thiazole (4-Isopropyl-1,3-thiazol-2-yl)methanol (10 g, 63.6011 mmol) dissolved in dichloromethane (60 ml) was added with thionyl chloride (7 ml, 95.40 mmol) under ice cooling, and then the reaction solution was returned to room temperature and stirred for 20 minutes. The reaction solution was concentrated under reduced pressure, and the residue was subjected to azeotropy with toluene and then diluted with diethyl ether, and further neutralized with saturated aqueous sodium hydrogencarbonate. The organic layer was washed with saturated brine, then dried over magnesium sulfate and concentrated under reduced pressure. The title compound was obtained as the residue without purification (11 g, 100%).

$^1$H-NMR (CDCl$_3$) δ: 1.30 (6H, d, J=7.08 Hz), 3.09 (1H, qu, J=7.08 Hz), 4.83 (2H, s), 6.91 (1H, s) EI/MS; m/z: 176 (M$^+$+1)

(E) Ethyl 4-[(4-isopropyl-1,3-thiazol-2-yl)methoxy]-2-pyridinecarboxylate

Ethyl 4-hydroxy-2-pyridinecarboxylate (19.5 g, 0.057 mol) dissolved in dimethylformamide (200 ml) was added with a solution of 2-(chloromethyl)-4-isopropyl-1,3-thiazole (11 g, 0.063 mol) in dimethylformamide (150 ml). The mixture was added with potassium iodide (9.5 g) and potassium carbonate (12 g) at room temperature, then heated to 110° C. and stirred for 1 hour. The reaction solution was returned to room temperature, and the solvent was evaporated under reduced pressure. The residue was diluted with chloroform and washed with water. The resulting organic layer was washed with saturated brine, and the organic layer was dried over magnesium sulfate and concentrated under reduced pressure. The residue was purified by silica gel chromatography (chloroform) to obtain 8.049 g (46%) of the title compound.

$^1$H-NMR (CDCl$_3$) δ: 1.32 (6H, d, J=6.86 Hz), 1.44 (3H, t, J=7.10 Hz), 3.12 (1H, qu, J=6.86 Hz), 4.47 (2H, q, J=7.10 Hz), 5.44 (2H, s), 6.94 (1H, s), 7.09 (1H, dd, J=2.694, 5.63 Hz), 7.80 (1H, d, J=2.694 Hz), 8.58 (1H, d, J=5.63 Hz) EI/MS; m/z: 307 (M$^+$+1)

(F) 4-[(4-Isopropyl-1,3-thiazol-2-yl)methoxy]-2-pyridinecarboxylic acid

Ethyl 4-[(4-isopropyl-1,3-thiazol-2-yl)methoxy]-2-pyridinecarboxylate (7.44 g, 24.28 mmol) dissolved in ethanol (50 ml) was added dropwise with 1 N sodium hydroxide (27 ml, 26.70 mmol) at room temperature, and stirred at room temperature for 1 hour and 30 minutes. The solvent was evaporated under reduced pressure, and the resulting Na salt crystals were washed with ethyl acetate.

The crystals were added with 4 N hydrochloric acid (27 ml) and 1,4-dioxane (40 ml), stirred and concentrated under reduced pressure. The residue was subjected to azeotropy with toluene, and the solvent was completely evaporated. The resulting crystals were filtered with chloroform:methanol=10:1, and the filtrate was concentrated under reduced pressure. The resulting pale yellow crystals were purified by silica gel column chromatography (chloroform:methanol=20:1→10:1→5:1) to obtain 6.7 g (100%) of the title compound as white crystals.

$^1$H-NMR (CD$_3$OD) δ: 1.37 (6H, d, J=6.83 Hz), 3.22 (1H, qu, J=6.83 Hz), 5.96 (2H, s), 7.54 (1H, s), 7.92 (1H, dd, J=2.68, 6.83 Hz), 8.22 (1H, d, J=2.68 Hz), 8.80 (1H, d, J=6.83 Hz) EI/MS; m/z: 279 (M$^+$+1).

(G) tert-Butyl N-{4-[(4-isopropyl-1,3-thiazol-2-yl)methoxy]-2-pyridyl}carbamate

4-[(4-Isopropyl-1,3-thiazol-2-yl)methoxy]-2-pyridinecarboxylic acid (50 mg, 0.18 mmol) was added with toluene (12 ml), triethylamine (63 pl, 0.45 mmol) and diphenyl phosphorylazide (78 μl, 0.36 mmol) and refluxed by heating at 140° C. for 7 hours. The reaction solution was returned to room temperature, added with tert-butanol (12 ml) and refluxed again by heating at 140° C. The reaction solution was stirred for 18 hours and then returned to room temperature, and the solvent was evaporated under reduced pressure. The residue was purified by thin layer silica gel chromatography (chloroform:methanol=40:1) to obtain 33 mg (53%) of the title compound.

$^1$H-NMR (CDCl$_3$) δ: 1.32 (6H, d, J=6.86 Hz), 1.53 (9H, s), 3.11 (1H, qu, J=6.86 Hz), 5.40 (2H, s), 6.60 (1H, dd, J=2.45, 5.88 Hz), 6.91 (1H, s), 7.73 (1H, s), 8.15 (1H, dd, J=2.45, 5.88 Hz) EI/MS; m/z: 350 (M$^+$+1)

(H) 4-[(4-Isopropyl-1,3-thiazol-2-yl)methoxy]-2-pyridinamine tert-Butyl N-{4-[(4-isopropyl-1,3-thiazol-2-yl)methoxy]-2-pyridyl}carbamate (706 mg, 2.202 mmol) dissolved in dichloromethane (20 ml) was added dropwise with trifluoroacetic acid (20 ml) under ice cooling, then warmed to room temperature and stirred for 2 hours. The reaction solution was concentrated under reduced pressure, diluted with chloroform, then neutralized with saturated aqueous sodium hydrogencarbonate and extracted with chloroform. The organic layer was dried over magnesium sulfate and concentrated under reduced pressure. The residue was purified by silica gel column chromatography (chloroform→chloroform:methanol=50:1→30:1→20:1) to obtain 331 mg (66%) of the title compound.

$^1$H-NMR (CDCl$_3$) δ: 1.32 (6H, d, J=6.83 Hz), 3.11 (1H, qu, J=6.83 Hz), 5.31 (2H, s), 6.08 (1H, d, J=1.95 Hz), 6.35 (1H, dd, J=1.95, 5.85 Hz), 6.91 (1H, s), 7.91 (1H, d, J=5.85 Hz)

(I) 2-Hydroxy-8-[(4-isopropyl-1,3-thiazol-2-yl)methoxy]-4H-pyrido[1,2-a]pyrimidin-4-one 4-[(4-Isopropyl-1,3-thiazol-2-yl)methoxy]-2-pyridinamine (378 mg, 1.52 mmol) dissolved in xylene (15 ml) was added with trichlorophenyl malonate (750 mg, 1.62 mmol) and refluxed by heating at 140° C. for 1 hour and 30 minutes. The reaction solution was returned to room temperature and concentrated under reduced pressure, and the residue was purified by silica gel column chromatography (chloroform→chloroform:methanol=100:1→80:1→50:1) to obtain 307 mg (64%) of the title compound.

$^1$H-NMR (CDCl$_3$) δ: 1.33 (6H, d, J=6.84 Hz), 3.15 (1H, qu, J=6.84 Hz), 5.23 (1H, s), 5.60 (2H, s), 6.95 (1H, dd, J=2.44, 7.57 Hz), 7.01 (1H, s), 7.06 (1H, d, J=2.44 Hz), 8.99 (1H, d, J=7.57 Hz) EI/MS; m/z: 318 (M$^+$+1)

(J) 2-Hydroxy-8-[(4-isopropyl-1,3-thiazol-2-yl)methoxy]-4-oxo-4 H-pyrido[1,2-a]-pyrimidine-3-carbaldehyde Dimethylformamide (3 ml) was added with phosphorus oxychloride (130 μl, 1.42 mmol) under ice cooling, and further added dropwise with 2-hydroxy-8-[(4-isopropyl-1,3-thiazol-2-yl)methoxy]-4H-pyrido[1,2-a]pyrimidin-4-one (300 mg, 0.945 mmol) dissolved in dimethylformamide (6 ml) under ice cooling. Then, the reaction solution was returned to room temperature and stirred for 1 hour. The reaction was stopped with saturated aqueous sodium hydrogencarbonate, and the reaction solution was extracted with chloroform. The resulting organic layer was washed with saturated brine, dried over sodium sulfate and concentrated under reduced pressure. The residue was purified by silica gel column chromatography (chloroform→chloroform:methanol=50:1→30:1→10:1) to obtain 45 mg (14%) of the title compound.

$^1$H-NMR (CDCl$_3$) δ: 1.32 (6H, d, J=6.84 Hz), 3.13 (1H, qu, J=6.84 Hz), 5.50 (2H, s), 6.94 (1H, d, J=6.85 Hz), 6.99 (2H, s), 8.92 (1H, d, J=6.85 Hz), 10.13 (1H, s) EI/MS; m/z: 346 (M$^+$+1)

(K) tert-Butyl (E)-3-{2-hydroxy-8-[(4-isopropyl-1,3-thiazol-2-yl)methoxy]-4-oxo-4H-pyrido[1,2-a]pyrimidin-3-yl}-2-propenoate 2-Hydroxy-8-[(4-isopropyl-1,3-thiazol-2-yl)methoxy]-4-oxo-4H-pyrido[1,2-a]pyrimidin-3-carbaldehyde (45 mg, 0.13 mmol) dissolved in tetrahydrofuran (2 ml) and dimethylformamide (1 ml) was added with (tert-butoxycarbonylmethylene)triphenyl-phosphorane (60 mg, 0.16 mmol) and refluxed by heating at 100° C. for 2 hours. The reaction solution was returned to room temperature and concentrated under reduced pressure, and the residue was purified by thin layer silica gel chromatography (chloroform:methanol=20:1) to obtain 36 mg (62%) of the title compound.

$^1$H-NMR (CDCl$_3$) δ: 1.26 (6H, d, J=6.86 Hz), 1.44 (9H, s), 3.08 (1H, qu, J=6.86 Hz), 5.57 (2H, s), 6.82 (1H, d,

J=15.92 Hz), 6.90 (1H, d, J=7.83 Hz), 6.96 (1H, s), 7.01 (1H, s, 7.69 (1H, d, J=15.92 Hz), 8.95 (1H, d, J=7.83 Hz) EI/MS; m/z: 444 (M$^+$+1)

(L) tert-Butyl (E)-3-{2-(3-hydroxypiperidino)-8-[(4-isopropyl-1,3-thiazol-2-yl)methoxy]-4-oxo-4H-pyrido[1,2-a]pyrimidin-3-yl}-2-propenoate Reactions were performed in the same manner as in Example 1, (G) by using tert-butyl (E)-3-{2-hydroxy-8-[(4-isopropyl-1,3-thiazol-2-yl)methoxy]-4-oxo-4H-pyrido-[1,2-a]pyrimidin-3-yl}-2-propenoate (26 mg, 0.059 mmol) to obtain 24 mg (78%) of the title compound as yellow oily compound.

$^1$H-NMR (CDCl$_3$) δ: 1.33 (6H, d, J=7.08 Hz), 1.51 (9H, s), 1.60 (2H, m), 1.83 (2H, m), 3.14 (1H, qu, J=7.08 Hz), 3.56 (3H, m), 3.92 (1H, dd, J=3.91, 13.67 Hz), 4.02 (1H, m), 5.44 (2H, s), 6.75 (1H, dd, J=2.68, 7.32 Hz), 6.76 (1H, s), 6.97 (1H, s), 6.98 (1H, d, J=15.62 Hz), 7.48 (1H, d, J=15.62 Hz), 8.86 (1H, d, J=7.32 Hz) EI/MS; m/z: 527 (M$^+$+1)

(M) (E)-3-{2-(3-Hydroxypiperidino)-8-[(4-isopropyl-1,3-thiazol-2-yl)methoxy]-4-oxo-4H-pyrido[1,2-a]pyrimidin-3-yl}-2-propenoic acid tert-Butyl (E)-3-{2-(3-hydroxypiperidino)-8-[(4-isopropyl-1,3-thiazol-2-yl)-methoxy]-4-oxo-4H-pyrido[1,2-a]pyrimidin-3-yl}-2-propenoate (24 mg, 0.046 mmol) was added with a mixture of 4 N hydrochloric acid and dioxane (1 ml) and stirred at room temperature for 3 hours. The reaction solution was concentrated under reduced pressure, and the residue was purified by thin layer silica gel chromatography (chloroform:methanol=15:1) to obtain 24 mg (100%) of the title compound as yellow crystals.

$^1$H-NMR (CD$_3$OD) δ: 1.33 (6H, d, J=7.08 Hz), 1.57 (1H, m), 1.69 (1H, m), 1.89 (1H, m), 2.07 (1H, m), 3.14 (1H, qu, J=7.08 Hz), 3.16 (1H, m), 3.17 (1H, m), 3.82 (2H, m), 4.04 (1H, d, J=9.52 Hz), 5.54 (2H, s), 6.87 (1H, d, J=7.81 Hz), 6.92 (1H, d, J=15.38 Hz), 6.95 (1H, s), 7.18 (1H, s), 7.61 (1H, d, J=15.38 Hz), 8.81 (1H, d, J=7.81 Hz) EI/MS; m/z: 471 (M$^+$+1)

Example 6

(E)-3-{8-[2-(4-Ethyl-2-thienyl)ethyl]-2-morpholino-4-oxo-4H-pyrido[1,2-a]-pyrimidin-3-yl}-2-propenoic acid (A) 4-Ethyl-2-thiophenecarbaldehyde 3-Ethylthiophene (2 g, 17.8 mmol) dissolved in diethyl ether (18 ml) was added with a solution of n-butyl lithium in hexane (1.5 M, 14 ml, 21.4 mmol) at room temperature and refluxed by heating at 60° C. for 15 minutes. The reaction solution was returned to room temperature and added dropwise with dimethylformamide (2 ml, 23.2 mmol) dissolved in diethyl ether. After the reaction solution was stirred for 2 hours at room temperature, the reaction was stopped with saturated aqueous ammonium chloride, and the reaction solution was extracted with chloroform. The collected organic layer was washed with saturated brine, then dried over magnesium sulfate and concentrated under reduced pressure.

The residue was purified by silica gel column chromatography (hexane:ethyl acetate=20:1→10:1) to obtain 2 g (80%) of the title compound.

$^1$H-NMR (CDCl$_3$) δ: 1.27 (3H, t, J=7.59 Hz), 2.68 (2H, q, J=7.59 Hz), 7.39 (1H, s), 7.63 (1H, s), 9.87 (1H, s)

(B) (4-Ethyl-2-thienyl)methanol

4-Ethyl-2-thiophenecarbaldehyde (1 g, 7.13 mmol) dissolved in methanol (7 ml) was added with sodium borohydride (135 mg, 3.57 mmol) under ice cooling, stirred for 10 minutes and then further added with sodium borohydride (150 mg, 3.96 mmol) at 0° C. After the reaction solution was stirred under ice cooling for 30 minutes, the reaction was stopped with saturated aqueous ammonium chloride and the reaction solution was extracted with chloroform. The organic layer collected was dried over magnesium sulfate and concentrated under reduced pressure to obtain 1 g (100%) of the title compound without purification.

$^1$H-NMR (CDCl$_3$) δ: 1.22 (3H, t, J=7.56 Hz), 2.59 (2H, q, J=7.56 Hz), 4.75 (2H, s), 6.86 (2H, s)

(C) tert-Butyl N-{4-[2-(3-bromo-4-ethyl-2-thienyl)ethyl]-2-pyridyl}carbamate (4-Ethyl-2-thienyl)methanol (1 g, 7.03 mmol) dissolved in dichloromethane (7 ml) was added with thionyl bromide (0.8 ml, 10.55 mmol) under ice cooling and then warmed to room temperature. The reaction solution was stirred for 20 minutes and then concentrated under reduced pressure, and the residue was neutralized by adding saturated aqueous sodium hydrogencarbonate and extracted with diethyl ether. The organic layer was washed with saturated brine, dried over magnesium sulfate and concentrated under reduced pressure. The residue was used in the subsequent reaction without purification.

tert-Butyl N-(4-methyl-2-pyridyl)carbamate (800 mg, 3.84 mmol) dissolved in tetrahydrofuran (15 ml) was cooled to −78° C. and then added dropwise with a solution of n-butyl lithium in hexane (1.5 M, 6.4 ml, 9.6 mmol). The reaction solution was stirred at room temperature for 1 hour, then cooled to −78° C. again and added dropwise with a solution of the above obtained 3-bromo-2-(bromomethyl)-4-ethylthiophene in tetrahydrofuran (14 ml). After the reaction solution was stirred at −78° C. for 1 hour and the reaction was stopped with saturated brine, the reaction solution was extracted with ethyl acetate. The organic layer collected was dried over magnesium sulfate and concentrated under reduced pressure. The resulting residue was purified by silica gel column chromatography (chloroform) to obtain 1.3 g (85%) of the title compound.

$^1$H-NMR (CDCl$_3$) δ: 1.15 (3H, t, J=7.57 Hz), 1.55 (9H, s), 2.52 (2H, q, J=7.57 Hz), 2.92 (2H, t, J=8.55 Hz), 3.04 (2H, t, J=8.55 Hz), 6.50 (1H, s), 6.77 (1H, d, J=5.13 Hz), 7.87 (1H, s), 8.18 (1H, d, J=5.13 Hz) EI/MS; m/z: 411 (M$^+$)

(D) 4-[2-(3-Bromo-4-ethyl-2-thienyl)ethyl]-2-pyridylamine tert-Butyl N-{4-[2-(3-bromo-4-ethyl-2-thienyl)ethyl]-2-pyridyl}carbamate (1.34 g, 4.04 mmol) dissolved in dichloromethane (40 ml) was added with trifluoroacetic acid (40 ml) at 0° C. and stirred at 0° C. for 3 hours. The reaction solution was concentrated under reduced pressure, neutralized with saturated sodium hydrogencarbonate and extracted with chloroform, and then the organic layer was dried over magnesium sulfate and concentrated under reduced pressure. The residue was purified by silica gel column chromatography (chloroform:ethyl acetate=3:1→1:1→ethyl acetate only) to obtain 524 mg (56%) of the title compound.

$^1$H-NMR (CD$_3$OD) δ: 1.12 (3H, t, J=7.56 Hz), 2.48 (2H, q, J=7.56 Hz), 2.79 (2H, t, J=7.56 Hz), 3.01 (2H, t, J=7.56 Hz), 6.40 (1H, s), 6.46 (1H, d, J=5.36 Hz), 6.53 (1H, s), 7.76 (1H, d, J=5.36 Hz) EI/MS; m/z: 310 (M$^+$−1)

(E) 8-[2-(3-Bromo-4-ethyl-2-thienyl)ethyl]-2-hydroxy-4H-pyrido[1,2-a]pyrimidin-4-one Reactions were performed in the same manner as in Example 4, (B) by using 4-[2-(3-bromo-4-ethyl-2-thienyl)ethyl]-2-pyridylamine as a starting material. After the reaction was completed, the reaction solution was concentrated under reduced pressure and the crystals in the resulting turbid solution was removed by filtration. The filtrate was concentrated under reduced pressure, and the resulting residue was purified by silica gel column chromatography (chloroform→chloroform:ethyl acetate=1:1→ethyl acetate→ethyl acetate:methanol=50:1→30:1→10:1) to obtain 180 mg (38%) of the title compound.

$^1$H-NMR (CDCl$_3$) δ: 1.14 (3H, t, J=7.56 Hz), 2.49 (2H, q, J=7.56 Hz), 3.15 (4H, s), 5.31 (1H, s), 6.53 (1H, s), 7.12 (1H, d, J=7.07 Hz), 7.24 (1H, s), 8.98 (1H, d, J=7.07 Hz)

(F) 8-[2-(4-Ethyl-2-thienyl)ethyl]-2-hydroxy-4H-pyrido[1,2-a]pyrimidin-4-one 8-[2-(3-Bromo-4-ethyl-2-thienyl)ethyl]-2-hydroxy-4H-pyrido[1,2-a]pyrimidin-4-one (96 mg, 0.25 mmol) dissolved in toluene (6 ml) was added with tributyltin hydride (75 μl) and 2,2-azobisisobutyronitrile (4 mg, 0.025 mmol) and refluxed by heating at 140° C. Then 2,2-azobisisobutyronitrile and tributyltin hydride were further added until the reaction was completed while the progress of the reaction was monitored by LC-MS. 34 mg (0.22 mmol) of 2,2-azobisisobutyronitrile and 350 μl (1.30 mmol) of tributyltin hydride were used. The reaction solution was returned to room temperature and the reaction was stopped with an aqueous solution of potassium fluoride. The reaction solution was extracted with ethyl acetate, and the organic layer was washed with saturated brine. Then, the aqueous layer was extracted with ethyl acetate. The organic layer collected was dried over magnesium sulfate and concentrated under reduced pressure. The residue was purified by thin layer silica gel chromatography (chloroform:methanol=20:1) to obtain 119 mg of the title compound with contained impurities.

$^1$H-NMR (CDCl$_3$) δ: 1.28 (3H, t, J=7.32 Hz), 2.56 (2H, q, J=7.32 Hz), 3.04 (2H, t, J=8.06 Hz), 3.17 (2H, t, J=8.06 Hz), 5.34 (1H, s), 5.63 (1H, s), 6.74 (1H, d, J=4.88 Hz), 7.04 (1H, d, J=7.08 Hz), 7.35 (1H, s), 9.02 (1H, d, J=7.08 Hz) ES-MS: 301 (M$^+$+1)

(G) 8-[2-(4-Ethyl-2-thienyl)ethyl]-2-morpholino-4H-pyrido[1,2-a]pyrimidin-4-one Reactions were performed in the same manner as in Example 2, (A) by using 8-[2-(4-ethyl-2-thienyl)ethyl]-2-hydroxy-4H-pyrido[1,2-a]pyrimidin-4-one (122 mg, 0.406 mmol) as a starting material. As a result, 122 mg of the title compound was obtained as a yellow oily substance in a mixture with impurities.

$^1$H-NMR (CDCl$_3$) δ: 1.20 (3H, t, J=7.57 Hz), 2.56 (2H, q, J=7.57 Hz), 3.01 (2H, t, J=7.32 Hz), 3.16 (2H, t, J=7.32 Hz), 3.66 (4H, t, J=4.88 Hz), 3.78 (4H, t, J=4.88 Hz), 5.62 (1H, s), 6.64 (1H, s), 6.73 (2H, m), 7.11 (1H, s), 8.79 (1H, d, J=7.08 Hz) ES-MS; m/z: 370 (M$^+$+1)

(H) 8-[2-(4-Ethyl-2-thienyl)ethyl]-2-morpholino-4-oxo-4H-pyrido[1,2-a]pyrimidin-3-carbaldehyde Reactions were performed in the same manner as in Example 1, (I) by using 8-[2-(4-ethyl-2-thienyl)ethyl]-2-morpholino-4H-pyrido[1,2-a]pyrimidin-4-one (122 mg, 0.33 mmol) as a starting material. As a result, 52 mg (40% for the three steps) of the title compound in orange color was obtained.

$^1$H-NMR (CDCl$_3$) δ: 1.20 (3H, t, J=7.56 Hz), 2.56 (2H, q, J=7.56 Hz), 3.02 (2H, t, J=8.04 Hz), 3.17 (2H, t, J=8.04 Hz), 3.73 (4H, d, J=4.88 Hz), 3.82 (4H, d, J=4.88 Hz), 6.64 (1H, s), 6.74 (1H, s), 6.76 (1H, dd, J=1.95, 7.07 Hz), 7.03 (1H, s), 8.74 (1H, d, J=7.07 Hz), 10.11 (1H, s) EI/MS; m/z: 398 (M$^+$+1)

(I) tert-Butyl (E)-3-{8-[2-(4-ethyl-2-thienyl)ethyl]-2-morpholino-4-oxo-4H-pyrido-[1,2-a]pyrimidin-3-yl}-2-propenoate Reactions were performed in the same manner as in Example 1, (J) by using 8-[2-(4-ethyl-2-thienyl)ethyl]-2-morpholino-4-oxo-4H-pyrido[1,2-a]pyrimidine-3-carbaldehyde (52 mg, 0.13 mmol) as a starting material. As a result, 65 mg of the title compound was obtained as an orange oily substance in a mixture with triphenylphosphine oxide.

$^1$H-NMR (CDCl$_3$) δ: 1.20 (3H, t, J=7.59 Hz), 1.51 (9H, s), 2.56 (2H, q, J=7.59 Hz), 3.04 (2H, t, J=8.08 Hz), 3.17 (2H, t, J=8.08 Hz), 3.60 (4H, t, J=4.41 Hz), 3.83 (4H t, J=4.41 Hz), 6.63 (1H, s), 6.73 (1H, s), 6.82 (1H, dd, J=1.96, 7.35 Hz), 7.05 (1H, d, J=15.68 Hz), 7.17 (1H, s), 7.69 (1H, d, J=15.68 Hz), 8.87 (1H, d, J=7.35 Hz) EI/MS; m/z: 496 (M$^+$+1)

(J) (E)-3-{8-[2-(4-Ethyl-2-thienyl)ethyl]-2-morpholino-4-oxo-4H-pyrido[1,2-a]-pyrimidin-3-yl}-2-propenoic acid Reactions were performed in the same manner as in Example 1, (L) by using tert-butyl (E)-3-{8-[2-(4-ethyl-2-thienyl)ethyl]-2-morpholino-4-oxo-4H-pyrido[1,2-a]-pyrimidin-3-yl}-2-propenoate (65 mg, 0.13 mmol) as a starting material. As a result, 32 mg (56%) of yellow crystals were obtained.

$^1$H-NMR (CDCl$_3$) δ: 1.20 (3H, t, J=7.57 Hz), 2.56 (2H, q, J=7.57 Hz), 3.05 (2H, t, J=7.81 Hz), 3.18 (2H, t, J=7.81 Hz), 3.63 (4H, t, J=4.40 Hz), 3.84 (4H, t, J=4.40 Hz), 6.63 (1H, s), 6.74 (1H, s), 6.84 (1H, dd, J=1.95, 7.32 Hz), 7.11 (1H, d, J=15.38 Hz), 7.18 (1H, s), 7.69 (1H, d, J=15.38 Hz), 8.88 (1H, d, J=7.32 Hz) EI/MS; m/z: 440 (M$^+$+1)

Example 7

(E)-3-[8-({[4-(tert-Butyl)-1,3-thiazol-2-yl]amino}carbonyl)-2-morpholino-4-oxo-4H-pyrido[1,2-a]pyrimidin-3-yl]-2-propenoic acid

(A) 2-(Acetylamino)isonicotinic acid

N1-(4-Methyl-2-pyridyl)acetamide (25 g, 0.168 mol) suspended in water (250 ml) was added with potassium permanganate (76.1 g, 0.50 mol) at 100° C. over 1 hour and then stirred for 40 minutes. The reaction solution was returned to room temperature, and black crystals were removed by filtration. The resulting filtrate was added with 12 N hydrochloric acid until pH of the solution became 3 to 4. After the reaction solution was stirred for about 15 minutes, the deposited white crystals were collected by filtration, washed with water, and dried by using a vacuum pump to obtain 7.65 g (25%) of the title compound without purification.

$^1$H-NMR (CD$_3$OD) δ: 2.20 (3H, s), 7.59 (1H, dd, J=1.47, 5.13 Hz), 8.42 (1H, dd, J=0.73, 5.13 Hz), 8.63 (1H, s) EI/MS; m/z: 179 (M$^+$)

(B) N4-[4-(tert-Butyl)-1,3-thiazol-2-yl]-2-(acetylamino)isonicotinamide 2-(Acetylamino)isonicotinic acid (500 mg, 2.8 mmol) was added dropwise with thionyl chloride (15 ml, 68.5 mmol) at room temperature, warmed to 80° C. and stirred for 30 minutes. The reaction solution was returned to room temperature, concentrated under reduced pressure, and the residue was subjected to azeotropy with toluene to evaporate excessive thionyl chloride. The resulting yellow crystals was added to a mixed solution of pyridine (0.25 ml), dichloromethane (5 ml) and 4-(tert-butyl)-1,3-thiazol-2-amine (525 mg, 3.35 mmol) under ice cooling. The mixture was stirred at 0° C. for 30 minutes, then warmed to room temperature, and further stirred for 2 hours and 30 minutes. The reaction solution was added with water and extracted with chloroform. The organic layer was dried over magnesium sulfate and concentrated under reduced pressure. The resulting residue was purified by silica gel column chromatography (chloroform→chloroform:methanol=80:1→50:1) to obtain 545.8 mg (61%) of the title compound.

$^1$H-NMR (CDCl$_3$) δ: 1.31 (9H, s), 2.26 (3H, s), 6.61 (1H, s), 7.63 (1H, dd, J=0.49, 5.14 Hz), 8.44 (1H, d, J=5.14 Hz), 8.51 (1H, brd), 8.72 (1H, s) EI/MS; m/z: 319 (M$^+$+1)

(C) N4-[4-(tert-Butyl)-1,3-thiazol-2-yl]-2-aminoisonicotinamide

N4-[4-(tert-Butyl)-1,3-thiazol-2-yl]-2-(acetylamino)isonicotinamide (546 mg) dissolved in ethanol (12 ml) was added dropwise with concentrated hydrochloric acid (1.2 ml) at room temperature and stirred at 80–90° C. for 1 hour. The reaction solution was returned to room temperature, concentrated under reduced pressure, neutralized with 1 N sodium hydroxide and extracted with chloroform. The organic layer was dried over magnesium sulfate and concentrated under reduced pressure, and the resulting residue was purified by silica gel column chromatography (chloroform→chloroform:methanol=60:1→20:1) to obtain 247.2 mg (52%) of the title compound as white crystals.

$^1$H-NMR (CD$_3$OD) δ: 1.33 (9H, s), 6.63 (1H, d, J=0.73 Hz), 7.05 (1H, t, J=0.73 Hz), 7.09 (1H, ddd, J=0.73, 1.46, 5.36 Hz), 8.13 (1H, dd, J=0.73, 5.36 Hz) EI/MS; m/z: 275 (M$^+$−1)

(D) N8-[4-(tert-Butyl)-1,3-thiazol-2-yl]-2,4-dioxo-3,4-dihydro-2H-pyrido[1,2-a]-pyrimidine-8-carboxamide N4-[4-(tert-Butyl)-1,3-thiazol-2-yl]-2-aminoisonicotinamide (200 mg, 0.724 mmol) was added with xylene (20 ml) and trichlorophenyl malonate (370 mg, 0.796 mmol) and refluxed by heating at 130° C. The reaction solution was stirred for 1 hour, then returned to room temperature and concentrated under reduced pressure. The resulting orange crystals was taken by filtration, washed with chloroform, dried under reduced pressure to obtain 209 mg (84%) of the title compound as orange crystals without purification.

$^1$H-NMR (DMSO-d$_6$) δ: 1.31 (9H, s), 3.45 (2H, m), 6.88 (1H, s), 7.77 (1H, d, J=7.08 Hz), 8.02 (1H, s), 8.99 (1H, d, J=7.08 Hz) EI/MS; m/z: 345 (M$^+$+1)

(E) N8-[4-(tert-Butyl)-1,3-thiazol-2-yl]-2-morpholino-4-oxo-4H-pyrido[1,2-a]-pyrimidine-8-carboxamide Reactions were performed in the same manner as in Example 2, (A) by using N8-[4-(tert-Butyl)-1,3-thiazol-2-yl]-2,4-dioxo-3,4-dihydro-2H-pyrido[1,2-a]pyrimidine-8-carboxamide (209 mg, 0.607 mmol). The resulting crude product was purified by silica gel column chromatography (chloroform:methanol=50:1→30:1) to obtain 147 mg of the title compound in a mixture with byproducts.

$^1$H-NMR (CD$_3$OD) δ: 1.36 (9H, s), 3.46 (4H, t, J=4.64 Hz), 3.58 (4H, t, J=4.64 Hz), 5.71 (1H, s), 6.64 (1H, s), 7.51 (1H, d, J=7.57 Hz), 7.99 (1H, s), 8.89 (1H, d, J=7.57 Hz) EI/MS; m/z: 414 (M$^+$+1)

(F) N8-[4-(tert-Butyl)-1,3-thiazol-2-yl]-3-formyl-2-morpholino-4-oxo-4H-pyrido[1,2-a]-pyrimidine-8-carboxamide Dimethylformamide (1 ml) was added dropwise with phosphorus oxychloride (66 μl, 0.712 mmol) under ice cooling, then warmed to room temperature, and stirred for 15 minutes. The reaction solution was cooled to 0° C. with ice, added with N8-[4-(tert-butyl)-1,3-thiazol-2-yl]-2-morpholino-4-oxo-4H-pyrido[1,2-a]pyrimidine-8-carboxamide (147 mg, 0.356 mmol) dissolved in dimethylformamide (4 ml) under ice cooling, and stirred at 0° C. for 2 hours and 30 minutes. The reaction solution was neutralized with saturated aqueous sodium hydrogencarbonate and concentrated under reduced pressure. The resulting residue was added with chloroform for extraction, and the organic layer was dried over magnesium sulfate and concentrated under reduced pressure. The resulting residue was purified by thin layer silica gel chromatography (chloroform:methanol=40:1) to obtain 98.2 mg of the title compound as yellow crystals in a mixture with dimethylformamide.

$^1$H-NMR (CDCl$_3$) δ: 1.34 (9H, s), 3.78 (4H, d, J=4.88 Hz), 3.82 (4H, d, J=4.88 Hz), 6.59 (1H, s), 7.44 (1H, dd, J=1.71, 7.32 Hz), 7.86 (1H, s), 8.87 (1H, d, J=7.32 Hz), 10.16 (1H, s) EI/MS; m/z: 442 (M$^+$+1)

(G) Methyl (E)-3-[8-({[4-(tert-butyl)-1,3-thiazol-2-yl]amino}carbonyl)-2-morpholino-4-oxo-4H-pyrido[1,2-a]pyrimidin-3-yl]-2-propenoate N8-[4-(tert-Butyl)-1,3-thiazol-2-yl]-3-formyl-2-morpholino-4-oxo-4H-pyrido-[1,2-a]pyrimidine-8-carboxamide (98.2 mg, 0.223 mmol) was added with tetrahydrofuran (6 ml), lithium chloride (30 mg, 0.669 mmol) and bis(2,2,2-trifluoroethyl)(methoxycarbonylmethyl)-phosphonate (142 μl, 0.669 mmol), then added dropwise with 1,8-diazabicyclo[5.4.0]undec-7-ene (92 μl, 0.669 mmol) at room temperature, stirred at room temperature for 1 hour, and further added with bis(2,2,2-trifluoroethyl)(methoxycarbonylmethyl)-phosphonate (75 μl) and 1,8-diazabicyclo[5.4.0]undec-7-ene (45 μl). The reaction solution was further stirred at room temperature for 30 minutes and concentrated under reduced pressure. The resulting residue was purified by thin layer silica gel chromatography (chloroform:methanol=40:1) to obtain 145.8 mg of the title compound in a mixture with 1,8-diazabicyclo[5.4.0]undec-7-ene.

$^1$H-NMR (CD$_3$OD) δ: 1.35 (9H, s), 3.70 (4H, m), 3.78 (4H, m), 3.86 (3H, s), 6.62 (1H, s), 7.12 (1H, d, J=15.63 Hz), 7.41 (1H, s), 7.58 (1H, d, J=7.57 Hz), 7.59 (1H, d, J=15.63 Hz), 8.98 (1H, d, J=7.57 Hz) EI/MS; m/z: 498 (M$^+$+1)

(H) (E)-3-[8-({[4-(tert-Butyl)-1,3-thiazol-2-yl]amino}carbonyl)-2-morpholino-4-oxo-4H-pyrido[1,2-a]pyrimidin-3-yl]-2-propenoic acid Methyl (E)-3-[8-({[4-(tert-butyl)-1,3-thiazol-2-yl]aminolcarbonyl)-2-morpholino-4-oxo-4H-pyrido[1,2-a]pyrimidin-3-yl]-2-propenoate (145.8 mg, 0.293 mmol) was added with methanol (2 ml), tetrahydrofuran (5 ml) and water (1 ml), and then added dropwise with 1 N sodium hydroxide (1 ml) at room temperature. After the reaction solution was stirred at room temperature for 1 hour, the solution was further added with 1 N sodium hydroxide (2 ml) and further stirred at room temperature for 15 hours. The reaction solution was added with 1 N hydrochloric acid until pH of the solution became 4 and extracted with chloroform. The organic layer was dried over magnesium sulfate and concentrated under reduced pressure. The resulting residue was purified by thin layer silica gel chromatography (chloroform:methanol=20:1) to obtain 15.4 mg (5% for the four steps) of the title compound as yellow crystals.

$^1$H-NMR (DMSO-$d_6$) δ: 1.27 (9H, s), 3.70 (4H, m), 3.78 (4H, m), 6.54 (1H, brd), 6.93 (1H, d, J=15.38 Hz), 7.48 (1H, d, J=15.38 Hz), 7.78 (1H, d, J=7.08 Hz), 8.05 (1H, s), 8.88 (1H, d, J=7.08 Hz) ES-MS: 484 (M$^+$+1), 482 (M$^+$−1)

Example 8

(E)-3-[8-{[(4-Cyclobutyl-1,3-thiazol-2-yl)amino]carbonyl}-2-(3-hydroxy-piperidino)-4-oxo-4H-pyrido[1,2-a]pyrimidin-3-yl]-2-propenoic acid (A) 4-Cyclobutyl-1,3-thiazol-2-amine Thiourea (2.3 g, 30.0 mmol) was dissolved in ethanol (100 ml), added with 2-bromo-1-cyclobutyl-1-ethanone synthesized in the same manner as in Example 1, (E), and then heated to 100° C. The reaction solution was stirred for 1 hour, then returned to room temperature, neutralized with saturated sodium hydrogencarbonate and extracted with chloroform. The collected organic layer was washed with saturated brine, dried over magnesium sulfate and then concentrated under reduced pressure. The title compound was obtained as the residue without purification as a brown oily substance (5.4 g, 100%).

$^1$H-NMR (CDCl$_3$) δ: 1.86 (1H, m), 1.98 (1H, qu, J=9.31 Hz), 2.12–2.37 (4H, m), 3.38 (1H, qu, J=8.08 Hz), 5.36 (2H, brd), 6.07 (1H, s)

(B) N4-(4-Cyclobutyl-1,3-thiazol-2-yl)-2-(acetylamino)isonicotinamide

Reactions were performed in the same manner as in Example 7, (B) by using 2-(acetylamino)isonicotinic acid (3.3 g, 18.42 mmol) as the starting material and 4-cyclobutyl-1,3-thiazol-2-amine (3 g, 18.42 mmol) to obtain 3.76 g (65%) of the title compound.

$^1$H-NMR (CDCl$_3$) δ1.91 (1H, m), 2.03 (1H, qu, J=9.03 Hz), 2.15–2.42 (4H, m), 2.23 (3H, s), 3.55 (1H, qu, J=8.55 Hz), 6.63 (1H, s), 7.56 (1H, d, J=5.13 Hz), 8.37 (1H, s), 8.66 (1H, s) EI/MS; m/z: 317 (M$^+$+1)

(C) N4-(4-Cyclobutyl-1,3-thiazol-2-yl)-2-aminoisonicotinamide

Reactions were performed in the same manner as in Example 7, (C) by using N4-(4-cyclobutyl-1,3-thiazol-2-yl)-2-(acetylamino)isonicotinamide (3.76 g, 11.9 mmol) to obtain 1.73 g (53%) of the title compound.

$^1$H-NMR (CDCl$_3$) δ: 1.94–2.37 (6H, m), 3.58 (1H, qu, J=8.57 Hz), 6.67 (1H, s), 7.07 (1H, s), 7.09 (1H, d, J=5.14 Hz), 8.10 (1H, d, J=5.14 Hz) EI/MS; m/z: 273 (M$^+$−1)

(D) N8-(4-Cyclobutyl-1,3-thiazol-2-yl)-2,4-dioxo-3,4-dihydro-2H-pyrido[1,2-a]-pyrimidine-8-carboxamide Reactions were performed in the same manner as in Example 7, (D) by using N4-(4-cyclobutyl-1,3-thiazol-2-yl)-2-aminoisonicotinamide (1.73 g, 6.3 mmol) to obtain 1.85 g (86%) of the title compound as brown solid.

$^1$H-NMR (DMSO-$d_6$) δ: 1.85–1.98 (2H, m), 2.16–2.27 (4H, m), 3.47 (2H, m), 3.57 (1H, m), 6.91 (1H, s), 7.74 (1H, d, J=7.35 Hz), 8.27 (1H, s), 8.97 (1H, d, J=7.35 Hz EI/MS; m/z: 343 (M$^+$+1)

(E) N8-(4-Cyclobutyl-1,3-thiazol-2-yl)-2-(3-hydroxypiperidino)-4-oxo-4H-pyrido-[1,2-a]pyrimidine-8-carboxamide N8-(4-Cyclobutyl-1,3-thiazol-2-yl)-2,4-dioxo-3,4-dihydro-2H-pyrido[1,2-a]-pyrimidine-8-carboxamide (100 mg, 0.29 mmol) was added with acetonitrile (2 ml) and dimethylformamide (1 ml), cooled to −10° C. with ice, then added with diphenyl chlorophosphate (0.2 ml, 0.96 mmol), and further added dropwise with diisopropylethylamine (0.3 ml, 1.74 mmol). The reaction solution was stirred at −10° C. for 30 minutes, then added with 3-hydroxypiperidine (90 mg, 0.89 mmol), warmed to room temperature, and then further warmed to 80° C. As the reaction was not completed, the reaction solution was further added with 3-hydroxypiperidine (60 mg), stirred for 1 hour, and further added with 3-hydroxypiperidine (70 mg). After the disappear of the starting material was observed, the reaction was stopped with saturated aqueous sodium hydrogencarbonate, and the reaction solution was extracted with chloroform. The organic layer was dried over magnesium sulfate and concentrated under reduced pressure. The resulting residue was purified by thin layer silica gel chromatography (chloroform:methanol=15:1) to obtain 85.2 mg (69%) of the title compound as yellow crystals.

$^1$H-NMR (CDCl$_3$) δ: 1.60–2.06 (6H, m), 2.21–2.35 (4H, m), 3.57 (4H, m), 3.95 (2H, m), 5.75 (1H, s), 6.62 (1H, s), 7.28 (1H, dd, J=1.71, 7.56 Hz), 7.74 (1H, s), 8.87 (1H, d, J=7.56 Hz) EI/MS; m/z: 426 (M$^+$+1)

(F) N8-(4-Cyclobutyl-1,3-thiazol-2-yl)-3-formyl-2-(3-hydroxypiperidino)-4-oxo-4H-pyrido[1,2-a]pyrimidine-8-carboxamide Reactions were performed in the same manner as in Example 7, (F) by using N8-(4-cyclobutyl-1,3-thiazol-2-yl)-2-(3-hydroxypiperidino)-4-oxo-4H-pyrido[1,2-a]-pyrimidine-8-carboxamide (85.2 mg, 0.20 mmol) to obtain 27.5 mg (30%) of the title compound.

$^1$H-NMR (CDCl$_3$) δ: 1.84–2.38 (10H, m), 3.43–3.63 (4H, m), 3.90 (1H, m), 4.08 (1H, m), 6.61 (1H, s), 7.39 (1H, d, J=7.07 Hz), 7.82 (1H, s), 8.87 (1H, d, J=7.07 Hz), 10.09 (1H, s), EI/MS; m/z: 454 (M$^+$+1)

(G) Methyl (E)-3-[8-{[(4-cyclobutyl-1,3-thiazol-2-yl)amino]carbonyl}-2-(3-hydroxy-piperidino)-4-oxo-4H-pyrido[1,2-a]pyrimidin-3-yl]-2-propenoate Reactions were performed in the same manner as in Example 7, (G) by using N8-(4-cyclobutyl-1,3-thiazol-2-yl)-3-formyl-2-(3-hydroxypiperidino)-4-oxo-4H-pyrido-[1,2-a]pyrimidine-8-carboxamide (27.5 mg, 0.061 mmol) to obtain 16.3 mg (53%) of the title compound.

$^1$H-NMR (CDCl$_3$) δ: 1.91 (5H, m), 2.06 (1H, m), 2.20 (2H, m), 2.38 (2H, m), 3.61 (4H, m), 3.68 (3H, s), 3.88 (1H, m), 4.04 (1H, m), 6.60 (1H, s), 7.14 (1H, d, J=15.63 Hz), 7.47 (1H, dd, J=1.95, 7.57 Hz), 7.57 (1H, d, J=15.63 Hz), 7.94 (1H, s), 8.99 (1H, d, J=7.57 Hz) EI/MS; m/z: 510 (M$^+$+1)

(H) (E)-3-[8-{[(4-Cyclobutyl-1,3-thiazol-2-yl)amino]carbonyl}-2-(3-hydroxypiperidino)-4-oxo-4H-pyrido[1,2-a]pyrimidin-3-yl]-2-propenoic acid Reactions were performed in the same manner as in Example 7, (H) by using methyl (E)-3-[8-{[(4-cyclobutyl- 1,3-thiazol-2-yl)amino]carbonyl}-2-(3-hydroxy-piperidino)-4-oxo-4H-pyrido[1,2-a]pyrimidin-3-yl]-2-propenoate (16.3 mg, 0.032 mmol) to obtain 11 mg (69%) of the title compound as orange crystals.

$^1$H-NMR (CD$_3$OD) δ: 1.59–2.08 (6H, m), 2.27–2.37 (4H, m), 3.62 (3H, s), 3.87 (2H, m), 4.08 (1H, d, J=12.21 Hz), 6.69 (1H, s), 7.09 (1H, d, J=15.87 Hz), 7.48 (1H, d, J=15.87 Hz), 7.60 (1H, dd, J=1.95, 7.32 Hz), 8.07 (1H, s), 8.94 (1H, d, J=7.32 Hz) EI/MS; m/z: 496 (M$^+$+1)

Example 9

(E)-3-[8-{[(4-Cyclobutyl-1,3-thiazol-2-yl)amino]carbonyl}-2-(4-methylpiperazino)-4-oxo-4H-pyrido[1,2-a]pyrimidin-3-yl]-2-propenoic acid (A) N8-(4-Cyclobutyl-1,3-thiazol-2-yl)-2-(4-methylpiperazino)-4-oxo-4H-pyrido[1,2-a]-pyrimidine-8-carboxamide Reactions were performed in the same manner as in Example 8, (E) by using N8-(4-cyclobutyl-1,3-thiazol-2-yl)-2,4-dioxo-3,4-dihydro-2H-pyrido[1,2-a]pyrimidine-8-carboxamide (60 mg, 0.174 mmol) and N-methylpiperazine (60 μl, 1, 0.52 mmol) as regents to obtain 51.2 mg (69%) of the title compound.

$^1$H-NMR (CDCl$_3$) δ: 1.94 (1H, m), 2.04 (1H, m), 2.23 (2H, m), 2.34 (2H, m), 2.35 (3H, s), 2.50 (4H, t, J=5.13 Hz), 3.57 (1H, qu, J=8.30 Hz), 3.72 (4H, brd), 5.68 (1H, s) s), 7.30 (1H.dd, J=1.95, 7.32 Hz), 7.80 (1H, s), 8.95 (1H, d, J=7.32 Hz) EI/MS; m/z: 425 (M$^+$+1)

(B) Methyl (E)-3-[8-{[(4-cyclobutyl-1,3-thiazol-2-yl)amino]carbonyl}-2-(4-methylpiperazino)-4-oxo-4H-pyrido[1,2-a]pyrimidin-3-yl]-2-propenoate Reactions were performed in the same manner as in Example 7, (F) by using N8-(4-cyclobutyl-1,3-thiazol-2-yl)-2-(4-methylpiperazino)-4-oxo-4H-pyrido[1,2-a]-pyrimidine-8-carboxamide (51.2 mg, 0.1206 mmol), and the product was used without purification to perform reactions in the same manner as in Example 7, (G) to obtain 24.7 mg (40% for the two steps) of the title compound.

$^1$H-NMR (CDCl$_3$) δ1.94 (1H, m), 2.05 (1H, m), 2.23 (2H, m), 2.34 (3H, s), 2.35 (2H, m), 2.54 (4H, m), 3.58 (1H, qu, J=8.54 Hz), 3.68 (4H, m), 3.81 (3H, s), 6.62 (1H, s), 7.16 (1H, d, J=15.63 Hz), 7.43 (1H, dd, J=1.95, 7.57 Hz), 7.57 (1H, d, J=15.63 Hz), 7.88 (1H, s), 8.99 (1H, d, J=7.57 Hz) EI/MS; m/z: 509 (M$^+$+1)

(C) (E)-3-[8-{[(4-Cyclobutyl-1,3-thiazol-2-yl)amino]carbonyl}-2-(4-methylpiperazino)-4-oxo-4H-pyrido[1,2-a]pyrimidin-3-yl]-2-propenoic acid Reactions were performed in the same manner as in Example 7, (H) by using methyl (E)-3-[8-{[(4-cyclobutyl-1,3-thiazol-2-yl)amino]carbonyl}-2-(4-methylpiperazino)-4-oxo-4H-pyrido[1,2-a]pyrimidin-3-yl]-2-propenoate (24.7 mg, 0.049 mmol) to obtain 14.1 mg (59%) of the title compound in yellow color.

$^1$H-NMR (CD$_3$OD) δ: 1.96–2.38 (6H, m), 2.37 (3H, s), 2.61 (4H, m), 3.59 (1H, m), 3.67 (4H, m), 6.66 (1H, s), 7.08 (1H, d, J=15.63 Hz), 7.48 (1H, d, J=15.63 Hz), 7.61 (1H.dd, J=1.71, 7.57 Hz), 8.09 (1H, s), 8.96 (1H, d, J=7.57 Hz) EI/MS; m/z: 495 (M$^+$+1)

Example 10

N8-[4-(tert-Butyl)-1,3-thiazol-2-yl]-4-oxo-3-(2H-1,2,3,4-tetrazol-5-yl)-4H-pyrido[1,2-a]pyrimidine-8-carboxamide (A) Ethyl 2-[2-(4-methoxybenzyl)-2H-1,2,3,4-tetrazol-5-yl]acetate Ethyl 1H-tetrazole-5-acetate (30 g, 0.192 mol) was dissolved in dimethylformamide (100 ml), cooled with ice, and added with potassium carbonate (32 g, 0.231 mol). The mixture was added dropwise with 4-methoxybenzochloride (31 ml, 0.231 mol) and stirred at room temperature for 21 hours. The reaction solution was concentrated under reduced pressure and subjected to azeotropy with toluene. The resulting residue was diluted with ethyl acetate and washed with water, and the compound dissolved in the aqueous layer was extracted with ethyl acetate. The organic layer collected was dried over magnesium sulfate. The organic layer was concentrated under reduced pressure, and then the residue was purified by silica gel column chromatography (hexane:ethyl acetate=2:1) to obtain 24 g (46%) of the title compound as a colorless transparent substance.

$^1$H-NMR (CDCl$_3$) δ: 1.25 (3H, t, J=7.07 Hz), 3.79 (3H, s), 3.93 (2H, s), 4.18 (2H, qu, J=7.07 Hz), 5.68 (2H, s), 6.88 (2H, d, J=8.78 Hz), 7.31 (2H, d, J=8.78 Hz) EI/MS; m/z: 275 (M$^+$–1)

(B) Ethyl 3-(dimethylamino)-2-[2-(4-methoxybenzyl)-2H-1,2,3,4-tetrazol-5-yl]-2-propenoate Dimethylformamide dimethylacetal (13 ml, 97.3 mmol) was dissolved in ethyl 2-[2-(4-methoxybenzyl)-2H-1,2,3,4-tetrazol-5-yl]acetate (24 g, 88.4 mmol) and heated to 100° C. for 3 hours with stirring. The reaction solution was purified by silica gel column chromatography (hexane:ethyl acetate=3:1→1:1→1:3) to obtain 14 g (48%) of yellow crystals.

$^1$H-NMR (CDCl$_3$) δ: 1.26 (3H, t, J=7.07 Hz), 2.04 (6H, s), 3.79 (3H, s), 4.11 (2H, qu, J=7.07 Hz), 5.70 (2H, s), 6.86 (2H, d, J=9.02 Hz), 7.30 (2H, d, J=9.02 Hz), 7.73 (1H, s), EI/MS; m/z: 332 (M$^+$+1)

(C) Ethyl 2-aminoisonicotinate 2-(Acetylamino)isonicotinic acid (13 g, 73.60 mmol) synthesized by the method of Example 7, (A) was added with ethanol (50 ml) and toluene (150 ml) and heated to 100–110° C. The mixture was added dropwise with concentrated sulfuric acid (7 ml) and heated for 11 hour with stirring. The reaction solution was returned to room temperature and poured into saturated aqueous sodium hydrogencarbonate cooled with ice. The mixture was extracted with chloroform and the collected organic layer was dried over magnesium sulfate and concentrated under reduced pressure to obtain 7.6 g (23% for the two steps) of the title compound as pale yellow crystals without purification.

$^1$H-NMR (CDCl$_3$) δ: 1.39 (3H, t, J=7.07 Hz), 4.37 (2H, qu, J=7.07 Hz), 4.63 (2H, brd), 7.07 (1H, s), 7.17 (1H, dd, J=0.98, 5.12 Hz), 8.18 (1H, d, J=5.12 Hz) EI/MS; m/z: 165 (M$^+$–1)

(D) Ethyl 3-[2-(4-methoxybenzyl)-2 H-1,2,3,4-tetrazol-5-yl]-4-oxo-4H-pyrido[1,2-a]-pyrimidine-8-carboxylate Ethyl 2-aminoisonicotinate (6.5 g, 39.23 mmol) was added with acetic acid (500 ml) and ethyl 3-(dimethylamino)-2-[2-(4-methoxybenzyl)-2H-1,2,3,4-tetrazol-5-yl]-2-propenoate (13 g, 39.23 mmol) and refluxed by heating at 130° C. for 5 hours. The reaction solution was returned to room temperature and poured into water, and this was extracted with chloroform. The resulting organic layer was washed with saturated brine, and the collected organic layer was dried over magnesium sulfate. The organic layer was concentrated under reduced pressure and subjected to azeotropy with toluene, and the resulting residue was purified by silica gel column chromatography (chloroform→chloroform:methanol=80:1→50:1→30:1) to obtain 8.6 g of the title compound.

$^1$H-NMR (CDCl$_3$) δ: 1.45 (3H, t, J=7.08 Hz), 3.79 (3H, s), 4.49 (2H,q, J=7.08 Hz), 5.82 (2H, s)6.89 (2H, d, J=8.54 Hz), 7.30 (2H, d, J=8.54 Hz), 7.74 (1H, d, J=6.59 Hz), 8.39 (1H, s), 9.28 (1H, s), 9.29 (1H, d, J=6.59 Hz) EI/MS; m/z: 407 (M$^+$+1)

(E) 3-[2-(4-Methoxybenzyl)-2 H-1,2,3,4-tetrazol-5-yl]-4-oxo-4H-pyrido[1,2-pyrimidine-8-carboxylic acid Ethyl 3-[2-(4-methoxybenzyl)-2 H-1,2,3,4-tetrazol-5-yl]-4-oxo-4H-pyrido[1,2-a]-pyrimidine-8-carboxylate (8.6 g, 21.1 mmol) was dissolved in tetrahydrofuran (170 ml) and added dropwise with 0.5 N aqueous sodium hydroxide (65 ml) at room temperature. The reaction solution was stirred for 1 hour and 30 minutes, then added with 1 N hydrochloric acid (55 ml) and water (250 ml) under ice cooling and warmed to room temperature with stirring. The deposited yellow crystals were taken by filtration, washed with water, dissolved in ethanol and concentrated under reduced pressure. The resulting crystals were dried under reduced pressure to obtain 4 g (27% for the two steps) of the title compound without purification.

$^1$H-NMR (CDCl$_3$) δ: 3.81 (3H, s), 5.83 (2H, s), 6.92 (2H, d, J=8.55 Hz), 7.43 (2H, d, J=8.55 Hz), 7.83 (1H, dd, J=1.22, 7.32 Hz), 8.40 (1H, s), 9.23 (1H, s), 9.31 (1H, d, J=7.32 Hz) EI/MS; m/z: 379 (M$^+$+1)

(F) N8-[4-(tert-Butyl)-1,3-thiazol-2-yl]-4-oxo-3-(2H-1,2,3,4-tetrazol-5-yl)-4H-pyrido-[1,2-a] pyrimidine-8-carboxamide 3-[2-(4-Methoxybenzyl)-2H-1,2,3,4-tetrazol-5-yl]-4-oxo-4H-pyrido[1,2-a]-pyrimidine-8-carboxylic acid (40 mg, 0.114 mmol) was added with dimethylformamide (2 ml), 4-(tert-butyl)-1,3-thiazol-2-amine (20 mg, 0.125 mmol), 1-hydroxybenzotriazole (20 mg, 0.136 mmol) and 4-dimethylaminopyridine (21 mg, 0.170 mmol) at room temperature, then added with 1-ethyl-3-(3-dimethylaminopropyl)carbodiimide hydrochloride (35 mg, 0.170 mmol) at room temperature, and stirred at room temperature for 24 hours. The reaction solution was added dropwise with 1 N hydrochloric acid (3 ml) at room temperature, and the deposited yellow crystals were taken by filtration and washed with water. The crystals were dissolved in chloroform and ethanol, concentrated under reduced pressure, and dried to obtain the title compound as yellow crystals without purification. The product was dissolved in anisole (0.2 ml) and trifluoroacetic acid (5 ml), stirred at room temperature for 5 hours, and added with water. The deposited yellow crystals were collected by filtration and washed with water, and the resulting crystals were dissolved in chloroform and ethanol and concentrated under reduced pressure. The crude crystals was added with ethanol, taken by filtration and washed with diethyl ether to obtain 28 mg (67% for the two steps) of the title compound as yellow crystals.

$^1$H-NMR (CD$_3$OD) δ: 1.38 (9H, s), 6.66 (1H, s), 8.10 (1H, d, J=8.30 Hz), 8.57 (1H, s), 9.38 (1H, d, J=8.30 Hz), 9.39 (1H, s) EI/MS; m/z: 397 (M$^+$+1)

Example 11

N8-[4-(4-Pyridyl)-1,3-thiazol-2-yl]-4-oxo-3-(2 H-1, 2,3,4-tetrazol-5-yl)-4H-pyrido[1,2-a]pyrimidine-8-carboxamide (A) 2-Bromo-1-(4-pyridyl)-1-ethanone 4-Acetylpyridine (3.62 g, 29.9 mmol) was added with acetic acid (30 ml) and 47% hydrobromic acid (5.3 ml) at room temperature, subsequently added dropwise with bromine (1.6 ml in total) four times at an interval of 5 minutes, stirred at room temperature for 2 hours and 30 minutes. The mixture was further added with bromine (1.6 ml), and stirred at room temperature for 20 hours. The reaction solution was filtered, and the resulting crystals were washed with diethyl ether and dried to obtain 12.43 g of the title compound as a salt of hydrogen bromide in the form of orange crystals without purification.

$^1$H-NMR (CD$_3$OD) δ: 3.73 (2H, dd, J=1.21,28.76 Hz), 8.26 (2H, d, J=6.83 Hz), 8.89 (2H, d, J=6.83 Hz) EI/MS; m/z: 279 (M$^+$−1)

(B) 4-(4-Pyridyl)-1,3-thiazol-2-amine

Reactions were performed in the same manner as in Example 8, (A) by using 2-bromo-1-(4-pyridyl)-1-ethanone (1 g, 3.56 mmol) to obtain 410 mg (65%) of the title compound.

$^1$H-NMR (CD$_3$OD) δ: 7.26 (1H, s), 7.80 (2H, d, J=6.35 Hz), 8.50 (2H, d, J=6.35 Hz) EI/MS; m/z: 176 (M$^+$−1)

(C) N8-[4-(4-Pyridyl)-1,3-thiazol-2-yl]-4-oxo-3-(2 H-1,2,3,4-tetrazol-5-yl)-4H-pyrido-[1,2-a] pyrimidine-8-carboxamide Reactions were performed in the same manner as in Example 10, (F) by using 3-[2-(4-methoxybenzyl)-2H-1,2, 3,4-tetrazol-5-yl]-4-oxo-4H-pyrido[1,2-a]pyrimidine-8-carboxylic acid (120 mg, 0.32 mmol) and 4-(4-pyridyl)-1, 3-thiazol-2-amine (62 mg, 0.35 mmol) to obtain 35.7 mg (27% for the two steps) of the title compound as orange crystals.

$^1$H-NMR (DMSO-d$_6$) δ: 8.03 (3H, m), 8.29 (1H, s), 8.66 (1H, d, J=0.977 Hz), 8.73 (2H, d, J=5.62 Hz), 9.29 (1H, s), 9.32 (1H, d, J=6.54 Hz) ES-MS; m/z: 418 (M$^+$+1) IR (cm$^{-1}$): 1668, 1633, 1567, 1492, 1288

Example 12

N8-(1,3-Benzothiazol-2-yl)-4-oxo-3-(2H-1,2,3,4-tetrazol-5-yl)-4H-pyrido-[1,2-a]pyrimidine-8-carboxamide Reactions were performed in the same manner as in Example 10, (F) by using 3-[2-(4-methoxybenzyl)-2H-1,2, 3,4-tetrazol-5-yl]-4-oxo-4H-pyrido[1,2-a]pyrimidine-8-carboxylic acid (60 mg, 0.16 mmol) and 2-aminobenzothiazole (30 mg, 0.17 mmol) to obtain 2 mg (3% for the two steps) of an orange compound.

$^1$H-NMR (DMSO-d$_6$) δ: 7.39 (1H, t, J=7.57 Hz), 7.52 (1H, t, J=7.57 Hz), 7.78 (1H, d, J=7.57 Hz), 8.05 (2H, d, J=7.57 Hz), 8.61 (1H, s), 9.28 (1H, s), 9.31 (1H, d, J=7.57 Hz) ES-MS; m/z: 391 (M$^+$+1)

Example 13

N8-(4-Cyclobutyl-1,3-thiazol-2-yl)-2-(4-methylpiperazino)-4-oxo-4H-pyrido[1,2-a] pyrimidine-8-carboxamide Reactions were performed in the same manner as in Example 9, (A) by using N8-(4-cyclobutyl-1,3-thiazol-2-yl)-2,4-dioxo-3,4-dihydro-2H-pyrido[1,2-a]pyrimidine-8-carboxamide (40 mg, 0.12 mmol), and the resulting compound was added with 4 N hydrochloric acid solution in dioxane (2 ml) and stirred to obtain 12 mg (24%) of the title compound as hydrochloride.

NMR for free form and Mass:
¹H-NMR (CDCl₃) δ: 1.94 (1H, m), 2.04 (1H, m), 2.23 (2H, m), 2.34 (2H, m), 2.35 (3H, s), 2.50 (4H, t, J=5.13 Hz), 3.57 (1H, qu, J=8.30 Hz), 3.72 (4H, brd), 5.68 (1H, s), 6.63 (1H, s), 7.30 (1H.dd, J=1.95, 7.32 Hz), 7.80 (1H, s), 8.95 (1H, d, J=7.32 Hz) EI/MS; m/z: 425 (M⁺+1)

Example 14

N8-(4-Isopropyl-1,3-thiazol-2-yl)-4-oxo-3-(2 H-1,2,3,4-tetrazol-5-yl)-4H-pyrido[1,2-a]pyrimidine-8-carboxamide (A) N8-(4-Isopropyl-1,3-thiazol-2-yl)-3-[2-(4-methoxybenzyl)-2H-1,2,3,4-tetrazol-5yl]-4-oxo-4H-pyrido[1,2-a]pyrimidine-8-carboxamide 3-[2-(4-Methoxybenzyl)-2H-1,2,3,4-tetrazol-5-yl]-4-oxo-4H-pyrido[1,2-a]-pyrimidine-8-carboxylic acid (250 mg, 0.66 mmol) was dissolved in dimethylformamide (6 ml), added with N,N-carbonylbis-1H-imidazole (abbreviated as "CDI" hereinafter, 160 mg, 0.991 mmol) and heated to 90° C. with stirring. After 1 hour and 30 minutes, the reaction solution was further added with CDI (170 mg), further stirred for 1 hour, and then further added with CDI (170 mg). The reaction solution was stirred further 2 hours, then returned to room temperature, added with 4-isopropyl-1,3-thiazol-2-amine hydrobromide (1.32 mmol) and stirred at room temperature for 2 hours and 30 minutes. The reaction solution was added with 2 N hydrochloric acid (7 ml), and the deposited crystals were collected by filtration and washed with water. The resulting yellow crystals were dissolved in chloroform and washed with saturated brine, and the collected organic layer was dried over magnesium sulfate and concentrated under reduced pressure to obtain the title compound as yellow crystals without purification.
¹H-NMR (CD₃OD) δ: 1.34 (6H, d, J=6.83 Hz), 3.00 (1H, qu, J=6.83 Hz), 3.80 (3H, s), 5.85 (2H, s), 6.63 (1H, s), 6.92 (2H, d, J=8.78 Hz), 7.44 (2H, d, J=8.78 Hz), 8.04 (1H, dd, J=1.46, 7.56 Hz), 8.50 (1H, s), 9.20 (1H, s), 9.34 (1H, d, J=7.56 Hz) EI/MS; m/z: 503 (M⁺+1)

(B) N8-(4-Isopropyl-1,3-thiazol-2-yl)-4-oxo-3-(2H-1,2,3,4-tetrazol-5-yl)-4H-pyrido-[1,2-a]pyrimidine-8-carboxamide N8-(4-Isopropyl-1,3-thiazol-2-yl)-3-[2-(4-methoxybenzyl)-2H-1,2,3,4-tetrazol-5-yl]-4-oxo-4H-pyrido[1,2-a]pyrimidine-8-carboxamide (330 mg, 0.66 mmol) was added with trifluoroacetic acid (10 ml) at room temperature and stirred for 3 days. The reaction solution was poured into ice water, and the deposited yellow crystals were collected by filtration, washed with water, then dissolved in chloroform and ethanol, and concentrated under reduced pressure. The resulting yellow crystals were suspended in a small amount of ethanol, and the crystals were taken by filtration and washed with diethyl ether to obtain 54 mg (21% for the two steps) of the title compound as yellow crystals.
¹H-NMR (DMSO-d₆) δ: 1.27 (6H, d, J=6.84 Hz), 2.93 (1H, m), 6.90 (1H, s), 8.02 (1H, d, J=7.08 Hz), 8.55 (1H, s), 9.26 (1H, s), 9.29 (1H, d, J=7.08 Hz) ES-MS; m/z: 383 (M⁺+1)

Example 15

(E)-3-(2-{3-[(Aminocarbonyl)oxy]piperidino}-8-{[(4-cyclobutyl-1,3-thiazol-2-yl)amino]carbonyl}-4-oxo-4H-pyrido[1,2-a]pyrimidin-3-yl)-2-propenoic acid (A) 1-(8{[(4-Cyclobutyl-1,3-thiazol-2-yl)amino]carbonyl}-3-formyl-4-oxo-4H-pyrido-[1,2-a]pyrimidin-2-yl)-3-piperidyl formate Reactions were performed in the same manner as in Example 7, (F) by using N8-(4-cyclobutyl-1,3-thiazol-2-yl)-2-(3-hydroxypiperidino)-4-oxo-4H-pyrido[1,2-a]-pyrimidine-8-carboxamide (85 mg, 0.20 mmol) to obtain 21 mg (22%) of the title compound.
¹H-NMR (CDCl₃) δ: 1.92–2.41 (10H, m), 3.58–3.68 (3H, m), 3.93 (2H, m), 5.10 (1H, m), 6.61 (1H, s), 7.39 (1H, dd, J=1.95, 7.31 Hz), 7.79 (1H, d, J=1.95 Hz), 8.01 (1H, s), 8.89 (1H, d, J=7.31 Hz), 10.14 (1H, s) EI/MS; m/z: 482 (M⁺+1)

(B) tert-Butyl (E)-3-[8-{[(4-cyclobutyl-1,3-thiazol-2-yl)amino]carbonyl}-2-(3-formyloxy-piperidino)-4-oxo-4H-pyrido[1,2-a]pyrimidin-3-yl]-2-propenoate Reactions were performed in the same manner as in Example 1, (J) by using 1-(8-{[(4-cyclobutyl-1,3-thiazol-2-yl)amino]carbonyl}-3-formyl-4-oxo-4H-pyrido[1,2-a]pyrimidin-2-yl)-3-piperidyl formate (36 mg, 0.075 mmol), and the resulting reaction solution was purified by thin layer silica gel chromatography (chloroform:methanol=30:1) to obtain 35 mg of the title compound as orange crystals in a mixture with triphenylphosphine oxide.
¹H-NMR (CDCl₃) δ: 1.52 (9H, s), 1.94–2.00 (6H, m), 2.23–2.34 (4H, m), 3.57–3.83 (5H, m), 5.15 (1H, m), 6.62 (1H, s), 7.09 (1H, d, J=15.63 Hz), 7.48 (1H, dd, J=1.71, 7.32 Hz), 7.49 (1H, d, J=15.63 Hz), 7.91 (1H, s), 8.09 (1H, s), 8.98 (1H, d, J=7.32 Hz)

(C) tert-Butyl (E)-3-[8-{[(4-cyclobutyl-1,3-thiazol-2-yl)amino]carbonyl}-2-(3-hydroxy-piperidino)-4-oxo-4H-pyrido[1,2-a]pyrimidin-3-yl]-2-propenoate Reactions were performed in the same manner as in Example 1, (K) by using tert-butyl (E)-3-[8-{[(4-cyclobutyl-1,3-thiazol-2-yl)amino]carbonyl}-2-(3-formyloxy-piperidino)-4-oxo-4H-pyrido[1,2-a]pyrimidin-3-yl]-2-propenoate (35 mg, 0.060 mmol), and the resulting crude crystals were purified by thin layer silica gel chromatography (chloroform:methanol=40:1) to obtain 16 mg (40% for the two steps) of the title compound as yellow crystals.
¹H-NMR (CDCl₃) δ: 1.52 (9H, s), 1.72–2.07 (6H, m), 2.17–2.38 (4H, m), 3.60 (4H, m), 3.80 (1H, m), 4.02 (1H, m), 6.61 (1H, s), 7.10 (1H, d, J=15.60 Hz), 7.48 (1H, dd, J=1.71, 7.31 Hz), 7.49 (1H, d, J=15.60 Hz), 7.97 (1H, s), 9.00 (1H, d, J=7.31 Hz) EI/MS; m/z: 552 (M⁺+1)

(D) tert-Butyl (E)-3-(2-{3-[(aminocarbonyl)oxy]piperidino}-8-{[(4-cyclobutyl-1,3-thiazol-2-yl)amino]carbonyl}-4-oxo-4H-pyrido[1,2-a]pyrimidin-3-yl)-2-propenoate tert-Butyl (E)-3-[8-{[(4-cyclobutyl-1,3-thiazol-2-yl)amino]carbonyl}-2-(3-hydroxypiperidino)-4-oxo-4H-pyrido[1,2-a]pyrimidin-3-yl]-2-propenoate (16 mg, 0.029 mmol) was dissolved in ethyl acetate (3 ml), added with trichloroacetyl isocyanate (10 μl) under ice cooling, stirred at 0° C. for 1 hour, then further added with trichloroacetyl isocyanate (10 μl), and further stirred for 30 minutes. Then, the reaction solution was concentrated under reduced pressure, and the resulting residue was added with methanol (2 ml), water (0.2 ml) and sodium formate (12 mg) at room temperature and stirred at room temperature for 7 hours. The reaction solution was concentrated under reduced pressure, and the residue was purified by thin layer silica gel chromatography (chloroform:methanol=30:1) to obtain 20 mg of the title compound.
¹H-NMR (CDCl₃) δ: 1.51 (9H, s), 1.90–2.36 (10H, m), 3.36–3.77 (4H, m), 4.04 (1H, m), 4.92 (1H, m), 6.62 (1H, s), 7.10 (1H, d, J=15.38 Hz), 7.54 (1H, d, J=7.57 Hz), 7.60 (1H, d, J=15.38 Hz), 8.07 (1H, s), 9.00 (1H, d, J=7.57 Hz) EI/MS; m/z: 595 (M⁺+1)

(E) (E)-3-(2-{3-[(Aminocarbonyl)oxy]piperidino}-8-{[(4-cyclobutyl-1,3-thiazol-2-yl)-amino]carbonyl}-4-oxo-4H-pyrido[1,2-a]pyrimidin-3-yl)-2-propenoic acid tert-Butyl (E)-3-(2-{3-[(aminocarbonyl)oxy]piperidino}-8-{[(4-cyclobutyl-1,3-thiazol-2-yl)amino]carbonyl}-4-oxo-4H-pyrido[1,2-a]pyrimidin-3-yl)-2-propenoate (20 mg, 0.034 mmol) was added with a mixed solution of 4 N hydrochloric acid and dioxane (1.5 ml) at room temperature and stirred for 2 hours. The reaction solution was concentrated under reduced pressure, and the resulting residue was purified by thin layer silica gel chromatography (chloroform:methanol=10:1) to obtain 9 mg (58% for the two steps) of the title compound as yellow crystals.

$^1$H-NMR (CD$_3$OD) δ: 1.68 (2H, m), 1.94–2.10 (4H, m), 2.23 (2H, m), 2.38 (2H, m). 3.39–3.72 (4H, m), 3.98 (1H, dd, J=5.86, 11.70 Hz), 4.86 (1H, m), 6.64 (1H, s), 7.10 (1H, d, J=15.63 Hz), 7.56 (1H, d, J=7.32 Hz), 7.68 (1H, d, J=15.63 Hz), 8.07 (1H, S), 8.96 (1H, d, J=7.32 Hz) ES-MS; m/z: 539 (M$^+$+1)

Example 16

2-{8-[2-(4-Isopropyl-1,3-thiazol-2-yl)ethyl]-2-morpholino-4-oxo-4H-pyrido-[1,2-a]pyrimidin-3-yl}-1-cyclopropanecarboxylic acid

(A) 3-[(E)-3-Hydroxy-1-propenyl]-8-[2-(4-isopropyl-1,3-thiazol-2-yl)ethyl]-2-morpholino-4H-pyrido[1,2-a]pyrimidin-4-one (E)-3-{8-[2-(4-Isopropyl-1,3-thiazol-2-yl)ethyl]-2-morpholino-4-oxo-4H-pyrido-[1,2-a]pyrimidin-3-yl}-2-propenoic acid (222.7 mg, 0.49 mmol) dissolved in tetrahydrofuran (8 ml) was added with triethylamine (342 μl) and ethyl chloroformate (141 μl) at −20° C., then stirred at room temperature for 1 hour, and subsequently added with aqueous sodium borohydride (0.8 M, 4 ml) at room temperature. The aqueous sodium borohydride was occasionally added until the reaction was completed, and the completion of the reaction was confirmed by TLC. Then, the reaction solution was added with water and extracted with chloroform and chloroform:methanol=10:1, and the organic layer collected was dried over magnesium sulfate and concentrated under reduced pressure. The resulting residue was purified by silica gel column chromatography (chloroform→chloroform:methanol=100:1→60:1→30:1) to recover 81 mg (37%) of the title compound and 82 mg of the starting material.

$^1$H-NMR (CDCl$_3$) δ: 1.29 (6H, d, J=6.83 Hz), 3.07 (1H, qu, J=6.83 Hz), 3.19 (2H, t, J=7.80 Hz), 3.36 (2H, t, J=7.80 Hz), 3.53 (4H, t, J=4.88 Hz), 3.80 (4H, t, J=4.88 Hz), 4.35 (2H, d, J=5.85 Hz), 6.44 (1H, d, J=15.60 Hz), 6.72 (1H, s), 6.83 (1H, dd, J=1.95, 7.31 Hz), 7.00 (1H, dt, J=5.85, 15.60 Hz) 7.21 (1H, s), 8.87 (1H, d, J=7.31 Hz) EI/MS; m/s: 441 (M$^+$+1)

(B) 3-[2-(Hydroxymethyl)cyclopropyl]-8-[2-(4-isopropyl-1,3-thiazol-2-yl)ethyl]-2-morpholino-4H-pyrido[1,2-a]pyrimidin-4-one 3-[(E)-3-Hydroxy-1-propenyl]-8-[2-(4-isopropyl-1,3-thiazol-2-yl)ethyl]-2-morpholino-4H-pyrido[1,2-a]pyrimidin-4-one (81 mg, 0.18 mmol) was added with dichloromethane (3 ml) and a solution of diethyl zinc in hexane (1.02 M, 270 μl, 0.275 mmol) and subsequently added dropwise with iodomethane (30 μl, 0.366 mmol) at room temperature. After the reaction solution was stirred for 2 hours, the reaction was stopped with saturated aqueous ammonium chloride, and the reaction solution was extracted with chloroform. The organic layer was dried over magnesium sulfate and concentrated under reduced pressure. The resulting residue was purified by thin layer silica gel chromatography (chloroform:methanol=15:1) to obtain 61 mg (73%) of the title compound.

$^1$H-NMR (CDCl$_3$) δ: 0.90 (1H, m), 1.04 (2H, m), 1.29 (6H, d, J=6.84 Hz), 1.52 (1H, dt, J=5.62, 7.57 Hz), 3.07 (1H, qu, J=6.84 Hz), 3.17 (2H, t, J=7.32 Hz), 3.35 (2H, t, J=7.32 Hz), 3.56 (2H, m), 3.84 (6H, m), 4.12 (1H, d, J=9.52 Hz), 4.68 (1H, brd), 6.73 (1H, dd, J=1.71, 7.32 Hz), 7.16 (1H, s), 8.80 (1H, d, J=7.32 Hz) EI/MS; m/s: 455 (M$^+$+1)

(C) 2-{8-[2-(4-Isopropyl-1,3-thiazol-2-yl)ethyl]-2-morpholino-4-oxo-4H-pyrido[1,2-a]-pyrimidin-3-yl}-1-cyclopropanecarboxylic acid 3-[2-(Hydroxymethyl)cyclopropyl]-8-[2-(4-isopropyl-1,3-thiazol-2-yl)ethyl]-2-morpholino-4H-pyrido[1,2-a]pyrimidin-4-one (55 mg, 0.121 mmol) dissolved in acetone (10 ml) was added dropwise with Jones' reagent (130 μl, 0.363 mmol) under ice cooling with and stirred for 2 hours. Then, the reaction solution was further added with Jones' reagent (165 μl) and stirred for 2 hours. Then, the reaction was stopped with saturated sodium thiosulfate, and the reaction solution was extracted with chloroform. The organic layer was dried over magnesium sulfate and concentrated under reduced pressure. The resulting residue was purified by thin layer silica gel chromatography (chloroform:methanol=10:1) to obtain 2.2 mg (4%) of the title compound as yellow crystals.

$^1$H-NMR (CDCl$_3$) δ: 1.29 (6H, d, J=7.07 Hz), 1.35 (1H, dt, J=4.39, 7.80 Hz), 1.63 (1H, dt, J=4.39, 8.53 Hz), 1.85 (1H, dt, J=3.90, 8.53 Hz), 2.34 (1H, dt, J=3.90, 7.80 Hz), 3.07 (1H, qu, J=7.07 Hz), 3.18 (2H, t, J=7.07 Hz), 3.35 (2H, t, J=7.07 Hz), 3.58 (2H, m), 3.77 (6H, m), 6.72 (1H, s), 6.80 (1H, dd, J=1.46, 7.31 Hz), 7.17 (1H, s), 8.81 (1H, d, J=7.31 Hz) EI/MS; m/s: 469 (M$^+$+1)

Example 17

(E)-3-{8-({[4-(tert-Butyl)-1,3-thiazol-2-yl]amino}carbonyl)-2-[(3R)-3-hydroxyhexahydro-1-pyridinyl]-4-oxo-4H-pyrido[1,2-a]pyrimidin-3-yl}-2-propenoic acid

(A) N8-[4-(tert-Butyl)-1,3-thiazol-2-yl]-2-[(3R)-3-hydroxyhexahydro-1-pyridinyl]-4-oxo-4H-pyrido[1,2-a]pyrimidine-8-carboxamide Reactions were performed in the same manner as in Example 8, (E) by using N8-[4-(tert-butyl)-1,3-thiazol-2-yl]-2,4-dioxo-3,4-dihydro-2H-pyrido[1,2-a]pyrimidine-8-carboxamide (300 mg, 0.871 mmol) and (R)-(+)-3-hydroxypiperidine (530 mg, 5.226 mmol) to obtain 241.8 mg (65%) of the title compound.

$^1$H-NMR (CDCl$_3$) δ: 1.34 (9H, s), 1.57 (1H, m), 1.76 (1H, m), 1.96 (2H, m), 3.61 (3H, m), 3.90 (2H, m), 5.69 (1H, s), 6.60 (1H, s), 7.31 (1H, dd, J=1.71, 7.32 Hz), 7.76 (1H, s), 8.86 (1H, d, J=7.32 Hz) EI/MS; m/s: 428 (M$^+$+1)

(B) (3R)-1-[8-({[4-(tert-Butyl)-1,3-thiazol-2-yl]amino}carbonyl)-3-formyl-4-oxo-4H-pyrido[1,2-a]pyrimidin-2-yl]hexahydro-3-pyridinyl formate Reactions were performed in the same manner as in Example 7, (F) by using N8-[4-(tert-butyl)-1,3-thiazol-2-yl]-2-[(3R)-3-hydroxyhexahydro-1-pyridinyl]-4-oxo-4H- pyrido[1,2-a]pyrimidine-8-carboxamide (295 mg, 0.690 mmol) and phosphorus oxychloride (130 μl, 1.38 mmol) to obtain 277 mg (68%) of the title compound.

$^1$H-NMR (CDCl$_3$) δ: 1.34 (9H, s), 1.70 (1H, m), 1.87–2.03 (3H, m), 3.66 (2H, m), 3.91 (2H, m), 5.09 (1H, brd), 6.58 (1H, s), 7.52 (1H, dd, J=1.71, 7.32 Hz), 7.96 (1H, s), 8.01 (1H, s), 8.87 (1H, d, J=7.32 Hz), 10.14 (1H, s) EI/MS; m/s: 484 (M$^+$+1)

(C) tert-Butyl (E)-3-{8-({[4-(tert-butyl)-1,3-thiazol-2-yl]amino}carbonyl)-2-[(3R)-3-formyloxyhexahydro-1-pyridinyl]-4-oxo-4H-pyrido[1,2-a]pyrimidin-3-yl}-2-propenoate Reactions were performed in the same manner as in Example 1, (J) by using (3R)-1-[8-({[4-(tert-butyl)-1,3-thiazol-2-yl]amino}carbonyl)-3-formyl-4-oxo-4H-pyrido-[1,2-a]pyrimidin-2-yl]hexahydro-3-pyridinyl formate (277 mg, 0.5723 mmol), and the resulting residue was purified by silica gel column chromatography (chloroform→chloroform:methanol=100:1→70:1→50:1) to obtain 559 mg (100% or more) of the title compound as a brown oily substance in a mixture with byproducts.

$^1$H-NMR (CDCl$_3$) δ: 1.28 (9H, s), 1.53 (9H, s), 1.71–1.97 (4H, m), 3.46–3.73 (4H, m), 5.09 (1H, brd), 6.56 (1H, s), 7.09 (1H, d, J=15.60 Hz), 7.64 (1H, dd, J=1.95, 7.31 Hz), 7.65 (1H, d, J=15.60 Hz), 8.01 (1H, s), 8.05 (1H, s), 8.82 (1H, d, J=7.31 Hz) EI/MS; m/s: 580 (M$^+$−1)

(D) tert-Butyl (E)-3-{8-({[4-(tert-butyl)-1,3-thiazol-2-yl]amino}carbonyl)-2-[(3R)-3-hydroxyhexahydro-1-pyridinyl]-4-oxo-4H-pyrido[1,2-a]pyrimidin-3-yl}-2-propenoate Reactions were performed in the same manner as in Example 1, (K) by using tert-butyl (E)-3-{8-({[4-(tert-butyl)-1,3-thiazol-2-yl]amino}carbonyl)-2-[(3R)-3-formyloxyhexahydro-1-pyridinyl]-4-oxo-4H-pyrido[1,2-a]pyrimidin-3-yl}-2-propenoate (559 mg, 0.961 mmol) to obtain 368 mg (69%) of the title compound as an orange oily substance.

$^1$H-NMR (CDCl$_3$) δ: 1.32 (9H, s), 1.52 (9H, s), 1.77–1.90 (4H, m), 3.54-3.73 (4H, m), 4.01 (1H, brd), 6.54 (1H, s), 7.04 (1H, d, J=15.63 Hz), 7.64 (1H, dd, J=1.95, 7.32 Hz), 7.65 (1H, d, J=15.63 Hz), 8.00 (1H, s), 8.84 (1H, d, J=7.32 Hz)

(E) (E)-3-{8-({[4-(tert-Butyl)-1,3-thiazol-2-yl]amino}carbonyl)-2-[(3R)-3-hydroxy-hexahydro-1-pyridinyl]-4-oxo-4H-pyrido[1,2-a]pyrimidin-3-yl}-2-propenoic acid Reactions were performed in the same manner as in Example 15, (E) by using tert-butyl (E)-3-{8-({[4-(tert-butyl)-1,3-thiazol-2-yl]amino}carbonyl)-2-[(3R)-3-hydroxy-hexahydro-1-pyridinyl]-4-oxo-4H-pyrido[1,2-a]pyrimidin-3-yl}-2-propenoate (140 mg, 0.253 mmol) as a mixture containing triphenylphosphine oxide to obtain 42 mg (33%) of the title compound as orange crystals.

$^1$H-NMR (CD$_3$OD) δ: 1.36 (9H, s), 1.61 (2H, m), 1.92 (1H, m), 2.06 (1H, m), 3.21 (1H, dd, J=8.55, 12.94 Hz), 3.36 (1H, m), 3.86 (2H, m), 4.10 (1H, d, J=12.94 Hz), 6.68 (1H, s), 7.05 (1H, d, J=15.63 Hz), 7.60 (1H, dd, J=1.95, 7.32 Hz), 7.61 (1H, d, J=15.63 Hz), 8.05 (1H, s), 8.95 (1H, d, J=7.32 Hz) ES-MS; m/s: 498 (M$^+$+1)

Example 18

(E)-3-[2-{(3R)-3-[(Aminocarbonyl)oxy]hexahydro-1-pyridinyl}-8-({[4-(tert-butyl)-1,3-thiazol-2-yl]amino}carbonyl)-4-oxo-4H-pyrido[1,2-a]pyrimidin-3-yl]-2-propenoic acid (A) tert-Butyl (E)-3-[2-{(3R)-3-[(aminocarbonyl)oxy]hexahydro-1-pyridinyl}-8-({[4-(tert-butyl)-1,3-thiazol-2-yl]amino}carbonyl)-4-oxo-4H-pyrido[1,2-a]pyrimidin-3-yl]-2-propenoate Reactions were performed in the same manner as in Example 15, (D) by using tert-butyl (E)-3-{8-({[4-(tert-butyl)-1,3-thiazol-2-yl]amino}carbonyl)-2-[(3R)-3-hydroxy-hexahydro-1-pyridinyl]-4-oxo-4H-pyrido[1,2-a]pyrimidin-3-yl}-2-propenoate (240 mg, 0.436 mmol) to obtain 254 mg (98%) of an orange oily compound.

$^1$H-NMR (CDCl$_3$) δ: 1.30 (9H, s), 1.49 (9H, s), 1.69–2.17 (4H, m), 3.34 (1H, m), 3.54 (1H, m), 3.65 (1H, m), 3.87 (1H, m), 4.93 (1H, brd), 6.60 (1H, s), 7.07 (1H, d, J=15.63 Hz), 7.56 (1H, dd, J=1.95, 7.33 Hz), 7.68 (1H, d, J=15.63 Hz), 8.06 (1H, s), 8.96 (1H, d, J=7.33 Hz)

(B) (E)-3-[2-{(3R)-3-[(Aminocarbonyl)oxy]hexahydro-1-pyridinyl}-8-({[4-(tert-butyl)-1,3-thiazol-2-yl]amino}carbonyl)-4-oxo-4H-pyrido[1,2-a]pyrimidin-3-yl]-2-propenoic acid Reactions were performed in the same manner as in Example 15, (E) by using tert-butyl (E)-3-[2-{(3R)-3-[(aminocarbonyl)oxy]hexahydro-1-pyridinyl}-8-({[4-(tert-butyl)-1,3-thiazol-2-yl]amino}carbonyl)-4-oxo-4H-pyrido[1,2-a]pyrimidin-3-yl]-2-propenoate (254 mg, 0.426 mmol) containing byproducts to obtain 51 mg (22%) of the title compound as orange crystals.

$^1$H-NMR (CD$_3$OD) δ: 1.35 (9H, s), 1.68 (1H, m), 1.94 (3H, m), 3.46 (1H, m), 3.66 (3H m), 3.98 (1H, dd, J=4.88, 13.43 Hz), 4.87 (1H, s), 6.63 (1H, s), 7.10 (1H, d, J=15.63 Hz), 7.56 (1H, dd, J=1.95, 7.33 Hz), 7.68 (1H, d, J=15.63 Hz), 8.06 (1H, s), 8.96 (1H, d, J=7.33 Hz) EI/MS; m/s: 541 (M$^+$+1)

Example 19

(E)-3-[2-{(3S)-3-[(Aminocarbonyl)oxy]hexahydro-1-pyridinyl}-8-({[4-(tert-butyl)-1,3-thiazol-2-yl]amino}carbonyl)-4-oxo-4H-pyrido[1,2-a]pyrimidin-3-yl]-2-propenoic acid (A) N8-[4-(tert-Butyl)-1,3-thiazol-2-yl]-2-[(3S)-3-hydroxyhexahydro-1-pyridinyl]-4-oxo-4H-pyrido[1,2-a]pyrimidine-8-carboxamide Reactions were performed in the same manner as in Example 8, (E) by using N8-[4-(tert-butyl)-1,3-thiazol-2-yl]-2,4-dioxo-3,4-dihydro-2H-pyrido[1,2-a]pyrimidine-8-carboxamide (600 mg, 1.74 mmol) and (S)-(−)-3-hydroxypiperidine hydrochloride (360 mg, 2.61 mmol) to obtain 463 mg (62%) of the title compound.

$^1$H-NMR (CDCl$_3$) δ: 1.35 (9H, s), 1.59 (1H, brd), 1.73–1.99 (3H, m), 3.61 (3H, m), 3.93 (2H, m), 5.71 (1H, s), 6.61 (1H, s), 7.31 (1H, d, J=7.32 Hz), 7.77 (1H, s), 8.89 (1H, d, J=7.32 Hz) EI/MS; m/s: 428 (M$^+$+1)

(B) (3S)-1-[8-({[4-(tert-Butyl)-1,3-thiazol-2-yl]amino}carbonyl)-3-formyl-4-oxo-4H-pyrido[1,2-a]pyrimidin-2-yl]hexahydro-3-pyridinyl formate Reactions were performed in the same manner as in Example 7, (F) by using N8-[4-(tert-butyl)-1,3-thiazol-2- yl]-2-[(3S)-3-hydroxyhexahydro-1-pyridinyl]-4-oxo-4H-pyrido[1,2-a]pyrimidine-8-carboxamide (463 mg, 1.08 mmol) and phosphorus oxychloride (0.3 ml, 3.25 mmol) to obtain 600 mg (100%) of the title compound as a substance containing dimethylformamide without purification.

$^1$H-NMR (CDCl$_3$) δ: 1.32 (9H, s), 1.72 (1H, m), 1.89–2.04 (3H, m), 3.68 (2H, m), 3.92 (2H, d, J=3.90 Hz), 5.09 (1H, brd), 6.59 (1H, s), 7.47 (1H, dd, J=1.95, 7.31 Hz), 7.89 (1H, s), 8.01 (1H, s), 8.88 (1H, d, J=7.31 Hz), 10.14 (1H, s)

(C) tert-Butyl (E)-3-{8-({[4-(tert-butyl)-1,3-thiazol-2-yl]amino}carbonyl)-2-[(3S)-3-formyloxyhexahydro-1-pyridinyl]-4-oxo-4H-pyrido[1,2-a]pyrimidin-3-yl}-2-propenoate Reactions were performed in the same manner as in Example 1, (J) by using (3S)-1-[8-({[4-(tert-butyl)-1,3-thiazol-2-yl]amino}carbonyl)-3-formyl-4-oxo-4H-pyrido-[1,2-a]pyrimidin-2-yl]hexahydro-3-pyridinyl formate (524 mg, 1.083 mmol), and the resulting residue was purified by silica gel column chromatography (chloroform→chloroform:methanol=100:1→70:1→50:1) to obtain 742 mg (100% or more) of the title compound as a brown oily substance in a mixture containing byproducts.

$^1$H-NMR (CDCl$_3$) δ: 1.28 (9H, s), 1.53 (9H, s), 1.68–2.03 (4H, m), 3.48–3.71 (4H, m), 5.10 (1H, m), 6.57 (1H, s), 7.09 (1H, d, J=15.63 Hz), 7.64 (1H, dd, J=1.95, 7.32 Hz), 7.65 (1H, d, J=15.63 Hz), 7.99 (1H, s), 8.06 (1H, s), 8.85 (1H, d, J=7.32 Hz) EI/MS; m/s: 580 (M$^+$−1)

(D) tert-Butyl (E)-3-{8-({[4-(tert-butyl)-1,3-thiazol-2-yl]amino}carbonyl)-2-[(3S)-3-hydroxyhexahydro-1-pyridinyl]-4-oxo-4H-pyrido[1,2-a]pyrimidin-3-yl}-2-propenoate Reactions were performed in the same manner as in Example 1, (K) by using tert-butyl (E)-3-{8-({[4-(tert-butyl)-1,3-thiazol-2-yl]amino}carbonyl)-2-[(3S)-3-formyloxyhexahydro-1-pyridinyl]-4-oxo-4H-pyrido[1,2-a]pyrimidin-3-yl}-2-propenoate (630 mg, 1.083 mmol) to obtain 439 mg (73%) of the title compound as an orange oily substance.

$^1$H-NMR (CDCl$_3$) δ: 1.34 (9H, s), 1.52 (9H, s), 1.78–1.90 (4H, m), 3.54 (2H, brd), 3.65–3.74 (2H, m), 4.02 (1H, brd), 6.53 (1H, s), 7.03 (1H, d, J=15.60 Hz), 7.56 (1H, d, J=7.31 Hz), 7.60 (1H, d, J=15.60 Hz), 7.99 (1H, s), 8.84 (1H, d, J=7.31 Hz) EI/MS; m/s: 554 (M$^+$+1)

(E) tert-Butyl (E)-3-[2-{(3S)-3-[(aminocarbonyl)oxy]hexahydro-1-pyridinyl}-8-({[4-(tert-butyl)-1,3-thiazol-2-yl]amino}carbonyl)-4-oxo-4H-pyrido[1,2-a]pyrimidin-3-yl]-2-propenoate Reactions were performed in the same manner as in Example 15, (D) by using tert-butyl (E)-3-{8-({[4-(tert-butyl)-1,3-thiazol-2-yl]amino}carbonyl)-2-[(3S)-3-hydroxy-hexahydro-1-pyridinyl]-4-oxo-4H-pyrido[1,2-a]pyrimidin-3-yl}-2-propenoate (140 mg, 0.2529 mmol) to obtain 131 mg (87%) of an orange oily compound.

$^1$H-NMR (CDCl$_3$) δ: 1.30 (9H, s), 1.49 (9H, s), 1.70–2.00 (4H, m), 3.35 (1H, m), 3.54 (1H, d, J=12.43 Hz), 3.67 (1H, m), 3.88 (1H, m), 4.92 (1H, brd), 6.60 (1H, s), 7.05 (1H, d, J=15.60 Hz), 7.55 (1H, dd, J=1.95, 7.31 Hz), 7.68 (1H, d, J=15.60 Hz), 8.05 (1H, s), 8.97 (1H, d, J=7.31 Hz) EI/MS; m/s: 597 (M$^+$+1)

(F) (E)-3-[2-{(3S)-3-[(Aminocarbonyl)oxy]hexahydro-1-pyridinyl}-8-({[4-(tert-butyl)-1,3-thiazol-2-yl]amino}carbonyl)-4-oxo-4H-pyrido[1,2-a]pyrimidin-3-yl]-2-propenoic acid Reactions were performed in the same manner as in Example 15, (E) by using tert-butyl (E)-3-[2-{(3S)-3-[(aminocarbonyl)oxy]hexahydro-1-pyridinyl}-8-({[4-(tert-butyl)-1,3-thiazol-2-yl]amino}carbonyl)-4-oxo-4H-pyrido[1,2-a]pyrimidin-3-yl]-2-propenoate (131 mg, 0.219 mmol) containing by products to obtain 40 mg (3.4%) of the title compound as orange crystals.

$^1$H-NMR (CD$_3$OD) δ: 1.35 (9H, s), 1.68 (1H, m), 1.93 (3H, m), 3.49 (1H, m), 3.69 (2H, m), 3.96 (1H, dd, J=5.36, 12.92 Hz), 4.86 (1H, brd), 6.62 (1H, s), 7.11 (1H, d, J=15.60 Hz), 7.55 (1H, dd, J=1.95, 7.56 Hz), 7.68 (1H, d, J=15.60 Hz), 8.06 (1H, s), 8.96 (1H, d, J=7.56 Hz) EI/MS; m/s: 541 (M$^+$+1)

Example 20

(E)-3-{8-({[4-(tert-butyl)-1,3-thiazol-2-yl]amino}carbonyl)-2-[(3S)-3-hydroxyhexahydro-1-pyridinyl]-4-oxo-4H-pyrido[1,2-a]pyrimidin-3-yl}-2-propenoic acid Reactions were performed in the same manner as in Example 15, (E) by using tert-butyl(E)-3-{8-({[4-(tert-butyl)-1,3-thiazol-2-yl]amino}carbonyl)-2-[(3S)-3-hydroxyhexahydro-1-pyridinyl]-4-oxo-4H-pyrido[1,2-a]pyrimidin-3-yl}-2-propenoate (50 mg, 0.090 mmol) containing triphenylphosphine oxide as a mixture to obtain 17 mg (38%) of the title compound as orange crystals.

$^1$H-NMR (CD$_3$OD) δ: 1.39 (9H, s), 1.65 (2H, m), 1.92 (1H, m), 2.04 (1H, m), 3.82–4.03 (5H, m), 6.62 (1H, s), 7.07 (1H, d, J=15.43 Hz), 7.56 (1H, d, J=7.35 Hz), 7.60 (1H, d, J=15.43 Hz), 8.03 (1H, s), 8.95 (1H, d, J=7.35 Hz) ES-MS; m/s: 498 (M$^+$+1)

Example 21

(E)-3-{2-[(3R)-3-(Dimethylamino)tetrahydro-1H-1-pyrrolyl]-8-[2-(4-isopropyl-1,3-thiazol-2-yl)ethyl]-4-oxo-4H-pyrido[1,2-a]pyrimidin-3-yl}-2-propenoic acid tert-Butyl (E)-3-{8-[2-(4-isopropyl-1,3-thiazol-2-yl)ethyl]-2-[(4-methylphenyl)-sulfonyl]oxy-4-oxo-4H-pyrido[1,2-a]pyrimidin-3-yl}-2-propenate (31.4 mg, 0.053 mmol) was dissolved in dimethylformamide (1 ml), added with (3R)-(+)-3-(dimethylamino)-pyrrolidine (30.1 mg, 0.26 mmol), and stirred at room temperature for 4 hours. The solvent was evaporated, and the residue was purified by preparative TLC (chloroform:methanol=10:1, v/v) to obtain 16.8 mg of yellow oil.

The product was added with 4 N hydrochloric acid solution in dioxane (2 ml), and stirred at room temperature for 4 hours. The solvent was evaporated, and the residue was purified by preparative TLC (chloroform:methanol=10:1, v/v). The residue was lyophilized to obtain 11.3 mg (44.5% for the two steps) of the title compound as yellow powder.

$^1$H-NMR (DMSO-d$_6$) δ: 1.20 (6H, d, J=6.8 Hz), 1.68–1.80 (1H, m), 2.03–2.15 (1H, m), 2.19 (6H, s), 2.62–2.75 (1H, m), 2.92–3.01 (1H, m), 3.14 (2H, t, J=7.7 Hz), 3.49–3.58 (1H, m), 3.62–3.78 (3H, m), 6.79 (1H, d, J=15.1 Hz), 7.07 (1H, s), 7.08 (1H, dd, J=7.3, 1.7 Hz), 7.22 (1H, s), 7.68 (1H, d, J=15.1 Hz), 8.72 (1H, d, J=7.3 Hz) ESI/MS; m/z: 482 (MH$^+$) EI/MS; m/z: 481 (M$^+$) FAB/MS; m/z: 482 (MH$^+$) H-R FAB/MS: Calcd. for C$_{25}$H$_{31}$N$_5$O$_3$S: 482.2226, Found: 482.2230

In a similar manner, the following compounds were synthesized in which the substituent at the 2-position was converted.

Example 22

(E)-3-{8-[2-(4-Isopropyl-1,3-thiazol-2-yl)ethyl]-2-[3-(oxymethyl)-piperidino]-4-oxo-4H-pyrido[1,2-a]pyrimidin-3-yl}-2-propenoic acid $^1$H-NMR (DMSO-d$_6$) δ: 1.20 (6H, d, J=6.9 Hz), 1.15–1.32 (2H, m), 1.52–1.83 (5H, m), 2.85 (1H, t, J=11.4

Hz), 2.90–3.10 (2H, m), 3.16 (2H, t, J=7.3 Hz), 3.85 (1H, brd, J=11.8 Hz), 4.01 (1H, brd, J=12.0 Hz), 4.56 (1H, brs), 6.85 (1H, d, J=15.4 Hz), 7.07 (1H, s), 7.15 (1H, dd, J=7.3 Hz), 7.28 (1H, s), 7.42 (1H, d, J=15.7 Hz), 8.75 (1H, d, J=7.1 Hz) ESI/MS; m/z: 483 (MH$^+$) FAB/MS; m/z: 483 (MH$^+$), 505 (M$^+$+Na) Anal. Calcd. for $C_{25}H_{30}N_4O_4S$i.5/4H$_2$O: C, 50.45; H, 6.49; N, 11.09, Found: C, 50.35; H, 6.16; N, 10.68

Example 23

(E)-3-{2-[2-(Hydroxymethyl)morpholino]-8-[2-(4-isopropyl-1,3-thiazol-2-yl)ethyl]-4-oxo-4H-pyrido[1,2-a]pyrimidin-3-yl}-2-propenoic acid $^1$H-NMR (DMSO-d$_6$) δ: 1.20 (6H, d, J=7.1 Hz), 2.91–3.02 (2H, m), 3.12–3.22 (4H, m), 3.42–3.67 (2H, m), 3.75–3.82 (1H, m), 3.87–3.97 (2H, m), 4.77–4.82 (1H, d, J=15.5 Hz), 7.07 (1H, s), 7.20 (1H, dd, J=7.3, 2.0 Hz), 7.34 (1H, s), 7.46 (1H, d, J=15.5 Hz), 8.79 (1H, d, J=7.3 Hz), 11.88 (1H, brs) ESI/MS; m/z: 485 (MH$^+$) FAB/MS; m/z: 485 (MH$^+$) H-RFAB/MS: Calcd. for $C_{24}H_{28}N_4O_5S$: 485.1859, Found: 485.1862

Example 24

(E)-3-{2-(3-Hydroxytetrahydro-1H-1-pyrrolyl)-8-[2-(4-isopropyl-1,3-thiazol-2-yl)ethyl]-4-oxo-4H-pyrido[1,2-a]pyrimidin-3-yl}-2-propenoic acid $^1$H-NMR (DMSO-d$_6$) δ: 1.20 (6H, d, J=6.9 Hz), 1.78–2.00 (2H, m), 2.92–3.02 (1H, m), 3.10–3.18 (3H, m), 3.55–3.64 (1H, m), 3.78–2.92 (2H, m), 4.39–4.46 (1H, m), 5.00 (1H, brd, J=3.4 Hz), 6.79 (1H, d, J=15.2 Hz), 7.06 (1H, d, J=1.7 Hz), 7.07 (1H, dd, J=7.3, 0.7 Hz), 7.18 (1H, d, J=1.7 Hz), 7.68 (1H, d, J=15.2 Hz), 8.70 (1H, d, J=7.3 Hz) EI/MS; m/z: 436 (M$^+$–H$_2$O) FAB/MS; m/z: 455 (MH$^+$), 477 (M$^+$+Na) H-R FAB/MS: Calcd. for $C_{23}H_{26}N_4O_4S$: 455.1753, Found: 455.1753

Example 25

(E)-3-{8-[2-(4-Isopropyl-1,3-thiazol-2-yl)ethyl]-4-oxo-2-[(3pyridylmethyl)-amino]-4H-pyrido[1,2-a]pyrimidin-3-yl}-2-propenoic acid $^1$H-NMR (DMSO-d$_6$) δ: 1.19 (6H, d, J=6.8 Hz), 2.90–3.10 (1H, m), 3.13 (2H, t, J=7.5 Hz), 4.69 (2H, d, J=5.9 Hz), 7.06 (1H, s), 7.10 (1H, dd, J=7.3, 2.0 Hz), 7.13 (1H, d, J=14.9 Hz), 7.21 (1H, s), 7.32 (1H, dd, J=7.8, 4.9 Hz), 7.74 (1H, d, J=14.9 Hz), 7.75 (1H, brs), 8.32–8.39 (1H, m), 8.40–8.47 (1H, m), 8.58–8.62 (1H, m), 8.73 (1H, d, J=7.3 Hz), 11.82 (1H, brs) EI/MS; m/z: 431 (M$^+$–CO$_2$) FAB/MS; m/z: 476 (MH$^+$) H-R FAB/MS: Calcd. for $C_{25}H_{25}N_5O_3S$: 476.1756, Found: 476.1757

Example 26

(E)-3-{8-[2-(4-Isopropyl-1,3-thiazol-2-yl)ethyl]-2-(3-hydroxypiperidino-4-oxo-4H-pyrido[1,2-a]pyrimidin-3-yl}-2-propenoic acid $^1$H-NMR (DMSO-d$_6$) δ: 1.19 (6H, d, J=6.8 Hz), 1.30–1.48 (1H, m), 1.48–1.62 (1H, m), 1.73–1.88 (1H, m), 1.88–1.98 (1H, m), 2.92–3.01 (2H, m), 3.10–3.21 (3H, m), 3.37 (2H, t, J=7.6 Hz), 3.54–3.65 (1H, m), 3.65–3.75 (1H, m), 3.84–3.92 (1H, m), 3.85–3.63 (1H, m), 6.85 (1H, d, J=15.5 Hz), 7.07 (1H, s), 7.15 (1H, dd, J=7.4, 1.7 Hz), 7.28 (1H, brs), 7.42 (1H, d, J=15.5 Hz), 8.75 (1H, d, J=7.4 Hz) FAB/MS; m/z: 469 (MH$^+$) H-R FAB/MS: Calcd. for $C_{24}H_{28}N_4O_4S$: 469.1910, Found: 469.1927

Example 27

(E)-3-{2-[(3R)-3-Aminotetrahydro-1H-1-pyrrolyl]-8-[2-(4-isopropyl-1,3-thiazol-2-yl)ethyl]-4-oxo-4H-pyrido[1,2-a]pyrimidin-3-yl}-2-propenoic acid $^1$H-NMR (DMSO-d$_6$) δ: 1.21 (6H, d, J=6.8 Hz), 2.00–2.10 (1H, m), 2.17–2.27 (1H, m), 2.93–3.03 (1H, m), 3.16 (2H, t, J=7.2 Hz), 3.65–3.75 (2H, m), 3.84–3.98 (1H, m), 6.86 (1H, d, J=15.2 Hz), 7.09 (1H, s), 7.13 (1H, d, J=7.3 Hz), 7.25 (1H, s), 7.70 (1H, d, J=15.2 Hz), 8.13–7.28 (2H, br), 8.75 (1H, d, J=7.3 Hz) LC/MS; m/z: 454 (MH$^+$) FAB/MS; m/z: 454 (MH$^+$) H-R FAB/MS: Calcd. for $C_{23}H_{27}N_5O_3S$: 454.1913, Found: 454.1920

Example 28

(E)-3-{8-[2-(4-Isopropyl-1,3-thiazol-2-yl)ethyl]-4-oxo-2-piperazino-4H-pyrido[1,2-a]pyrimidin-3-yl}-2-propenoic acid $^1$H-NMR (DMSO-d$_6$) δ: 1.20 (6H, d, J=6.8 Hz), 2.92–3.02 (1H, m), 3.13–3.27 (6H, m), 3.21 (2H, t, J=7.2 Hz), 6.92 (1H, d, J=15.6 Hz), 7.10 (1H, s), 7.27 (1H, d, J=7.1 Hz), 7.40 (1H, s), 7.43 (1H, d, J=15.6 Hz), 8.85 (1H, d, J=7.3 Hz), 9.17 (1H, br) LC/MS; m/z: 454 (MH$^+$) EI/MS; m/z: 453 (M$^+$) FAB/MS; m/z: 454 (MH$^+$), 476 (M$^+$+Na) H-R FAB/MS: Calcd. for $C_{23}H_{27}N_5O_3S$: 454.1913, Found: 454.1912

Example 29

(E)-3-{2-(3,5-cis-Dimethylpiperazino)-8-[2-(4-isopropyl-1,3-thiazol-2-ethyl]-4-oxo-4H-pyrido[1,2-a]pyrimidin-3-yl}-2-propenoic acid $^1$H-NMR (DMSO-d$_6$) δ: 1.21 (6H, d, J=6.9 Hz), 1.26 (3H, s), 1.27 (3H, s), 2.92–3.02 (1H, m), 3.12–3.25 (4H, m), 3.90–3.98 (2H, m), 6.90 (1H, d, J=15.7 Hz), 7.09 (1H, s), 7.26 (1H, dd, J=7.3, 1.7 Hz), 7.42 (1H, d, J=15.7 Hz), 7.41 (1H, s), 8.83 (1H, d, J=7.3 Hz), 9.03 (1H, d, J=9.6 Hz), 9.50 (1H, br) EI/MS; m/z: 481 (M$^+$) H-R EI/MS: Calcd. for $C_{25}H_{31}N_5O_3S$: 481.2148, Found: 481.2150

Example 30

(E)-3-{2-[4-(Dimethylamino)piperidino]-8-[2-(4-isopropyl-1,3-thiazol-2-yl)ethyl]-4-oxo-4H-pyrido[1,2-a]pyrimidin-3-yl}-2-propenoic acid $^1$H-NMR (DMSO-d$_6$) δ: 1.21 (6H, d, J=6.8 Hz), 1.64–1.78 (2H, m), 2.10–2.19 (2H, m), 2.73 (3H, s), 2.75 (3H, s), 2.93–3.02 (1H, m), 3.03–3.14 (2H, m), 3.19 (2H, t, J=7.2 Hz), 3.38 (2H, t, J=7.2 Hz), 4.02–4.11 (1H, m), 6.91 (1H, d, J=15.5 Hz), 7.09 (1H, s), 7.22 (1H, dd, J=7.3, 1.7 Hz), 7.34 (1H, s), 7.43 (1H, d, J=15.5 Hz), 8.81 (1H, d, J=7.3 Hz), 10.19–10.27 (1H, m) FAB/MS; m/z: 496 (MH$^+$) H-R FAB/MS: Calcd. for $C_{26}H_{33}N_5O_3S$: 496.2382, Found: 496.2386

Example 31

(E)-3-{2-[2-(Aminomethyl)morpholino]-8-[2-(4-isopropyl-1,3-thiazol-2-yl)-ethyl]-4-oxo-4H-pyrido[1,2-a]pyrimidin-3-yl}-2-propenoic acid $^1$H-NMR (DMSO-d$_6$) δ: 1.20 (6H, d, J=6.9 Hz), 2.84–3.14 (5H, m), 3.20 (2H, t, J=7.1 Hz), 3.63–3.85 (3H, m), 3.85–3.92 (1H, m), 3.97–4.03 (1H, m), 6.90 (1H, d, J=15.5 Hz), 7.08 (1H, s), 7.25 (1H, d, J=7.3 Hz), 7.33 (1H, s), 7.45 (1H, d, J=15.5 Hz), 7.92 (2H, br), 8.82 (1H, d, J=7.6

Hz) FAB/MS; m/z: 484 (MH$^+$) H-R EI/MS: Calcd. for C$_{24}$H$_{29}$N$_5$O$_4$S: 484.2019, Found: 484.1999

Example 32

(E)-3-{8-[2-(4-Isopropyl-1,3-thiazol-2-yl)ethyl]-2-[(3R)-3-(methylamino)-tetrahydro-1H-1-pyrrolyl]-4-oxo-4H-pyrido[1,2-a]pyrimidin-3-yl}-2-propenoic acid $^1$H-NMR (DMSO-d$_6$) δ: 1.20 (6H, d, J=6.8 Hz), 2.11–2.31 (2H, m), 2.58–2.64 (3H, m), 2.92–3.02 (1H, m), 3.13–3.21 (2H, m), 3.35–3.42 (2H, m), 3.44–3.52 (1H, m), 3.65–3.75 (1H, m), 3.80–4.05 (3H, m), 6.86 (1H, d, J=15.2 Hz), 7.11 (1H, s), 7.14 (1H, dd, J=7.3, 1.7 Hz), 7.26 (1H, s), 7.68 (1H, d, J=15.2 Hz), 8.76 (1H, d, J=7.3 Hz), 9.05–9.30 (1H,br), FAB/MS; m/z: 468 (MH$^+$) H-R FAB/MS: Calcd. for C$_{24}$H$_{29}$N$_5$O$_3$S: 468.2069, Found: 468.2085

Example 33

((E)-3-{2-[(3S)-3-(Dimethylamino)tetrahydro-1H-1-pyrrolyl]-8-[2-(4-isopropyl-1,3-thiazol-2-yl)ethyl]-4-oxo-4H-pyrido[1,2-a]pyrimidin-3-yl}-2-propenoic acid $^1$H-NMR (DMSO-d$_6$) δ: 1.20 (6H, d, J=6.8 Hz), 1.68–1.80 (1H, m), 2.03–2.12 (1H, m), 2.18 (6H, s), 2.64–2.73 (1H, m), 2.92–3.03 (1H, m), 3.10–3.18 (2H, m), 2.49–2.58 (1H, m), 2.62–2.79 (3H, m), 6.78 (1H, d, J=15.1 Hz), 7.05–7.08 (2H, m), 7.22 (1H, s), 7.68 (1H, d, J=15.1 Hz), 8.71 (1H, d, J=7.3 Hz) FAB/MS; m/z: 482 (MH$^+$), 504 (M$^+$+Na). H-R FAB/MS: Calcd. for C$_{25}$H$_{31}$N$_5$O$_3$S: 482.2226, Found: 482.2231

Example 34

(E)-3-{8-[2-(4-Isopropyl-1,3-thiazol-2-yl)ethyl]-2-(4-methyl-1,4-diazepan-1-yl)-4-oxo-4H-pyrido[1,2-a]pyrimidin-3-yl}-2-propenoic acid $^1$H-NMR (DMSO-d$_6$) δ: 1.21 (6H, d, J=6.8 Hz), 2.08–2.10 (1H, m), 2.12–2.37 (1H, m), 2.77 (3H, s), 2.92–3.03 (1H, m), 3.12–3.20 (2H, m), 3.50–3.72 (5H, m), 3.75–3.87(2H, m), 4.08–4.17 (1H, m), 6.80 (1H, d, J=15.4 Hz), 7.10 (1H, s), 7.16 (1H, dd, J=7.3, 1.2 Hz), 7.28 (1H, s), 7.48 (1H, d, J=15.4 Hz), 8.77 (1H, d, J=7.3 Hz), 10.38 (1H, br) FAB/MS; m/z: 482 (MH$^+$), 504 (M$^+$+Na) H-R FAB/MS: Calcd. for C$_{25}$H$_{31}$N$_5$O$_3$S: 482.2226, Found: 482.2234

Example 35

(E)-3-{2-(4-Aminopiperidino)-8-[2-(4-isopropyl-1,3-thiazol-2-yl)ethyl]-4-oxo-4H-pyrido[1,2-a]pyrimidin-3-yl}-2-propenoic acid $^1$H-NMR (DMSO-d$_6$) δ: 1.21 (6H, d, J=7.1 Hz), 1.58–1.72 (2H, m), 1.97–2.08 (2H, m), 2.93–3.03 (1H, m), 3.06–3.17 (2H, m), 3.17–3.23 (2H, m), 3.23–3.55 (3H, m), 3.60–3.75 (2H, m), 6.91 (1H, d, J=15.5 Hz), 7.15 (1H, s), 7.21 (1H, d, J=7.1 Hz), 7.34 (1H, s), 7.42 (1H, d, J=15.5 Hz), 8.19 (2H, br), 8.80 (1H, d, J=7.3 Hz) FAB/MS; m/z: 468 (MH$^+$) H-R FAB/MS: Calcd. for C$_{24}$H$_{29}$N$_5$O$_3$S: 468.2069, Found: 468.2069

Example 36

(E)-3-{2-[4-(Hydroxymethyl)piperidino]-8-[2-(4-isopropyl-1,3-thiazol-2-yl)ethyl]-4-oxo-4H-pyrido[1,2-a]pyrimidin-3-yl}-2-propenoic acid $^1$H-NMR (DMSO-d$_6$) δ: 1.20 (6H, d, J=6.9 Hz), 1.12–1.35 (2H, m), 1.68–1.82 (3H, m), 2.92–3.07 (3H, m), 3.12–3.21 (2H, m), 3.95–4.03 (2H, m), 4.52–4.57 (1H, m), 6.87 (1H, d, J=15.5 Hz), 7.07 (1H, s), 7.16 (1H, d, J=6.6 Hz), 7.28 (1H, s), 7.41 (1H, d, J=15.5 Hz), 8.75 (1H, d, J=7.1 Hz) FAB/MS; m/z: 483 (MH$^+$), 505 (M$^+$+Na) H-R FAB/MS: Calcd. for C$_{25}$H$_{30}$N$_4$O$_4$S: 483.2066, Found: 483.2064

Example 37

(E)-3-{2-(3-Aminopiperidino)-8-[2-(4-isopropyl-1,3-thiazol-2-yl)ethyl]4-oxo-4H-pyrido[1,2-a]pyrimidin-3-yl}-2-propenoic acid $^1$H-NMR (DMSO-d$_6$) δ: 1.21 (6H, d, J=6.8 Hz), 1.58–1.72 (2H, m), 1.77–1.88 (1H, m), 2.00–2.14 (1H, m), 2.92–3.05 (1H, m), 3.03–3.55 (8H, m), 6.91 (1H, d, J=15.5 Hz), 7.13 (1H, s), 7.24 (1H, d, J=6.8 Hz), 7.37 (1H, s), 7.45 (1H, d, J=15.5 Hz), 8.25 (3H, br), 8.82 (1H, d, J=6.8 Hz) FAB/MS; m/z: 468 (MH$^+$) H-R FAB/MS: Calcd. for C$_{24}$H$_{29}$N$_5$O$_3$S: 468.2069, Found: 468.2073

Example 38

(E)-3-{8-[2-(4-Isopropyl-1,3-thiazol-2-yl)ethyl]-2-[3-(methylamino)-piperidino]-4-oxo-4H-pyrido[1,2-a]pyrimidin-3-yl}-2-propenoic acid $^1$H-NMR (DMSO-d$_6$) δ: 1.21 (6H, d, J=6.8 Hz), 1.55–1.78 (2H, m), 1.78–1.89 (1H, m), 2.05–2.20 (1H, m), 2.62 (3H, s), 2.92–3.03 (1H, m), 3.05-3.55 (8H, m), 3.98–4.07 (1H, m), 6.91 (1H, d, J=15.5 Hz), 7.11 (1H, s), 7.24 (1H, d, J=7.3 Hz), 7.38 (1H, s), 7.44 (1H, d, J=15.5 Hz), 8.82 (1H, d, J=7.3 Hz), 8.90 (1H, br), 9.07 (1H, br) EI/MS; m/z: 481 (M$^+$) FAB/MS; m/z: 482 (MH$^+$) H-R FAB/MS: Calcd. for C$_{25}$H$_{31}$N$_5$O$_3$S: 482.2226, Found: 482.2244

Example 39

(E)-3-{2-[3-(Dimethylamino)piperidino]-8-[2-(4-isopropyl-1,3-thiazol-2-yl)ethyl]-4-oxo-4H-pyrido[1,2-a]pyrimidin-3-yl}-2-propenoic acid $^1$H-NMR (CDCl$_3$) δ: 1.29 (6H, d, J=6.8 Hz), 1.52–1.80 (2H, m), 1.82–1.93 (1H, m), 2.14–2.23 (1H, m), 2.49 (6H, s), 2.80–2.90 (1H, m), 2.90–3.01 (2H, m), 3.01–3.12 (1H, m), 3.17–3.24 (2H, m), 3.32–3.40 (2H, m), 4.02–4.12 (1H, m), 4.27–4.36 (1H, s), 6.83 (1H, dd, J=7.3, 1.7 Hz), 7.08 (1H, d, J=15.6 Hz), 7.19 (1H, s), 7.56 (1H, J=15.6 Hz), 8.85 (1H, d, J=7.3 Hz) EI/MS; m/z: 495 (M$^+$) FAB/MS; m/z: 496 (MH$^+$) H-R FAB/MS: Calcd. for C$_{26}$H$_{33}$N$_5$O$_3$S: 496.2382, Found: 496.2383

Example 40

(E)-3-{2-[3-(Aminocarbonyl)piperidino]-8-[2-(4-isopropyl-1,3-thiazol-2-yl)-ethyl]-4-oxo-4H-pyrido[1,2-a]pyrimidin-3-yl}-2-propenoic acid $^1$H-NMR (DMSO-d$_6$) δ: 1.20 (6H, d, J=6.9 Hz), 1.55–1.67 (2H, m), 1.67–1.84 (1H, m), 1.88–2.00 (1H, m), 2.40–2.50 (1H, m), 2.90–3.12 (3H, m), 3.12–3.22 (2H, m), 3.81–3.91 (1H, m), 4.00–4.12 (1H, m), 6.86 (1H, d, J=15.5 Hz), 6.89 (1H, s), 7.07 (1H, s), 7.17 (1H, d, J=7.1 Hz), 7.29 (1H, br), 7.34 (1H, s), 7.41 (1H, d, J=15.5 Hz), 8.76 (1H, d, J=7.1 Hz), 11.89 (1H, br) FAB/MS; m/z: 496 (MH$^+$) H-R FAB/MS: Calcd. for C$_{25}$H$_{29}$N$_5$O$_4$S: 496.2019, Found: 496.2018

Example 41

(E)-3-{2-[4-(Aminocarbonyl)piperidino]-8-[2-(4-isopropyl-1,3-thiazol-2-yl-ethyl]-4-oxo-4H-pyrido[1,2-a]pyrimidin-3-yl}-2-propenoic acid ¹H-NMR (DMSO-d₆) δ: 1.20 (6H, d, J=6.9 Hz), 1.60–1.76 (2H, m), 1.76–1.85 (2H, m), 2.35–2.46 (1H, m), 2.92–3.09 (3H, m), 3.12–3.20 (2H, m), 3.92–4.00 (2H, m), 6.82 (1H, s), 6.87 (1H, d, J=15.5 Hz), 7.07 (1H, s), 7.17 (1H, dd, J=7.3, 1.7 Hz), 7.22–7.33 (2H, m), 7.42 (1H, d, J=15.5 Hz), 8.77 (1H, d, J=15.5 Hz), 11.88 (1H, br) FAB/MS; m/z: 496 (MH⁺) H-R FAB/MS: Calcd. for $C_{25}H_{29}N_5O_4S$: 496.2019, Found: 496.2015

Example 42

(E)-3-{2-[(7S)-7-Amino-5-azaspiro[2,4]hept-5-yl]-8-[2-(4-isopropyl-1,3-thiazol-2-yl)ethyl]-4-oxo-4H-pyrido[1,2-a]pyrimidin-3-yl}-2-propenoic acid ¹H-NMR (DMSO-d₆) δ: 1.70–1.90 (3H, m), 1.00–1.09 (1H, m), 1.20 (6H, d, J=6.9 Hz), 2.91–3.02 (1H, m), 3.13–3.22 (2H, m), 3.22–3.28 (1H, m), 3.62–3.75 (1H, m), 3.77–3.85 (1H, m), 4.19–4.32 (2H, m), 6.87 (1H, d, J=15.2 Hz), 7.08 (1H, s), 7.14 (1H, d, J=6.9 2.2 Hz), 7.25 (1H, s), 7.68 (1H, d, J=15.2 Hz), 8.16 (2H, br), 8.75 (1H, d, J=6.9 Hz) FAB/MS; m/z: 480 (MH⁺) H-R FAB/MS: Calcd. for $C_{25}H_{29}N_5O_3S$: 480.2069, Found: 480.2062

Example 43

(E)-3-{2-[(3S,4S)-3-Amino-4-(fluoromethyl)tetrahydro-1H-1-pyrrolyl]-8-[2-(4-isopropyl-1,3-thiazol-2-yl)ethyl]-4-oxo-4H-pyrido[1,2-a]pyrimidin-3-yl}-2-propenoic acid ¹H-NMR (DMSO-d₆) δ: 1.21 (6H, d, J=6.9 Hz), 2.83–3.07 (2H, m), 3.12–3.20 (2H, m), 3.34–3.42 (2H, m), 3.65–3.83 (2H, m), 3.87–4.10 (3H, m), 4.62–4.70 (1H, m), 4.72–4.81 (1H, m), 6.88 (1H, d, J=15.3 Hz), 7.09 (1H, s), 7.14 (1H, dd, J=7.3, 1.7 Hz), 7.27 (1H, s), 7.68 (1H, d, J=15.3 Hz), 8.29 (2H, br), 8.75 (1H, d, J=7.3 Hz) FAB/MS; m/z: 486 (MH⁺) H-R FAB/MS: Calcd. for $C_{24}H_{28}FN_5O_3S$: 486.1975, Found: 486.1974

Example 44

(E)-3-{2-[(3R)-3-Piperidino]-8-[2-(4-isopropyl-1,3-thiazol-2-oxo-4H-pyrido[1,2-a]pyrimidin-3-yl}-2-propenoic acid ¹H-NMR (DMSO-d₆) δ: 1.19 (6H, d, J=6.9 Hz), 1.30–1.60 (2H, m), 1.73–1.83 (1H, m), 1.83–1.96 (1H, m), 2.90–3.00 (2H, m), 3.08–3.21 (3H, m), 3.52–3.61 (1H, m), 3.63–3.72 (1H, m), 3.82–3.91 (1H, m), 4.85–4.93 (1H, m), 6.84 (1H, d, J=15.4 Hz), 7.07 (1H, s), 7.14 (1H, d, J=6.9 Hz), 7.27 (1H, s), 7.41 (1H, d, J=15.4 Hz), 8.74 (1H, d, J=7.8 Hz), 11.85 (1H, br). FAB/MS; m/z: 469 (MH⁺) H-R FAB/MS: Calcd. for $C_{24}H_{28}N_4O_4S$: 469.1910, Found: 469.1901

Example 45

(E)-3-{2-[(3S)-3-Hydroxypiperidino]-8-[2-(4-isopropyl-1,3-thiazol-2-yl)-ethyl]-4-oxo-4H-pyrido[1,2-a]pyrimidin-3-yl}-2-propenoic acid ¹H-NMR (DMSO-d₆) δ: 1.20 (6H, d, J=6.9 Hz), 1.31–1.61 (2H, m), 1.74–1.85 (1H, m), 1.85–1.98 (1H, m), 2.90–3.00 (2H, m), 3.08–3.21 (3H, m), 3.53–3.63 (1H, m), 3.63–3.75 (1H, m), 3.83–3.92 (1H, m), 4.86–4.95 (1H, m), 6.85 (1H, d, J=15.7 Hz), 7.07 (1H, s), 7.15 (1H, d, J=6.6 Hz), 7.28 (1H, s), 7.42 (1H, d, J=15.7 Hz), 8.75 (1H, d, J=7.3 Hz), 11.88 (1H, br) FAB/MS; m/z: 469 (MH⁺) H-R FAB/MS: Calcd. for $C_{24}H_{28}N_4O_4S$: 469.1910, Found: 469.1921

Example 46

(E)-3-{2-(3-Amino-1-azetanyl)-8-[2-(4-isopropyl-1,3-thiazol-2-yl)ethyl]-4-oxo-4H-pyrido[1,2-a]pyrimidin-3-yl}-2-propenoic acid ¹H-NMR (DMSO-d₆) δ: 1.21 (6H, d, J=6.8 Hz), 2.93–3.03 (1H, m), 3.13–3.23 (2H, m), 3.43–3.53 (2H, m), 3.65–3.85 (2H, m), 4.25–4.35 (2H, m), 4.50–4.58 (1H, m), 6.92 (1H, d, J=15.2 Hz), 7.10 (1H, s), 7.16 (1H, d, J=7.6 Hz), 7.28 (1H, s), 7.50 (1H, d, J=15.2 Hz), 8.49 (1H, br), 8.77 (1H, d, J=7.1 Hz) FAB/MS; m/z: 440 (MH⁺) H-R FAB/MS: Calcd. for $C_{22}H_{25}N_5O_3S$: 440.1756, Found: 440.1768

Example 47

(E)-3-{2-(4-Fluoropiperidino)-8-[2-(4-isopropyl-1,3-thiazol-2-yl)ethyl]-4-oxo-4H-pyrido[1,2-a]pyrimidin-3-yl}-2-propenoic acid ¹H-NMR (DMSO-d₆) δ: 1.20 (6H, d, J=6.8 Hz), 1.75–1.88 (2H, m), 1.93–2.10 (2H, m), 2.91–3.01 (1H, m), 3.14–3.21 (2H, m), 3.32–3.40 (2H, m), 3.40–3.52 (2H, m), 3.52–3.68 (2H, m), 4.83–4.92 (0.5H, m), 4.95–5.04 (0.5H, m), 6.88 (1H, d, J=15.6 Hz), 7.07 (1H, s), 7.19 (1H, dd, J=7.1, 1.5 Hz), 7.33 (1H, s), 7.44 (1H, d, J=15.6 Hz), 8.79 (1H, d, J=7.1 Hz), 11.91 (1H, br) FAB/MS; m/z: 470 (MH⁺) H-R FAB/MS: Calcd. for $C_{24}H_{27}FN_4O_3S$: 470.1788, Found: 470.1779

Example 48

(E)-3-{8-[2-(4-Isopropyl-1,3-thiazol-2-yl)ethyl]-4-oxo-2-(4-oxopiperidino)-4H-pyrido[1,2-a]pyrimidin-3-yl]-2-propenoic acid ¹H-NMR (DMSO-d₆) δ: 1.20 (6H, d, J=6.8 Hz), 2.91–3.01 (1H, m), 3.15–3.22 (2H, m), 3.30–3.41 (6H, m), 3.79–3.87 (4H, m), 6.91 (1H, d, J=15.4 Hz), 7.07 (1H, s), 7.22 (1H, dd, J=7.3, 1.8 Hz), 7.37 (1H, s), 7.52 (1H, d, J=15.4 Hz), 8.81 (1H, d, J=7.3 Hz), 11.94 (1H, br) FAB/MS; m/z: 467 (MH⁺) H-R FAB/MS: Calcd. for $C_{24}H_{26}N_4O_4S$: 467.1753, Found: 467.1765

Example 49

(E)-3-(8-[2-(4-Isopropyl-1,3-thiazol-2-yl)ethyl]-4-oxo-2-{4-[(2R,3R,4S,5S,6R)-3,4,5-trihydroxy-6-(hydroxymethyl)tetrahydro-2H-2-pyranyl]-piperazino}-4H-pyrido[1,2-a]pyrimidin-3-yl)-2-propenoic acid ¹H-NMR (CD₃OD) δ: 1.35 (6H, d, J=6.8 Hz), 3.12–3.23 (2H, m), 3.25–3.43 (4H, m), 3.53–3.90 (18H, m), 7.10 (1H, d, J=15.7 Hz), 7.18 (1H, s), 7.35 (1H, dd, J=7.12, 2.4 Hz), 7.42 (1H, s), 7.57 (1H, d, J=15.7 Hz), 8.94 (1H, d, J=7.1 Hz) LC-MS; m/z: 616 (MH⁺)

Example 50

(E)-3-[8-[2-(4-Isopropyl-1,3-thiazol-2-yl)ethyl]-4-oxo-2-(4-{[(2R,3R,4S,5R,6R)-3,4,5-trihydroxy-6-(hydroxymethyl)tetrahydro-2H-2-pyranyl]oxy}-piperidino)-4H-pyrido[1,2-a]pyrimidin-3-yl]-2-propenoic acid ¹H-NMR (CD₃OD) δ: 1.26 (6H, d, J=6.8 Hz), 1.70–1.92 (2H, m), 1.92–2.10 (2H, m), 2.98–3.10 (1H, m), 3.17–3.25 (2H, m), 3.36–3.58 (7H, m), 3.68–3.78 (2H, m), 3.82–3.98 (3H, m), 4.00–4.12 (1H, m), 4.39 (1H, d, J=7.3 Hz), 6.95 (1H, d, J=15.6 Hz), 6.96 (1H, s), 7.04 (1H, dd, J=7.3, 1.7 Hz), 7.21 (1H, s), 7.60 (1H, d, J=15.6 Hz), 8.79 (1H, d, J=7.3 Hz) FAB/MS; m/z: 631 (MH⁺) H-R FAB/MS: Calcd. for $C_{30}H_{38}N_4O_9S$: 631.2438, Found: 631.2485

Example 51

(E)-3-{2-[cis-3,4-Dihydroxyhexahydro-1-pyridinyl]-8-[2-(4-isopropyl-1,3-thiazol-2-yl)ethyl]-4-oxo-4H-pyrido[1,2-a]pyrimidin-3-yl}-2-propenoic acid ¹H-NMR (DMSO-d₆) δ: 1.19 (6H, d, J=7.1 Hz), 1.60–1.72 (1H, m), 1.77–1.88 (1H, m), 2.90–3.01 (1H, m), 3.12–3.20 (2H, m), 3.35–3.42 (2H, m), 3.45–3.66 (3H, m), 3.72–3.80 (1H, m), 4.57–4.60 (1H, m), 4.60–4.70 (1H, m), 6.83 (1H, d, J=15.5 Hz), 7.06 (1H, s), 7.13 (1H, d, J=7.6 Hz), 7.26 (1H, s), 7.42 (1H, d, J=15.5 Hz), 8.73 (1H, d, J=7.1 Hz) FAB/MS; m/z: 485 (MH$^+$) H-R FAB/MS: Calcd. for $C_{24}H_{28}N_4O_5S$: 485.1859, Found: 485.1882

Example 52

3-{8-[2-(4-Isopropyl-1,3-thiazol-2-yl)ethyl]-2-morpholino-4-oxo-4H-pyrido-[1,2-a]pyrimidin-3-yl}-2-propanoic acid (A) tert-Butyl 3-{8-[2-(4-isopropyl-1,3-thiazol-2-yl)ethyl]-4-oxo-4H-pyrido[1,2-a]-pyrimidin-3-yl}-2-propanoate ]tert-Butyl (E)-3-{8-[2-(4-isoprolyl-1,3-thiazol-2-yl)ethyl]-2-morpholino-4-oxo-4H-pyrido[1,2-a]pyrimidin-3-yl}-2-propenate (29.8 mg, 0.058 mmol) was dissolved in methanol (20 ml), added with 10% palladium/carbon (6.0 mg) and stirred at room temperature under hydrogen flow for 4 hours and 30 minutes. After the catalyst was removed by filtration, the solvent was evaporated and the residue was purified by preparative TLC (chloroform:methanol=30:1, v/v) to obtain the title compound (8.0 mg, 26.7%) as a pale yellow oily substance.

$^1$H-NMR (CDCl$_3$) δ: 1.29 (6H, d, J=6.8 Hz), 1.43 (9H, s), 2.62–2.70 (2H, m), 2.87–2.93 (2H, m), 3.02–3.12 (1H, m), 3.16–3.23 (2H, m), 3.32–3.47 (6H, m), 3.80–3.80–3.86 (4H, m), 6.73 (1H, s), 6.82 (1H, dd, J=7.3, 1.7 Hz), 7.22 (1H, s), 8.81 (1H, d, J=7.3 Hz)

(B) 3-{8-[2-(4-Isopropyl-1,3-thiazol-2-yl)ethyl]-2-morpholino-4-oxo-4H-pyrido[1,2-a]-pyrimidin-3-yl}-2-propanoic acid The tert-Butyl 3-{8-[2-(4-isopropyl-1,3-thiazol-2-yl)ethyl]-4-oxo-4H-pyrido-[1,2-a]pyrimidin-3-yl}-2-propanoate (8.0 mg, 0.016 mmol) obtained in (A) was added with 4 N hydrochloric acid in dioxane (1 ml), stirred at room temperature for 3 hours, further added with 4 N hydrochloric acid in dioxane (1 ml), and stirred for further 4 hours. The solvent was evaporated, and the residue was purified by preparative TLC (chloroform:methanol=10:1, v/v) and lyophilized from dioxane to obtain the title compound (4.3 mg, 60.4%) as pale yellow powder.

$^1$H-NMR (CDCl$_3$) δ: 1.29 (6H, d, J=6.9 Hz), 2.76 (2H, t, J=6.9 Hz), 2.92 (2H, t, J=6.9 Hz), 3.02–3.12 (1H, m), 3.18–3.25 (2H, m), 3.3.4–3.56 (6H, m), 3.78–3.86 (4H, m), 6.73 (1H, s), 6.88 (1H, dd, J=7.3, 1.7 Hz), 7.26 (1H, s), 8.82 (1H, d, J=7.1 Hz) LC/MS; m/z: 457 (MH$^+$), 455 (M$^+$–1) EI/MS; m/z: 456 (MH$^+$) H-R EI/MS: Calcd. for $C_{23}H_{28}N_4O_4S$: 456.1831, Found: 456.1848

Example 53

(E)-3-{2-(4,4-Dimethylhexahydropyrazin-4-ium-1-yl)-8-[2-(4-isopropyl-1,3-thiazol-2-yl)ethyl]-4-oxo-4H-pyrido[1,2-a]pyrimidin-3-yl}-2-propenoic acid (E)-3-{8-[2-(4-Isopropyl-1,3-thiazol-2-yl)ethyl]-2-(4-methyl)piperazino-4-oxo-4H-pyrido[1,2-a]pyrimidin-3-yl}-2-propenoic acid (19.9 mg, 0.043 mmol) was dissolved in dimethylformamide (1 ml), added dropwise with methyl iodide (0.1 ml, 1.61 mmol), sealed with a stopper and left in a refrigerator for 14 hours. The solvent and excessive reagents were evaporated, and the residue was lyophilized from dioxane/water to obtain the title compound (29.7 mg, quantitative).

$^1$H-NMR (DMSO-d$_6$) δ: 1.21 (6H, d, J=6.9 Hz), 2.55 (6H, s), 2.91–3.02 (1H, m), 3.15–3.26 (2H, m), 3.45–3.55 (4H, m), 3.82–3.92 (4H, m), 6.93 (1H, d, J=15.5 Hz), 7.09 (1H, s), 7.29 (1H, d, J=7.1 Hz), 7.41 (1H, s), 7.45 (1H, d, J=15.5 Hz), 8.14 (1H, br), 8.85 (1H, d, J=7.3 Hz) FAB/MS; m/z: 482 (M$^+$) H-R FAB/MS: Calcd. for $C_{25}H_{32}N_5O_3S$: 482.2226, Found: 482.2216

Example 54

(E)-3-{12-{(3R)-3-[(Aminocarbonyl)oxy]piperidino}-8-[2-(4-isopropyl-1,3-thiazol-2-yl)ethyl]-4-oxo-4H-pyrido[1,2-a]pyrimidin-3-yl}-2-propenoic acid (A) tert-Butyl (E)-3-{2-[(3R)-3-hydroxyhexahydro-1-pyridinyl]-8-[2-(4-isopropyl-1,3-thiazol-2-yl)ethyl]-4-oxo-4 H-pyrido[1,2-a]pyrimidin-3-yl}-2-propenate tert-Butyl (E)-3-{8-[2-(4-isopropyl-1,3-thiazol-2-yl)ethyl]-2-[(4-methylphenyl)-sulfonyl]oxy-4-oxo-4H-pyrido[1,2-a]pyrimidin-3-yl}-2-propenate (111.4 mg, 0.19 mmol) was dissolved in dimethylformamide (3 ml), added dropwise with triethylamine (130.4 μl, 0.93 mmol), added with R-(+)-3-hydroxypiperidine hydrochloride (128.7 mg, 0.93 mmol), and stirred at room temperature for 17 hours. The solvent was evaporated, and then the residue was purified by preparative TLC (chloroform:methanol=30:1, v/v) to obtain the title compound (91.4 mg, 93.2%) as yellow oil.

$^1$H-NMR (CDCl$_3$) δ: 1.29 (6H, d, J=6.8 Hz), 1.51 (9H, s), 1.72-1.95 (4H, m), 3.01–3.11 (1H, m), 3.16–3.23 (2H, m), 3.32–3.40 (2H, m), 3.49–3.68 (3H, m), 3.88–3.97 (1H, m), 3.97–4.07 (1H, m), 6.74 (1H, s), 6.86 (1H, d, J=7.3 Hz), 7.03 (1H, d, J=15.6 Hz), 7.19 (1H, s), 7.49 (1H, d, J=15.6 Hz), 8.85 (1H, d, J=7.3 Hz)

(B) tert-Butyl (E)-3-{2-(3R)-3-[(aminocarbonyl)oxy]hexahydro-1-pyridinyl-8-[2-(4-isopropyl-1,3-thiazol-2-yl)ethyl]-4-oxo-4 H-pyrido[1,2-a]pyrimidin-3-yl}-2-propenate The tert-Butyl (E)-3-{2-[(3R)-3-hydroxyhexahydro-1-pyridinyl]-8-[2-(4-isopropyl-1,3-thiazol-2-yl)ethyl]-4-oxo-4 H-pyrido[1,2-a]pyrimidin-3-yl}-2-propenate (38.9 mg, 0.074 mmol) obtained in (A) was dissolved in ethyl acetate (3 ml), added with trichloroacetyl isocyanate (9.7 μl, 0.082 mmol) under ice cooling, and stirred at the same temperature for 1 hour. The reaction solution was further added with trichloroacetyl isocyanate (9.7 μl, 0.082 mmol), stirred at the same temperature for further 1 hour, and added with chloroform/methanol (10:1, v/v, 6 ml), and the solvent was evaporated. The residue was dissolved in methanol (1.5 ml), added with water (0.2 ml) and sodium formate (9.6 mg, 0.14 mmol) stirred at room temperature for 2 hours and 30 minutes. The mixture was further added with sodium formate (9.6 mg, 0.14 mmol), and stirred at room temperature for further 20 hours. The solvent was evaporated, and the residue was purified by preparative TLC (chloroform:methanol=30:1, v/v) to obtain the title compound (74.9 mg, quantitative) as yellow solid.

$^1$H-NMR (CDCl$_3$) δ: 1.29 (6H, d, J=6.9 Hz), 1.50 (9H, s), 1.80–2.10 (4H, m), 3.02–3.12 (1H, m), 3.15–3.23 (2H, m), 3.23–3.40 (3H, m), 3.45–3.63 (1H, m), 3.65–3.77 (2H, m), 4.75–4.85 (1H, m), 6.73 (1H, s), 6.85 (1H, dd, J=7.3, 1.7 Hz), 7.08 (1H, d, J=15.7 Hz), 7.22 (1H, s), 7.73 (1H, d, J=15.7 Hz), 8.86 (1H, d, J=7.1 Hz)

(C) (E)-3-{2-{(3R)-3-[(Aminocarbonyl)oxy]hexahydro-1-pyridinyl}-8-[2-(4-isopropyl-1,3-thiazol-2-yl)ethyl]-4-oxo-4H-pyrido[1,2-a]pyrimidin-3-yl}-2-propenic acid The tert-Butyl (E)-3-{2-(3R)-3-[(aminocarbonyl)oxy]hexahydro-1-pyridinyl-8-[2-(4-isopropyl-1,3-thiazol-2-yl)

ethyl]-4-oxo-4H-pyrido[1,2-a]pyrimidin-3-yl}-2-propenate (74.9 mg, 0.074 mmol) obtained in (B) was dissolved in 4 N hydrochloric acid solution in dioxane and stirred at room temperature for 5 hours. After the solvent was evaporated, the residue was purified by preparative TLC (chloroform:methanol=10:1, v/v) and lyophilized from dioxane to obtain the title compound (17.6 mg, 67.5%) as yellow powder.

$^1$H-NMR (DMSO-d$_6$) δ: 1.20 (6H, d, J=6.9 Hz), 1.55–1.70 (2H, m), 1.80–1.90 (1H, m), 1.90–2.02 (1H, m), 2.90–3.01 (1H, m), 3.13–3.20 (2H, m), 3.30–3.42 (3H, m), 3.45–3.60 (2H, m), 3.80–3.88 (1H, m), 4.54–4.62 (1H, m), 6.49 (2H, br), 6.87 (1H, d, J=15.4 Hz), 7.07 (1H, s,), 7.17 (1H, dd, J=7.3, 1.7 Hz), 7.32 (1H, s), 7.44 (1H, d, J=15.4 Hz), 8.76 (1H, d, J=7.3 Hz), 11.89 (1H, br) FAB/MS; m/z: 512 (MH$^+$) H-R FAB/MS: Calcd. for C$_{25}$H$_{29}$N$_5$O$_5$S: 512.1968, Found: 512.1970

Example 55

(E)-3-{2-{(3S)-3-[(Aminocarbonyl)oxy]piperidino}-8-[2-(4-isopropyl-1,3-thiazol-2-yl)ethyl]-4-oxo-4H-pyrido[1,2-a]pyrimidin-3-yl}-2-propenoic acid The title compound was synthesized in the same manner as in Example 54.

$^1$H-NMR (DMSO-d$_6$) δ: 1.20 (6H, d, J=6.9 Hz), 1.53–1.70 (2H, m), 1.80–1.90 (1H, m), 1.90–2.02 (1H, m), 2.91–3.01 (1H, m), 3.13–3.20 (2H, m), 3.30–3.42 (3H, m), 3.45–3.62 (2H, m), 3.80–3.88 (1H, m), 4.53–4.63 (1H, m), 6.49 (2H, br), 6.87 (1H, d, J=15.4 Hz), 7.07 (1H, s,), 7.17 (1H, dd, J=7.3, 1.7 Hz), 7.32 (1H, s), 7.44 (1H, d, J=15.4 Hz), 8.76 (1H, d, J=7.3 Hz), 11.89 (1H, br) FAB/MS; m/z: 512 (MH$^+$) H-R FAB/MS: Calcd. for C$_{25}$H$_{29}$N$_5$O$_5$S: 512.1968, Found: 512.1968

Example 56

(E)-3-{2-{4-[(Aminocarbonyl)oxy]hexahydro-1-pyridinyl}-8-[2-(4-isopropyl-1,3-thiazol-2-yl)ethyl]-4-oxo-4H-pyrido[1,2-a]pyrimidin-3-yl}-2-propenoic acid The title compound was synthesized in the same manner as in Example 54.

$^1$H-NMR (DMSO-d$_6$) δ: 1.20 (6H, d, J=6.9 Hz), 1.57–1.70 (2H, m), 1.91–2.01 (2H, m), 2.91–3.01 (1H, m), 3.13–3.20 (2H, m), 3.27–3.40 (4H, m), 3.72–3.82 (2H, m), 4.69–4.78 (1H, m), 6.50 (2H, br), 6.86 (1H, d, J=15.4 Hz), 7.07 (1H, s), 7.18 (1H, dd, J=7.3, 2.0 Hz), 7.32 (1H, s), 7.44 (1H, d, J=15.4 Hz), 8.77 (1H.d, J=7.3 Hz), 11.90 (1H, br) FAB/MS; m/z: 512 (MH$^+$) H-R FAB/MS: Calcd. for C$_{25}$H$_{29}$N$_5$O$_5$S: 512.1968, Found: 512.1964

Example 57

8-[2-(4-Isopropyl-1,3-thiazol-2-yl)ethyl]-2-morpholino-3-[2-(2 H-1,2,3,4-tetrazol-5-yl)acetyl]-4H-pyrido[1,2-a]pyrimidin-4-one (A) Ethyl 2-[2-(4-methoxybenzyl)-2 H-1,2,3,4-tetrazol-5-yl]acetate Ethyl 2-(1H-1,2,3,4-tetrazol-5-yl)acetate (5.0 g, 32.0 mmol) was dissolved in dimethylformamide (20 ml), added with potassium carbonate (5.75 g, 41.6 mmol). The mixture was further added dropwise with 4-methoxybenzyl chloride (5.21 ml, 38.4 mmol) under ice cooling and stirred at the same temperature for 1 hour and 30 minutes and at room temperature for 15 hours. The solvent was evaporated, and the residue was diluted with toluene, washed with water and saturated brine, and dried over anhydrous sodium sulfate. Then, the solvent was evaporated and the residue was purified by silica gel column chromatography (hexane:ethyl acetate=2:1, v/v) to obtain the title compound (3.78 g, 42.7%) as colorless oil.

$^1$H-NMR (CDCl$_3$) δ: 1.25 (3H, t, J=7.1 Hz), 3.79 (3H, s), 3.94 (2H, s), 4.19 (2H, q, J=7.1 Hz), 5.68 (2H, s), 6.82–6.92 (2H, m), 7.28–7.38 (2H, m)

(B) 2-[2-(4-Methoxybenzyl)-2H-1,2,3,4-tetrazol-5-yl]acetic acid

The ethyl 2-[2-(4-methoxybenzyl)-2H-1,2,3,4-tetrazol-5-yl]acetate (2.15 g, 7.78 mmol) obtained in (A) was dissolved in tetrahydrofuran/methanol (3:1, v/v, 60 ml), added dropwise with a solution of lithium hydroxide (359.2 mg, 8.56 mmol) in water (15 ml) under ice cooling and then stirred at room temperature for 2 hours. The solvent was evaporated, and the residue was added with 1 N aqueous hydrochloric acid to obtain pH of about 1. The solution was extracted with ethyl acetate, and the organic layer was washed with saturated brine and dried over anhydrous sodium sulfate. Then, the solvent was evaporated to obtain the title compound (1.91 g, 98.8%).

$^1$H-NMR (CDCl$_3$) δ: 3.79 (3H, s), 3.99 (2H, s), 5.68 (2H, s), 6.85–6.95 (2H, m), 7.29–7.39 (2H, m)

(C) 2-[2-(4-Methoxybenzyl)-2 H-1,2,3,4-tetrazol-5-yl]ethanoyl chloride

The 2-[2-(4-methoxybenzyl)-2H-1,2,3,4-tetrazol-5-yl] acetic acid (262.0 mg, 1.05 mmol) obtained in (B) was added dropwise with thionyl chloride (615.9 μl, 8.44 mmol) under ice cooling and stirred at room temperature for 30 minutes. Excessive regents were evaporated to obtain the title compound (0.27 g, quantitative) as pale yellow oil.

(D) 8-[2-(4-Isopropyl-1,3-thiazol-2-yl)ethyl]-3-{2-[2-(4-methoxybenzyl)-2H-1,2,3,4-tetrazol-5-yl] acetyl}-2-morpholino-4 H-pyrido[1,2-a]pyrimidin-4-one The 2-[2-(4-methoxybenzyl)-2H-1,2,3,4-tetrazol-5-yl] ethanoyl chloride (0.27 g, 1.05 mmol) obtained in (C) was dissolved in methylene chloride (3 ml), added dropwise with pyridine (170.2 μl, 2.10 mmol) under ice cooling, and added dropwise with a solution of 8-[2-(4-isopropyl-1,3-thiazol-2-yl)ethyl]-2-morpholino-4 H-pyrido-[1,2-a]pyrimidin-4-one (80.9 mg, 0.21 mmol) in methylene chloride (3 ml). The reaction solution was stirred at room temperature for 23 hours, then further added with a solution of 2-[2-(4-methoxybenzyl)-2H-1,2,3,4-tetrazol-5-yl]ethanoyl chloride (0.27 g, 1.05 mmol) in methylene chloride (2 ml) and pyridine (170.2 μl, 2.10 mmol) under ice cooling. Further, the reaction solution was added with the same amounts of the acid chloride and pyridine twice every 24 hours, and stirred at room temperature. The solvent was evaporated, and the residue was added with saturated aqueous sodium hydrogencarbonate and extracted with ethyl acetate. The organic layer was washed with saturated brine and dried over anhydrous sodium sulfate. The solvent was evaporated and the residue was purified by preparative TLC (hexane:ethyl acetate=1:1, v/v and chloroform:methanol= 30:1, v/v) to obtain the title compound (10.1 mg, 7.8%) as yellow oil.

$^1$H-NMR (CDCl$_3$) δ: 1.29 (6H, d, J=6.8 Hz), 3.02–3.12 (1H, m), 3.12–3.20 (2H, m), 3.31–3.38 (2H, m), 3.60–3.75

(8H, m), 3.79 (3H, s), 4.68 (2H, s), 5.66 (2H, s), 6.72 (1H, dd, J=7.3, 1.5 Hz), 6.73 (1H, s), 6.86 (2H, d, J=8.6 Hz), 7.03 (1H, s), 7.29 (2H, d, J=8.6 Hz), 8.71 (1H, d, J=7.3 Hz)

(E) 8-[2-(4-Isopropyl-1,3-thiazol-2-yl)ethyl]-2-morpholino-3-[2-(2H-1,2,3,4-tetrazol-5-yl)acetyl]-4 H-pyrido[1,2-a]pyrimidin-4-one The 8-[2-(4-isopropyl-1,3-thiazol-2-yl)ethyl]-3-{2-[2-(4-methoxybenzyl)-2H -1,2,3,4-tetrazol-5-yl]acetyl}-2-morpholino-4 H-pyrido[1,2-a]pyrimidin-4-one (8.9 mg, 0.014 mmol) obtained in (D) was dissolved in trifluoroacetic acid (5 ml)and stirred at room temperature for 18 hours. The solvent was evaporated, and the residue was purified by preparative TLC (chloroform:methanol=10:1, v/v) and lyophilized from dioxane to obtain the title compound (4.8 mg, 67.0%) as pale yellow powder.

$^1$H-NMR (CDCl$_3$) δ: 1.29 (6H, d, J=6.9 Hz), 3.01–3.12 (1H, m), 3.17–3.23 (2H, m), 3.32–3.40 (2H, m), 3.55–3.63 (4H, m), 3.67–3.76 (4H, m), 4.75 (2H, s), 6.74 (1H, s), 6.80 (1H, d, J=7.3 Hz), 7.07 (1H, s), 8.73 (1H, d, J=7.3 Hz) FAB/MS; m/z: 495 (MH$^+$) H-R FAB/MS: Calcd. for C$_{23}$H$_{26}$N$_5$O$_3$S: 495.1927, Found: 495.1955

Example 58

(E)-3-(8-({[4-(tert-Butyl)-1,3-thiazol-2-yl]amino}carbonyl)-2-{3-[(dimethylamino)carbonyl]piperidino}-4-oxo-4 H-pyrido[1,2-a]pyrimidin-3-yl)-2-propenoic acid (A) N$^8$-[4-(tert-Butyl)-1,3-thiazol-2-yl]-2-{3-[(dimethylamino)carbonyl]piperidino}-4-oxo-4 H-pyrido[1,2-a]pyrimidine-8-carboxamide N$^8$-[4-(tert-butyl)-1,3-thiazol-2-yl]-2,4-dioxo-3,4-dihydro-2 H-pyrido[1,2-a]-pyrimidine-8-carboxamide (301.9 mg, 0.88 mmol) was suspended in dimethylformamide (6 ml) and acetonitrile (12 ml), added dropwise with diisopropylethylamine (1.83 ml, 10.5 mmol) and diphenyl chlorophosphate (545.1 µl, 2.63 mmol) at −10° C. under an argon flow, and stirred at the same temperature for 5 minutes and at room temperature for 15 minutes. The reaction solution was cooled to −10° C. again, added dropwise with a solution of 3-[(dimethylamino)carbonyl]piperidine trifluoroacetic acid salt (1.18 g, 4.38 mmol) in dimethylformamide (5 ml), and stirred at room temperature for 1 hour and at about 80° C. for 2 hours. The reaction solution was heated to about 100° C., heated for 30 minutes with stirring, then added with diisopropylethylamine (1.83 ml, 10.5 mmol), and further heated at 100° C. for 3 hours and 30 minutes with stirring. After cooling, the solution was added with saturated aqueous sodium hydrogencarbonate and extracted with chloroform. The organic layer was washed with saturated brine and dried over anhydrous sodium sulfate and the solvent was evaporated. The residue was purified by silica gel column chromatography (chloroform→chloroform:methanol=50:1→20:1, v/v) and preparative TLC (chloroform:methanol=20:1, v/v) to obtain the title compound (85.9 mg, 20.3%) as yellow orange oil.

$^1$H-NMR (CDCl$_3$) δ: 1.33 (9H, s), 1.42–1.62 (1H, m), 1.70–2.08 (3H, m), 2.57–3.20 (3H, m), 2.99 (3H, s), 3.12 (3H, s), 4.03–4.90 (2H, m), 5.69 (1H, s), 6.60 (1H, s) 7.36–7.22 (1H, m), 7.89 (1H, s), 8.97 (1H, d, J=7.3 Hz) LC-MS; m/z: 483 (MH$^+$)

(B) N$^8$-[4-(tert-Butyl)-1,3-thiazol-2-yl]-2-{3-[(dimethylamino)carbonyl]piperidino}-3-formyl-4-oxo-4 H-pyrido[1,2-a]pyrimidine-8-carboxamide Dimethylformamide (2 ml) was added dropwise with phosphorus oxychloride (24.9 µl, 0.27 mmol) under ice cooling, and stirred at room temperature for 30 minutes. The reaction solution was cooled with ice again, added dropwise with a solution of the N$^8$-[4-(tert-butyl)-1,3-thiazol-2-yl]-2-{3-[(dimethylamino)carbonyl]-piperidino}-4-oxo-4H-pyrido[1,2-a]pyrimidine-8-carboxamide (85.9 mg, 0.18 mmol) obtained in (A) in dimethylformamide (2 ml) and stirred at the same temperature for 2 hours. The reaction solution was added with saturated aqueous sodium hydrogencarbonate and extracted with chloroform. The organic layer was washed with saturated brine and dried over anhydrous sodium sulfate, and the solvent was evaporated to obtain the title compound (84.2 mg, quantitative) as yellow oil.

$^1$H-NMR (CDCl$_3$) δ: 1.34 (9H, s), 1.57–2.10 (4H, m), 2.89 (3H, s), 2.97 (3H, s), 3.00–3.28 (3H, m), 4.10–4.45 (2H, m), 6.59 (1H, s), 7.35–7.45 (1H, m), 7.82 (1H, s), 8.95 (1H, s), 8.86 (1H, d, J=7.3 Hz), 10.12 (1H, s) ESI/MS; m/z: 511 (MH$^+$)

(C) Methyl (E)-3-(8-({[4-(tert-Butyl)-1,3-thiazol-2-yl]amino}carbonyl)-2-{3-[(dimethyl-amino)carbonyl]piperidino}-4-oxo-4 H-pyrido[1,2-a]pyrimidin-3-yl)-2-propenoate The N$^8$-[4-(tert-butyl)-1,3-thiazol-2-yl]-2-{3-[(dimethylamino)carbonyl]-piperidino}-3-formyl-4-oxo-4 H-pyrido[1,2-a]pyrimidine-8-carboxamide (84.2 mg, 0.18 mmol) obtained in (B) was dissolved in tetrahydrofuran (10 ml), added with lithium chloride (45.3 mg, 1.07 mmol), and added dropwise with bis(2,2,2-trifluoroethyl)-(methoxycarbonylmethyl)phosphonate (112.9 µl, 0.53 mmol) and 1,8-diazabicyclo-[5,4,0]undec-7-ene (73.4 µl, 0.53 mmol). After the reaction solution was stirred at room temperature for 2 hours, the solvent was evaporated, and the residue was purified by preparative TLC (chloroform:methanol=20:1, v/v) to obtain the title compound (63.7 mg, 68.2%) as a mixture of orange oil and solid.

$^1$H-NMR (CDCl$_3$) δ: 1.35 (9H, s), 1.56–1.70 (1H, m), 1.70–2.00 (3H, m), 2.92–3.20 (3H, m), 2.99 (3H, s), 3.19 (3H, s), 3.78 (3H, s), 3.97–4.03 (1H, m), 4.22–4.30 (1H, m), 6.60 (1H, s), 7.10 (1H, d, J=15.6 Hz), 7.45 (1H, dd, J=7.3, 1.7 Hz), 7.49 (1H, d, J=15.6 Hz), 7.85 (1H, d, J=1.7 Hz), 8.96 (1H, d, J=7.3 Hz)

(D) (E)-3-(8-({[4-(tert-Butyl)-1,3-thiazol-2-yl]amino}carbonyl)-2-{3-[(dimethylamino)-carbonyl]piperidino}-4-oxo-4 H-pyrido[1,2-a]pyrimidin-3-yl)-2-propenoic acid The methyl (E)-3-(8-({[4-(tert-butyl)-1,3-thiazol-2-yl]amino}carbonyl)-2-{3-[(dimethylamino)carbonyl]piperidino}-4-oxo-4H-pyrido[1,2-a]pyrimidin-3-yl)-2-propenoate (63.7 mg, 0.11 mmol) obtained in (C) was dissolved in methanol (10 ml), added dropwise with 1 N aqueous sodium hydroxide (562.0 µl, 0.56 mmol), and stirred at room temperature for 1 hour. The reaction solution was further added with 1 N aqueous sodium hydroxide (5.62 ml, 5.62 mmol), stirred at room temperature for 2 hours, further added with 1 N aqueous sodium hydroxide (2.81 ml, 2.81 mmol), and stirred at room temperature for 3 hours. The reaction solution was adjusted to about pH 2 with 1 N hydrochloric acid aqueous solution and extracted with chloroform/methanol (10:1, v/v). The organic layer was washed with saturated brine and dried over anhydrous sodium sulfate, and the solvent was evaporated. The residue was purified by preparative TLC (chloroform:methanol= 20:1, v/v) and lyophilized from dioxane to obtain the title compound (37.6 mg, 38.5%, for the three steps) as yellow orange powder.

¹H-NMR (DMSO-d₆) δ: 1.31 (9H, s), 1.60–1.80 (3H, m), 1.85–1.94 (1H, m), 2.84 (3H, s), 2.97–3.05 (1H, m), 3.12 (3H, s), 3.30–3.45 (2H, m), 3.95-4.03 (1H, m), 4.08–4.15 (1H, m), 6.82–6.95 (1H, m), 6.93 (1H, d, J=15.6 Hz), 7.44 (1H, d, J=15.6 Hz), 7.60–7.67 (1H, m), 8.12–8.18 (1H, m), 8.90 (1H, d, J=7.3 Hz) FAB/MS; m/z: 553 (MH⁺) H-R FAB/MS: Calcd. for $C_{27}H_{32}N_6O_5S$: 553.2233, Found: 553.2236

Example 59

(E)-3-[8-({[4-(tert-Butyl)-1,3-thiazol-2-yl]amino}carbonyl)-4-oxo-2-piperidino-4H-pyrido[1,2-a]pyrimidin-3-yl]-2-propenoic acid The title compound was synthesized in the same manner as in Example 58.

¹H-NMR (DMSO-d₆) δ: 1.31 (9H, s), 1.62–1.72 (6H, m), 3.53–3.62 (4H, m), 6.82–6.92 (1H, m), 6.93 (1H, d, J=15.6 Hz), 7.45 (1H, d, J=15.6 Hz), 7.57–7.62 (1H, m), 8.14–8.20 (1H, m), 8.89 (1H, d, J=7.3 Hz) FAB/MS; m/z: 482 (MH⁺) H-R FAB/MS: Calcd. for $C_{24}H_{27}N_5O_4S$: 482.1862, Found: 482.1844

Example 60

(E)-3-(8-({[4-(tert-Butyl)-1,3-thiazol-2-yl]amino}carbonyl)-2-{3-[(methylamino)carbonyl]piperidino}-4-oxo-4 H-pyrido[1,2-a]pyrimidin-3-yl)-2-propenoic acid The title compound was synthesized in the same manner as in Example 58.

¹H-NMR (DMSO-d₆) δ: 1.31 (9H, s), 1.58–1.80 (3H, m), 1.89–1.97 (1H, m), 2.59 (3H, d, J=4.4 Hz), 3.18–3.20 (2H, m), 3.30–3.42 (2H, m), 3.90–3.97 (1H, m), 4.11–4.18 (1H, m), 6.79–6.89 (1H, m), 6.93 (1H, d, J=15.6 Hz), 7.43 (1H, d, J=15.6 Hz), 7.60–7.66 (1H, m), 7.77–7.83 (1H, m), 8.19–8.26 (1H, m), 8.90 (1H, d, J=7.6 Hz) FAB/MS; m/z: 539 (MH⁺) H-R FAB/MS: Calcd. for $C_{26}H_{30}N_6O_5S$: 539.2077, Found: 539.2112

Example 61

(E)-3-{8-[2-(4-Isopropyl-1,3-thiazol-2-yl)ethyl]-2-morpholino-4-oxo-4H-pyrido[1,2-a]pyrimidin-3-yl}-2-propenoic acid (A) 2-Hydroxy-8-[2-(4-isopropyl-1,3-thiazol-2-yl)ethyl]-4H-pyrido[1,2-a]pyrimidin-4-one 2-Amino-4-[2-(4-isopropyl-1,3-thiazol-2-yl)ethyl]-2-pyridine (9.8 g) and bis(2,4,6-trichlorophenyl) malonate (18 g) were refluxed by heating in xylene for 30 minutes and left stand for cooling. The reaction mixture was added with ether, and the deposited crystals were collected by filtration, washed with ethyl acetate and dried to obtain the title compound (10.3 g). The reaction solution was combined and the solvent was evaporated. The residue was purified by silica gel column chromatography to further obtain the title compound (1.5 g).

¹H-NMR (CDCl₃): 1.29 (6H, d, J=6.8 Hz), 3.06 (1H, m), 3.34 (2H, m), 3.38 (2H, m), 5.34 (1H, s), 6.74 (1H, s), 7.10 (1H, dd, J=7.1,1.7 Hz), 7.37 (1H, s), 9.02 (1H, d, J=7.1 Hz)

(B) 8-[2-(4-Isopropyl-1,3-thiazol-2-yl)ethyl]-2-morpholino-4H-pyrido[1,2-a]pyrimidin-4-one The 2-hydroxy-8-[2-(4-isopropyl-1,3-thiazol-2-yl)ethyl]-4 H-pyrido[1,2-a]-pyrimidin-4-one (500 mg) obtained in (A) was dissolved in methylene chloride (20 ml), added with triethylamine (0.26 ml) and p-toluenesulfonyl chloride (360 mg) and stirred for 24 hours under nitrogen atmosphere. The reaction solution was added with morpholine (0.83 ml) and stirred for 12 hours, and the solvent was evaporated. The residue was purified by silica gel column chromatography to obtain the title compound (273 mg).

¹H-NMR (CDCl₃): 1.30 (s, 3H), 1.33 (s, 3H), 3.07 (m, 1H), 3.18 (m, 2H), 3.48 (m, 2H), 3.67 (m, 4H), 3.79 (m, 4H), 5.59 (s, 1H), 6.77 (s, 1H), 6.78 (d, 1H), 7.11 (s, 1H, 8.80 (d, 1H)

(C) 8-[2-(4-Isopropyl-1,3-thiazol-2-yl)ethyl]-2-morpholino-4-oxo-4H-pyrido[1,2-a]-pyrimidine-3-carbaldehyde Dimethylformamide (10 ml) was added with phosphorus oxychloride (0.60 ml) under ice cooling, stirred for 30 minutes, then added with the 8-[2-(4-isopropyl-1,3-thiazol-2-yl)ethyl]-2-morpholino-4H-pyrido[1,2-a]pyrimidin-4-one (1.0 g) obtained in (B), stirred for 1 hour, and added with saturated aqueous sodium hydrogencarbonate to adjust the reaction solution to pH of about 8. The reaction solution was extracted with ethyl acetate, and the organic layer was washed with saturated brine and dried over sodium sulfate. The solvent was evaporated under reduced pressure to obtain the title compound (1.07 g).

¹H-NMR (CDCl₃): 1.31 (s, 3H), 1.33 (s, 3H), 3.10 (m, 1H), 3.22 (m, 2H), 3.42 (m, 2H), 3.73 (m, 4H), 3.81 (m, 4H), 6.80 (s, 1H), 6.82 (d, 1H), 7.09 (s, 1H), 8.75 (d, 1H), 10.11 (s, 1H)

(D) tert-Butyl (E)-3-(8-[2-(4-isopropyl-1,3-thiazol-2-yl)ethyl]-2-morpholino-4-oxo-4-H-pyrido[1,2-a]pyrimidin-3-yl)-2-propenoate The 8-[2-(4-isopropyl-1,3-thiazol-2-yl)ethyl]-2-morpholino-4-oxo-4 H-pyrido[1,2-a]pyrimidine-3-carbaldehyde (110 mg) obtained in (C) and (tert-butoxycarbonylmethylene)triphenylphosphorane (441 mg) were stirred in tetrahydrofuran (5 ml) at 80° C. for 15 hours. After the solvent was evaporated, the residue was purified by silica gel column chromatography to obtain the title compound (150 mg) as yellow powder.

¹H-NMR (CDCl₃): 1.29 (6H, d, J=6.8 Hz), 1.51 (9H, s), 3.05 (1H, m), 3.20 (2H, m), 3.37 (2H, m), 3.60 (4H, m), 3.83 (4H, m), 6.73 (1H, s), 6.85 (1H, d, J=6.8 Hz), 7.05 (1H, d. J=15.4 Hz), 7.20 (1H, s), 7.50 (1H, d, J=15.4 Hz), 8.87 (1H, d, J=7.1 Hz)

(E) (E)-3-{8-[2-(4-Isopropyl-1,3-thiazol-2-yl)ethyl]-2-morpholino-4-oxo-4 H-pyrido-[1,2-a]pyrimidin-3-yl}-2-propenoic acid The tert-butyl (E)-3-{8-[2-(4-isopropyl-1,3-thiazol-2-yl)ethyl]-2-morpholino-4-oxo-4H-pyrido[1,2-a]pyrimidin-3-yl}-2-propenoate (39 mg) obtained in (D) was stirred in formic acid (1 ml) for 4.5 hours, and the solvent was evaporated under reduced pressure to obtain the title compound (30 mg).

¹H-NMR (CD₃OD): 1.26 (6H, d, J=6.8 Hz), 3.03 (1H, m), 3.20 (2H, m), 3.31 (2H, m), 3.56 (4H, m), 3.79 (4H, m), 6.94 (1H, d, J=15.6 Hz), 6.96 (1H, s), 7.05 (1H, d, J=6.6 Hz), 7.21 (1H, s), 7.55 (1H, d, J=15.6 Hz), 8.76 (1H, d, J=7.1 Hz)

The compounds of Examples 62 to 77 mentioned below were synthesized in the same manner as in Example 61.

Example 62

(E)-3-(2-Morpholino-4-oxo-8-{2-[4-(trifluoromethyl)-1,3-thiazol-2-yl]-ethyl}-4 H-pyrido[1,2-a]pyrimidin-3-yl)-2-propenoic acid ¹H-NMR (CD₃OD) δ: 3.26 (m, 2H), 3.50 (m, 2H), 3.61 (m, 4H), 3.81 (m, 4H), 6.68 (d, J=15.6 Hz, 1H), 7.12 (d, 1H, 7.32 (s, 1H), 7.62 (d, J=16 Hz, 1H), 8.03 (s, 1H), 8.84 (d, 1H) MS (ES+) m/z 481 (M⁺+1)

Example 63

(E)-3-{8-[2-(4-tert-Butyl-1,3-thiazol-2-yl)ethyl]-2-morpholino-4-oxo-4 H-pyrido[1,2-a]pyrimidin-3-yl}-2-propenoic acid ¹H-NMR (CDCl₃) δ: 1.31 (s, 9H), 3.19 (t, 2H), 3.35 (t, 2H), 3.59 (m, 4H), 3.79 (m, 4H), 6.72 (s, 1H), 6.85 (d, 1H), 7.07 (d, J=16 Hz, 1H), 7.18 (s, ¹H), 7.62 (d, J=16 Hz, 1H), 8.84 (d, 1H) MS (ES+) m/z 469 (M⁺+1); MS (ES−) m/z 467 (M⁺−1)

Example 64

(E)-3-{8-(2-[4-(1-Methylcyclopropyl)-1,3-thiazol-2-yl]ethyl)-2-morpholino-4-oxo-4H-pyrido[1,2-a]pyrimidin-3-yl}-2-propenoic acid ¹H-NMR (CD₃OD) δ: 0.70 (m, 2H), 1.03 (m, 2H), 1.41 (s, 3H), 3.18 (t, 2H), 3.37 (t, 2H), 3.59 (m, 4H), 3.80 (m, 4H), 6.92 (s, 1H), 6.98 (d, J=16 Hz, 1H), 7.08 (s, 1H), 7.25 (s, 1H), 7.60 (d, J=16 Hz, 1H), 8.82 (d, 1H) MS (ES+) m/z 467 (M⁺+1); MS (ES−) m/z 465 (M⁺−1)

Example 65

(E)-3-{8-[2-(4-Isopropyl-1,3-thiazol-2-yl)ethyl]-2-(3-carboxypiperidino)-4-oxo-4 H-pyrido[1,2-a]pyrimidin-3-yl}-2-propenoic acid ¹H-NMR (CDCl₃) δ: 1.26 (d, 6H), 2.38 (m, 1H), 2.55 (m, 1H), 2.67 (m, 1H), 2.82 (m, 1H), 3.08 (m, 1H), 3.12 (m, 2H), 3.39 (m, 3H), 3.56 (m, 2H), 3.82 (m, 2H), 3.92 (m, 1H), 6.75 (s, 1H), 6.84 (d, 1H), 7.07 (d, J=14 Hz, 1H), 7.21 (s, 1H), 7.33 (s, 1H), 7.20 (s, 1H), 7.65 (m, 2H), 8.82 (d, 1H) MS (ES+) m/z 497 (M⁺+1); MS (ES−) m/z 495 (M⁺−1)

Example 66

(E)-3-{8-[2-(4-Isopropyl-1,3-thiazol-2-yl)ethyl]-2-(4-carboxypiperidino)-4-oxo-4 H-pyrido[1,2-a]pyrimidin-3-yl}-2-propenoic acid ¹H-NMR (CDCl₃) δ: 1.29 (d, 6H), 2.00 (m, 2H), 2.13 (m, 2H), 2.62 (m, 1H), 3.10 (m, 3H), 3.20 (m, 2H), 3.39 (m, 2H), 4.08 (m, 2H), 6.75 (s, 1H), 6.83 (d, 1H), 7.08 (d, J=15.6 Hz, 1H), 7.22 (s, 1H), 7.69 (d, J=15.6 Hz, 1H), 8.86 (d, 1H) MS (ES+) m/z 497 (M⁺+1); MS (ES−) m/z 495 (M⁺−1)

Example 67

(E)-3-{8-[2-(4-Isopropyl-1,3-thiazol-2-yl)ethyl]-4-oxo-2-(1,2,3,4-tetrahydro-2-isoquinolinyl)-4-H-pyrido[1,2-a]pyrimidin-3-yl}-2-propenoic acid ¹H-NMR (CDCl₃) δ: 1.33 (d, 6H), 2.95 (m, 1H), 3.12 (m, 2H), 3.23 (m, 2H), 3.56 (t, 2H), 3.88 (t, 2H), 4.81 (s, 2H), 6.88 (m, 2H), 7.11 (d, J=15 Hz, 1H), 7.19 (m, 6H), 7.79 (d, J=15 Hz, 1H), 8.86 (d, 1H) MS (ES+) m/z 501 (M⁺+1)

Example 68

(E)-3-{8-[2-(4-Isopropyl-1,3-thiazol-2-yl)ethyl]-4-oxo-2-(3-hydroxy-3-methylpiperidino)-4 H-pyrido[1,2-a]pyrimidin-3-yl}-2-propenoic acid ¹H-NMR (CD₃OD) δ: 1.12 (s, 3H), 1.23 (d, 6H), 1.65 (m, 2H), 1.97 (m, 1H), 3.08 (m, 1H), 3.2 (m, 3H), 3.39 (m, 4H), 3.68 (m, 2H), 6.95 (d, J=14 Hz, 1H), 6.98 (s, 1H), 7.02 (d, 1H), 7.21 (s, 1H), 7.62 (d, J=14 Hz, 1H), 8.78 (d, 1H) MS (ES+) m/z 483 (M⁺+1); MS (ES−) m/z 481 (M⁺−1)

Example 69

(E)-3-{8-[2-(4-Isopropyl-1,3-thiazol-2-yl)ethyl]-4-oxo-2-(3-cyanopiperidino)-4H-pyrido[1,2-a]pyrimidin-3-yl}-2-propenoic acid ¹H-NMR (CDCl₃) δ: 1.30 (d, 6H), 1.65 (m, 1H), 1.90 (m, 2H), 2.00 (m, 1H), 2.98 (m, 1H), 3.08 (m, 1H), 3.22 (m, 2H), 3.40 (m, 2H), 3.52 (m, 1H), 3.65 (m, 1H), 3.83 (m, 1H), 4.18 (m, 1H), 6.75 (s, 1H), 6.92 (d, 1H), 7.11 (d, J=15.6 Hz, 1H), 7.25 (s, with CDCl₃, 1H), 7.63 (d, J=15.6 Hz, 1H), 8.88 (d, 1H) MS (ES+) m/z 478 (M⁺+1); MS (ES−) m/z 476 (M⁺−1)

Example 70

(E)-3-{8-[2-(4-Isopropyl-1,3-thiazol-2-yl)ethyl]-4-oxo-2-(4-cyanopiperidino)-4 H-pyrido[1,2-a]pyrimidin-3-yl}-2-propenoic acid ¹H-NMR (CDCl₃) δ: 1.33 (d, 6H), 2.04 (m, 4H), 2.95 (m, 1H), 3.21 (m, 3H), 3.55 (m, 4H), 3.79 (m, 2H), 6.92 (m, 2H), 7.08 (d, J=15.6 Hz, 1H), 7.26 (1Hs, with CHCl₃, 1H), 7.62 (d, J=15.6 Hz, 1H), 8.89 (d, 1H) MS (ES+) m/z 478 (M⁺+1)

Example 71

(E)-3-{8-[2-(4-Isopropyl-1,3-thiazol-2-yl)ethyl]-4-oxo-2-(3-cyanomorpholino)-4 H-pyrido[1,2-a]pyrimidin-3-yl}-2-propenoic acid ¹H-NMR (CDCl₃) δ: 1.29 (d, 6H), 3.05 (m, 1H), 3.22 (t, 2H), 3.40 (t, 2H), 3.46 (m, 1H), 3.7–4.0 (m, 4H), 4.08 (m, 1H), 4.72 (m, 1H), 6.74 (s, 1H), 6.97 (d, 1H), 7.14 (d, J=15.6 Hz, 1H), 7.28 (s, 1H), 7.67 (d, J=15.6 Hz, 1H), 8.90 (d, 1H) MS (ES+) m/z 480 (M⁺+1); MS (ES−) m/z 478 (M⁺−1)

Example 72

(E)-3-{8-[2-(4-Isopropyl-1,3-thiazol-2-yl)ethyl]-2-(3-aminocarbonylpiperazino)-4-oxo-4H-pyrido[1,2-a]pyrimidin-3-yl}-2-propenoic acid ¹H-NMR (CD₃OD) δ: 1.25 (d, 6H), 3.02 (m, 1H), 3.2–3.4 (m, with CHD₂OD), 4.24 (m, 1H), 6.96 (s, 1H), 7.04 (d, J=16 Hz, 1H), 7.14 (m, 1H), 7.37 (s, 1H), 7.58 (d, J=16 Hz, 1H), 8.84 (d, 1H) MS (ES+) m/z 497 (M⁺+1)

Example 73

(E)-3-{8-[2-(4-Isopropyl-1,3-thiazol-2-yl)ethyl]-2-(3-carboxypiperazino)-4-oxo-4H-pyrido[1,2-a]pyrimidin-3-yl}-2-propenoic acid ¹H-NMR (CD₃OD) δ: 1.23 (d, 6H), 3.02 (m, 1H), 3.15–3.42 (m, with CHD₂OD), 3.62 (m, 1H), 3.95 (m, 1H), 4.75 (m, 1H), 6.96 (s, 1H), 7.05 (m, 2H), 7.37 (m, 2H), 8.82 (d, 1H) MS (ES+) m/z 520 (M⁺+Na); MS (ES−) m/z 496 (M⁺−1)

Example 74

(E)-3-{8-[2-(4-Isopropyl-1,3-thiazol-2-yl)ethyl]-2-(3-cyanopiperazino)-4oxo-4H-pyrido[1,2-a]pyrimidin-3-yl}-2-propenoic acid ¹H-NMR (300 MHz, CD₃OD) δ: 1.23 (d, 6H), 3.02 (m, 1H), 3.15–3.42 (m, with CHD₂OD), 3.71 (m, 1H), 3.92 (m, 1H), 4.12 (m, 1H), 6.81 (s, 1H), 7.00 (m, 2H), 7.25 (m, 1H), 752 (d, J=16 Hz, 1H), 8.82 (d, 1H)

Example 75

(E)-3-{8-[2-(4-Isopropyl-1,3-thiazol-2-yl)ethyl]-2-(3-carboxymorpholino)-4-oxo-4H-pyrido[1,2-a]pyrimidin-3-yl}-2-propenoic acid $^1$H-NMR (CDCl$_3$+CD$_3$OD) δ: 1.22 (d, 6H), 3.0 (m, 1H), 3.14 (t, 2H), 3.31 (m, 4H), 3.73 (m, 2H), 4.02 (m, 1H), 4.12 (m, 2H), 6.70 (s, 1H), 6.88 (d, 1H), 6.97 (d, J=15.6 Hz, 1H), 7.21 (s, 1H), 7.53 (d, J=15.6 Hz, 1H), 8.78 (d, 1H). MS (ES+) m/z 499 (M$^+$+1)

Example 76

(E)-3-{8-[2-(4-Isopropyl-1,3-thiazol-2-yl)ethyl]-2-(3-aminocarbonyl-morpholino)-4-oxo-4H-pyrido[1,2-a]pyrimidin-3-yl}-2-propenoic acid $^1$H-NMR (CDCl$_3$) δ: 1.30 (d, 6H), 3.0–3.2 (m, 5H), 3.47 (m, 2H), 3.81 (m, 2H), 4.02 (m, 1H), 4.21 (m, 1H), 4.42 (m, 1H), 6.82 (s, 1H), 6.92 (d, 1H), 7.08 (d, J=15.6 Hz, 1H), 7.26 (s, with CHCl$_3$, 1H), 7.64 (d, J=15.6 Hz, 1H), 8.87 (d, 1H) MS (ES+) m/z 498 (M$^+$+1); MS (ES−) m/z 496 (M$^+$−1)

Example 77

(E)-3-{8-[2-(4-Isopropyl-1,3-thiazol-2-yl)ethyl-4-oxo-2-([(2S,3R, 4R,5S,6S)-3,4,5,6-tetrahydroxytetrahydro-2H-2-pyranyl]methylamino)-4H-pyrido[1,2-a]-pyrimidin-3-yl]-2-propenoic acid $^1$H-NMR (CD$_3$OD) δ: 1.23 (d, 6H), 3.02 (m, 1H), 3.18 (m, 2H), 3.4 (m, 3H), 3.75 (m, 1H), 3.98 (m, 1H), 4.5 & 5.12 (2 doublets, mixture of anomers, 1H), 6.98 (s, 1H), 7.02 (m, 2H), 7.18 (s, 1H), 7.73 (d, J=16 Hz, 1H), 8.75 (d, 1H) MS (ES+) m/z 547 (M$^+$+1); MS (ES−) m/z 545 (M$^+$−1)

Example 78

(E)-3-{2-[4-((2 S)-2-Amino-5-{[amino(imino)methyl]amino}pentanoyl)-piperazino]-8-[(E)-2-(4-isopropyl-1,3-thiazol-2-yl)-1-ethenyl]-4-oxo-4H-pyrido[1,2-a]-pyrimidin-3-yl}-2-propenoic acid tert-Butyl (E)-3-{8-[(E)-2-(4-isopropyl-1,3-thiazol-2-yl)-1-ethenyl]-4-oxo-2-piperazino-4H-pyrido[1,2-a]pyrimidin-3-yl}-2-propenoate (10 mg, 0.0197 mmol) and N-α, ω-1, ω-2-tri-tert-butoxycarbonyl-L-arginine (BOC-Arg, (BOC)$_2$OH, 14 mg, 0.0295 mmol) were added with methylene chloride (1 ml). The mixture was further added with 1-ethyl-3-(3-dimethylaminopropyl)carbodiimide hydrochloride (EDC HCl, 11 mg, 0.0591 mmol) and stirred at room temperature overnight. The reaction solution was diluted with methylene chloride, washed with 5% aqueous citric acid, saturated aqueous sodium hydrogencarbonate and saturated brine, and dried over sodium sulfate. The solvent was evaporated under reduced pressure, and then the residue was added with trifluoroacetic acid (1 ml) and stirred in the dark for 1 hour. The reaction solution was added with toluene, and the solvent was evaporated under reduced pressure. The residue was purified by medium pressure column chromatography (Amberkron column, gradient 100% 0.1% TFA in H$_2$O to 100% CH$_3$CN over 80 minutes, 3 ml/minute) to obtain the title compound (7.0 mg).

$^1$H-NMR (CD$_3$OD): 1.34 (d, 6H), 1.70 (m, 2H), 1.90 (m, 2H), 3.10 (m, 1H), 3.70 (m, 8H), 3.92 (m, 1H), 4.54 (t, 1H), 7.08 (d, 1H), 7.28 (s, 1H), 7.52 (d, 1H), 7.55 (m, 2H), 7.66 (d, 1H), 7.72 (d, 1H), 8.93 (d, 1H) MS (ES+): 631 (M+Na)

The compounds of Examples 79 to 91 mentioned below were synthesized in the same manner as in Example 78.

Example 79

(E)-3-{2-[4-((2 S)-2-Amino-5-{[amino(imino)methyl]amino}pentanoyl)-piperazino]-8-[(E)-2-(4-isopropyl-1,3-thiazol-2-yl)ethyl]-4-oxo-4H-pyrido[1,2-a]-pyrimidin-3-yl}-2-propenoic acid $^1$H-NMR (CD$_3$OD): 1.26 (d, 6H), 1.70 (m, 2H), 1.90 (m, 2H), 3.03 (m, 1H), 3.20–3.42 (m, 7H), 3.50–3.80 (m, 8H), 3.90 (m, 1H), 4.53 (t, 1H), 6.98 (s, 1H), 7.05 (d, 1H), 7.15 (d, 1H), 7.30 (s, 1H), 7.64 (d, 1H), 8.87 (d, 1H) MS (ES+): 610

Example 80

(E)-3-{2-[4-((2S)-2-Amino-5-{[amino(imino)methyl]amino}pentanoyl)-piperazino]-8-[(E)-2-(4-tert-butyl-1,3-thiazol-2-yl)ethyl]-4-oxo-4H-pyrido[1,2-a]-pyrimidin-3-yl}-2-propenoic acid $^1$H-NMR (CD$_3$OD): 1.29 (s, 9H), 1.69 (m, 2H), 1.88 (m, 2H), 3.10–3.50 (m, 5H), 3.50–3.80 (m, 10H), 3.90 (m, 2H), 4.53 (m, 1H), 6.96 (s, 1H), 7.05 (d, 1H), 7.16 (d, 1H), 7.30 (s, 1H), 7.65 (d, 1H), 8.88 (d, 1H) MS (ES+): 624

Example 81

(E)-3-{8-[2-(4-Isopropyl-1,3-thiazol-2-yl)ethyl]-4-oxo-2-(3-dimethylaminoethylaminocarbonylpiperidino)-4H-pyrido[1,2-a]pyrimidin-3-yl}-2-propenoic acid $^1$H-NMR (CD$_3$OD) δ: 1.26 (d, J=7 Hz, 6H), 1.80 (m, 4H), 2.05 (m, 1H), 2.65 (m, 1H), 2.94 (s, 6H), 3.05 (m, 2H), 3.15–3.25 (m, 4H), 3.42 (t, 2H), 3.58 (t, 2H), 4.10 (m, 2H), 6.98 (d, J=15.6 Hz , 1H), 7.03 (s, 1H), 7.06 (dd, 1H), 7.23 (s, 1H), 7.58 (d, J=15.6 Hz, 1 H), 8.80 (d, 1H) MS (ES+) m/z 567 (M$^+$+1)

Example 82

(E)-3-{8-[2-(4-Isopropyl-1,3-thiazol-2-yl)ethyl]-4-oxo-2-(4-dimethylaminoethylaminocarbonylpiperidino)-4H-pyrido[1,2-a]pyrimidin-3-yl}-2-propenoic acid $^1$H-NMR (CD$_3$OD) δ: 1.26 (d, J=7 Hz, 6H), 1.88 (m, 4H), 2.53 (m, 1H), 2.94 (s, 6H), 3.02 (m, 2H), 3.0–3.25 (m, 6H), 3.41 (t, 2H), 3.55 (t, 2H), 4.15 (m, 2H), 6.97 (m, 2H), 7.04 (dd, 1H), 7.22 (s, 1H), 7.60 (d, J=15.6 Hz , 1H), 8.80 (d, 1H) MS (ES+) m/z 567 (M$^+$+1)

Example 83

(E)-3-{8-[2-(4-Isopropyl-1,3-thiazol-2-yl)ethyl]-4-oxo-2-(4-dimethylaminoacetylpiperazino)-4H-pyrido[1,2-a]pyrimidin-3-yl}-2-propenoic acid $^1$H-NMR (CD$_3$OD) δ: 1.23 (d, 6H), 2.95 (s, 6H), 3.02 (m, 1H), 3.2–3.35 (m, with CHD$_2$OD), 3.42 (m, 1H), 3.58 (m, 1H), 3.63 (m, 2H), 3.80 (m, 1H), 4.28 (s, 2H), 6.96 (s, 1H), 7.05 (d, J=13 Hz, 1H), 7.14 (d, 1H), 7.29 (s, 1H), 7.62 (d, J=13 Hz, 1H), 8.85 (d, 1H)

Example 84

(E)-3-{8-[2-(4-Isopropyl-1,3-thiazol-2-yl)ethyl]-4-oxo-2-(aminoethylthioethylamino )-4H-pyrido[1,2-a]pyrimidin-3-yl}-2-propenoic acid $^1$H-NMR (CD$_3$OD) δ: 1.26 (d, J=7 Hz, 6H), 2.85 (m, 4H), 3.02 (m, 1H), 3.2 (m, 4H), 3.40 (t, 2H), 3.78 (t, 2H), 6.99 (m, 2H), 7.11 (d, J=15.6 Hz 1H), 7.15 (s, 1H), 7.73 (d, J=15.6 Hz, 1H), 8.78 (d, 1H) MS (ES+) m/z 488 (M$^+$+1)

Example 85

(E)-3-{8-[2-(4-Isopropyl-1,3-thiazol-2-yl)ethyl]-4-oxo-2-(3-aminopropylaminocarbonylpiperidino)-4H-pyrido[1,2-a]pyrimidin-3-yl}-2-propenoic acid $^1$H-NMR (CD$_3$OD) δ: 1.26 (d, J=7 Hz, 6H), 1.84 (m, 3H), 2.06 (m, 1H), 2.68 (m, 1H), 2.93 (m, 2H), 3.02 (m, 2H), 3.2–3.3 (m, with CD$_3$OD), 3.42 (m, 3H), 4.08 (m, 2H), 6.9–7.02 (m, 2H), 7.07 (dd, 1H), 7.25 (s, 1H), 7.58 (d, J=15.6 Hz, 1H), 8.81 (d, 1H) MS (ES+) m/z 553 (M$^+$+1)

Example 86

(E)-3-{8-[2-(4-Isopropyl-1,3-thiazol-2-yl)ethyl]-4-oxo-2-(3-amininoethylaminocarbonylpiperidino)-4H-pyrido[1,2-a]pyrimidin-3-yl}-2-propenoic acid $^1$H-NMR (CD$_3$OD) δ: 1.26 (d, J=7 Hz, 6H), 1.79 (m, 3H), 2.06 (m, 1H), 2.68 (m, 1H), 3.0–3.1 (m, 4H), 3.15–3.28 (m, 3H), 3.45 (m, 4H), 4.1 (m, 2H), 6.97 (d, J=15.6 Hz, 1H), 7.06 (m, 2H), 7.25 (s, 1H), 7.58 (d, J=15.6 Hz, 1H), 8.79 (d, 1H) MS (ES+) m/z 539 (M$^+$+1)

Example 87

(E)-3-{8-[2-(4-Isopropyl-1,3-thiazol-2-yl)ethyl]-4-oxo-2-(3-[(tetrahydro-1H-2-pyrrolylmethyl)amino]carbonylpiperidino)-4H-pyrido[1,2-a]pyrimidin-3-yl}-2-propenoic acid $^1$H-NMR (CD$_3$OD) δ: 1.26 (d, J=7 Hz, 6H), 1.79 (m, 4H), 2.04 (m, 4H), 2.68 (m, 1H), 2.9–3.1 (m, 2H), 3.15–3.35 (m, with CD$_3$OD), 3.35–3.55 (m, 4H), 3.68 (m, 1H), 4.1 (m, 2H), 6.99 (m, 2H), 7.08 (d, 1H), 7.25 (s, 1H), 7.59 (d, J=15.6 Hz, 1H), 8.81 (d, 1H) MS (ES+) m/z 579 (M$^+$+1)

Example 88

(E)-3-{8-[2-(4-Isopropyl-1,3-thiazol-2-yl)ethyl]-4-oxo-2-(4-aminomethylcarbonylpiperazino)-4H-pyrido[1,2-a]pyrimidin-3-yl}-2-propenoic acid $^1$H-NMR (CD$_3$OD) δ: 1.26 (d, J=7 Hz, 6H), 3.02 (m, 1H), 3.23 (t, 2H), 3.42 (t, 2H), 3.62 (m, 6H), 3.78 (m, 2H), 3.99 (s, 2H), 6.98 (s, 1H), 7.02 (d, J=15.6 Hz, 1H), 7.13 (d, 1H), 7.27 (s, 1H), 7.63 (d, J=15.6 Hz, 1H), 8.84 (d, 1H) MS (ES+) m/z 511 (M$^+$+1)

Example 89

(E)-3-{8-[2-(4-Isopropyl-1,3-thiazol-2-yl)ethyl]-4-oxo-2-(4-prolyl-piperazino)-4H-pyrido[1,2-a]pyrimidin-3-yl}-2-propenoic acid $^1$H-NMR (CD$_3$OD) δ: 1.26 (d, J=7 Hz, 6H), 1.9–2.1 (m, 3H), 2.52 (m, 1H), 3.02 (m, 1H), 3.25 (t, 2H), 3.42 (t, 2H), 3.5–3.9 (m, 10H), 4.68 (m, 1H), 6.97 (s, 1H), 7.03 (d, 15.6 Hz, 1H), 7.14 (d, 1H), 7.28 (s, 1H), 7.63 (d, J=15.6 Hz, 1H), 8.83 (d, 1H, d) MS (ES+) m/z 551 (M$^+$+1)

Example 90

(E)-3-{8-[2-(4-Isopropyl-1,3-thiazol-2-yl)ethyl]-4-oxo-2-(4-lysypiperazino)-4H-pyrido[1,2-a]pyrimidin-3-yl}-2-propenoic acid $^1$H-NMR (CD$_3$OD) δ: 1.26 (d, J=7 Hz, 6H), 1.51 (m, 2H), 1.72 (m, 2H), 1.90 (m, 2H), 2.95 (m, 2H), 3.02 (m, 1H), 3.25 (t, 2H), 3.42 (t, 2H), 3.5–3.8 (m, 7H), 3.95 (m, 1H), 4.50 (m, 1H), 6.98 (s, 1H), 7.04 (d, J=15.6 Hz, 1H), 7.14 (d, 1H), 7.28 (s, 1H), 7.64 (d, J=15.6 Hz, 1H), 8.85 (d, 1H) MS (ES+) m/z 582 (M$^+$+1)

Example 91

(E)-3-{8-[2-(4-Isopropyl-1,3-thiazol-2-yl)ethyl]-4-oxo-2-(4-ornithylpiperazino)-4H-pyrido[1,2-a]pyrimidin-3-yl}-2-propenoic acid $^1$H-NMR (CD$_3$OD) δ: 1.26 (d, J=7 Hz, 6H), 1.80 (m, 2H), 1.92 (m, 2H), 2.99 (m, 3H), 3.22 (t, 2H), 3.42 (t, 2H), 3.5–3.8 (m, 7H), 3.94 (m, 1H), 4.58 (m, 1H), 6.99 (s, 1H), 7.04 (d, J=15.6 Hz, 1H), 7.14 (d, 1H), 7.28 (s, 1H), 7.64 (d, J=15.6 Hz, 1H), 8.85 (d, 1H) MS (ES+) m/z 568 (M$^+$+1)

Example 92

(E)-3-{2-(4-[2-(4-Aza-1-azoniabicyclo[2.2.2]oct-1-yl)acetyl]piperazine)-8-[2-(4-isopropyl-1,3-thiazol-2-yl)ethyl]-4-oxo-4H-pyrido[1,2-a]pyrimidin-3-yl}-2-propenoic acid (A) tert-Butyl (E)-3-{2-[4-(2-chloroacetyl)piperazino]-8-[2-(4-isopropyl-1,3-thiazol-2-yl)ethyl]-4-oxo-4H-pyrido[1,2-a]pyrimidin-3-yl}-2-propenoate tert-Butyl (E)-3-{8-[(E)-2-(4-isopropyl-1,3-thiazol-2-yl)ethyl]-4-oxo-2-piperazino-4H-pyrido[1,2-a]pyrimidin-3-yl}-2-propenoate (206 mg, 0.405 mmol) was dissolved in methylene chloride (8 ml), added with triethylamine (170 ml) and chloroacetyl chloride (64 ml) at −78° C., and then stirred overnight at room temperature in the dark. The reaction solution was diluted with methylene chloride, washed with water, 5% aqueous citric acid, saturated aqueous sodium hydrogencarbonate and then with saturated brine, and the solution was dried over magnesium sulfate. Then, the solvent was evaporated under reduced pressure. The residue was purified by silica gel column chromatography to obtain the title compound (260 mg).

$^1$H-NMR (CDCl$_3$): 1.28 (d, 6H), 1.51 (s, 9H), 3.06 (m, 1H), 3.21 (m, 2H), 3.37 (m, 2H), 3.62 (brm, 6H), 3.78 (brm, 2H), 4.10 (s, 2H), 6.72 (s, 1H), 6.89 (d, 1H), 7.07 (d, 1H), 7.24 (d, 1H), 7.49 (d, 1H), 8.88 (d, 1H)

(B) tert-Butyl (E)-3-{2-[4-(2-iodoacetyl)piperazino]-8-[2-(4-isopropyl-1,3-thiazol-2-yl)-ethyl]-4-oxo-4H-pyrido[1,2-a]pyrimidin-3-yl}-2-propenoate The tert-butyl (E)-3-{2-[4-(2-chloroacetyl)piperazino]-8-[2-(4-isopropyl-1,3-thiazol-2-yl)ethyl]-4-oxo-4H-pyrido[1,2-a] pyrimidin-3-yl}-2-propenoate (240 mg, 0.405 mmol) obtained in (A) and NaI (300 mg, 2.03 mmol) were refluxed by heating in acetone (8 ml) for 3 hours in the dark. The reaction solution was cooled, then diluted with methylene chloride, washed with water and saturated brine, and dried over sodium sulfate. Then, the solvent was evaporated under reduced pressure to obtain the title compound (226 mg) as a yellow amorphous substance.

$^1$H-NMR (CDCl$_3$): 1.28 (d, 6H), 1.52 (s, 9H), 3.10 (m, 1H), 3.22 (m, 2H), 3.38 (m, 2H), 3.60 (m, 4H), 3.79 (s, 2H), 6.73 (s, 1H), 6.90 (d, 1H), 7.08 (d, 1H), 7.50 (d, 1H), 8.88 (d, 1H)

(C) (E)-3-{2-(4-[2-(4-Aza-1-azoniabicyclo[2.2.2]oct-1-yl)acetyl]piperazino)-8-[2-(4-isopropyl-1,3-thiazol-2-yl)ethyl]-4-oxo-4H-pyrido[1,2-a]pyrimidin-3-yl}-2-propenoic acid The tert-butyl (E)-3-{2-[4-(2-iodoacetyl)piperazino]-8-[2-(4-isopropyl-1,3-thiazol-2-yl)ethyl]-4-oxo-4H-pyrido[1, 2-a]pyrimidin-3-yl}-2-propenoate (226 mg, 0.33 mmol) obtained in (B) and 1,4-diazabicyclo[2.2.2]octane (187 mg, 1.67 mmol) were stirred overnight in tetrahydrofuran (9 ml) under nitrogen atmosphere, then the solvent was evaporated, and the residue was stirred in trifluoroacetic acid (TFA, 4 ml) for 1 hour. The solvent was evaporated under reduced pressure, and the residue was purified by medium pressure reverse phase chromatography (Amberkron column, gradient 100% 0.1% TFA in H$_2$O to 100% CH$_3$CN over 80 minutes, 3 ml/minute) to obtain the title compound (150 mg, 75%, for the two steps).

$^1$H-NMR (CD$_3$OD) δ1.27 (d, 6H), 3.02 (m, 1H), 3.26 (t, 2H), 3.43 (t, 2H), 3.62 (m, 5H), 3.78 (m, 6H), 4.43 (s, 2H), 7.00 (s, 1H), 7.02 (d, J=15.6 Hz, 1H), 7.13 (d, J=7 Hz, 1H), 7.29 (s, 1H), 7.63 (d, J=15.6 Hz, 1H), 8.85 (d, J=7 Hz, 1H) MS (ES+) m/z 606 (M$^+$+1)

The compounds of Examples 93 to 97 mentioned below were synthesized in the same manner as in Example 92.

Example 93

(E)-3-8-[2-(4-Isopropyl-1,3-thiazol-2-yl)ethyl]-2-(4-[2-(1-methyl-1H-imidazol-3-ium-3-yl)acetyl] piperazino)-4-oxo-4H-pyrido[1,2-a]pyrimidin-3-yl}-2-propenoic acid $^1$H-NMR (CDCl$_3$+CD$_3$OD) δ: 1.23 (d, J=7 Hz, 6H), 3.02 (m, 1H), 3.17 (t, 2H), 3.34 (t, 2H), 3.57 (m, 2H), 3.6–3.8 (m, 6H), 3.92 (s, 3H), 5.40 (s, 2H), 6.72 (s, 1H), 6.88 (d, J=7.2 Hz, 1H), 7.00 (d, J=15.6 Hz, 1H), 7.20 (m, 2H), 7.37 (s, 1H), 7.55 (d, J=15.6 Hz, 1H), 8.81 (d, J=7.2 Hz, 1H), 9.24 (s, 1H) MS (ES+) m/z 576 (M$^+$+1)

Example 94

(E)-3-{2-4-[2-(1-Azabicyclo[2.2.2]oct-1-yl)acetyl] piperazino-8-[2-(4-isopropyl-1,3-thiazol-2-yl)ethyl]-4-oxo-4H-pyrido[1,2-a]pyrimidin-3-yl}-2-propenoic acid $^1$H-NMR (CD$_3$OD): 1.26 (d, 6H), 2.05 (brm, 7H), 2.19 (m, 1H), 3.03 (m, 1H), 3.22 (m, 2H), 3.39 (m, 2H), 3.61 (brm, 6H), 3.67 (m, 8H), 4.26 (s, 2H), 6.97 (s, 1H), 6.99 (d, 1H), 7.12 (d, 1H), 7.28 (s, 1H), 7.62 (d, 1H), 8.85 (d, 1H) MS (ES+): 605

Example 95

(E)-3-{8-[2-(4-Isopropyl-1,3-thiazol-2-yl)ethyl]-4-oxo-2-(4-[2-(1-pyridinium)acetyl]piperazino)-4H-pyrido[1,2-a]pyrimidin-3-yl}-2-propenoic acid $^1$H-NMR (CD$_3$OD): 1.27 (d, 6H), 3.02 (m, 1H), 3.25 (m, 2H), 3.40 (m, 2H), 5.80 (s, 2H), 6.98 (s, 1H), 7.02 (d, 1H), 7.17 (d, 1H), 7.31 (s, 1H), 7.65 (d, 1H), 8.20 (m, 2H), 8.65 (m, 1H), 8.88 (m, 2H) MS (ES+): 573

Example 96

(E)-3-{2-(4-[2-(1-Azabicyclo[2.2.2]oct-1-yl) butanoyl]piperazino)-8-[2-(4-isopropyl-1,3-thiazol-2-yl)ethyl]-4-oxo-4H-pyrido[1,2-a]pyrimidin-3-yl}-2-propenoic acid $^1$H-NMR (CD$_3$OD): 1.25 (d, 6H), 2.07 (m, 1H), 2.58 (m, 1H), 3.02 (m, 1H), 3.20–3.80 (m, 24H), 6.99 (s, 1H), 7.02 (d, 1H), 7.12 (d, 1H), 7.28 (s, 1H), 7.64 (d, 1H), 8.86 (d, 1H)

Example 97

(E)-3-{2-(4-[2-(4-Aza-1-azoniabicyclo[2.2.2]oct-1-yl)acetyl]piperazino-8(2-[4-(tert-butyl)-1,3-thiazol-2-yl]ethyl)-4-oxo-4H-pyrido[1,2-a]pyrimidin-3-yl)-2-propenoic acid $^1$H-NMR (CD$_3$OD): 1.29 (s, 9H), 3.20–3.41 (m, 5H), 3.50–3.79 (m, 20H), 4.39 (s, 2H), 6.96 (s, 1H), 7.02 (d, 1H), 7.13 (d, 1H), 7.29 (s, 1H), 7.64 (d, 1H), 8.86 (d, 1H) MS (ES+): 620

Example 98

N-((E)-3-{8-[2-(4-Isopropyl-1,3-thiazol-2-yl)ethyl]-2-morpholino-4-oxo-4H-pyrido[1,2-a]pyrimidin-3-yl}-2-propenoyl)methanesulfonamide (E)-3-{8-[2-(4-Isopropyl-1,3-thiazol-2-yl)ethyl]-2-morpholino-4-oxo-4-H-pyrido-[1,2-a]pyrimidin-3-yl}-2-propenoic acid (24 mg) was dissolved in dimethylformamide (2 ml), added with methanesulfonamide (15 mg), dimethylaminopyridine (20 mg) and 1-ethyl-3-(3-dimethylaminopropyl)carbodiimide hydrochloride (31 mg), and then the mixture was stirred at room temperature for 24 hours. The reaction solution was added with ethyl acetate and hexane, washed with 0.2 M hydrochloric acid, and dried over sodium over sodium sulfate, and the solvent was evaporated under reduced pressure. The residue was purified by silica gel column chromatography to obtain the title compound (14 mg) as yellow powder.

$^1$H-NMR (CDCl$_3$) δ: 1.21 (d, 6H), 3.02 (m, 1H), 3.15 (m, 2H), 3.19 (s, 3H), 3.36 (m, 2H), 3.53 (m, 4H), 3.70 (m, 4H), 6.78 (s, 1H), 6.86 (d, 1H), 6.92 (d, J=16 Hz, 1H), 7.17 (s, 1H), 7.53 (d, J=16 Hz, 1H), 8.67 (d, 1H) MS (ES+) m/z 532 (M$^+$+1)

Example 99

N-((E)-3-{8-[2-(4-Isopropyl-1,3-thiazol-2-yl)ethyl]-4-oxo-4H-pyrido[1,2-a]-pyrimidin-3-yl}-2-propenoyl)methanesulfonamide $^1$H-NMR (CDCl$_3$) δ: 1.28 (d, 6H), 3.04 (m, 1H), 3.11 (s, 3H), 3.37 (m, 4H), 6.73 (s, 1H), 7.19 (d, J=7 Hz, 1H), 7.32 (d, J=14 Hz, 1H), 7.59 (s, 1H), 7.72 (d, J=14 Hz, 1H), 8.48 (s, 1H), 9.08 (d, J=7 Hz, 1H) MS (ES+) m/z 447 (M$^+$+1); MS (ES−) m/z 445 (M$^+$−1)

Example 100

N-((E)-3-{8-[2-(4-Isopropyl-1,3-thiazol-2-yl)ethyl]-2-morpholino-4-oxo-4H-pyrido[1,2-a]pyrimidin-3-yl}-2-propenoyl)-3-amino-1-propanesulfonamide (A) N-((E)-3-{8-[2-(4-Isopropyl-1,3-thiazol-2-yl) ethyl]-2-morpholino-4-oxo-4H-pyrido-[1,2-a]pyrimidin-3-yl}-2-propenoyl)-3-(tert-butoxycarbonylamino)-1-propane-sulfonamide (E)-3-{8-[2-(4-Isopropyl-1,3-thiazol-2-yl)ethyl]-2-morpholino-4-oxo-4H-pyrido -[1,2-a]pyrimidin-3-yl}-2-propenoic acid (53 mg) was dissolved in dimethylformamide (2 ml), added with 3-(N-tert-butoxycarbonylamino) propanesulfonamide (55 mg) and 1-ethyl-3-(3-dimethylaminopropyl)carbodiimide hydrochloride (67 mg), and the mixture was stirred at room temperature for 24 hours. The reaction solution was added with ethyl acetate and hexane, washed with 0.2 M hydrochloric acid, and dried over sodium sulfate, and the solvent was evaporated under reduced pressure. The residue was purified by silica gel column chromatography to obtain the title compound (32 mg) as yellow powder.

$^1$H-NMR (300 MHz) δ: 1.22 (d, J=7.2 Hz, 6H), 1.40 (s, 9H), 1.90–2.05 (m, 2H), 3.00–3.80 (m, 17H), 6.70 (s, 1H), 6.85 (d, J=7.5 Hz, 1H), 7.20 (s, 1H), 7.35 (d, J=15.4 Hz, 1H), 7.65 (d, J=15.4 Hz, 1H), 9.00–9.10 (m, 2H)

(B) N-((E)-3-{8-[2-(4-Isopropyl-1,3-thiazol-2-yl) ethyl]-2-morpholino-4-oxo-4H-pyrido -[1,2-a] pyrimidin-3-yl}-2-propenoyl)-3-amino-1-propanesulfonamide The N-((E)-3-{8-[2-(4-isopropyl-1,3-thiazol-2-yl)ethyl]-2-morpholino-4-oxo-4H-pyrido -[1,2-a]pyrimidin-3-yl}-2- propenoyl)-3-(tert-butoxycarbonylamino)-1-propane-sulfonamide (32 mg) obtained in (A) was dissolved in trifluoroacetic acid (2 ml) and stirred for 40 minutes. The solvent was evaporated under reduced pressure, and the residue was purified by medium pressure reverse phase column chromatography to obtain the title compound (quantitative).

$^1$H-NMR (CD$_3$OD) δ: 1.25 (d, 6H), 2.18 (m, 2H), 3.02 (m, 1H), 3.1–3.45 (m, with CHD$_2$OD), 3.60 (m, 4H), 3.80 (m, 4H), 6.98 (s, 1H), 7.12 (s, 1H), 7.16 (d, J=16 Hz, 1H), 7.26 (s, 1H), 7.75 (d, J=16 Hz, 1H), 8.82 (d, 1H) MS (ES+) m/z 575 (M$^+$+1); MS (ES−) m/z 573 (M$^+$−1)

Example 101

(E)-3-{8-[(E)-2-(4-Isopropyl-1,3-thiazol-2-yl)-1-ethenyl]-2-morpholine-4-oxo-4H-pyrido[1,2-a]pyrimidin-3-yl}-2-propenoic acid (A) tert-Butyl (E)-3-{8-[(E)-2-(4-isopropyl-1,3-thiazol-2-yl)-1-ethenyl]-2-{[(4-methyl-phenyl)sulfonyl]oxy}-4-oxo-4H-pyrido[1,2-a]pyrimidin-3-yl}-2-propenoate 4-[(E)-2-(4-Isopropyl-1,3-thiazol-2-yl)-1-ethenyl]-2-pyridinamine (100 mg, 0.408 mmol) was dissolved in xylene (1.2 ml), added with trichlorophenyl malonate (208 mg, 0.448 mmol), and then the mixture was refluxed by heating for 1.3 hours. The reaction mixture was added with n-hexane, and the deposited solid was collected by filtration. Dimethylformamide (110 μl) was added with phosphorus oxychloride (190 μl, 2.04 mmol) under ice cooling and stirred at room temperature for 30 minutes. The mixture was added with the solid dissolved in dichloromethane (3.0 ml) under ice cooling, and stirred at room temperature for 1.5 hours. The reaction mixture was added with saturated aqueous sodium hydrogencarbonate and extracted with chloroform. The organic layer was dried over magnesium sulfate, and the solvent was evaporated under reduced pressure. The residue was suspended in anhydrous tetrahydrofuran (4.0 ml), added with (tert-butoxycarbonylmethylene)triphenylphosphorane (460 mg, 1.22 mmol), and stirred at 80° C. for 5 days. The reaction solution was concentrated, and then the residue was purified by silica gel column chromatography (chloroform:methanol=100:0→100:10, v/v) and thin layer chromatography (chloroform:methanol=10:1, v/v). The resulting compound was dissolved in anhydrous tetrahydrofuran (600 μl) and dimethylformamide (600 μl), added with 4-dimethylaminopyridine (10.2 mg, 0.0831 mmol) and p-toluenesulfonyl chloride (13.4 mg, 0.0703 mmol), and stirred at room temperature for 2 hours. The reaction mixture was added with water and extracted with chloroform. The organic layer was dried over magnesium sulfate, and the solvent was evaporated under reduced pressure. The residue was purified by thin layer chromatography (n-hexane:ethyl acetate=2:1, v/v) to obtain the title compound (9.0 mg, 3.7%).

$^1$H-NMR (CDCl$_3$) δ: 1.37 (6H, d, J=6.8 Hz), 1.51 (9H, s), 2.48 (3H, s), 3.14–3.21 (1H, m), 7.03 (1H, s), 7.18 (1H, d, J=15.9 Hz), 7.38–7.42 (4H, m), 7.52 (1H, d, J=1.5 Hz), 7.56 (1H, d, J=16.1 Hz), 7.67 (1H, d, J=15.9 Hz), 8.05 (2H, d, J=8.3 Hz), 9.02 (1H, d, J=7.6 Hz)

(B) tert-Butyl (E)-3-{8-[(E)-2-(4-isopropyl-1,3-thiazol-2-yl)-1-ethenyl]-2-morpholino-4-oxo-4H-pyrido[1,2-a]pyrimidin-3-yl}-2-propenoate The tert-butyl (E)-3-{8-[(E)-2-(4-isopropyl-1,3-thiazol-2-yl)-1-ethenyl]-2-{[(4-methylphenyl)sulfonyl]oxy}-4-oxo-4H-pyrido[1,2-a]pyrimidin-3-yl}-2-propenoate (9.0 mg, 0.0152 mmol) obtained in (A) was dissolved in dimethylformamide (0.75 ml), added with morpholine (13.2 μl, 0.152 mmol), and stirred overnight at room temperature. The reaction mixture was concentrated, and then the residue was purified by thin layer chromatography (n-hexane:ethyl acetate=1:1, v/v) to obtain the title compound (6.7 mg, 87%).

$^1$H-NMR (CDCl$_3$) δ: 1.33 (6H, d, J=6.8 Hz), 1.52 (9H, s), 3.12–3.19 (1H, m), 3.62–3.64 (4H, m), 3.73–3.75 (4H, m), 6.97 (1H, s), 7.08 (1H, d, J=15.9 Hz), 7.16 (1H, dd, J=1.5, 7.6 Hz), 7.34–7.38 (2H, m), 7.50 (2H, d, J=15.9 Hz), 8.91 (1H, d, J=7.6 Hz)

(C) (E)-3-}8-[(E)-2-(4-Isopropyl-1,3-thiazol-2-yl)-1-ethenyl]-2-morpholino-4-oxo-4H-pyrido[1,2-a]pyrimidin-3-yl}-2-propenoic acid The tert-butyl (E)-3-{8-[(E)-2-(4-isopropyl-1,3-thiazol-2-yl)-1-ethenyl]-2-morpholino-4-oxo-4H-pyrido[1,2-a]pyrimidin-3-yl}-2-propenoate (6.7 mg, 0.0132 mmol) obtained in (B) was dissolved in 1,4-dioxane (260 μl), added with 4 N hydrochloric acid solution in 1,4-dioxane (260 μl), and stirred at room temperature for 7 hours. The reaction solution was concentrated, and the residue was purified by thin layer chromatography (chloroform:methanol=10:1, v/v) to obtain the title compound (4.8 mg, 81%).

$^1$H-NMR (CDCl$_3$+CD$_3$OD) δ: 1.36 (6H, d, J=6.8 Hz), 3.13–3.20 (1H, m), 3.67 (4H, t, J=4.4 Hz), 3.86 (4H, t, J=4.4 Hz), 7.04 (1H, d, J=15.6 Hz), 7.07 (1H, s), 7.33 (1H, dd, J=1.6, 7.5 Hz), 7.40 (1H, d, J=16.2 Hz), 7.47 (1H, d, J=6.6 Hz), 7.58 (1H, d, J=16.2 Hz), 7.62 (1H, d, J=15.6 Hz), 8.89 (1H, d, J=7.5 Hz) FAB-MS; m/z: 453 (M$^+$+1) FAB-HRMS; Calcd. for C$_{23}$H$_{25}$O$_4$N$_4$S+H$^+$: 453.1597, Found: 453.1602

Example 102

(E)-3-{2-(3-Hydroxypiperidino)-8-[(E)-2-(4-isopropyl-1,3-thiazol-2-yl)-1-ethenyl]-4-oxo-4H-pyrido[1,2-a]pyrimidin-3-yl}-2-propenoic acid (A) 4-Isopropyl-1,3-thiazole-2-carbaldehyde (4-Isopropyl-1,3-thiazol-2-yl)methanol (5.20 g, 33.0 mmol) was dissolved in methylene chloride (100 ml), added with pyridinium dichromate (14.9 g, 39.7 mmol), and stirred at room temperature for 19 hours stirred. After insoluble solids were removed, the reaction solution was evaporated, and the residue was purified by silica gel column chromatography (chloroform) to obtain the title compound (3.32 g, 65%).

$^1$H-NMR (CDCl$_3$) δ: 1.37 (6H, d, J=6.8 Hz), 3.18–3.25 (1H, m), 7.34 (1H, s), 9.98 (1H, s)

(B) tert-Butyl N-4-[2-hydroxy-2-(4-isopropyl-1,3-thiazol-2-yl)ethyl]-2-pyridylcarbamate tert-Butyl N-(4-methyl-2-pyridyl)carbamate (6.24 g, 30.0 mmol) was dissolved in anhydrous tetrahydrofuran (100 ml), added with n-butyl lithium (1.59 M in n-hexane, 47.1 ml, 74.9 mmol) at −78° C. under argon atmosphere, and then stirred at room temperature for 1.5 hours. The reaction solution was cooled to −78° C. again, then added with a solution of the 4-isopropyl-1,3-thiazole-2-carbaldehyde (4.65 g, 30.0 mmol) obtained in (A) in anhydrous tetrahydrofuran (50.0 ml), and then the mixture was stirred for 3 hours. The reaction mixture was added with saturated aqueous ammonium chloride, warmed to room temperature, and then extracted with ethyl acetate. The organic layer was dried over magnesium sulfate, and the solvent was evaporated under reduced pressure. The residue was purified by silica gel column chromatography (n-hexane:ethyl acetate=3:1→1:1, v/v) to obtain the title compound (5.42 g, 50%).

$^1$H-NMR (CDCl$_3$) δ: 1.29 (6H, d, J=6.8 Hz), 1.53 (9H, s), 3.03–3.11 (2H, m), 3.28–3.32 (2H, m), 5.24 (1H, dd, J=4.2, 8.5 Hz), 6.82 (1H, d, J=0.7 H), 6.85 (1H, dd, J=1.6, 5.2 Hz), 7.90 (1H, s), 8.10 (1H, s), 8.14 (1H, d, J=5.2 Hz) ESI-MS; m/z: 364 (M$^+$+1)

(C) tert-Butyl N-4-[(E)-2-(4-isopropyl-1,3-thiazol-2-yl)-1-ethenyl]-2-pyridylcarbamate The tert-butyl N-4-[2-hydroxy-2-(4-isopropyl-1,3-thiazol-2-yl)ethyl]-2-pyridyl-carbamate (5.30 g, 14.6 mmol) obtained in (B) was dissolved in anhydrous tetrahydrofuran (100 ml), added with triethylamine (5.08 ml, 36.5 mmol) and methanesulfonyl chloride (1.35 ml, 17.5 mmol), and then the mixture was stirred at room temperature for 1 hour. After insoluble solids were removed, the reaction solution was washed with tetrahydrofuran, and the solvent was evaporated under reduced pressure. The residue was dissolved in toluene (100 ml), added with 1,8-diazabicyclo[5.4.0]undec-7-ene (10.9 ml, 72.9 mmol), and refluxed by heating for 30 minutes. The reaction solution was concentrated, then added with 1 N hydrochloric acid and extracted with chloroform. The organic layer was washed with saturated aqueous sodium hydrogencarbonate and dried over magnesium sulfate, and the solvent was evaporated under reduced pressure. The residue was purified by silica gel column chromatography (n-hexane:ethyl acetate=5:1→3:1, v/v) to obtain the title compound (3.76 g, 75%).

$^1$H-NMR (CDCl$_3$) δ: 1.34 (6H, d, J=6.8 Hz), 1.56 (9H, s), 3.07–3.18 (1H, m), 6.87 (1H, s), 7.07 (1H, dd, J=1.2, 5.1 Hz), 7.31 (1H, d, J=16.1 Hz), 7.50 (1H, d, J=16.1 Hz), 8.12 (1H, s), 8.25 (1H, s), 8.26 (1H, s)

(D) 4-[(E)-2-(4-Isopropyl-1,3-thiazol-2-yl)-1-ethenyl]-2-pyridinamine

The tert-butyl N-4-[(E)-2-(4-isopropyl-1,3-thiazol-2-yl)-1-ethenyl]-2-pyridylcarbamate (3.75 g, 10.9 mmol) obtained in (C) was dissolved in dichloromethane (50.0 ml), added with trifluoroacetic acid (50.0 ml), and then the mixture was stirred at room temperature for 30 minutes. The reaction solution was concentrated, then neutralized with saturated aqueous sodium hydrogencarbonate, and extracted with chloroform. The organic layer was dried over magnesium sulfate, and then the solvent was evaporated under reduced pressure to obtain the title compound (2.65 g, 100%).

$^1$H-NMR (CDCl$_3$) δ: 1.34 (6H, d, J=6.8 Hz), 3.09–3.16 (1H, m), 4.67 (1H, br, s), 6.57 (1H, s), 6.80 (1H, dd, J=1.3, 5.5 Hz), 6.87 (1H, s), 7.18 (1H, d, J=16.1 Hz), 7.37 (1H, d, J=16.1 Hz), 8.04 (1H, d, J=5.5 Hz)

(E) 2-Hydroxy-8-[(E)-2-(4-isopropyl-1,3-thiazol-2-yl)-1-ethenyl]-4H-pyrido[1,2-a]-pyrimidin-4-one The 4-[(E)-2-(4-isopropyl-1,3-thiazol-2-yl)-1-ethenyl]-2-pyridinamine (2.65 g, 10.8 mmol) obtained in (D) was dissolved in toluene (100 ml), added with trichlorophenyl malonate (5.50 g, 11.9 mmol), and refluxed by heating for 1.5 hours. After the reaction mixture was concentrated, the deposited solid was collected by filtration and washed with n-hexane and ether to obtain the title compound (3.14 g, 93%) as yellow solid.

$^1$H-NMR (CDCl$_3$) δ: 1.37 (6H, d, J=6.8 Hz), 3.14–3.21 (1H, m), 5.41 (1H, s), 7.05 (1H, s), 7.40 (1H, dd, J=1.5, 7.4 Hz), 7.46 (1H, d, J=16.1 Hz), 7.51 (1H, d, J=1.5 Hz), 7.66 (1H, d, J=16.1 Hz), 9.09 (1H, d, J=7.4 Hz)

(F) 2-(3-Hydroxypiperidino)-8-[(E)-2-(4-isopropyl-1,3-thiazol-2-yl)-1-ethenyl]-4H-pyrido[1,2-a]pyrimidin-4-one The 2-hydroxy-8-[(E)-2-(4-isopropyl-1,3-thiazol-2-yl)-1-ethenyl]-4H-pyrido[1,2-a]-pyrimidin-4-one (1.00 g, 3.19 mmol) obtained in (E) was dissolved in anhydrous tetrahydrofuran (15.0 ml) and anhydrous dimethylformamide (15.0 ml), added with 4-dimethylaminopyridine (585 mg, 4.79 mmol) and p-toluenesulfonyl chloride (730 mg, 3.83 mmol), and then the mixture was stirred at room temperature for 50 minutes. Subsequently, the reaction solution was added with 3-hydroxypiperidine (646 mg, 6.38 mmol) and stirred at room temperature for 16 hours, and then added with 3-hydroxypiperidine (968 mg, 9.57 mmol) and stirred at 60° C. for 1.5 hours. After the reaction mixture was concentrated, the residue was purified by silica gel column chromatography (chloroform:methanol=100:0→100:1→100:2→100:5→100:10, v/v) to obtain the title compound (865 mg, 68%).

$^1$H-NMR (CDCl$_3$) δ: 1.35 (6H, d, J=7.1 Hz), 1.54–1.72 (1H, m), 1.86–2.01 (3H, m), 3.11–3.21 (1H, m), 3.39–3.45 (1H, m), 3.55 (1H, dd, J=7.1,13.2 Hz), 3.73–3.78 (1H, m), 3.85–3.89 (1H, m), 4.00 (1H, dd, J=3.1,12.9 Hz), 5.65 (1H, m), 6.94 (1H, m), 7.03 (1H, dd, J=2.0, 7.6 Hz), 7.32 (1H, d, J=16.1 Hz), 7.45 (1H, d, J=16.1 Hz), 8.82 (1H, d, J=7.3 Hz) ESI-MS; m/z: 397 (M$^+$+1)

(G) tert-Butyl (E)-3-{2-(3-formyloxypiperidino)-8-[(E)-2-(4-isopropyl-1,3-thiazol-2-yl)-1-ethenyl]-4-oxo-4H-pyrido[1,2-a]pyrimidin-3-yl}-2-propenoate Dimethylformamide (15.0 ml) was added with phosphorus oxychloride (608 µl, 6.52 mmol) under ice cooling and stirred at room temperature for 40 minutes. The mixture was added to a solution of the 2-(3-hydroxypiperidino)-8-[(E)-2-(4-isopropyl-1,3-thiazol-2-yl)-1-ethenyl]-4H-pyrido[1,2-a]pyrimidin-4-one (862 mg, 2.17 mmol) obtained in (F) in dimethylformamide (15.0 ml) under ice cooling, and then the mixture was stirred at room temperature for 1.5 hours. The reaction mixture was added with saturated aqueous sodium hydrogencarbonate and extracted with chloroform. The organic layer was dried over magnesium sulfate, and the solvent was evaporated under reduced pressure. The residue was suspended in anhydrous tetrahydrofuran (20 ml) and anhydrous N,N-dimethylformamide (10 ml), added with (tert-butoxycarbonyl-methylene)triphenylphosphorane (1.64 g, 4.35 mmol), and stirred at 50° C. for 16 hours. The reaction mixture was concentrated, and the residue was purified by silica gel column chromatography (n-hexane:ethyl acetate=10:1→5:1→3:1→2:1, v/v) to obtain the title compound (488 mg, 41%).

$^1$H-NMR (CDCl$_3$) δ: 1.35 (6H, d, J=6.8 Hz), 1.52 (9H, s), 1.72–1.75 (1H, m), 1.81–1.85 (1H, m), 1.94–2.03 (2H, m), 3.12–3.18 (1H, m), 3.51–3.60 (2H, m), 3.71 (1H, dd, J=6.3, 13.4 Hz), 3.82 (1H, dd, J=3.1,13.4 Hz), 5.13–5.16 (1H, m), 6.97 (1H, s), 7.07 (1H, d, J=15.6 Hz), 7.15 (1H, dd, J=1.7, 7.6 Hz), 7.34–7.37 (2H, m), 7.49 (1H, d, J=16.1 Hz), 7.51 (1H, d, J=15.6 Hz), 8.10 (1H, s), 8.89 (1H, d, J=7.6 Hz) ESI-MS; m/z: 551 (M$^+$+1)

(H) tert-Butyl (E)-3-{2-(3-hydroxypiperidino)-8-[(E)-2-(4-isopropyl-1,3-thiazol-2-yl)-1-ethenyl]-4-oxo-4H-pyrido[1,2-a]pyrimidin-3-yl}-2-propenoate The tert-butyl (E)-3-{2-(3-formyloxypiperidino)-8-[(E)-2-(4-isopropyl-1,3-thiazol-2-yl)-1-ethenyl]-4-oxo-4H- pyrido[1,2-a]pyrimidin-3-yl}-2-propenoate (184 mg, 0.334 mmol) obtained in (G) was dissolved in methanol (3.0 ml), added with 1 N aqueous sodium hydroxide (1.0 ml), and then the mixture was stirred at room temperature for 10 minutes. The reaction mixture was added with 1 N hydrochloric acid (1.0 ml) and extracted with chloroform. The organic layer was dried over magnesium sulfate and the solvent was evaporated under reduced pressure. The residue was purified by silica gel column chromatography (n-hexane:ethyl acetate=2:1→2:1→1:2, v/v) to obtain the title compound (174 mg, 100%).

$^1$H-NMR (CDCl$_3$) δ: 1.35 (6H, d, J=6.8 Hz), 1.52 (9H, s), 1.68–1.89 (4H, m), 3.12–3.18 (1H, m), 3.55–3.66 (3H, m), 3.93–3.96 (1H, m), 4.03 (1H, br s), 6.97 (1H, s), 7.06 (1H, d, J=15.6 Hz), 7.16 (1H, dd, J=1.6, 7.5 Hz), 7.34 (1H, d, J=16.1 Hz), 7.34 (1H, d, J=1.6 Hz), 7.49 (1H, d, J=16.1 Hz), 7.50 (1H, d, J=15.6 Hz), 8.89 (1H, d, J=7.5 Hz) ESI-MS; m/z: 523 (M$^+$+1)

(I) (E)-3-{2-(3-Hydroxypiperidino)-8-[(E)-2-(4-isopropyl-1,3-thiazol-2-yl)-1-ethenyl]-4-oxo-4H-pyrido[1,2-a]pyrimidin-3-yl}-2-propenoic acid The tert-Butyl (E)-3-{2-(3-hydroxypiperidino)-8-[(E)-2-(4-isopropyl-1,3-thiazol-2-yl)-1-ethenyl]-4-oxo-4H-pyrido[1,2-a]pyrimidin-3-yl}-2-propenoate (43.4 mg, 0.0830 mmol) obtained in (H) was dissolved in 1,4-dioxane (200 μl), added with 4 N hydrochloric acid solution in 1,4-dioxane, and stirred at room temperature for 3.5 hours. The reaction solution was concentrated, and the residue was purified by thin layer chromatography (chloroform:methanol:water=10:1:0→8:3:0.1→7:3:1, v/v) to obtain the title compound (18.9 mg, 49%).

$^1$H-NMR (DMSO-d$_6$) δ: 1.29 (6H, d, J=6.6 Hz), 1.42–1.47 (1H, m), 1.55–1.59 (1H, m), 1.81 (1H, m), 1.90–1.95 (1H, m), 2.97–3.74 (4H, m), 3.89–3.92 (1H, m), 4.95 (1H, br s), 6.89 (1H, d, J=15.1 Hz), 7.42–7.46 (2H, m), 7.54–7.62 (3H, m), 7.87 (1H, d, J=16.6 Hz), 8.76 (1H, d, 7.8 Hz) ESI-MS; m/z: 467 (M$^+$+1)

Example 103

(E)-3-(2-{3-[(Aminocarbonyl)oxy]piperidino}-8-[(E)-2-(4-isopropyl-1,3-thiazol-2-yl)-1-ethenyl]-4-oxo-4H-pyrido[1,2-a]pyrimidin-3-yl)-2-propenoic acid (A) tert-Butyl (E)-3-(2-{3-[(aminocarbonyl)oxy] piperidino}-8-[(E)-2-(4-isopropyl-1,3-thiazol-2-yl)-1-ethenyl]-4-oxo-4H-pyrido[1,2-a]pyrimidin-3-yl)-2-propenoate tert-Butyl (E)-3-{2-(3-hydroxypiperidino)-8-[(E)-2-(4-isopropyl-1,3-thiazol-2-yl)-1-ethenyl]-4-oxo-4H-pyrido[1,2-a]pyrimidin-3-yl}-2-propenoate (138 mg, 0.264 mmol) was dissolved in ethyl acetate (2.6 ml), added with trichloroacetyl isocyanate (62.6 μl, 0.528 mmol) under ice cooling, and then the mixture was stirred at room temperature for 15 minutes. The reaction mixture was concentrated, dissolved in methanol (5.0 ml) and water (0.5 ml), and then added with sodium formate (71.8 mg, 1.06 mmol), and stirred overnight at room temperature. The reaction mixture was further added with chloroform (3.0 ml) and sodium formate (71.8 mg, 1.06 mmol) and stirred overnight. The reaction mixture was concentrated, and the residue was purified by silica gel column chromatography (chloroform:methanol= 100:0→100:1→100:2, v/v) to obtain the title compound (150 mg, 100%).

$^1$H-NMR (CDCl$_3$) δ: 1.35 (6H, d, J=6.8 Hz), 1.50 (9H, s), 1.70–2.04 (4H, m), 3.11–3.18 (1H, m), 3.27–3.33 (1H, m), 3.52–3.56 (1H, m), 3.68–3.74 (2H, m), 4.85 (1H, br s), 5.15 (2H, br s), 6.97 (1H, s), 7.11 (1H, d, J=15.6 Hz), 7.15 (1H, dd, J=1.8, 7.6 Hz), 7.34 (1H, d, J=16.5 Hz), 7.37 (1H, s), 7.49 (1H, d, J=16.5 Hz), 7.72 (1H, d, J=15.6 Hz), 8.89 (1H, d, J=7.6 Hz) ESI-MS; m/z: 566 (M$^+$+1)

(B) (E)-3-(2-{3-[(Aminocarbonyl)oxy]piperidino}-8-[(E)-2-(4-isopropyl-1,3-thiazol-2-yl)-1-ethenyl]-4-oxo-4H-pyrido[1,2-a]pyrimidin-3-yl)-2-propenoic acid The tert-butyl (E)-3-(2-{3-[(aminocarbonyl)oxy] piperidino}-8-[(E)-2-(4-isopropyl-1,3-thiazol-2-yl)-1-ethenyl]-4-oxo-4H-pyrido[1,2-a]pyrimidin-3-yl)-2-propenoate obtained in (B) was dissolved in 1,4-dioxane (100 μl), added with 4 N hydrochloric acid solution in 1,4-dioxane (400 μl), and stirred at room temperature for 15 hours. The reaction solution was further added with 4 N hydrochloric acid solution in 1,4-dioxane (400 μl) and stirred at room temperature for 7 hours. The reaction solution was concentrated, and the residue was subjected to azeotropy with toluene. The product was added with saturated aqueous sodium hydrogencarbonate, neutralized with phosphate buffer (pH 7–8), and extracted with a mixture of chloroform/methanol (10:1, v/v). The organic layer was dried over magnesium sulfate, and the solvent was evaporated under reduced pressure. The residue was purified by thin layer chromatography (chloroform:methanol=20:1, v/v) to obtain the title compound (8.1 mg, 36%).

$^1$H-NMR (CDCl$_3$+CD$_3$OD) δ: 1.35 (6H, d, J=7.1 Hz), 1.71 (1H, m), 1.90–1.96 (3H, m), 3.12–3.19 (1H, m), 3.38–3.40 (1H, m), 3.58–3.81 (3H, m), 4.87 (1H, br s), 6.99 (1H, s), 7.11 (1H, d, J=15.6 Hz), 7.21 (1H, d, J=7.7 Hz), 7.35 (1H, d, J=16.1 Hz), 7.40 (1H, s), 7.52 (1H, d, J=16.1 Hz), 7.76 (1H, d, J=15.6 Hz), 8.88 (1H, d, J=7.7 Hz) ESI-MS; m/z: 510 (M$^+$+1)

Example 104

2-(3-Hydroxypiperidino)-8-[(E)-2-(4-isopropyl-1,3-thiazol-2-yl)-1-ethenyl]-3-[(E)-2-(1H-1,2,3,4-tetrazol-5-yl)-1-ethenyl]-4H-pyrido[1,2-a]pyrimidin-4-one (A) tert-Butyl (E)-3-{2-[(3-acetyloxy)piperidino]-8-[(E)-2-(4-isopropyl-1,3-thiazol-2-yl)-1-ethenyl]-4-oxo-4H-pyrido[1,2-a]pyrimidin-3-yl}-2-propenoate tert-Butyl (E)-3-{2-(3-formyloxypiperidino)-8-[(E)-2-(4-isopropyl-1,3-thiazol-2-yl)-1-ethenyl]-4-oxo-4H-pyrido[1,2-a]pyrimidin-3-yl}-2-propenoate (115 mg, 0.209 mmol) was dissolved in methanol (2.0 ml), added with 1 N aqueous sodium hydroxide (627 μl), and stirred at room temperature for 10 minutes. The reaction solution was added with 1 N hydrochloric acid (627 μl) and extracted with chloroform. The organic layer was dried over magnesium sulfate, and the solvent was evaporated under reduced pressure. The residue was dissolved in dichloromethane (2.0 ml), added with 4-dimethylaminopyridine (51.0 mg, 0.418 mmol) and acetic anhydride (29.6 μl), and then the mixture was stirred at room temperature for 10 minutes. The reaction mixture was added with 1 N hydrochloric acid and extracted with chloroform. The organic layer was dried over magnesium sulfate, and the solvent was evaporated under reduced pressure. The residue was purified by silica gel column chromatography (n-hexane:ethyl acetate=5:1→3:1→2:1, v/v) to obtain the title compound (121 mg, quantitative).

¹H-NMR (CDCl₃) δ: 1.35 (6H, d, J=6.8 Hz), 1.52 (9H, s), 1.70–1.78 (2H, m), 1.90–2.02 (2H, m), 2.06 (3H, s), 3.12–3.19 (1H, m), 3.47–3.52 (1H, m), 3.61 (2H, dd, J=7.1, 13.2 Hz), 3.88 (1H, dd, J=3.3, 13.2 H), 4.96–5.00 (1H, m), 6.96 (1H, s), 7.06 (1H, d, J=15.6 Hz), 7.13 (1H, dd, J=2.0, 7.6 Hz), 7.33–7.37 (2H, m), 7.48 (1H, d, J=16.1 Hz), 7.50 (1H, d J=15.6 Hz), 7.50 (1H, d, J=15.6 Hz), 8.89 (1H, d, J=7.6 Hz) ESI-MS; m/z: 565 (M⁺+1)

(B) 1-(3-{(E)-3-[(2-Cyanoethyl)amino]-3-oxo-1-propenyl}-8-[(E)-2-(4-isopropyl-1,3-thiazol-2-yl)-1-ethenyl]-4-oxo-4H-pyrido[1,2-a]pyrimidin-2-yl)-3-piperidyl acetate The tert-Butyl (E)-3-{2-[(3-acetyloxy)piperidino]-8-[(E)-2-(4-isopropyl-1,3-thiazol-2-yl)-1-ethenyl]-4-oxo-4H-pyrido[1,2-a]pyrimidin-3-yl}-2-propenoate (121 mg, 0.214 mmol) obtained in (A) was dissolved in 1,4-dioxane (1.0 ml), added with 4 N hydrochloric acid solution in 1,4-dioxane, and then the mixture was stirred overnight at room temperature. The reaction mixture was concentrated, and the residue was suspended in dichloromethane (2.0 ml), added with 2-cyanoethylamine (79 μl, 1.07 mmol), BOPCl (109 mg, 0.429 mmol) and diisopropylethylamine (187 μl, 1.07 mmol), and stirred for 1 hour. The reaction mixture was further added with 2-cyanoethylamine (79 μl, 1.07 mmol), BOPCl (109 mg, 0.429 mmol) and diisopropylethylamine (187 μl, 1.07 mmol) and stirred overnight. The reaction mixture was added with saturated aqueous sodium hydrogencarbonate and extracted with a mixture of chloroform/methanol (10:1, v/v). The organic layer was dried over magnesium sulfate, and the solvent was evaporated under reduced pressure. The residue was purified by column chromatography (chloroform:methanol, 100:0→100:1→100:2, v/v) to obtain the title compound (53.3 mg, 48%).

¹H-NMR (CDCl₃) δ: 1.35 (6H, d, J=6.8 Hz), 1.70–1.79 (2H, m), 1.90–1.93 (1H, m) 2.01–2.04 (1H, m), 2.06 (3H, s), 2.71 (2H, t, J=6.5 Hz), 3.11–3.18 (1H, m), 3.46–3.51 (1H, m), 3.56–3.68 (4H, m), 3.92 (1H, dd, J=3.1,13.1 Hz), 4.95–5.00 (1H, m), 6.58–6.61 (1H, m), 6.96 (1H, s), 7.13 (1H, d, J=7.6 Hz), 7.25 (1H, d, J=15.1 Hz), 7.31–7.34 (2H, m), 7.47 (1H, d, J=16.4 Hz), 7.47 (1H, d, J=15.1 Hz), 7.52 (1H, d, J=15.1 H), 8.83 (1H, d, J=7.6 Hz) ESI-MS; m/z: 561 (M⁺+1)

(C) 1-(3-{(E)-2-[1-(2-Cyanoethyl)-1H-1,2,3,4-tetrazol-5-yl]-1-ethenyl}-8-[(E)-2-(4-isopropyl-1,3-thiazol-2-yl)-1-ethenyl]-4-oxo-4H-pyrido[1,2-a]pyrimidin-2-yl)-3-piperidyl acetate The 1-(3-{(E)-3-[(2-cyanoethyl)amino]-3-oxo-1-propenyl}-8-[(E)-2-(4-isopropyl -1,3-thiazol-2-yl)-1-ethenyl]-4-oxo-4H-pyrido[1,2-a]pyrimidin-2-yl)-3-piperidyl acetate (57.3 mg, 0.102 mmol) obtained in (B) was suspended in acetonitrile (3.0 ml), added with sodium azide (13.3 mg, 0.204 mmol) and trifluoromethanesulfonic acid anhydride (25.8 μl, 0.153 mmol) under ice cooling, and then the mixture was stirred at room temperature for 1 hour. The reaction mixture was further added with sodium azide (13.3 mg, 0.204 mmol) and trifluoromethanesulfonic acid anhydride (25.8 μl, 0.153 mmol), and stirred for 3 hours. The reaction mixture was added with saturated aqueous sodium hydrogencarbonate and extracted with chloroform, and the organic layer was dried over magnesium sulfate. The solvent was evaporated under reduced pressure, and the residue was purified by thin layer chromatography (hexane:ethyl acetate=1:2→1:3→0:1, v/v) to obtain the title compound (26.8 mg, 45%).

¹H-NMR (CDCl₃) δ: 1.36 (6H, d, J=6.9 Hz), 1.73–1.80 (4H, m), 2.04 (3H, s), 3.10 (2H, t, J=7.0 Hz), 3.13–3.19 (1H, m), 3.57–3.73 (3H, m), 3.91 (1H, dd, J=2.8, 13.1 Hz), 4.69 (2H, t, J=7.0 Hz), 4.95–4.98 (1H, m), 6.97 (1H, s), 7.17 (1H, dd, J=1.5, 7.5 Hz), 7.36 (1H, d, J=1.5 Hz), 7.36 (1H, d, J=16.0 Hz), 7.50 (1H, d, J=16.0 Hz), 7.75 (1H, d, J=15.3 Hz), 7.83 (1H, d, J=15.3 Hz), 8.86 (1H, d, J=7.5 Hz)

(D) 2-(3-Hydroxypiperidino)-8-[(E)-2-(4-isopropyl-1,3-thiazol-2-yl)-1-ethenyl]-3-[(E)-2-(1H-1,2,3,4-tetraazol-5-yl)-1-ethenyl]-4H-pyrido[1,2-a]pyrimidin-4-one The 1-(3-{(E)-2-[1-(2-cyanoethyl)-1H-1,2,3,4-tetraazol-5-yl]-1-ethenyl}-8[(E)-2-(4-isopropyl-1,3-thiazol-2-yl)-1-ethenyl]-4-oxo-4H-pyrido[1,2-a]pyrimidin-2-yl)3-piperidyl acetate (25.9 mg, 0.0442 mmol) obtained in (C) was suspended in methanol (0.5 ml) and anhydrous tetrahydrofuran (1.0 ml), added with sodium methoxide (4.8 mg, 0.0884 mmol) under ice cooling, and then stirred for 4 hours. The reaction solution was further added with sodium methoxide (4.8 mg, 0.0884 mmol) and stirred for 1 hour. The reaction mixture was added with saturated aqueous ammonium chloride and extracted with chloroform, and the organic layer was dried over magnesium sulfate. Then, the solvent was evaporated under reduced pressure, and the residue was purified by thin layer chromatography (chloroform:methanol=10:1, v/v) to obtain the title compound (12.7 mg, 59%).

¹H-NMR (CD₃OD) δ: 1.32 (6H, d, J=7.1 Hz), 1.56–1.61 (1H, m), 1.67–1.71 (1H, m), 1.89–1.92 (1H, m), 2.03–2.07 (1H, m), 3.08–3.19 (2H, m), 3.45 (1H, s), 3.76–3.80 (1H, m), 3.84–3.88 (1H, m), 4.00 (1H, dd, J=2.9, 12.9 Hz), 7.19 (1H, s), 7.34-7.36 (2H, m), 7.39 (1H, d, J=16.4 Hz), 7.51 (1H, d, J=16.1 Hz), 7.57 (1H, d, J=16.4 Hz), 7.74 (1H, d, J=16.1 Hz), 8.76 (1H, d, J=7.6 Hz) ESI-MS; m/z: 491 (M⁺+1)

Example 105

(E)-3-{2-[(3R)-3-Hydroxyhexahydro-1-pyridinyl]-8-[(E)-2-(4-isopropyl-1,3-thiazol-2-yl)-1-ethenyl]-4-oxo-4H-pyrido[1,2-a]pyrimidin-3-yl}-2-propenoic acid (A) tert-Butyl (E)-3-{2-[(3R)-3-Formyloxyhexahydro-1-pyridinyl]-8-[(E)-2-(4-isopropyl-1,3-thiazol-2-yl)-1-ethenyl]-4-oxo-4H-pyrido[1,2-a]pyrimidin-3-yl}-2-propenoate 2-Hydroxy-8-[(E)-2-(4-isopropyl-1,3-thiazol-2-yl)-1-ethenyl]-4H-pyrido[1,2-a]-pyrimidin-4-one (500 mg, 1.60 mmol) was treated in the same manner as in Example 102, (F) and (G) to obtain the title compound (488 mg, 56%).

¹H-NMR (CDCl₃) δ: 1.35 (6H, d, J=6.8 Hz), 1.52 (9H, s), 1.73–1.75 (1H, m), 1.83–1.85 (1H, m), 1.95–2.03 (2H, m), 3.13–3.17 (1H, m), 3.54–3.60 (2H, m), 3.71 (1H, dd, J=6.2, 13.5 Hz), 3.82 (1H, dd, J=3.2, 13.5 Hz), 5.14–5.16 (1H, m), 6.97 (1H, s), 7.07 (1H, d, J=15.6 Hz), 7.14 (1H, dd, J=1.6, 7.6 Hz), 7.34–7.37 (2H, m), 7.49 (1H, d, J=16.0 Hz), 7.51 (1H, d, J=15.6 Hz), 8.10 (1H, s), 8.89 (1H, d, J=7.6 Hz)

(B) tert-Butyl (E)-3-{2-[(3R)-3-Hydroxyhexahydro-1-pyridinyl]-8-[(E)-2-(4-isopropyl-1,3-thiazol-2-yl)-1-ethenyl]-4-oxo-4H-pyrido[1,2-a]pyrimidin-3-yl}-2-propenoate The tert-butyl (E)-3-{2-[(3R)-3-formyloxyhexahydro-1-pyridinyl]-8-[(E)-2-(4-isopropyl-1,3-thiazol-2-yl)-1- ethenyl]-4-oxo-4H-pyrido[1,2-a]pyrimidin-3-yl}-2-propenoate (488 mg, 0.886 mmol) obtained in (A) was treated in the same manner as in Example 102, (H) to obtain the title compound (373 mg, 81%).

$^1$H-NMR (CDCl$_3$) δ: 1.35 (6H, d, J=6.8 Hz), 1.52 (9H, s), 1.82–1.88 (4H, m), 3.11–3.18 (1H, m), 3.54–3.67 (3H, m), 3.95–3.98 (1H, m), 4.03 (1H, br s), 6.97 (1H, s), 7.05 (1H, d, J=15.7 Hz), 7.16 (1H, dd, J=1.8, 7.6 Hz), 7.34 (1H, d, J=16.1 Hz), 7.34 (1H, s), 7.49 (1H, d, J=16.1 Hz), 7.50 (1H, d, J=15.7 Hz), 8.89 (1H, d, J=7.6 Hz)

(C) (E)-3-{2-[(3R)-3-Hydroxyhexahydro-1-pyridinyl]-8-[(E)-2-(4-isopropyl-1,3-thiazol-2-yl)-1-ethenyl]-4-oxo-4H-pyrido[1,2-a]pyrimidin-3-yl}-2-propenoic acid tert-Butyl (E)-3-{2-[(3R)-3-hydroxyhexahydro-1-pyridinyl]-8-[(E)-2-(4-isopropyl-1,3-thiazol-2-yl)-1-ethenyl]-4-oxo-4H-pyrido[1,2-a]pyrimidin-3-yl}-2-propenoate (105 mg, 0.201 mmol) obtained in (B) was treated in the same manner as in Example 102, (I) to obtain the title compound (64.0 mg, 68%).

$^1$H-NMR (DMSO-d$_6$) δ: 1.27 (6H, d, J=6.8 Hz), 1.40–1.45 (1H, m), 1.54-1.57 (1H, m), 1.80–1.83 (1H, m), 1.89–1.93 (1H, m), 2.96–3.19 (2H, m), 3.60 (1H, m), 3.88–3.90 (1H, m,), 4.92 (1H, br s), 6.87 (1H, d, J=15.5 Hz), 7.40 (1H,S), 7.43 (1H, d, J=15.5 Hz), 7.54 (1H, d, J=16.1 Hz), 7.58–7.59 (2H, m), 7.85 (1H, d, J=16.1 Hz), 8.74 (1H, d, 8.1 Hz)

Example 106

(E)-3-{2-[(3S)-3-Hydroxyhexahydro-1-pyridinyl]-8-[(E)-2-(4-isopropyl-1,3-thiazol-2-yl)-1-ethenyl]-4-oxo-4H-pyrido[1,2-a]pyrimidin-3-yl}-2-propenoic acid (A) tert-Butyl (E)-3-{2-[(3S)-3-formyloxyhexahydro-1-pyridinyl]-8-[(E)-2-(4-isopropyl-1,3-thiazol-2-yl)-1-ethenyl]-4-oxo-4H-pyrido[1,2-a]pyrimidin-3-yl}-2-propenoate 2-Hydroxy-8-[(E)-2-(4-isopropyl-1,3-thiazol-2-yl)-1-ethenyl]-4H-pyrido[1,2-a]-pyrimidin-4-one(500 mg, 1.60 mmol) was treated in the same manner as in Example 102, (F) and (G) to obtain the title compound (164 mg, 19%).

$^1$H-NMR (CDCl$_3$) δ: 1.35 (6H, d, J=6.9 Hz), 1.52 (9H, s), 1.73–1.75 (1H, m), 1.81–1.85 (1H, m), 1.96–2.05 (2H, m), 3.11–3.18 (1H, m), 3.54–3.57 (2H, m), 3.70 (1H, dd, J=6.5, 13.1 Hz), 3.82 (1H, d, J=13.5 Hz), 5.15 (1H, m), 6.96 (1H, s), 7.06 (1H, d, J=15.4 Hz), 7.14 (1H, dd, J=1.6, 7.4 Hz), 7.32–7.36 (2H, m), 7.48 (1H, d, J=15.9 Hz), 7.51 (1H, d, J=15.4 Hz), 8.10 (1H, s), 8.87 (1H, d, J=7.4 Hz)

(B) tert-Butyl (E)-3-{2-[(3S)-3-hydroxyhexahydro-1-pyridinyl]-8-[(E)-2-(4-isopropyl-1,3-thiazol-2-yl)-1-ethenyl]-4-oxo-4H-pyrido[1,2-a]pyrimidin-3-yl}-2-propenoate The tert-butyl (E)-3-{2-[(3S)-3-formyloxyhexahydro-1-pyridinyl]-8-[(E)-2-(4-isopropyl-1,3-thiazol-2-yl)-1-ethenyl]-4-oxo-4H-pyrido[1,2-a]pyrimidin-3-yl}-2-propenoate (164 mg, 0.298 mmol) obtained in (A) was treated in the same manner as in Example 102, (H) to obtain the title compound (156 mg, 100%).

$^1$H-NMR (CDCl$_3$) δ: 1.35 (6H, d, J=6.8 Hz), 1.52 (9H, s), 1.81–1.91 (4H, m), 3.11–3.18 (1H, m), 3.60–3.63 (3H, m), 3.86–3.89 (1H, m), 4.02 (1H, brs), 6.97 (1H, s), 7.04 (1H, d, J=15.6 Hz), 7.13 (1H, dd, J=1.7, 7.6 Hz), 7.31 (1H, d, J=1.7 Hz), 7.32 (1H, d, J=16.0 Hz), 7.48 (1H, d, J=16.0 Hz), 7.49 (1H, d, J=15.6 Hz), 8.87 (1H, d, J=7.6 Hz)

(C) (E)-3-{2-[(3S)-3-Hydroxyhexahydro-1-pyridinyl]-8-[(E)-2-(4-isopropyl-1,3-thiazol-2-yl)-1-ethenyl]-4-oxo-4H-pyrido[1,2-a]pyrimidin-3-yl}-2-propenoic acid The tert-butyl (E)-3-{2-[(3S)-3-hydroxyhexahydro-1-pyridinyl]-8-[(E)-2-(4-isopropyl-1,3-thiazol-2-yl)-1-ethenyl]-4-oxo-4H-pyrido[1,2-a]pyrimidin-3-yl}-2-propenoate (72.7 mg, 0.139 mmol) obtained in (B) was treated in the same manner as in Example 102, (I) to obtain the title compound (35.5 mg, 55%).

$^1$H-NMR (DMSO-d$_6$) δ: 1.29 (6H, d, J=6.8 Hz), 1.42–1.45 (1H, m), 1.56–1.59 (1H, m), 1.81–1.85 (1H, m), 1.93–1.95 (1H, m), 2.97–3.20 (3H, m), 3.62 (1H, m), 3.69–3.74 (1H, m), 3.89–3.92 (1H, m), 4.90 (1H, br s), 6.89 (1H, d, J=15.4 Hz), 7.42-7.46 (1H, m), 7.55 (1H, d, J=16.2 Hz), 7.61–7.62 (2H, m), 7.87 (1H, d, J=16.2 Hz), 8.76 (1H, d, 7.6 Hz), 11.84 (1H, br s)

Example 107

(E)-3-(2-{(3R)-3-[(Aminocarbonyl)oxy]hexahydro-1-pyridinyl}-8-[(E)-2-(4-isopropyl-1,3-thiazol-2-yl)-1-ethenyl]-4-oxo-4H-pyrido[1,2-a]pyrimidin-3-yl)-2-propenoic acid The tert-butyl (E)-3-{2-[(3R)-3-hydroxyhexahydro-1-pyridinyl]-8-[(E)-2-(4-isopropyl-1,3-thiazol-2-yl)-1-ethenyl]-4-oxo-4H-pyrido[1,2-a]pyrimidin-3-yl}-2-propenoate (109 mg, 0.209 mmol) was treated in the same manner as in Example 103, (A) and (B) to obtain the title compound (89.7 mg, 84%).

$^1$H-NMR (DMSO-d$_6$) δ: 1.29 (6H, d, J=6.9 Hz), 1.66 (2H, m), 1.88–1.98 (2H, m), 3.05–3.12 (1H, m), 3.36–3.54 (3H, m), 3.86 (1H, d, J=10.0 Hz), 4.60 (1H, m), 6.47 (2H, br s), 6.90 (1H, d, J=15.2 Hz), 7.42 (1H, s), 7.45 (1H, d, J=15.2 Hz), 7.55 (1H, d, J=16.2 Hz), 7.62–7.64 (2H, m), 7.88 (1H, d, J=16.2 Hz), 8.77 (1H, d, J=7.3 Hz), 11.90 (1H, br s)

Example 108

(E)-3-(2-{(3S)-3-[(Aminocarbonyl)oxy]hexahydro-1-pyridinyl}-8-[(E)-2-(4-isopropyl-1,3-thiazol-2-yl)-1-ethenyl]-4-oxo-4H-pyrido[1,2-a]pyrimidin-3-yl)-2-propenoic acid The tert-butyl (E)-3-{2-[(3S)-3-hydroxyhexahydro-1-pyridinyl]-8-[(E)-2-(4-isopropyl-1,3-thiazol-2-yl)-1-ethenyl]-4-oxo-4H-pyrido[1,2-a]pyrimidin-3-yl}-2-propenoate (83.6 mg, 0.160 mmol) was treated in the same manner as in Example 103 (A) and (B) to obtain the title compound (59.4 mg, 73%).

$^1$H-NMR (DMSO-d$_6$) δ: 1.29 (6H, d, J=6.6 Hz), 1.66 (2H, m), 1.88 (1H, m), 1.98 (1H, m), 3.06–3.13 (1H, m), 3.43–3.51 (3H, m), 3.86 (1H, d, J=11.7 Hz), 4.61 (1H, m), 6.47 (2H, brs), 6.90 (1H, d, J=15.6 Hz), 7.42 (1H, s), 7.46 (1H, d, J=15.6 Hz), 7.55 (1H, d, J=16.1 Hz), 7.62–7.64 (2H, m), 7.88 (1H, d, J=16.1 Hz), 8.77 (1H, d, J=7.3 Hz), 11.90 (1H, brs)

Example 109

(E)-3-(2-{3-[(Dimethylamino)carbonyl]piperidino}-8-[(E)-2-(4-isopropyl-1,3-thiazol-2-yl)-1-ethenyl]-4-oxo-4H-pyrido[1,2-a]pyrimidin-3-yl)-2-propenoic acid (A) N3,N3-Dimethyl-1-{8-[(E)-2-(4-isopropyl-1,3-thiazol-2-yl)-1-ethenyl]-4-oxo-4H-pyrido[1,2-a]pyrimidin-2-yl}-3-piperidinecarboxamide The 2-hydroxy-8-[(E)-2-(4-isopropyl-1,3-thiazol-2-yl)-1-ethenyl]-4H-pyrido-[1,2-a]pyrimidin-4-one (164 mg, 0.523 mmol) obtained in Example 101, (E) was dissolved in anhydrous tetrahydrofuran (2.5 ml) and anhydrous dimethylformamide (2.5 ml), added with 4-dimethylaminopyridine (83.0 mg, 0.680 mmol) and p-toluenesulfonyl chloride (110 mg, 0.576 mmol), and then the mixture was stirred at 0° C. for 3 hours. Subsequently, the reaction solution was added with triethylamine (729 μl, 5.23 mmol) and N3,N3-dimethyl-3-piperidinecarboxamide trifluoroacetic acid salt (707 mg, 2.62 mmol) and stirred at 0° C. for 1 hour, at room temperature for 30 minutes and at 60° C. for 19 hours. Then, the reaction solution was added with triethylamine (40.0 μl , 0.287 mmol) and N3,N3-dimethyl-3-piperidinecarboxamide trifluoroacetic acid salt (400 mg, 1.48 mmol) and stirred at 60° C. for 5 hours. The reaction mixture was concentrated, added with saturated aqueous ammonium chloride, and then extracted with chloroform. The organic layer was dried over sodium sulfate, and the solvent was evaporated under reduced pressure. The residue was purified by silica gel column chromatography (chloroform:methanol=100:1→100:3, v/v) to obtain the title compound (168 mg, 71%).

$^1$H-NMR (CDCl$_3$) δ: 1.36 (6H, d, J=6.4 Hz), 1.52–1.62 (1H, m), 1.73 (1H, s), 1.81–1.97 (3H, m), 2.70–2.76 (1H, m), 2.99 (3H, s), 3.14 (3H, s), 3.04–3.18 (2H, m), 4.35 (1H, m), 4.65 (1H, m), 5.63 (1H, s), 6.95 (1H, s), 7.03 (1H, d, J=7.3 Hz), 7.23 (1H, d J=16.1 Hz), 7.45 (1H, d, J=16.1 Hz), 8.82 (1H, d, J=7.3 Hz)

(B) tert-Butyl (E)-3-(2-{3-[(dimethylamino)carbonyl]piperidino}-8-[(E)-2-(4-isopropyl-1,3-thiazol-2-yl)-1-ethenyl]-4-oxo-4H-pyrido[1,2-a]pyrimidin-3-yl)-2-propenoate Dimethylformamide (3.0 ml) was added with phosphorus oxychloride (104 μl, 1.12 mmol) under ice cooling and stirred at room temperature for 30 minutes. This was added to the N3,N3-dimethyl-1-{8-[(E)-2-(4-isopropyl-1,3-thiazol-2-yl)-1-ethenyl]-4-oxo-4H-pyrido[1,2-a]pyrimidin-2-yl}-3-piperidinecarboxamide (168 mg, 0.372 mmol) obtained in (A) and dissolved in dimethylformamide (4.0 ml) under ice cooling, and stirred at room temperature for 2 hours. The reaction mixture was concentrated, added with saturated aqueous sodium hydrogencarbonate, and then extracted with chloroform. The organic layer was dried over sodium sulfate, and the solvent was evaporated under reduced pressure. The residue was suspended in anhydrous tetrahydrofuran (3 ml) and anhydrous N,N-dimethylformamide (3 ml), added with (tert-butoxycarbonylmethylene)triphenylphosphorane (280 mg, 0.744 mmol), and stirred at 50° C. for 37 hours. The reaction mixture was further added with (tert-butoxycarbonylmethylene)triphenylphosphorane (280 mg, 0.744 mmol), stirred at 80° C. for 5 hours, and then concentrated, and the residue was purified by silica gel column chromatography (chloroform:methanol=100:1→100:2, v/v) to obtain the title compound (167 mg, 78%).

$^1$H-NMR (CDCl$_3$) δ: 1.36 (6H, d, J=6.8 Hz), 1.51 (9H, s), 1.65–1.68 (1H, m), 1.81–1.84 (1H, m), 1.89–1.94 (2H, m), 2.98 (3H, s), 3.04–3.17 (4H, m), 3.22 (3H, s), 4.05 (1H, m,), 4.24 (1H, m), 6.96 (1H, s), 7.06 (1H, d, J=15.6 Hz), 7.25 (1H, d, J=7.6), 7.34 (1H, d, J=16.1 Hz), 7.46 (1H, s), 7.47 (1H, d, J=16.1 Hz), 7.52 (1H, d, J=15.6), 8.89 (1H, d, J=7.6 Hz)

(C) (E)-3-(2-{3-[(Dimethylamino)carbonyl]piperidino}-8-[(E)-2-(4-isopropyl-1,3-thiazol-2-yl)-1-ethenyl]-4-oxo-4H-pyrido[1,2-a]pyrimidin-3-yl)-2-propenoic acid The tert-butyl (E)-3-(2-{3-[(dimethylamino)carbonyl]piperidino}-8-[(E)-2-(4-isopropyl-1,3-thiazol-2-yl)-1-ethenyl]-4-oxo-4H-pyrido[1,2-a]pyrimidin-3-yl)-2-propenoate (71.0 mg, 0.123 mmol) obtained in (B) was added with trifluoroacetic acid (3.0 ml) and stirred at room temperature for 2 hours. The trifluoroacetic acid in the reaction mixture was evaporated under reduced pressure, and the residue was neutralized with 0.1 N sodium hydroxide and phosphate buffer (pH 7–8) and extracted with chloroform. The organic layer was dried over sodium sulfate, and the solvent was evaporated under reduced pressure. The residue was purified by thin layer chromatography (chloroform:methanol and chloroform:methanol:water, 8:3:1, v/v, lower layer) to obtain the title compound (39.0 mg, 61%).

$^1$H-NMR (DMSO-d$_6$) δ: 1.29 (6H, d, J=6.8 Hz), 1.64 (1H, m), 1.72 (2H, m), 1.87 (1H, m), 2.84 (3H, s), 3.04 (2H, m), 3.07–3.11 (2H, m), 3.15 (3H, s), 3.92 (1H, m), 4.08 (1H, m), 6.89 (1H, d, J=15.4), 7.42 (1H, s), 7.43 (1H, d, J=15.4 Hz), 7.56 (1H, d, J=16.1 Hz), 7.60 (1H, s), 7.62 (1H, d, J=7.8 Hz), 7.87 (1H, d, J=16.1 Hz), 8.77 (1H, d, J=7.8 Hz) EI-MS; m/z: 522 (M$^+$+1)

Example 110

(E)-3-(8-[(E)-2-(4-Isopropyl-1,3-thiazol-2-yl)-1-ethenyl]-2-{3-[(methylamino)carbonyl]piperidino}-4-oxo-4H-pyrido[1,2-a]pyrimidin-3-yl)-2-propenoic acid (A) N3-Methyl-1-{8-[(E)-2-(4-isopropyl-1,3-thiazol-2-yl)-1-ethenyl]-4-oxo-4H-pyrido-[1,2-a]pyrimidin-2-yl}-3-piperidinecarboxamide 2-Hydroxy-8-[(E)-2-(4-isopropyl-1,3-thiazol-2-yl)-1-ethenyl]-4H-pyrido[1,2-a]-pyrimidin-4-one (157 mg, 0.501 mmol) was dissolved in anhydrous tetrahydrofuran (2.5 ml) and anhydrous dimethylformamide (2.5 ml), added with 4-dimethylamino-pyridine (80.0 mg, 0.651 mmol) and p-toluenesulfonyl chloride (105 mg, 0.551 mmol), and stirred at 0° C. for 1.5 hours. Subsequently, the reaction mixture was added with triethylamine (698 μl, 5.01 mmol) and N3-methyl-3-piperidinecarboxamide hydrochloride (448 mg, 2.50 mmol), and then the mixture was stirred at 60° C. for 5.5 hours. The reaction mixture was concentrated, added with saturated aqueous ammonium chloride, and then extracted with chloroform. The organic layer was dried over sodium sulfate, and the solvent was evaporated under reduced pressure. The residue was purified by silica gel column chromatography (chloroform:methanol= 100:2→100:3, v/v) to obtain the title compound (174 mg, 79%).

$^1$H-NMR (CDCl$_3$) δ: 1.35 (6H, d, J=6.8 Hz), 1.60 (1H, m), 1.73 (1H, m), 1.94 (1H, m), 2.02–2.05 (1H, m), 2.36–2.38 (1H, m), 2.83 (3H, d, J=4.9), 3.13–3.20 (2H, m), 3.59 (1H, dd, J=8.8, 13.7), 4.00 (1H, m), 4.24 (1H, m), 5.62 (1H, s), 6.95 (1H, s), 7.05 (1H, d, J=7.8 Hz), 7.27 (1H, s), 7.33 (1H, d, J=16.1 Hz), 7.46 (1H, d, J=16.1 Hz), 8.83 (1H, d, J=7.8 Hz)

(B) tert-Butyl (E)-3-(8-[(E)-2-(4-isopropyl-1,3-thiazol-2-yl)-1-ethenyl]-2-{3-[(methylamino)carbonyl]piperidino}-4-oxo-4H-pyrido[1,2-a]pyrimidin-3-yl)-2-propenoate Dimethylformamide (3.0 ml) was added with phosphorus oxychloride (111 μl, 1.19 mmol) under ice cooling and stirred at room temperature for 30 minutes. The mixture was added to the N3-methyl-1-{8-[(E)-2-(4-isopropyl-1,3-thiazol-2-yl)-1-ethenyl]-4-oxo-4H-pyrido[1,2-a]pyrimidin- 2-yl}-3-piperidinecarboxamide (174 mg, 0.398 mmol) obtained in (A) and dissolved in dimethylformamide (4.0 ml) under ice cooling, and then the mixture was stirred at room temperature for 2 hours. The reaction mixture was concentrated, added with saturated aqueous sodium hydrogencarbonate, and then extracted with chloroform. The organic layer was dried over sodium sulfate, and the solvent was evaporated under reduced pressure. The residue was suspended in anhydrous tetrahydrofuran (3 ml) and dimethylformamide (3 ml), added with (tert-butoxycarbonylmethylene)triphenylphosphorane (449 mg, 1.19 mmol) and stirred at 75° C. for 24 hours. The reaction mixture was concentrated, and the residue was purified by silica gel column chromatography (chloroform:methanol= 100:0→100:3, v/v) to obtain the title compound (192 mg, 86%).

$^1$H-NMR (CDCl$_3$) δ: 1.35 (6H, d, J=7.1 Hz), 1.54 (9H, m), 1.65–1.68 (1H, m), 1.85–1.90 (1H, m), 1.95–2.00 (2H, m), 2.77 (3H, d, J=4.6), 2.82 (1H, m), 2.92 (1H, m), 3.11–3.17 (2H, m), 3.90–4.00 (1H, m), 4.45–4.50 (1H, m), 6.97 (1H, s), 7.09 (1H, d, J=15.6 Hz), 7.12 (1H, d, J=1.7), 7.30 (1H, d, J=1.7 Hz), 7.34 (1H, d, J=16.1 Hz), 7.40–7.70 (2H, m), 8.86 (1H, d, J=7.3 Hz)

(C) (E)-3-(8-[(E)-2-(4-Isopropyl-1,3-thiazol-2-yl)-1-ethenyl]-2-{3-[(methylamino)-carbonyl]piperidino}-4-oxo-4H-pyrido[1,2-a]pyrimidin-3-yl)-2-propenoic acid The tert-butyl (E)-3-(8-[(E)-2-(4-isopropyl-1,3-thiazol-2-yl)-1-ethenyl]-2-{3-[(methylamino)carbonyl]piperidino}-4-oxo-4H-pyrido[1,2-a]pyrimidin-3-yl)-2-propenoate (192 mg, 0.341 mmol) obtained in (B) was added with trifluoroacetic acid (5.0 ml) and stirred at room temperature for 1.5 hours. After the reaction was completed, the trifluoroacetic acid was evaporated under reduced pressure, and the residue was neutralized with 0.1 N sodium hydroxide and phosphate buffer (pH 7–8) and extracted with chloroform. The organic layer was dried over sodium sulfate, and the solvent was evaporated under reduced pressure. The residue was purified by thin layer chromatography (chloroform:methanol and chloroform:methanol:water=8:3:1, v/v, lower layer) to obtain the title compound (49.0 mg, 28%).

$^1$H-NMR (DMSO-d$_6$) δ: 1.29 (6H, d, J=6.8 Hz), 1.62–1.71 (2H, m), 1.77 (1H, m), 1.90 (1H, m), 2.58 (3H, d, J=4.6 Hz), 3.05–3.13 (3H, m), 3.27 (1H, m), 3.89 (1H, m), 4.08 (1H, m), 6.89 (1H, d, J=15.6 Hz), 7.42 (1H, s), 7.42 (1H, d, J=15.6 Hz), 7.54 (1H, d, J=16.1 Hz), 7.62 (1H, d, J=7.6 Hz), 7.67 (1H, s), 7.79 (1H, s), 7.88 (1H, d, J=16.1 Hz), 8.77 (1H, d, J=7.6 Hz) EI-MS; m/z: 508 (M$^+$+1)

Example 111

8-(E)-2-[4-(tert-Butyl)-1,3-thiazol-2-yl]-1-ethenyl-3-(2H-1,2,3,4-tetraazol-5-yl)-4H-pyrido[1,2-a]pyrimidin-4-one (A) [4-(tert-Butyl)-1,3-thiazol-2-yl]methanol Ethyl thiooxamate (4.94 g, 37.1 mmol) was dissolved in anhydrous ethanol (250 ml), added with 1-bromopinacolone (4.99 ml, 37.1 mmol), and refluxed by heating for 4 hours. The reaction mixture was concentrated, neutralized with saturated aqueous sodium hydrogencarbonate, and extracted with ethyl acetate. The organic layer was dried over sodium sulfate, and then the solvent was evaporated under reduced pressure. The residue was dissolved in anhydrous ethanol (200 ml), added with sodium hydroboride (2.10 g, 55.6 mmol), and stirred at room temperature for 16 hours. The reaction solution was further added with sodium borohydride (500 mg, 13.2 mmol) and stirred at room temperature for 4 hours, and then the solvent was evaporated under reduced pressure. The residue was cooled to –78° C., and the resulting white solid was taken by filtration to obtain the title compound (2.77 g, 44%).

$^1$H-NMR (CDCl$_3$) δ: 1.33 (9H, s), 4.92 (2H, s), 6.86 (1H, s)

(B) 4-(tert-Butyl)-1,3-thiazol-2-carbaldehyde

[4-(tert-Butyl)-1,3-thiazol-2-yl]methanol (2.77 g, 16.2 mmol) obtained in (A) was dissolved in methylene chloride (45 ml), added with pyridinium dichromate (12.2 g, 32.3 mmol), and stirred at room temperature for 13.5 hours. After insoluble solids were removed, the reaction solution was evaporated, and the residue was purified by silica gel column chromatography (dichloromethane) to obtain the title compound (2.71 g, 99%).

$^1$H-NMR (CDCl$_3$) δ: 1.40 (9H, s), 7.36 (1H, s), 9.98 (1H, s)

(C) tert-Butyl N-(4-{2-[4-(tert-butyl)-1,3-thiazol-2-yl]-2-hydroxyethyl}-2-pyridyl)-carbamate tert-Butyl N-(4-methyl-2-pyridyl)carbamate (3.11 g, 14.9 mmol) was dissolved in anhydrous tetrahydrofuran (50 ml), added with n-butyl lithium (1.59 M in n-hexane, 19.7 ml, 31.3 mmol) at –78° C. under argon atmosphere, and stirred at room temperature for 1.5 hours. The reaction mixture was cooled to –78° C. again, then added with a solution of the 4-(tert-butyl)-1,3-thiazol-2-carbaldehyde (2.30 g, 13.6 mmol) obtained in (B) in anhydrous tetrahydrofuran (10 ml), and stirred for 30 minutes. The reaction mixture was added with saturated aqueous ammonium chloride, warmed to room temperature and extracted with chloroform. The organic layer was dried over sodium sulfate, and the solvent was evaporated under reduced pressure. The residue was purified by silica gel column chromatography (n-hexane:ethyl acetate=2:1→1:1, v/v) to obtain the title compound (2.29 g, 45%).

$^1$H-NMR (CDCl$_3$) δ: 1.32 (9H, s), 1.53 (9H, s), 3.08 (1H, dd, J=8.4, 13.8 Hz), 3.29 (1H, dd, J=4.2, 13.8), 5.23 (1H, dd, J=4.2, 8.4 Hz), 6.83 (1H, s), 6.85 (1H, dd, J=1.5, 5.1 Hz), 7.67 (1H, s), 7.87 (1H, s), 8.13 (1H, d, J=5.1 Hz)

(D) tert-Butyl N-(4-(E)-{2-[4-(tert-butyl)-1,3-thiazol-2-yl]-1-ethenyl}-2-pyridyl)-carbamate The tert-butyl N-(4-{2-[4-(tert-butyl)-1,3-thiazol-2-yl]-2-hydroxyethyl}-2-pyridyl)carbamate (1.80 g, 4.77 mmol) obtained in (C) was dissolved in anhydrous tetrahydrofuran (20 ml), added with triethylamine (2.33 ml, 16.7 mmol) and methanesulfonyl chloride (738 μl, 9.54 mmol), and stirred at 0° C. for 3.5 hours. After insoluble solids were removed, the reaction mixture was washed with tetrahydrofuran, and the solvent was evaporated under reduced pressure. The residue was dissolved in toluene (30 ml), added with 1,8-diazabicyclo[5.4.0]undec-7-ene (1.07 ml, 7.15 mmol), and refluxed by heating for 1 hour. The reaction mixture was concentrated, and the residue was purified by silica gel column chromatography (n-hexane:ethyl acetate=3:1→2:1, v/v) to obtain the title compound (1.23 g, 72%).

$^1$H-NMR (CDCl$_3$) δ: 1.37 (9H, s), 1.55 (9H, s), 6.89 (1H, s), 7.08 (1H, dd, J=1.5, 5.4 Hz), 7.29 (1H, d, J=16.4 Hz), 7.51 (1H, d, J=16.4 Hz), 8.12 (1H, s), 8.09 (1H, s), 8.21 (1H, d, J=5.4 Hz)

(E) 4-(E)-2-[4-(tert-Butyl)-1,3-thiazol-2-yl]-1-ethenyl-2-pyridinamine

The tert-butyl N-(4-(E)-2-[4-(tert-butyl)-1,3-thiazol-2-yl]-1-ethenyl-2-pyridyl)-carbamate (585 mg, 1.63 mmol) obtained in (D) was dissolved in trifluoroacetic acid (15 ml) and stirred at room temperature for 1 hour. The reaction mixture was concentrated, neutralized with saturated aqueous sodium hydrogencarbonate, and extracted with chloroform. The organic layer was dried over sodium sulfate, and the solvent was evaporated under reduced pressure to obtain the title compound (422 mg, 100%).

$^1$H-NMR (CDCl$_3$) δ: 1.38 (9H, s), 6.62 (1H, s), 6.84 (1H, d, J=6.0 Hz), 6.93 (1H, s), 7.17 (1H, d, J=16.2 Hz), 7.42 (1H, d, J=16.2 Hz), 7.92 (1H, d, J=6.0 Hz)

(F) 8-(E)-2-[4-(tert-Butyl)-1,3-thiazol-2-yl]-1-ethenyl-3-(2H-1,2,3,4-tetraazol-5-yl)-4H-pyrido[1,2-a]pyrimidin-4-one Ethyl 3-(dimethylamino)-2-[2-(4-methoxybenzyl)-2H-1,2,3,4-tetraazol-5-yl]-2-propenoate (150 mg, 0.453 mmol) was dissolved in propionic acid (2.0 ml), added to the 4-(E)-2-[4-(tert-butyl)-1,3-thiazol-2-yl]-1-ethenyl-2-pyridinamine (98.0 mg, 0.378 mmol) obtained in (E), and refluxed by heating for 3 hours. The reaction mixture was concentrated, and the residue was purified by silica gel column chromatography (chloroform) to obtain the title compound (175 mg, 93%).

$^1$H-NMR (CDCl$_3$) δ: 1.40 (9H, s), 3.79 (3H, s), 5.81 (2H, s), 6.89 (2H, d, J=8.3 Hz), 7.02 (1H, s), 7.41 (1H, d, J=16.2 Hz), 7.42 (2H, d, J=8.3 Hz), 7.46 (1H, d, J=7.5), 7.60 (1H, d, J=16.2 Hz), 7.74 (1H, s), 9.21 (1H, d, J=7.5 Hz), 9.21 (1H, s)

(G) 8-(E)-2-[4-(tert-Butyl)-1,3-thiazol-2-yl]-1-ethenyl-3-(2H-1,2,3,4-tetraazol-5-yl)-4H-pyrido[1,2-a]pyrimidin-4-one The 8-(E)-2-[4-(tert-butyl)-1,3-thiazol-2-yl]-1-ethenyl-3-(2H-1,2,3,4-tetraazol-5-yl)-4H-pyrido[1,2-a]pyrimidin-4-one (170 mg, 0.340 mmol) obtained in (F) was added with trifluoroacetic acid (4.0 ml) and stirred at 60° C. for 3 hours. After the reaction was completed, the trifluoroacetic acid was evaporated under reduced pressure, and the residue was neutralized with 0.1 N sodium hydroxide and phosphate buffer (pH 7–8) and extracted with chloroform. The organic layer was dried over sodium sulfate, and the solvent was evaporated under reduced pressure. The yellow solid deposited from the residue was collected by filtration to obtain the title compound (20.0 mg, 15%).

$^1$H-NMR (DMSO-d$_6$) δ: 1.35 (9H, s), 7.47 (1H, s), 7.67 (1H, d, J=16.1 Hz), 8.03 (1H, d, J=16.1 Hz), 8.04 (1H, d, J=1.9 Hz), 8.13 (1H, d, J=1.9 Hz), 9.11 (1H, d, J=7.3 Hz), 9.17 (1H, s) EI-MS; m/z: 380 (M$^+$+1)

Example 112

(E)-3-{8-[2-(4-Isopropyl-1,3-thiazol-2-yl)ethyl]-4-oxo-2-(tetrahydro-3-furanylmethoxy)-4H-pyrido[1,2-a]pyrimidin-3-yl}-2-propenoic acid (A) tert-Butyl (E)-3-{8-[2-(4-isopropyl-1,3-thiazol-2-yl)ethyl]-4-oxo-2-(tetrahydro-3-furanylmethoxy)-4H-pyrido[1,2-a]pyrimidin-3-yl}-2-propenoate tert-Butyl (E)-3-(2-hydroxy-8-[2-(4-isopropyl-1,3-thiazol-2-yl)ethyl]-4-oxo-4H-pyrido[1,2-a]pyrimidin-3-yl)-2-propenoate (17 mg) was added with dimethylformamide (3 ml), diisopropylethylamine (500 ml) and 3-(iodomethyl)tetrahydrofuran (50 ml), and then the mixture was stirred at 80° C. for 16 hours. The reaction mixture was added with ethyl acetate and saturated brine, and the organic layer was further washed twice with saturated brine and dried over magnesium sulfate. After the solvent was evaporated under reduced pressure, the residue was purified by silica gel column chromatography to obtain the title compound (14 mg).

$^1$H-NMR (CDCl$_3$) δ: 1.29 (6H, d, J=7.1 Hz), 1.52 (9H, s), 1.75 (1H, m), 2.16 (1H, m), 2.82 (1H, m), 3.07 (1H, m), 3.26 (2H, m), 3.39 (2H, m), 3.71 (1H, m), 3.80 (1H, m). 3.92 (2H, m), 4.42 (2H, m), 6.74 (1H, s), 7.02 (1H, m), 7.13 (1H, d, J=15.8 Hz), 7.34 (1H, s), 7.91 (1H, d, J=15.8 Hz), 8.99 (1H, d, J=7.3 Hz)

(B) (E)-3-{8-[2-(4-Isopropyl-1,3-thiazol-2-yl)ethyl]-4-oxo-2-(tetrahydro-3-furanylmethoxy)-4H-pyrido[1,2-a]pyrimidin-3-yl}-2-propenoic acid The tert-butyl (E)-3-{8-[2-(4-isopropyl-1,3-thiazol-2-yl)ethyl]-4-oxo-2-(tetrahydro-3-furanylmethoxy)-4H-pyrido[1,2-a]pyrimidin-3-yl}-2-propenoate (10 mg) obtained in (A) was dissolved in methylene chloride (1 ml) and formic acid (1 ml), and then the mixture was stirred for 5 hours. After the solvent was evaporated under reduced pressure, the residue was purified by silica gel column chromatography to obtain the title compound (14 mg).

$^1$H-NMR (CDCl$_3$) δ: 1.29 (6H, d, J=6.6 Hz), 1.79 (1H, m), 2.16 (1H, m), 2.83 (1H, m), 3.07 (1H, m), 3.26 (2H, m), 3.39 (2H, m), 3.73 (2H, m), 3.81 (1H, m), 3.93 (2H, m), 4.42 (2H, m), 6.73 (1H, s), 7.02 (1H, m), 7.15 (1H, d, J=15.8 Hz), 7.33 (1H, s), 8.05 (1H, d, J=15.8 Hz), 8.99 (1H, d, J=6.5 Hz)

Example 113

8-[2-(4-Isopropyl-1,3-thiazol-2-yl)ethyl]-3-[(E)-2-(1H-1,2,3,4-tetrazol-5-yl)-1-ethenyl]-2-(tetrahydro-3-furanylmethoxy)-4H-pyrido[1,2-a]pyrimidin-4-one (A) (E)-2-{8-[2-(4-Isopropyl-1,3-thiazol-2-yl)ethyl]-4-oxo-2-(tetrahydro-3-furanylmethoxy)-4H-pyrido[1,2-a]pyrimidin-3-yl}-1-ethenylcyanide (E)-2-{2-Hydroxy-8-[2-(4-isopropyl-1,3-thiazol-2-yl)ethyl]-4-oxo-4H-pyrido-[1,2-a]pyrimidin-3-yl}-1-ethenylcyanide (100 mg) was added with dimethylformamide (5 ml), diisopropylethylamine (500 ml) and 3-(iodomethyl)tetrahydrofuran (200 ml), and then the mixture was stirred at 80° C. for 2 hours and further stirred overnight at room temperature. After the reaction mixture was distributed between chloroform and water, the organic layer was dried over magnesium sulfate. After the solvent was evaporated under reduced pressure, the residue was purified by silica gel column chromatography to obtain the title compound (51 mg).

$^1$H-NMR (CDCl$_3$) δ: 1.29 (6H, d, J=6.8 Hz), 1.78 (1H, m), 2.16 (1H, m), 2.79 (1H, m), 3.05 (1H, m), 3.29 (2H, m), 3.38 (2H, m), 3.71 (1H, m), 3.82 (1H, m), 3.93 (2H, m), 4.42 (2H, m), 6.74 (1H, s), 6.68 (1H, d, J=16.3 Hz), 7.07 (1H, d, J=7.3 Hz), 7.37 (1H, s), 7.64 (1H, d, J=16.3 Hz), 8.97 (1H, d, J=7.3 Hz)

(B) 8-[2-(4-Isopropyl-1,3-thiazol-2-yl)ethyl]-3-[(E)-2-(1H-1,2,3,4-tetrazol-5yl)1-ethenyl]-2-(tetrahydro-3-furanylmethoxy)-4H-pyrido[1,2-a]pyrimidin-4-one $^1$H-NMR (CDCl$_3$) δ: 1.29 (6H, d, J=6.8 Hz), 1.80 (1H, m), 2.18 (1H, m), 2.86 (1H, m), 3.08 (1H, m), 3.27 (2H, m), 3.42 (2H, m), 3.80 (2H, m), 3.96 (2H, m), 4.47 (2H, m), 6.76 (1H, s), 7.04 (1H, m), 7.34 (1H, s), 7.90 (1H, d, J=16.3 Hz), 8.04 (1H, d, J=16.3 Hz), 8.99 (1H, d, J=7.0 Hz)

Example 114

(E)-3-{8-[2-(4-Isopropyl-1,3-thiazol-2-yl)ethyl]-4-oxo-2-(2-pyridylmethoxy)-4H-pyrido[1,2-a]pyrimidin-3-yl}-2-propenoic acid $^1$H-NMR (CD$_3$OD–CDCl$_3$) δ: 1.42 (6H, d, J=6.8 Hz), 3.29 (1H, m), 3.40 (2H, m), 3.77 (2H, m), 5.96 (2H, s), 7.18 (1H, d, J=15.9 Hz), 7.37 (1H, m), 7.44 (1H, s), 7.80 (1H, s), 8.02 (1H, d, J=15.9 Hz), 8.07 (1H, m), 8.31 (1H, m), 8.68 (1H, m), 8.92 (1H, m), 9.04 (1H, d, J=7.3 Hz)

Example 115

(E)-3-{8-[2-(4-Isopropyl-1,3-thiazol-2-yl)ethyl]-4-oxo-2-(3-pyridylmethoxy)-4H-pyrido[1,2-a]pyrimidin-3-yl}-2-propenoic acid $^1$H-NMR (CD$_3$OD-CDCl$_3$) δ: 1.42 (6H, d, J=6.8 Hz), 3.29 (1H, m), 3.45 (2H, m), 3.83 (2H, m), 5.85 (2H, s), 7.07 (1H, d, J=15.9 Hz), 7.39 (1H, d, J=7.3 Hz), 7.46 (1H, s), 7.78 (1H, s), 7.93 (1H, d, J=15.9 Hz), 8.18 (1H, m), 8.82 (2H, m), 9.01 (1H, d, J=7.1 Hz), 9.24 (1H, s)

Example 116

(E)-3-{8-[2-(4-Isopropyl-1,3-thiazol-2-yl)ethyl]-4-oxo-2-(4-pyridylmethoxy)-4H-pyrido[1,2-a]pyrimidin-3-yl}-2-propenoic acid $^1$H-NMR (CD$_3$OD) δ: 1.35 (6H, d, J=6.8 Hz), 3.29 (1H, m), 3.37 (2H, m), 3.70 (2H, m), 5.97 (2H, s), 7.16 (1H, d, J=15.9 Hz), 7.38 (1H, d, J=7.0 Hz), 7.52 (2H, s), 8.08 (1H, d, J=15.9 Hz), 8.20 (2H, m), 8.88 (2H, m), 9.06 (1H, d, J=7.0 Hz)

Example 117

(E)-3-{8-[(E)-2-(4-Isopropyl-1,3-thiazol-2-yl)-1-ethenyl]-4-oxo-2-(tetrahydro-3-furanylmethoxy)-4H-pyrido[1,2-a]pyrimidin-3-yl}-2-propenoic acid (A) 8-[(E)-2-(4-Isopropyl-1,3-thiazol-2-yl)-1-ethenyl]-2-(tetrahydro-3-furanylmethoxy)-4H-pyrido[1,2-a]pyrimidin-4-one 2-Hydroxy-8-[(E)-2-(4-isopropyl-1,3-thiazol-2-yl)-1-ethenyl]-4H-pyrido[1,2-a]-pyrimidin-4-one (210 mg, 0.670 mmol) was suspended in dimethylformamide (6.0 ml), added with diisopropylethylamine (600 μl) and 3-(iodomethyl)tetrahydrofuran (334 μl), and stirred overnight at 80° C. The reaction solution was further added with diisopropylethylamine (600 μl) and 3-(iodomethyl)tetrahydrofuran (334 μl) and stirred overnight at 80° C. The reaction mixture was concentrated, and the residue was purified by silica gel column chromatography (chloroform:methanol=100:0→100:1→100:2→100:5, v/v) to obtain the title compound (277 mg, quantitative).

(B) tert-Butyl (E)-3-{8-[(E)-2-(4-isopropyl-1,3-thiazol-2-yl)-1-ethenyl]-4-oxo-2-(tetrahydro-3-furanylmethoxy)-4H-pyrido[1,2-a]pyrimidin-3-yl}-2-propenoate Dimethylformamide (3.0 ml) was added with phosphorus oxychloride (187 μl, 2.02 mmol) under ice cooling and stirred at room temperature for 30 minutes. The mixture was added to 8-[(E)-2-(4-isopropyl-1,3-thiazol-2-yl)-1-ethenyl]-2-(tetrahydro-3-furanylmethoxy)-4H-pyrido[1,2-a]pyrimidin-4-one (277 mg) obtained in (A) and dissolved in dimethylformamide (3.0 ml) under ice cooling, and then the mixture was stirred at room temperature for 4 hours. The reaction mixture was added with saturated aqueous sodium hydrogencarbonate and extracted with chloroform. The organic layer was dried over magnesium sulfate, and the solvent was evaporated under reduced pressure. The residue was suspended in anhydrous tetrahydrofuran (6.0 ml) and anhydrous N,N-dimethylformamide (3.0 ml), added with (tert-butoxycarbonylmethylene)triphenylphosphorane (505 mg, 1.34 mmol) and stirred at 50° C. for 16 hours. The reaction mixture was concentrated, and then the residue was purified by silica gel column chromatography (n-hexane:ethyl acetate, 5:1→3:1→2:1→1:1, v/v) to obtain the title compound (215 mg, 61%).

$^1$H-NMR (CDCl$_3$) δ: 1.36 (6H, d, J=6.8 Hz), 1.53 (9H, s), 1.80 (1H, dt, J=7.3, 12.8 Hz), 2.12–2.21 (1H, m), 2.80–2.87 (1H, m), 3.12–3.19 (1H, m), 3.73 (1H, dd, J=5.4, 8.8 Hz), 3.81 (1H, dd, J=7.7, 15.2 Hz), 3.91–3.97 (2H, m), 4.44–4.47 (2H, m), 6.99 (1H, s), 7.16 (1H, d, J=16.3 Hz), 7.31 (1H, d, J=1.8, 7.5 Hz), 7.39 (1H, d, J=16.2 Hz), 7.48 (1H, d, J=1.5 Hz), 7.54 (1H, d, J=16.2 Hz), 7.92 (1H, d, J=16.3 Hz), 9.04 (1H, d, J=7.5 Hz) ESI-MS; m/z: 524 (M$^+$+1)

(C) (E)-3-{8-[(E)-2-(4-Isopropyl-1,3-thiazol-2-yl)-1-ethenyl]-4-oxo-2-(tetrahydro-3-furanylmethoxy)-4H-pyrido[1,2-a]pyrimidin-3-yl}-2-propenoic acid The tert-butyl (E)-3-{8-[(E)-2-(4-isopropyl-1,3-thiazol-2-yl)-1-ethenyl]-4-oxo-2-(tetrahydro-3-furanylmethoxy)-4H-pyrido[1,2-a]pyrimidin-3-yl}-2-propenoate (101 mg, 0.193 mmol) obtained in (B) was dissolved in 1,4-dioxane (1.6 ml), added with 4 N hydrochloric acid in 1,4-dioxane (3.2 ml), and then the mixture was stirred at room temperature for 16.25 hours. The reaction solution was concentrated, added with saturated aqueous sodium hydrogencarbonate, neutralized with phosphate buffer (pH 7–8), and then extracted with a mixture of chloroform/methanol (10:1, v/v). The organic layer was dried over magnesium sulfate, and then the solvent was evaporated under reduced pressure. The residue was purified by thin layer chromatography (chloroform:methanol=20:1, v/v) to obtain the title compound (77.1 mg, 86%).

$^1$H-NMR (CDCl$_3$+CD$_3$OD) δ: 1.36 (6H, d, J=6.8 Hz), 1.17–1.85 (1H, m), 2.13–2.22 (1H, m), 2.82–2.89 (1H, m), 3.13–3.19 (1H, m), 3.74 (1H, dd, J=5.4, 8.8 Hz), 3.82 (1H, dd, J=7.7, 15.5 Hz), 3.93–3.98 (2H, m), 4.44–4.52 (2H, m), 7.01 (1H, s), 7.16 (1H, d, J=15.9 Hz), 7.36–7.41 (2H, m), 7.50 (1H, s), 7.57 (1H, d, J=16.1 Hz), 8.03 (1H, d, J=15.9 Hz), 9.03 (1H, d, J=7.3 Hz) ESI-MS; m/z: 468 (M$^+$+1)

Example 118

8-[2-(4-Isopropyl-1,3-thiazol-2-yl)ethyl]-2-morpholino-3-(1H-1,2,3,4-tetrazol-5-yl)-4H-pyrido[1,2-a]pyrimidin-4-one (A) 8-[2-(4-Isopropyl-1,3-thiazol-2-yl)ethyl]-2-hydroxy-3-[(4-methoxybenzyl)tetrazol-5-yl]-4H-pyrido[1,2-a]pyrimidin-4-one 4-[2-(4-Isopropyl-1,3-thiazol-2-yl)ethyl]-2-aminopyridine (50 mg) and diethyl 2-[1-(4-methoxybenzyl)tetrazol-5-yl]malonate (141 mg) were heated to 150° C. in bromobenzene with stirring for 4 hours. After the solvent was evaporated, the residue was purified by silica gel column chromatography to obtain the title compound (73 mg) as cream solid.

$^1$H-NMR (CDCl$_3$) δ: 1.22 (d, J=6.6 Hz, 6H), 3.02 (m, 1H), 3.20-3.40 (m, 4H), 3.70 (s, 3H), 5.80 (s, 2H), 6.70 (s, 1H), 6.80 (bs, 2H), 7.00 (s, 1H), 7.30–7.50 (m, 3H), 9.00 (bs, 1H) MS(−), m/z, 502 (M−H$^+$)

(B) 8-[2-(4-Isopropyl-1,3-thiazol-2-yl)ethyl]-2-tosyloxy-3-[(4-methoxybenzyl)tetrazol-5-yl]-4H-pyrido[1,2-a]pyrimidin-4-one The 8-[2-(4-isopropyl-1,3-thiazol-2-yl)ethyl]-2-hydroxy-3-[(4-methoxybenzyl)-tetrazol-5-yl]-4H-pyrido[1,2-a]pyrimidin-4-one(73 mg) obtained in (A) was dissolved in methylene chloride (2 ml), added with dimethylaminopyridine (5 mg), triethylamine(40 ml) and p-toluenesulfonyl chloride (83 mg) at 0° C., and then the mixture was stirred at room temperature for 6 hours. The reaction solution was directly purified by silica gel column chromatography to obtain the title compound (61 mg, 64%) as pale yellow powder.

$^1$H-NMR (CDCl$_3$) δ: 1.22 (d, J=6.6 Hz, 6H), 2.42 (s, 3H), 3.05 (m, 1H), 3.25–3.32 (m, 4H), 3.80 (s, 3H), 5.75 (s, 2H), 6.75 (s, 1H), 6.85 (d, J=7.2 Hz, 2H), 7.15 (d, J=7.5 Hz, 1H), 7.24 (d, J=7.2 Hz, 2H), 7.35 (d, J=7.2 Hz, 2H), 7.42 (s, 1H), 7.90 (d, J=7.2 Hz, 2H), 9.01 (d, J=7.5 Hz, 1H)

(C) 8-[2-(4-Isopropyl-1,3-thiazol-2-yl)ethyl]-2-morpholino-3-(1-p-methoxybenzyl-1,2,3,4-tetrazol-5-yl)-4H-pyrido[1,2-a]pyrimidin-4-one The 8-[2-(4-isopropyl-1,3-thiazol-2-yl)ethyl]-2-tosyloxy-3-[(4-methoxybenzyl)-tetrazol-5-yl]-4H-pyrido[1,2-a]pyrimidin-4-one (61 mg) obtained in (B) was dissolved in tetrahydrofuran (1 ml), added with morpholine (40 ml) at room temperature, and stirred overnight at the same temperature. After the solvent was evaporated under reduced pressure, the residue was purified by silica gel column chromatography to obtain the title compound (31 mg, 59%).

$^1$H-NMR (CDCl$_3$) δ: 1.28 (d, J=6.6 Hz, 6H), 3.06 (m, 1H), 3.30–3.70 (m, 12H), 3.78 (s, 3H), 5.76 (s, 2H), 6.72 (s, 1H), 6.77 (d, J=7.5 Hz, 1H), 6.86 (d, J=7.2 Hz, 2H), 7.14 (s, 1H), 7.36 (d, J=7.2 Hz, 2H), 8.88 (m, J=7.5 Hz, 1H)

(D) 8-[2-(4-Isopropyl-1,3-thiazol-2-yl)ethyl]-2-morpholino-3-(1H-1,2,3,4-tetrazol-5-yl)-4H-pyrido[1,2-a]pyrimidin-4-one The 8-[2-(4-isopropyl-1,3-thiazol-2-yl)ethyl]-2-morpholino-3-(1-p-methoxybenzyl-1,2,3,4-tetrazol-5-yl)-4H-pyrido[1,2-a]pyrimidin-4-one (10 mg) obtained in (C) was dissolved in trifluoroacetic acid (1 ml) and added with anisole (50 ml), and then stirred at room temperature for 4 hours. After the solvent was evaporated, the residue was purified by silica gel column chromatography to obtain the title compound (7 mg) as yellow powder.

$^1$H-NMR (CDCl$_3$) δ: 1.25 (d, 6H), 3.04 (m, 1H), 3.22 (t, 2H), 3.38 (t, 2H), 3.66 (m, 4H), 3.82 (m, 4H), 6.73 (s, 1H), 6.89 (m, 1H), 7.22 (m, 1H), 8.83 (d, 1H) MS (ES−) m/z 451 (M$^+$−1)

In the following Examples 119 to 121, synthesis was performed in the same manner as in Example 118.

Example 119

8-[2-(4-Isopropyl-1,3-thiazol-2-yl)ethyl]-2-(3-pyridylmethoxy)-3-(1H-1,2,3,4-tetrazol-5-yl)-4H-pyrido[1,2-a]pyrimidin-4-one $^1$H-NMR (CDCl$_3$) δ: 1.21 (d, 6H), 2.98 (m, 1H), 3.25 (t, 2H), 3.36 (t, 2H), 5.73 (s, 2H), 6.71 (s, 1H), 7.16 (d, 1H), 7.31 (m, 1H), 7.42 (s, 1H), 8.10 (d, 1H), 8.41 (d, 1H), 8.69 (s, 1H), 8.99 (d, 1H) MS (ES+) m/z 475 (M$^+$+1); MS (ES−) m/z 473 (M$^+$−1)

Example 120

8-[2-(4-Isopropyl-1,3-thiazol-2-yl)ethyl]-2-dimethylamino-3-(1H-1,2,3,4-tetrazol-5-yl)-4H-pyrido[1,2-a]pyrimidin-4-one $^1$H-NMR (CD$_3$OD) δ:1.24 (d, 6H), 2.95 (s, 6H), 3.01 (m, 1H), 3.21 (t, 2H), 3.41 (t, 2H), 6.95 (s, 1H), 7.00 (m, 1H), 7.23 (s, 1H), 8.80 (d, 1H) MS (ES+) m/z 512 (M$^+$+1); MS (ES−) m/z 510 (M$^+$−1)

Example 121

8-[2-(4-Isopropyl-1,3-thiazol-2-yl)ethyl]-2-(4-cyanopiperidino)-3-(1H-1,2,3,4-tetrazol-5-yl)-4H-pyrido[1,2-a]pyrimidin-4-one $^1$H-NMR (CDCl$_3$) δ: 1.33 (d, 6H), 2.02 (m, 2H), 2.10 (m, 2H), 2.95 (m, 1H), 3.20 (m, 4H), 3.45 (m, 2H), 3.62 (m, 1H), 3.79 (m, 2H), 6.82 (s, 1H), 6.90 (d, 1H), 7.18 (s, 1H), 8.85 (d, 1H) MS (ES−) m/z 476 (M$^+$+1); 474 (M$^+$−1)

Example 122

4-Isopropyl-2-(2-(3-[([(4-methylphenyl)sulfonyl] aminocarbonyl)amino]-4-oxo-4H-pyrido[1,2-a] pyrimidin-8-yl)ethyl)-1,3-thiazole (A) tert-Butyl N-8-[2-(4-isopropyl-1,3-thiazol-2-yl) ethyl]-4-oxo-4H-pyrido[1,2-a]-pyrimidin-3-ylcarbamate 4-[2-(4-Isopropyl-1,3-thiazol-2-yl)ethyl]-2-aminopyridine (300 mg) and methyl 2-(t-butoxycarbonyl) amino-3-dimethylaminopropenoate (445 mg) were added with xylene (2 ml) and heated at 140° C. for 6.5 hours with stirring. After the solvent was evaporated, the residue was purified by silica gel column chromatography to obtain the title compound (200 mg) as yellow powder.

$^1$H-NMR (CDCl$_3$) δ: 1.21 (d, J=6.9 Hz, 6H), 3.01 (m, 1H), 3.22 (t, J=7.8 Hz, 2H), 3.37 (t, J=7.8 Hz, 2H), 6.72 (s, 1H), 6.96 (d, J=7.2 Hz, 1H), 7.25 (s, 1H), 7.47 (s, 1H), 8.83 (d, J=7.5 Hz, 1H), 9.14 (s, 1H) MS(+), m/z, 415 (M+H$^+$), 829 (2M+H$^+$)

(B) 3-Amino-8-[2-(4-isopropyl-1,3-thiazol-2-yl) ethyl]-4H-pyrido[1,2-a]pyrimidin-4-one The tert-butyl N-8-[2-(4-isopropyl-1,3-thiazol-2-yl) ethyl]-4-oxo-4H-pyrido-[1,2-a]pyrimidin-3-ylcarbamate (200 mg) obtained in (A) was treated with 2 ml of trifluoroacetic acid at room temperature for 1 hour, and the solvent was evaporated under reduced pressure. The residue was dissolved in ethyl acetate, washed with saturated sodium hydrogencarbonate and dried over sodium sulfate. The solvent was evaporated under reduced pressure, and the residue was purified by silica gel column chromatography to obtain the title compound (quantitative) as yellow powder.

$^1$H-NMR (CDCl$_3$) δ: 1.28 (d, J=6.9 Hz, 6H), 3.06 (m, 1H), 3.23 (t, J=7.8 Hz, 2H), 3.9 (t, J=7.8 Hz, 2H), 6.75 (s, 1H), 6.95 (d, J=7.5 Hz, 1H), 7.50 (s, 1H), 7.47 (s, 1H), 7.94 (s, 1H), 8.80 (d, J=7.5 Hz, 1H) MS(+), m/z, 315 (M+H$^+$)

(C) 4-Isopropyl-2-(2-3-[([(4-methylphenyl)sulfonyl] aminocarbonyl)amino]-4-oxo-4H-pyrido[1,2-a] pyrimidin-8-ylethyl)-1,3-thiazole The 3-amino-8-[2-(4-isopropyl-1,3-thiazol-2-yl)ethyl]-4H-pyrido[1,2-a]-pyrimidin-4-one (44 mg) obtained in (B)

and p-toluenesulfonyl isocyanate (42 mg) were dissolved in toluene (0.5 ml) and refluxed by heating for 2.5 hours. After the solvent was evaporated, the residue was purified by silica gel column chromatography to obtain the title compound (33 mg) as white powder.

$^1$H-NMR (CDCl$_3$) δ: 1.26 (d, 6H), 2.41 (s, 3H), 3.05 (m, 1H), 3.25 (t, 2H), 3.39 (t, 2H), 6.73 (s, 1H), 7.19 (dd, 1H), 7.31 (d, 1H), 7.56 (s, 1H), 7.96 (d, 1H), 8.71 (s,1H), 9.04 (d, 1H), 9.39 (s, 1H) MS (ES+) m/z 411 (M$^+$+1)

Example 123

(E)-3-{8-[2-(4-Isopropyl-1,3-thiazol-2-yl)ethyl]-4-oxo-4H-pyrido[1,2-a]-pyrimidin-3-yl}-2-propenoic acid (A) Ethyl (E)-3-{8-[2-(4-isopropyl-1,3-thiazol-2-yl) ethyl]-4-oxo-4H-pyrido[1,2-a]-pyrimidin-3-yl}-2-propenoate 4-[2-(4-Isopropyl-1,3-thiazol-2-yl)ethyl]-2-aminopyridine(200 mg), diethyl 4-dimethylaminomethyleneglutaconate (265 mg) was added with bromobenzene (2 ml) and heated at 120° C. for 1 hour and at 160° C. for 4 hours with stirring. The residue was purified by silica gel column chromatography to obtain the title compound (20 mg) as white powder.

$^1$H-NMR (CDCl$_3$) δ: 1.20–1.40 (m, 9H), 3.05 (m, 1H), 3.32 (t, J=6.6 Hz, 2H), 3.40 (t, J=6.6 Hz, 2H), 4.27 (q, J=7.2 Hz, 2H), 6.73 (s, 1H), 7.11 (d, J=7.2 Hz, 1H), 7.18 (d, J=15.9 Hz, 1H), 7.51 (s, 1H), 7.66 (d, J=15.9 Hz, 1H), 8.45 (s, 1H), 9.08 (s, 1H) MS(+), m/z, 398 (M+H$^+$), 420 (M+Na$^+$), MS(−), m/z, 396 (M−H$^+$)

(B) (E)-3-{8-[2-(4-Isopropyl-1,3-thiazol-2-yl)ethyl]-4-oxo-4H-pyrido[1,2-a]pyrimidin-3-yl}-2-propenoic acid The ethyl (E)-3-{8-[2-(4-Isopropyl-1,3-thiazol-2-yl) ethyl]-4-oxo-4H-pyrido-[1,2-a]pyrimidin-3-yl}-2-propenoate (15 mg) obtained in (A) was dissolved in tetrahydrofuran (1 ml) and methanol (0.5 ml), added with a solution of 8 mg of lithium hydroxide dissolved in 0.5 ml of water, and stirred at room temperature for 3.5 hours, and the solvent was concentrated under reduced pressure. The residue was distributed between ether and water, and the aqueous layer was separated, made pH 3 with hydrochloric acid, extracted with ethyl acetate, and dried over sodium sulfate. After the solvent was evaporated, the residue was purified by silica gel column chromatography to obtain the title compound.

$^1$H-NMR (CDCl$_3$) δ: 1.21 (d, 6H), 2.41 (s, 3H), 3.00 (m, 1H), 3.25 (t, 2H), 3.34 (t, 2H), 6.67 (s, 1H), 7.06–7.19 (m, 2H), 7.48 (s, 1H), 7.68 (d, J=16 Hz, 1H), 8.40 (s, 1H), 9.03 (d, J=7.5 Hz, 1H) MS (ES+) m/z 370 (M$^+$+1); MS (ES−) m/z 368 (M$^+$−1)

Example 124

2-{8-[2-(4-Isopropyl-1,3-thiazol-2-yl)ethyl]-4-oxo-4H-pyrido[1,2a]-pyrimidin-3-yloxy}acetic acid (A) Ethyl 2-{8-[2-(4-isopropyl-1,3-thiazol-2-yl) ethyl]-4-oxo-4H-pyrido[1,2-a]-pyrimidin-3-yloxy}acetate 4-[2-(4-Isopropyl-1,3-thiazol-2-yl)ethyl]-2-aminopyridine (100 mg) and ethyl 2-ethoxycarbonylmethoxy-3-methoxy-3-dimethylaminopropenoate (150 mg) were heated at 140° C. in xylene (1 ml) for 7 hours with stirring. After the solvent was evaporated under reduced pressure, the residue was purified by silica gel column chromatography to obtain the title compound (41 mg).

$^1$H-NMR(CDCl$_3$, 300 MHz) δ: 1.20–1.30 (m, 9H), 3.04 (m, 1H), 3.23 (t, J=7.8 Hz, 2H), 3.40 (t, J=7.8 Hz, 2H), 4.25 (q, J=7.2 Hz, 2H), 4.86 (s, 2H), 6.72 (s, 1H), 6.98 (d, J=7.5 Hz, 1H), 7.45 (s, 1H), 8.29 (s, 1H), 8.90 (d, J=7.5 Hz, 1H) MS(+), m/z, 401 (M+H$^+$)

(B) 2-(8-[2-(4-Isopropyl-1,3-thiazol-2-yl)ethyl]-4-oxo-4H-pyrido[1,2-a]pyrimidin-3-yloxy)acetic acid The ethyl 2-{8-[2-(4-isopropyl-1,3-thiazol-2-yl)ethyl]-4-oxo-4H-pyrido[1,2-a]-pyrimidin-3-yloxy}acetate (41 mg) obtained in (A) was dissolved in tetrahydrofuran (1 ml) and methanol (300 ml), added with a solution of lithium hydroxide (5 mg) dissolved in water (300 ml), and then the mixture was stirred at room temperature for 1 hour, and the solvent was concentrated under reduced pressure. The residue was distributed between ether and water, and the aqueous layer was separated and made pH 3 with hydrochloric acid, and then extracted with ethyl acetate. The organic layer was dried over sodium sulfate. After the solvent was evaporated, the residue was purified by silica gel column chromatography to obtain the title compound (quantitative).

$^1$H-NMR (DMSO-d$_6$) δ: 1.23 (d, 6H), 3.00 (m, 1H), 3.21 (t, 2H), 3.40 (t, 2H), 4.54 (s, 2H), 6.96 (s, 1H), 7.18 (d, 1H), 7.38 (s, 1H), 8.12 (s, 1H), 8.85 (d, 1H) MS (ES−) m/z 372 (M$^+$−1)

Example 125

5-{8-[2-(4-Isopropyl-1,3-thiazol-2-yl)ethyl]-4-oxo-4H-pyrido[1,2-a]-pyrimidin-3-yl}-2,3-dihydrol,3,4-oxadiazol-2-one Methyl 8-[2-(4-isopropyl-1,3-thiazol-2-yl)ethyl]-4-oxo-4H-pyrido[1,2-a]-pyrimidin-3-carboxylate (22 mg) and hydrazine (4 ml) were refluxed by heating in methanol (3ml) for 2.5 hours under nitrogen atmosphere. The reaction mixture was further added with hydrazine (10 ml) and refluxed by heating for 2 days. After the reaction mixture was cooled, insoluble solids were collected by filtration and suspended in methylene chloride (5 ml). The suspension was added with diphosgene (7 ml) and stirred for 30 minutes. Insoluble solids were removed by filtration, and the reaction mixture was concentrated to obtain the title compound (11 mg).

$^1$H-NMR (CD$_3$OD) δ: 1.36 (s, 3H), 1.39 (s, 3H), 3.22 (m, 1H), 3.53 (m, 2H), 3.77 (m, 2H); 7.58 (s, 1H); 7.75 (d, 1H), 7.91 (s, 1H), 8, 84 (s, 1H), 9.31 (d, 1H) MS (ES+) m/z 384 (M$^+$+1); MS (ES−) m/z 382 (M$^+$−1)

Example 126

(E)-3-{8-[2-(4-Isopropyl-1,3-thiazol-2-yl)ethyl]-4-oxo-4H-pyrido[1,2-a]-pyrimidin-3-yl}-2-methyl-2-propenoic acid (A) tert-Butyl (E)-3-{8-[2-(4-isopropyl-1,3-thiazol-2-yl)ethyl]-4-oxo-4H-pyrido[1,2-a]-pyrimidin-3-yl}-2-methyl-2-propenoate tert-Butyl 2-(diethylphosphono)propionate (70 mg) was dissolved in tetrahydrofuran(5 ml), added with sodium hydride (60% in oil, 40 mg), and stirred for 10 minutes. The reaction mixture was added with 8-(2-(4-isopropyl-1,3- thiazol-2-yl)-ethyl)-4-oxo-4H-pyrido[1,2-a]pyrimidine-3-carbaldehyde (56 mg), stirred for 10 minutes and added with acetic acid (0.2 ml), and then distributed between ethyl acetate and saturated aqueous sodium hydrogencarbonate. The organic layer was concentrated, and the residue was purified by silica gel column chromatography to obtain the title compound (70 mg) as yellow oil.

$^1$H-NMR (CDCl$_3$) δ: 1.27 (d, 6H), 1.51 (s, 9H), 2.07 (s, 3H), 3.05 (m, 1H), 3.3–3.5 (m, 4H), 6.72 (s, 1H), 7.07 (d, 1H), 7.52 (s, 1H), 7.68 (s, 1H), 8.41 (s, 1H), 9.00 (s, 1H)

(B) (E)-3-{8-[2-(4-Isopropyl-1,3-thiazol-2-yl)ethyl]-4-oxo-4H-pyrido[1,2-a]pyrimidin-3-yl}-2-methyl-2-propenoic acid The tert-butyl (E)-3-{8-[2-(4-isopropyl-1,3-thiazol-2-yl)ethyl]-4-oxo-4H-pyrido-[1,2-a]pyrimidin-3-yl}-2-methyl-2-propenoate (70 mg) obtained in (A) was dissolved in trifluoroacetic acid (1 ml) and stirred at room temperature for 1 hour, and then the solvent was evaporated under reduced pressure. The residue was purified by silica gel column chromatography to obtain the title compound (21 mg).

$^1$H-NMR (CDCl$_3$+CD$_3$OD) δ: 1.25 (d, 6H), 2.10 (s, 3H), 3.04 (m, 1H), 3.28 (t, 2H), 3.35–3.45 (m, with CD$_3$OD), 6.74 (s, 1H), 7.15 (d, 1H), 7.59 (s, 1H), 7.79 (s, 1H), 8.45 (s, 1H), 9.01 (d, 1H)

Example 127

(E)-2-(3-Chloroethyl)-3-{8-[2-(4-isopropyl-1,3-thiazol-2-yl)ethyl]4-oxo-4H-pyrido[1,2-a]pyrimidin-3-yl}-2-propenoic acid $^1$H-NMR (CDCl$_3$) δ: 1.28 (d, 6H), 2.10 (m, 2H), 2.70 (m, 2H), 3.05 (m, 1H), 3.30 (t, 2H), 3.40 (t, 2H), 3.60 (m, 2H), 6.75 (s, 1H), 7.10 (d, 1H), 7.54 (s, 1H), 7.94 (s, 1H), 8.51 (s, 1H), 9.03 (d, 1H) MS (ES+) m/z 446 (M$^+$+1); MS (ES−) m/z 444 (M$^+$−1)

Example 128

(E)-3-{8-[2-(4-Isopropyl)-1,3-thiazol-2-yl]ethyl}-4-oxo-2-phenyl-4H-pyrido[1,2-a]pyrimidin-3-yl}-2-propenoic acid (A) 2-Trifluoromethanesulfonyloxy-8-[2-(4-isopropyl-1,3-thiazol-2-yl)ethyl]-4H-pyrido[1,2-a]pyrimidin-4-one 2-Hydroxy-8-[2-(4-isopropyl-1,3-thiazol-2-yl)ethyl]-4H-pyrido[1,2-a]-pyrimidin-4-one (400 mg) and DMAP (310 mg) were dissolved in methylene chloride (8 ml), added with trifluoromethanesulfonic anhydride (427 ml) at −78 °C., and then the mixture was stirred overnight while the reaction temperature was gradually returned to room temperature. The reaction mixture was added with 0.2 M hydrochloric acid (50 ml) and extracted with methylene chloride, and the organic layer was dried over sodium sulfate. After the solvent was evaporated, the residue was purified by silica gel column chromatography to obtain the title compound (499 mg, 88%).

$^1$H-NMR (CDCl$_3$) δ: 1.22 (d, J=7.5 Hz, 6H), 3.10 (m, 1H), 3.25–3.40 (m, 4H), 6.10 (s, 1H), 6.75 (s, 1H), 7.18 (d, J=7.5 Hz, 1H), 7.55 (s, 1H), 8.95 (d, J=7.5 Hz, 1H)

(B) 2-Phenyl-8-[2-(4-isopropyl-1,3-thiazol-2-yl)ethyl]-4H-pyrido[1,2-a]pyrimidin-4-one The 2-trifluoromethanesulfonyloxy-8-[2-(4-isopropyl-1,3-thiazol-2-yl)ethyl]-4H-pyrido[1,2-a]pyrimidin-4-one (82 mg) obtained in (A), phenylboronic acid (45 mg), palladium tetrakistriphenylphosphine (11 mg), potassium bromide (24 mg) and potassium carbonate (38 mg) were stirred at 85° C. overnight in dioxane (4 ml) under a nitrogen flow. The reaction mixture was cooled and added with water (20 ml) and extracted with ethyl acetate, and then the organic layer was dried over sodium sulfate. The solvent was evaporated under reduced pressure, and the residue was purified by silica gel column chromatography to obtain the title compound (65 mg, 94%) as white powder.

$^1$H-NMR (CDCl$_3$) δ: 1.22 (d, J=7.5 Hz, 6H), 3.00–3.10 (m, 1H), 3.30–3.50 (m, 4H), 6.72 (s, 1H), 6.85 (s, 1H), 6.99 (d, J=7.5 Hz, 1H), 7.46–7.56 (m, 5H), 8.20–8.40 (m, 1H), 8.96 (d, J=7.5 Hz, 1H)

(C) tert-Butyl (E)-3-{2-phenyl-4-oxo-8-[2-(4-isopropyl-1,3-thiazol-2-yl)ethyl]-4H-pyrido[1,2-a]pyrimidin-3-yl}-2-propenoate Dimethylformamide (1 ml) and phosphorus oxychloride (25 ml) were mixed under ice cooling and stirred at room temperature for 30 minutes. The mixture was added with a solution of the 2-phenyl-8-[2-(4-isopropyl-1,3-thiazol-2-yl)ethyl]-4H-pyrido[1,2-a]pyrimidin-4-one (65 mg) obtained in (B) and dissolved in dimethylformamide (1 ml) and stirred at room temperature for 1 hour and at 95° C. for 1.5 hours on an outer bath. The reaction mixture was cooled and then added with ethyl acetate and hexane. Then, the organic layer was washed with saturated aqueous sodium hydrogencarbonate and water and dried over magnesium sulfate, and the solvent was evaporated under reduced pressure. The residue was added with tetrahydrofuran (2.5 ml) and dimethylformamide (0.5 ml), further added with (tert-butoxycarbonylmethylidene)triphenylphosphorane (240 mg), and stirred at 80° C. for 10 hours. The solvent was evaporated under reduced pressure, and the residue was purified by silica gel column chromatography to obtain the title compound (18 mg).

$^1$H-NMR (CDCl$_3$) δ: 1.22 (d, J=7.5 Hz, 6H), 3.00–310 (m, 1H), 3.30–3.50 (m, 4H), 6.82 (s, 1H), 6.99 (d, J=7.5 Hz, 1H), 7.40–7.66 (m, 7H), 8.05–8.10 (m, 1H), 8.95 (d, J=7.5 Hz, 1H)

(D) (E)-3-{8-[2-(4-Isopropyl)-1,3-thiazol-2-yl]ethyl}-4-oxo-2-phenyl-4H-pyrido[1,2-a]pyrimidin-3-yl}-2-propenoic acid The tert-butyl (E)-3-{2-phenyl-4-oxo-8-[2-(4-isopropyl-1,3-thiazol-2-yl)ethyl]-4H-pyrido[1,2-a]pyrimidin-3-yl}-2-propenoate (18 mg) obtained in (C) was added with trifluoroacetic acid (1 ml) and stirred at room temperature for 2 hours. The solvent was evaporated under reduced pressure, and the residue was purified by silica gel column chromatography to obtain the title compound (15 mg) as yellow powder.

$^1$H-NMR (CDCl$_3$) δ: 1.25 (d, 6H), 3.05 (m, 1H), 3.28 (t, 2H), 3.39 (t, 2H), 6.75 (s, 1H), 7.12 (d, 1H), 7.39 (d, J=16 Hz, 1H), 7.50 (m, 3H), 7.58 (m, 3H), 7.72 (d, J=16 Hz, 1H), 9.05 (d, 1H)

Example 129

(E)-3-{8-[2-(4-Isopropyl-1,3-thiazol-2-yl)ethyl]-4-oxo-2-(3-pyridyl)-4H-pyrido[1,2-a]pyrimidin-3-yl}-2-propenoic acid (A) 8-[2-(4-Isopropyl-1,3-thiazol-2-yl)ethyl]-2-(3-pyridyl)-4H-pyrido[1,2-a]pyrimidin-4-one 2-Trifluoromethanesulfonyloxy-8-[2-(4-isopropyl-1,3-thiazol-2-yl)ethyl]-4H-pyrido[1,2-a]pyrimidin-4-one(499 mg), pyridine-3-boronic acid 1,3-propanediol cyclic ester (364 mg), palladium tetrakistriphenylphosphine (65 mg), potassium bromide (146 mg) and potassium carbonate (231 mg) were added with dioxane(8 ml) and stirred overnight at 85° C. under nitrogen atmosphere. The reaction mixture was cooled and then added with ethyl acetate. Insoluble solids were removed by filtration, and the solvent of the filtrate was evaporated. The residue was purified by silica gel column chromatography to obtain the title compound (400 mg).

$^1$H-NMR (CDCl$_3$) δ: 1.18 (d, J=7.2 Hz, 6H), 2.98 (m, 1H), 3.05-3.30 (m, 4H), 6.66 (s, 1H), 6.75 (s, 1H), 7.02 (dd, J=7.5, 1.8 Hz, 1H), 7.38 (dd, J=7.5, 7.8 Hz, 1H), 7.49 (d, J=1.2 Hz, 1H), 8.30 (dt, J=7.5, 1.8 Hz, 1H), 8.55 (dd, J=7.5, 1.2 Hz, 1H), 8.86 (d, J=7.8 Hz, 1H), 9.11 (d, J=1.2 Hz, 1H).

(B) Methyl (E)-3-(8-[2-(4-isopropyl-1,3-thiazol-2-yl)ethyl]-4-oxo-2-(3-pyridyl)-4H-pyrido[1,2-a] pyrimidin-3-yl)-2-propenoate Phosphorus oxychloride (367 ml) was added to dimethylformamide (5 ml) under ice cooling and stirred at the same temperature for 10 minutes. The mixture was added with the 8-[2-(4-isopropyl-1,3-thiazol-2-yl)ethyl]-2-(3-pyridyl)-4H-pyrido-[1,2-a]pyrimidin-4-one (336 mg) obtained in (A) and stirred at 95° C. for 1.5 hours. The mixture was cooled, then slowly added with sodium carbonate and extracted with ethyl acetate. The organic layer was dried over sodium sulfate, and the solvent was evaporated under reduced pressure. The residue was purified by silica gel column chromatography to obtain yellow powder (58 mg). The resulting powder was dissolved in tetrahydrofuran (2.5 ml) and dimethylformamide (0.5 ml), added with methyl (triphenylphosphoranylidene)acetate (240 mg) and stirred at 90° C. for 10 hours. After the solvent was evaporated under reduced pressure, the residue was purified by silica gel column chromatography to obtain the title compound (19 mg) as yellow powder.

$^1$H-NMR (CDCl$_3$) δ: 1.22 (d, J=7.5 Hz, 6H), 3.05 (m, 1H), 3.30–3.50 (m, 4H), 3.75 (s, 3H), 6.88 (s, 1H), 7.15 (dd, J=7.2, 2.1 Hz, 1H), 7.40–7.60 (m, 4H), 7.93 (dt, J=7.8, 1.8 Hz, 1H), 8.75 (dd, J=5.1, 1.5 Hz, 1H), 8.87 (d, J=1.8 Hz, 1H), 9.08 (d, J=7.5 Hz, 1H)

(C) (E)-3-{8-[2-(4-Isopropyl-1,3-thiazol-2-yl)ethyl]-4-oxo-2-(3-pyridyl)-4H-pyrido-[1,2-a]pyrimidin-3-yl}-2-propenoic acid The methyl (E)-3-{8-[2-(4-isopropyl-1,3-thiazol-2-yl)ethyl]-4-oxo-2-(3-pyridyl)-4H-pyrido[1,2-a]pyrimidin-3-yl}-2-propenoate obtained in (B) was dissolved in tetrahydrofuran (2 ml) and methanol (0.5 ml), added with a solution (0.5 ml) containing lithium hydroxide (5.5 mg) and stirred at room temperature for 1 hour. The solvent was evaporated under reduced pressure, and the residue was distributed between water and diethyl ether. The aqueous layer was separated, made pH 4–5 with hydrochloric acid, and then extracted with ethyl acetate. The organic layer was dried over sodium sulfate, and the solvent was evaporated. The residue was purified by silica gel column chromatography to obtain the title compound (6.9 mg) as yellow powder.

$^1$H-NMR (CDCl$_3$) δ: 1.18 (d, 6H), 2.95 (m, 1H), 3.21 (t, 2H), 3.32 (t, 2H), 6.67 (s, 1H), 7.15 (d, 1H), 7.23 (d, J=13 Hz, 1H), 7.41 (d, J=13 Hz, 1H), 7.48 (s, 1H), 7.55 (m, 1H), 8.01 (m, 1H), 8.65 (m, 1H), 8.76 (s, 1H), 8.98 (d, 1H) MS (ES+) m/z 447 (M$^+$+1); MS (ES−) m/z 445 (M$^+$−1)

Example 130

(E)-3-{8-[2-(4-Isopropyl-1,3-thiazol-2-yl)ethyl]-4-oxo-2-(4H-pyrido[1,2-a]pyrimidin-3-yl}-2-propenoic acid $^1$H-NMR (CD$_3$OD) δ: 1.25 (d, 6H), 3.02 (m, 1H), 3.2–3.5 (m, withCHD$_2$OD), 6.87 (s, 1H), 7.33 (d, J=16 Hz, 1H), 7.38 (m, 1H), 7.45 (d, J=16 Hz, 1H), 7.59 (m, 2H), 7.72 (s, 1H), 8.72 (m, 2H), 9.13 (d, 1H) MS (ES+) m/z 447 (M$^+$+1); MS (ES−) m/z 445 (M$^+$−1)

Example 131

(E)-3-{8-[2-(4-Isopropyl-1,3-thiazol-2-yl)ethyl]-2-morpholino-4-oxo-4H-pyrido[1,2-a]pyrimidin-3-yl}-2-methyl-2-propenoic acid (A) Ethyl (E)-3-{8-[2-(4-isopropyl-1,3-thiazol-2-yl) ethyl]-2-morpholino-4-oxo-4H-pyrido[1,2-a] pyrimidin-3-yl}-2-methyl-2-propenoate Under nitrogen atmosphere, triethyl 2-phosphonopropionate (155 mg, 0.65 mmol) was dissolved in tetrahydrofuran (2 ml), added with n-butyl lithium (1 M, 0.65 ml) at −78° C., and stirred at the same temperature for 20 minutes. The reaction mixture was added with a solution of 8-[2-(4-isopropyl-1,3-thiazol-2-yl)ethyl]-2-morpholino-4-oxo-4H-pyrido[1,2-a]pyrimidine-3-carbaldehyde (50 mg) dissolved in tetrahydrofuran (1 ml). The cooling bath was removed, and the reaction mixture was warmed to room temperature and stirred overnight at room temperature. The reaction mixture was added with saturated aqueous sodium hydrogencarbonate and extracted with ethyl acetate. The organic layer was dried over magnesium sulfate, and the solvent was evaporated under reduced pressure. The residue was purified by silica gel column chromatography to obtain the title compound (14 mg).

$^1$H-NMR (CDCl$_3$) δ: 1.20–1.30 (m, 9H), 1.79 (s, 3H), 2.95 (m, 1H), 3.11 (t, J=7.5 Hz, 2H), 3.29 (t, J=7.5 Hz, 2H), 3.48 (t, J=4.8 Hz, 4H), 3.66 (t, J=4.8 Hz, 4H), 4.05–4.15 (m, 2H), 6.66 (s, 1H), 6.75 (d, J=7.5 Hz, 1H), 7.12 (s, 1H), 7.45 (s, 1H), 8.75 (d, J=7.5 Hz, 1H)

(B) (E)-3-{8-[2-(4-Isopropyl-1,3-thiazol-2-yl)ethyl]-2-morpholino-4-oxo-4H-pyrido-[1,2-a] pyrimidin-3-yl}-2-methyl-2-propenoic acid The ethyl (E)-3-{8-[2-(4-isopropyl-1,3-thiazol-2-yl) ethyl]-2-morpholino-4-oxo-4H-pyrido[1,2-a]pyrimidin-3-yl}-2-methyl-2-propenoate (14 mg) obtained in (A) was dissolved in tetrahydrofuran (4 ml) and methanol (1 ml), added with a solution of lithium hydroxide (1.4 mg) in water (1 ml) and stirred at room temperature for 1.5 hours. The reaction mixture was added with water and washed with ether, and then the aqueous layer was made acidic with diluted hydrochloric acid and extracted with ethyl acetate. The organic layer was dried over magnesium sulfate, and the solvent was evaporated under reduced pressure. The residue was purified by silica gel column chromatography to obtain the title compound (4.4 mg) as yellow powder.

$^1$H-NMR (CDCl$_3$) δ: 1.24 (d, 6H), 1.86 (s, 3H), 3.05 (m, 1H), 3.19 (t, 2H), 3.38 (t, 2H), 3.58 (m, 4H), 3.74 (m, 4H), 6.74 (s, 1H), 6.82 (d, 1H), 7.20 (s, 1H), 7.63 (s, 1H), 8.83 (d, 1H) MS (ES+) m/z 469 (M$^+$+1); MS (ES−) m/z 467 (M$^+$−1)

Example 132

(E)-2-Methyl-3-(8-{2-[4-(1-methylcyclopropyl)-1,3-thiazol-2-yl]ethyl}-2-morpholino-4-oxo-4H-pyrido [1,2-a]pyrimidin-3-yl)-2-propenoic acid $^1$H-NMR (CDCl$_3$) δ: 0.75 (m, 2H), 1.14 (m, 2H), 1.42 (s, 3H), 1.88 (s, 3H), 3.18 (t, 2H), 3.34 (t, 2H), 3.59 (m, 4H), 3.76 (m, 4H), 6.73 (s, 1H), 6.81 (d, 1H), 7.22 (s, 1H), 7.63 (s, 1H), 8.82 (d, 1H) MS (ES+) m/z 481

Example 133

(E)-3-{8-[2-(4-tert-Butyl-1,3-thiazol-2-yl)ethyl]-2-morpholino-4-oxo-4H-pyrido[1,2-a]pyrimidin-3-yl}-2-methyl-2-propenoic acid $^1$H-NMR (CDCl$_3$) δ: 1.35 (s, 9H), 1.85 (s, 3H), 3.20 (t, 2H), 3.36 (t, 2H), 3.58 (m, 4H), 3.75 (m, 4H), 6.73 (s, 1H), 6.81 (d, 1H), 7.20 (s, 1H), 7.61 (s, 1H), 8.81 (d, 1H) MS (ES+) m/z 483 (M$^+$+1); MS (ES−) m/z 481 (M$^+$−1)

Example 134

(E)-3-{8-[2-(4-Isopropyl-1,3-thiazol-2-yl)ethyl]-2-(3-aminopyrrolidino-4-oxo-4H-pyrido[1,2-a]pyrimidin-3-yl)-2-methyl-2-propenoic acid $^1$H-NMR (CD$_3$OD) δ: 1.20 (d, 6H), 1.59 (s, 3H), 1.95 (m, 1H), 2.23 (m, 1H), 2.98 (m, 1H), 3.10 (m, 2H), 3.35 (m, 2H), 3.43 (m, 1H), 3.62 (m, 2H), 3.75 (m, 2H), 6.88 (m, 2H), 7.08 (s, 1H), 7.36 (s, 1H), 8.62 (d, 1H) MS (ES+) m/z 468 (M$^+$+1)

Example 135

(Z)-2-Fluoro-3-{8-[2-(4-isopropyl-1,3-thiazol-2-yl)ethyl]-2-morpholino-4-oxo-4H-pyrido[1,2-a]pyrimidin-3-yl}-2-propenoic acid (A) Ethyl (Z)-2-fluoro-3-{8-[2-(4-isopropyl-1,3-thiazol-2-yl)ethyl]-2-hydroxy-4-oxo-4H-pyrido[1,2-a]pyrimidin-3-yl}-2-propenoate 2-Fluoro-2-phosphonoacetic acid triethyl ester (384 mg) was dissolved in tetrahydrofuran (3ml) and dimethylformamide (1.5 ml), added with n-butyl lithium (1.6 M, 1 ml) at −78° C. under nitrogen atmosphere, and then the mixture was stirred at the same temperature for 20 minutes. The reaction mixture was added with a solution of 8-[2-(4-isopropyl-1,3-thiazol-2-yl)ethyl]-2-hydroxy-4-oxo-4H-pyrido[1,2-a]-pyrimidine-3-carbaldehyde (108 mg) dissolved in tetrahydrofuran (2 ml). The reaction temperature was gradually raised to room temperature, and the reaction mixture was stirred overnight at the same temperature. The reaction mixture was added with water and extracted with methylene chloride, and the organic layer was dried over magnesium sulfate. Then, the solvent was evaporated under reduced pressure. The residue was purified by silica gel column chromatography to obtain the title compound (35 mg) as a mixture of (E)- and (Z)-isomers.

$^1$H-NMR (CDCl$_3$) δ: 1.20–1.30 (m, 9H), 3.05 (m, 1H), 3.20–3.30 (m, 4H), 4.05–4.15 (m, 2H), 6.70–6.80 (m, 2H), 7.14 (d, J=7.5 Hz, 1H), 7.41 (s, 1H), 9.00-9.05 (m, 1H) MS(+), m/z, 382 (M+H$^+$); MS(−), m/z, 380 (M−H$^+$)

(B) Ethyl (Z)-2-fluoro-3-(8-[2-(4-isopropyl-1,3-thiazol-2-yl)ethyl]-2-morpholino-4-oxo-4H-pyrido[1,2-a]pyrimidin-3-yl)-2-propenoate The ethyl 2-fluoro-3-(8-[2-(4-isopropyl-1,3-thiazol-2-yl)ethyl]-2-hydroxy-4-oxo-4H-pyrido[1,2-a]pyrimidin-3-yl)-2-propenoate (35 mg) obtained in (A) was dissolved in methylene chloride (2 ml), added with triethylamine(35 ml) and tosyl chloride (46 mg) under ice cooling, and then the mixture was stirred overnight at room temperature. The reaction mixture was added with morpholine (49 ml) and further stirred for 4 hours. After the solvent was evaporated under reduced pressure, the residue was purified by silica gel column chromatography to obtain yellow powder (28 mg). This was dissolved in methylene chloride (1 ml), added with a trace amount of iodine, and then the mixture was stirred at room temperature for 30 minutes, and the solvent was evaporated to obtain the title compound.

$^1$H-NMR (CDCl$_3$) δ: 1.20–1.30 (m, 9H), 3.05 (m, 1H), 3.20 (t, J=7.8 Hz, 2H), 3.36 (t, J=7.8 Hz, 2H), 3.55–3.80 (m, 8H), 4.20–4.35 (m, 2H), 6.70–6.82 (m, 2H), 7.19 (d, J=7.5 Hz, 1H), 7.35 (d, J=36.9 Hz, 1H), 8.75–8.85 (m, 1H)

(C) (Z)-2-Fluoro-3-{8-[2-(4-isopropyl-1,3-thiazol-2-yl)ethyl]-2-morpholino-4-oxo-4H-pyrido[1,2-a]pyrimidin-3-yl}-2-propenoic acid The ethyl (Z)-2-fluoro-3-{8-[2-(4-isopropyl-1,3-thiazol-2-yl)ethyl]-2-morpholino-4-oxo-4H-pyrido[1,2-a]pyrimidin-3-yl}-2-propenoate (28 mg) obtained in (B) was dissolved in tetrahydrofuran (2 ml) and methanol (0.5 ml), added with a solution of lithium hydroxide(5 mg) in water (0.5 ml), and then the mixture was stirred at room temperature for 1 hour. The reaction mixture was added with water and washed with ether. Then, the aqueous layer was made acidic with diluted hydrochloric acid and extracted with ethyl acetate. The organic layer was dried over magnesium sulfate, and the solvent was evaporated under reduced pressure. The residue was purified by silica gel column chromatography to obtain the title compound (26 mg) as yellow powder.

$^1$H-NMR (CD$_3$OD) δ: 1.24 (d, 6H), 3.03 (m, 1H), 3.18 (t, 2H), 3.37 (t, 2H), 3.62 (m, 4H), 3.72 (m, 4H), 6.88–7.0 (m, 3H), 7.18 (s, 1H), 8.72 (d, 1H) MS (ES+) m/z 473 (M$^+$+1); MS (ES−) m/z 471 (M$^+$−1)

Example 136

(Z)-2-Fluoro-3-{8-[2-(4-isopropyl-1,3-thiazol-2-yl)ethyl]-2-(3-hydroxy-piperidino)-4-oxo-4H-pyrido[1,2-a]pyrimidin-3-yl}-2-propenoic acid $^1$H-NMR (CD$_3$OD) δ: 1.2–1.4 (m, 7H), 1.52 (m, 2H), 1.80 (m, 1H), 2.0 (m, 1H), 3.0 (m, 2H), 3.2 (t, 2H), 3.38 (t, 2H), 3.65 (m, 1H), 3.9 (m, 1H), 4.15 (m, 1H), 6.97 (m, 2H), 7.15 (d, J=36 Hz, 1H), 7.15 (s, 1H), 8.66 (d, 1H)

Example 137

(Z)-2-Fluoro-3-{8-[2-(4-isopropyl-1,3-thiazol-2-yl)ethyl]-2-(3-aminocarbonylmorpholino)-4-oxo-4H-pyrido[1,2-a]pyrimidin-3-yl}-2-propenoic acid $^1$H-NMR (CD$_3$OD) δ: 1.24 (d, 6H), 3.0 (m, 2H), 3.2 (m, 3H), 3.38 (t, 2H), 3.68 (m, 1H), 4.0 (m, 3H), 4.46 (d, 1H), 6.97 (s, 1H), 7.03 (d, 1H), 7.13 (s, 1H), 7.19 (d, J=36 Hz, 1H), 7.25 (s, 1H), 8.75 (d, 1H) MS (ES−) m/z 514 (M$^+$−1)

Example 138

(Z)-2-Fluoro-3-{8-[2-(4-isopropyl-1,3-thiazol-2-yl)ethyl]-2-(3-cyanomorpholino)-4-oxo-4H-pyrido[1,2-a]pyrimidin-3-yl}-2-propenoic acid $^1$H-NMR (CDCl$_3$) δ: 1.22 (d, 6H), 3.0 (m, 1H), 3.15 (m, 2H), 3.25 (m, 4H), 3.70–4.0 (m, 4H), 4.26 (dd, 1H), 6.72 (s, 1H), 6.81 (d, 1H), 6.85 (d, J=36 Hz, 1H), 7.16 (s, 1H), 8.72 (d, 1H) MS (ES−) m/z 496 (M$^+$−1)

Example 139

(Z)-2-Fluoro-3-{8-[2-(4-isopropyl-1,3-thiazol-2-yl)ethyl]-2-(4-amino-methylcarbonylpiperazino)-4-oxo-4H-pyrido[1,2-a]pyrimidin-3-yl}-2-propenoic acid $^1$H-NMR (CD$_3$OD) δ: 1.22 (d, 6H), 3.02 (m, 1H), 3.21 (t, 2H), 3.39 (t, 2H), 3.53 (m, 2H), 3.65 (m, 6H), 3.98 (s, 2H), 6.98 (s, 1H), 7.05 (d, 1H), 7.22 (s, 1H), 7.26 (d, J=37 Hz, 1H), 8.77 (d, 1H) MS (ES+) m/z 529 (M$^+$+1); MS (ES−) m/z 527 (M$^+$−1)

Example 140

(Z)-3-{8-[2-(4-Isopropyl-1,3-thiazol-2-yl)ethyl]-2-morpholino-4-oxo-4H-pyrido[1,2-a]pyrimidin-3-yl}-2-methoxy-2-propenoic acid (A) Ethyl (Z)-3-{8-[2-(4-isopropyl-1,3-thiazol-2-yl)ethyl]-2-morpholino-4-oxo-4H-pyrido[1,2-a]pyrimidin-3-yl}-2-methoxy-2-propenoate 2-Methoxy-2-phosphonoacetic acid triethyl ester (92 mg) was dissolved in tetrahydrofuran (1 ml), added with n-butyl lithium (1.6 M, 0.23 ml) at −78° C. under nitrogen atmosphere, and then the mixture was stirred at the same temperature for 30 minutes. The reaction mixture was added with a solution of 8-[2-(4-isopropyl-1,3-thiazol-2-yl)ethyl]-2-morpholino-4-oxo-4H-pyrido[1,2-a]pyrimidine-3-carbaldehyde (50 mg) dissolved in tetrahydrofuran (1 ml). The reaction temperature was gradually raised to room temperature, and the reaction mixture was stirred overnight at the same temperature. The reaction mixture was added with water and extracted with methylene chloride. The organic layer was dried over magnesium sulfate, and the solvent was evaporated under reduced pressure. The residue was purified by silica gel column chromatography to obtain the title compound.

$^1$H-NMR (CDCl$_3$) δ: 1.20–1.30 (m, 9H), 3.05 (m, 1H), 3.15–3.35 (m, 4H), 3.50 (s, 3H), 3.55–3.70 (m, 8H), 4.05–4.15 (m, 2H), 6.70–6.80 (m, 2H), 7.14 (s, 1H), 7.21 (s, 1H), 8.78 (d, J=7.5 Hz, 1H)

(B) (Z)-3-{8-[2-(4-Isopropyl-1,3-thiazol-2-yl)ethyl]-2-morpholino-4-oxo-4H-pyrido-[1,2-a]pyrimidin-3-yl}-2-methoxy-2-propenoic acid The ethyl (Z)-3-{8-[2-(4-isopropyl-1,3-thiazol-2-yl)ethyl]-2-morpholino-4-oxo-4H-pyrido[1,2-a]pyrimidin-3-yl}-2-methoxy-2-propenoate obtained in (A) was dissolved in tetrahydrofuran (2 ml) and methanol (0.5 ml), added with a solution of lithium hydroxide (5 mg) in water (0.5 ml), and then the mixture was stirred at room temperature for 2.5 hours. The reaction mixture was added with water and washed with ether, and then the aqueous layer was made acidic with diluted with hydrochloric acid and extracted with ethyl acetate. The organic layer was dried over magnesium sulfate, and the solvent was evaporated under reduced pressure to obtain the title compound (6 mg, 10% for the two steps) as yellow powder.

$^1$H-NMR (CD$_3$OD) δ: 1.23 (d, 6H), 3.02 (m, 1H), 3.19 (t, 2H), 3.38 (t, 2H), 3.55 (s, 3H), 3.62 (m, 4H), 3.70 (m, 4H), 6.95 (s, 1H), 6.99 (m, 2H), 7.18 (s, 1H), 8.74 (d, 1H) MS (ES+) m/z 485 (M$^+$+1); MS (ES−) m/z 483 (M$^+$−1)

Example 141

5-(1-{8-[2-(4-Isopropyl-1,3-thiazol-2-yl)ethyl]-2-morpholino-4-oxo-4H-pyrido[1,2-a]pyrimidin-3-yl}methylidene)-1,3-thiazolidine-2,4-dione 8-[2-(4-Isopropyl-1,3-thiazol-2-yl)ethyl]-2-morpholino-4-oxo-4H-pyrido[1,2-a]-pyrimidine-3-carbaldehyde (18 mg) and 2,4-thiazolidinedione (53 mg) were added with benzene (10 ml), piperidine (one drop) and acetic acid (two drops) and refluxed by heating for 3 hours in a vessel provided with a Dean-Stark trap. After the solvent was evaporated under reduced pressure, the residue was purified by silica gel column chromatography to obtain the title compound (17 mg) as yellow powder.

$^1$H-NMR (CDCl$_3$) δ: 1.26 (d, 6H), 3.01 (m, 1H), 3.22 (t, 2H), 3.38 (t, 2H), 3.63 (m, 4H), 3.80 (m, 4H), 6.73 (s, 1H), 6.87 (d, 1H), 7.23 (s, 1H), 7.78 (s, 1H), 8.80 (d, 1H) MS (ES−) m/z 510 (M$^+$−1)

Example 142

(E)-3-{8-[2-(4-Isopropyl-1,3-thiazol-2-yl)ethyl]-2-methoxy-4-oxo-4H-pyrido[1,2-a]pyrimidin-3-yl}-2-propenoic acid (A) tert-Butyl (E)-3-{8-[2-(4-isopropyl-1,3-thiazol-2-yl)ethyl]-4 2-methoxy-4-oxo-4H-pyrido[1,2-a]pyrimidin-3-yl}-2-propenoate tert-Butyl (E)-3-{8-[2-(4-isopropyl-1,3-thiazol-2-yl)ethyl]-2-hydroxy-4-oxo-4H-pyrido[1,2-a]pyrimidin-3-yl}-2-propenoate (20 mg) and triethylamine (63 ml) were dissolved in dimethylformamide (1.5 ml) and stirred at room temperature for 20 minutes under nitrogen atmosphere. The reaction mixture was added with dimethyl sulfate (4.3 ml) and stirred in the dark for 2 days. The reaction mixture was further added with dimethyl sulfate (4.3 ml) and stirred for 2 days in the same manner. The reaction mixture was added with water and extracted with ethyl acetate. The organic layer was washed with 1% aqueous solution of lithium chloride and dried over magnesium sulfate, and the solvent was evaporated under reduced pressure. The residue was purified by silica gel column chromatography to obtain the title compound (6.7 mg) as yellow powder. The starting material (7.6 mg) was also recovered.

$^1$H-NMR (CDCl$_3$): 1.28 (s, 3H), 1.29 (s, 3H), 1.51 (s, 9H), 3.07 (m, 1H), 3.21 (m, 2H), 3.42 (m, 2H), 4.06 (s, 3H), 6.74 (s, 1H), 7.01 (d, 1H), 7.11 (d, 1H), 7.37 (s, 1H), 7.94 (d, 1H), 9.00 (d, 1H)

(B) (E)-3-{8-[2-(4-Isopropyl-1,3-thiazol-2-yl)ethyl]-2-methoxy-4-oxo-4H-pyrido[1,2-a]-pyrimidin-3-yl}-2-propenoic acid The tert-butyl (E)-3-{8-[2-(4-isopropyl-1,3-thiazol-2-yl)ethyl]-2-methoxy-4-oxo-4H-pyrido[1,2-a]pyrimidin-3-yl}-2-propenoate (6.7 mg) obtained in (A) was treated with trifluoroacetic acid (0.5 ml) in the dark for 30 minutes, and then the solvent was evaporated. The residue was added with methanol and methylene chloride, and insoluble matters were collected by filtration to obtain the title compound (7.2 mg).

$^1$H-NMR (CDCl$_3$): 1.30 (s, 3H), 1.32 (s, 3H), 3.11 (m, 1H), 3.31 (m, 2H), 3.45 (m, 2H), 4.07 (s, 3H), 6.77 (s, 1H), 7.05 (d, 1H), 7.18 (d, 1H), 7.39 (s, 1H), 8.10 (d, 1H), 9.02 (d, 1H) MS (ES−): 398

Example 143

(Z)-3-{8-[2-(4-Isopropyl-1,3-thiazol-2-yl)ethyl]-2-methoxy-4-oxo-4H-pyrido[1,2-a]pyrimidin-3-yl}-2-propenoic acid (E)-3-{8-[2-(4-Isopropyl-1,3-thiazol-2-yl)ethyl]-2-methoxy-4-oxo-4H-pyrido-[1,2-a]pyrimidin-3-yl}-2-propenoic acid (1 mg) was dissolved in CDCl$_3$ (0.5 ml) and irradiated with light from a fluorescent lamp for 19 hours. The solvent was evaporated to obtain the title compound (1 mg).

$^1$H-NMR (CDCl$_3$) δ: 1.28 (s, 3H), 1.29 (s, 3H), 3.12 (m, 1H), 3.38 (m, 2H), 3.61 (m, 2H), 4.06 (s, 3H), 6.19 (d, 1H), 6.80 (d, 1H), 6.90 (s, 1H), 7.05 (d, 1H), 7.40 (d, 1H), 7.50 (s, 1H), 9.04 (d, 1H) MS (ES−): 398

Example 144

(E)-3-{8-[2-(4-Isopropyl-1,3-thiazol-2-yl)ethyl]-2-hydroxy-4-oxo-4H-pyrido[1,2-a]pyrimidin-3-yl}-2-propenoic acid tert-Butyl (E)-3-{8-[2-(4-isopropyl-1,3-thiazol-2-yl)ethyl]-2-hydroxy-4-oxo-4H-pyrido[1,2-a]pyrimidin-3-yl}-2-propenoate (15 mg) was treated with formic acid (1 ml) in the dark for 1 hour, and added with toluene. The solvent was evaporated under reduced pressure to obtain the title compound (22 mg).

$^1$H-NMR (DMSO-d$_6$) δ: 1.18 (s, 3H), 1.21 (s, 3H), 2.99 (m, 1H), 3.23-3.40 (m, 4H), 6.82 (d, 1H), 7.10 (s, 1H), 7.20 (s, 1H), 7.42 (d, 1H), 7.85 (d, 1H), 8.91 (d, 1H) MS (ES−): 384

Example 145

(E)-3-{8-[2-(4-Isopropyl-1,3-thiazol-2-yl)ethyl]-4-oxo-9-methoxy-2-morpholino-4H-pyrido[1,2-a]pyrimidin-3-yl}-2-propenoic acid (A) 3-Methoxy-4-methyl-2-nitropyridine 3-Hydroxy-4-methyl-2-nitropyridine (5 g) was dissolved in dimethylformamide (50 ml), added with cesium carbonate (11.6 g) and methyl iodide (13.7 g), and then the mixture was stirred overnight at room temperature. The reaction mixture was added with ethyl acetate and hexane, washed with water and dried over magnesium sulfate, and then the solvent was evaporated under reduced pressure to obtain the title compound (quantitative).

$^1$H-NMR (CDCl$_3$) δ: 2.30 (s, 3H), 3.78 (s, 3H), 7.27 (d, J=4.8 Hz, 1H), 7.98 (d, J=4.8 Hz, 1H)

(B) 2-Amino-3-methoxy-4-methylpyridine

The 3-methoxy-4-methyl-2-nitropyridine (1 g) obtained in (A) was dissolved in methanol (50 ml), added with 5% Pd/C (200 mg), and stirred at a pressure of 40 psi for 2 hours under hydrogen atmosphere. After the catalyst was removed by filtration, the solvent was evaporated under reduced pressure to obtain the title compound (850 mg) as yellow oil.

$^1$H-NMR (CDCl$_3$) δ: 2.20 (s, 3H), 3.70 (s, 3H), 4.6 (s, 2H), 6.45 (d, J=4.8 Hz, 1H), 7.85 (d, J=4.8 Hz, 1H)

(C) 2-(tert-Butoxycarbonylamino)-3-methoxy-4-methylpyridine

The 2-amino-3-methoxy-4-methylpyridine (850 mg) obtained in (B) was dissolved in tert-butanol (10 ml), added with di-tert-butyl dicarbonate (2 g), and stirred at room temperature for 72 hours. After the solvent was evaporated under reduced pressure, the residue was purified by silica gel column chromatography to obtain the title compound (1.1 g).

$^1$H-NMR (CDCl$_3$) δ: 1.52 (s, 9H), 2.27 (s, 3H), 3.75 (s, 3H), 4.6 (s, 1H), 6.78 (d, J=4.8 Hz, 1H), 8.05 (d, J=4.8 Hz, 1H)

(D) tert-Butyl N-4-[2-(4-isopropyl-1,3-thiazol-2-yl)ethyl]-3-methoxy-2-pyridylcarbamate The 2-(tert-butoxycarbonylamino)-3-methoxy-4-methylpyridine (2.84 g) obtained in (C) was dissolved in anhydrous tetrahydrofuran (50 ml) and added dropwise with n-butyl lithium (1.6 M, 19 ml) at −78° C. under nitrogen atmosphere. Then, the reaction temperature was raised to room temperature. The reaction mixture was cooled to −78° C. again, added dropwise with a solution of 2-bromomethyl-4-isopropylthiazole (3.94 g) dissolved in tetrahydrofuran (10 ml) and stirred at the same temperature for 1 hour. Then, the reaction mixture was added with water and extracted with ethyl acetate. The organic layer was dried over sodium sulfate, and the solvent was evaporated under reduced pressure. The residue was purified by silica gel column chromatography to obtain the title compound (4.1 g).

$^1$H-NMR (CDCl$_3$) δ: 1.20 (d, J=6.9 Hz, 6H), 1.45 (s, 9H), 2.95–3.20 (m, 5H), 3.67 (s, 3H), 6.60 (s, 1H), 6.70 (d, J=4.8 Hz, 1H), 8.05 (d, J=4.8 Hz, 1H)

(E) 2-Amino-4-[2-(4-isopropyl-1,3-thiazol-2-yl)ethyl]-3-methoxypyridine

The tert-butyl N-4-[2-(4-isopropyl-1,3-thiazol-2-yl)ethyl]-3-methoxy-2-pyridylcarbamate (4.1 g) obtained in (D) was added with trifluoroacetic acid (20 ml) at room temperature and stirred overnight. Then, the reaction mixture was added with 50 ml of water and 5 ml of 6 M hydrochloric acid and washed with ether. The aqueous layer was carefully added with sodium hydrogencarbonate to make pH of the aqueous layer weakly alkaline, and then extracted with ethyl acetate. The organic layer was dried over sodium sulfate, and the solvent was evaporated under reduced pressure to obtain the title compound (2.7 g).

$^1$H-NMR (CDCl$_3$) δ: 1.20 (d, J=6.9 Hz, 6H), 3.00–3.30 (m, 5H), 3.70 (s, 3H), 4.6 (s, 2H), 6.50 (s, 1H), 6.70 (d, J=4.8 Hz, 1H), 7.75 (d, J=4.8 Hz, 1H)

(F) 2-Hydroxy-8-[2-(4-isopropyl-1,3-thiazol-2-yl)ethyl]-9-methoxy-4H-pyrido[1,2-a]-pyrimidin-4-one The 2-amino-4-[2-(4-isopropyl-1,3-thiazol-2-yl)ethyl]-3-methoxypyridine (2.35 g) obtained in (E) and bis-2,4,6-trichlorophenyl malonate (4.3 g) were refluxed by heating for 1 hour in toluene (25 ml), and then the solvent was evaporated under reduced pressure. The residue was purified by silica gel column chromatography to obtain the title compound (2.8 g).

$^1$H-NMR (CDCl$_3$) δ: 1.28 (d, J=6.9 Hz, 6H), 2.95–3.05 (m, 1H), 3.30–3.40 (m, 4H), 3.95 (s, 3H), 5.35 (s, 1H), 6.70 (s, 1H), 7.00 (d, J=7.2 Hz, 1H), 8.82 (d, J=7.2 Hz, 1H)

(G) 8-[2-(4-Isopropyl-1,3-thiazol-2-yl)ethyl]-9-methoxy-2-morpholino-4H-pyrido[1,2a]-pyrimidin-4-one The 2-hydroxy-8-[2-(4-isopropyl-1,3-thiazol-2-yl)ethyl]-9-methoxy-4H-pyrido-[1,2-a]pyrimidin-4-one (1.77 g) obtained in (F) was dissolved in methylene chloride (40 ml), added with triethylamine (1.5 ml) and tosyl chloride (1.96 g) under ice cooling, and then the mixture was stirred at room temperature. After disappearance of the starting material was observed, the reaction mixture was added with morpholine (2.2 ml) and stirred overnight. After the solvent was evaporated under reduced pressure, the residue was purified by silica gel column chromatography to obtain the title compound (0.99 g) as yellow powder.

$^1$H-NMR (CDCl$_3$) δ: 1.28 (d, J=6.9 Hz, 6H), 3.00–3.10 (m, 1H), 3.20 (t, J=7.2 Hz, 2H), 3.30 (t, J=7.2 Hz, 2H), 3.65–3.80 (m, 8H), 4.00 (s, 3H), 5.60 (s, 1H), 6.65–6.70 (m, 2H), 8.80 (d, J=7.2 Hz, 1H)

(H) 8-[2-(4-Isopropyl-1,3-thiazol-2-yl)ethyl]-9-methoxy-2-morpholino-4-oxo-4H-pyrido[1,2-a]pyrimidine-3-carbaldehyde Dimethylformamide (2 ml) was added with phosphorus oxychloride (0.6 ml) under ice cooling and stirred at room temperature for 20 minutes. This mixture was cooled again with ice, and added with a solution of the 8-[2-(4-isopropyl-1,3-thiazol-2-yl)ethyl]-9-methoxy-2-morpholino-4H-pyrido[1,2-a]pyrimidin-4-one (0.99 g) obtained in (G) in methylene chloride (10 ml). The reaction mixture was stirred at room temperature for 3 hours, added with water, then added with saturated aqueous sodium hydrogencarbonate and extracted with methylene chloride. After the organic layer was dried over sodium sulfate, the solvent was evaporated and the residue was purified by silica gel column chromatography to obtain the title compound (1.54 g).

$^1$H-NMR (CDCl$_3$) δ: 1.28 (d, J=6.9 Hz, 6H), 3.00–3.10 (m, 1H), 3.20 (t, J=7.2 Hz, 2H), 3.30 (t, J=7.2 Hz, 2H), 3.70–3.85 (m, 8H), 3.95 (s, 3H), 6.75 (d, J=7.5 Hz, 1H), 8.00 (s, 1H), 8.55 ((d, J=7.5 Hz), 10.05 (s, 1H)

(I) tert-Butyl (E)-3-{8-[2-(4-isopropyl-1,3-thiazol-2-yl)ethyl]-4-oxo-9-methoxy-2-morpholino-4H-pyrido[1,2-a]pyrimidin-3-yl}-2-propenoate The 8-[2-(4-isopropyl-1,3-thiazol-2-yl)ethyl]-9-methoxy-2-morpholino-4-oxo-4H-pyrido[1,2-a]pyrimidine-3-carbaldehyde (300 mg) obtained in (H) was dissolved in tetrahydrofuran (4 ml) and dimethylformamide (1 ml), added with (tert-butoxy-carbonylmethylene)triphenylphosphorane (767 mg), and stirred at 80° C. for 15 hours. After the solvent was evaporated, the residue was purified by silica gel column chromatography to obtain the title compound (209 mg) as yellow powder.

$^1$H-NMR (CDCl$_3$) δ: 1.25 (d, J=6.9 Hz, 6H), 1.5 (s, 9H), 3.00–3.10 (m, 1H), 3.20–3.35 (m, 4H), 3.60–3.85 (m, 8H), 4.00 (s, 3H), 6.70 (s, 1H), 6.80 (d, J=7.5 Hz, 1H), 7.05 (d, J=15.3 Hz, 1H), 7.50 (d, J=15.3 Hz, 1H), 8.65 (d, J=7.5 Hz, 1H)

(J) (E)-3-{8-[2-(4-Isopropyl-1,3-thiazol-2-yl)ethyl]-4-oxo-9-methoxy-2-morpholino-4H-pyrido[1,2-a]pyrimidin-3-yl}-2-propenoic acid The tert-butyl (E)-3-{8-[2-(4-isopropyl-1,3-thiazol-2-yl)ethyl]-4-oxo-9-methoxy-2-morpholino-4H-pyrido[1,2-a]pyrimidin-3-yl}-2-propenoate (209 mg) obtained in (I) was dissolved in trifluoroacetic acid (2 ml) and stirred at room temperature for 30 minutes. The solvent was evaporated under reduced pressure to obtain the title compound (180 mg) as yellow powder.

$^1$H-NMR (CDCl$_3$) δ: 1.22 (d, 6H), 3.00 (m, 1H), 3.16 (m, 2H), 3.25 (t, 2H), 3.55 (m, 4H), 3.78 (m, 4H), 3.98 (s, 3H), 6.68 (s, 1H), 6.94 (d, J=16 Hz, 1H), 7.58 (d, J=16 Hz, 1H), 8.58 (d, 1H) MS (ES+) m/z 485 (M$^+$+1), MS (ES−) m/z 483 (M$^+$−1)

Example 146

5-((Z)-1-{8-[2-(4-Isopropyl-1,3-thiazol-2-yl)ethyl]-4-oxo-4H-pyrido[1,2a]-pyrimidin-3-yl}methylidene)-1,3-thiazolidine-2,4-dione (A) Methyl 8-[2-(4-isopropyl-1,3-thiazol-2-yl)ethyl]-4-oxo-4H-pyrido[1,2-a]-pyrimidine-3-carboxylate 4-[2-(4-Isopropyl-1,3-thiazol-2-yl)ethyl]-2-aminopyridine (497 mg) and dimethyl methoxymethylenemalonate (425 mg) were dissolved in methylene chloride, and stirred at 90°0 C. for 2 hours while the solvent was evaporated. The reaction mixture was added with propionic acid (0.5 ml) and heated at 160° C. for 10 hours with stirring. The reaction mixture was cooled, then added with ethyl acetate, washed with saturated sodium hydrogencarbonate and dried over sodium over sodium sulfate. The solvent was evaporated under reduced pressure, and the residue was purified by silica gel column chromatography to obtain the title compound (416 mg).

$^1$H-NMR (CDCl$_3$) δ: 1.28 (s, 3H), 1.31 (s, 3H), 3.06 (m, 1H), 3.35 (m, 2H), 3.40 (m, 2H), 3.99 (s, 3H), 6.75 (s, 1H), 7.20 (d, 1H), 7.60 (s, 1H), 9.07 (s, 1H), 9.19 (d, 1H)

(B) 8-[2-(4-Isopropyl-1,3-thiazol-2-yl)ethyl]-4-oxo-4H-pyrido[1,2-a]pyrimidine-3-carbaldehyde The methyl 8-[2-(4-isopropyl-1,3-thiazol-2-yl)ethyl]-4-oxo-4H-pyrido[1,2-a]-pyrimidin-3-carboxylate (660 mg) obtained in (A) was dissolved in tetrahydrofuran (30 ml), added dropwise with diisopropylaluminum hydride (1 M solution in tetrahydrofuran, 9.2 ml) at −78° C., and then the mixture was stirred for 2 hours at the same temperature. The reaction mixture was added with saturated aqueous ammonium chloride (1 ml), then added with 12% aqueous hydrochloric acid, and stirred at room temperature for 1 hour. After insoluble solids were removed by filtration through a Celite layer, the solvent of the filtrate was evaporated, and the residue was dissolved in methylene chloride. This solution was added with active manganese dioxide (1.2 g) and stirred at room temperature for 16 hours. Then, insoluble matters were removed by filtration to obtain the title compound (390 mg) as yellow powder.

$^1$H-NMR (CDCl$_3$) δ: 1.27 (d, 6H), 3.05 (m, 1H), 3.3–3.5 (m, 4H), 6.74 (s, 1H), 7.25 (d, 1H), 7.63 (s, 1H), 8.87 (s, 1H), 9.16 (d, 1H), 10.36 (s, 1H)

(C) 5-((Z)-1-{8-[2-(4-Isopropyl-1,3-thiazol-2-yl)ethyl]-4-oxo-4H-pyrido[1,2a]-pyrimidin-3-yl}methylidene)-1,3-thiazolidine-2,4-dione The 8-[2-(4-isopropyl-1,3-thiazol-2-yl)ethyl]-4-oxo-4H-pyrido[1,2-a]pyrimidine-3-carbaldehyde (70 mg) obtained in (B) and 2,4-thiazolidinedione (360 mg) were added with benzene(10 ml), piperidine (one drop) and acetic acid (two drops) and refluxed by heating for 1 hour in a vessel provided with a Dean-Stark trap. After the solvent was evaporated under reduced pressure, the residue was purified by silica gel column chromatography to obtain the title compound (62 mg) as yellow powder.

$^1$H-NMR (CDCl$_3$+CD$_3$OD) δ: 1.22 (d, 6H), 3.00 (m, 1H), 3.2–3.4 (m, with CD$_3$OD), 6.72 (s, 1H), 7.18 (d, 1H), 7.51 (s, 1H), 7.86 (s, 1H), 8.42 (s, 1H), 8.98 (d, 1H) MS (ES+) m/z 427 (M$^+$+1), MS (ES−) m/z 425 (M$^+$−1)

Example 147

3-{8-[2-(4-Isopropyl-1,3-thiazol-2-yl)ethyl]-4-oxo-4H-pyrido[1,2-a]-pyrimidin-3-yl}-4,5-dihydro-1,2,4-oxadiazol-5-one (A) 8-[2-(4-Isopropyl-1,3-thiazol-2-yl)ethyl]-4-oxo-4H-pyrido[1,2-a]pyrimidine-3-carboxamide A mixture of methyl 8-[2-(4-isopropyl-1,3-thiazol-2-yl)ethyl]-4-oxo-4H-pyrido-[1,2-a]pyrimidine-3-carboxylate (400 mg), concentrated aqueous ammonia (6 ml) and methanol (9 ml) was stirred overnight. Insoluble solids were collected by filtration to obtain the title compound (117 mg). The reaction mixture was concentrated and the residue was purified by silica gel column chromatography to further obtain the title compound (69 mg).

$^1$H-NMR (CDCl$_3$) δ: 1.29 (s, 3H), 1.31 (s, 3H), 3.09 (m, 1H), 3.39 (m, 2H), 3.48 (m, 2H), 5.73 (brs, 1H), 6.79 (s, 1H), 7.29 (d, 1H), 7.66 (s, 1H), 8.71 (brs, 1H), 9.14 (d, 1H), 9.30 (s, 1H) MS (ES+) m/z 343 (M$^+$+1), MS (ES−) m/z 341 (M$^+$−1)

(B) 8-[2-(4-Isopropyl-1,3-thiazol-2-yl)ethyl]-4-oxo-4H-pyrido[1,2-a]pyrimidine-3-carbonitrile A mixture of the 8-[2-(4-isopropyl-1,3-thiazol-2-yl)ethyl]-4-oxo-4H-pyrido[1,2-a]pyrimidine-3-carboxamide (186 mg) obtained in (A), p-toluenesulfonyl chloride (207 mg) and pyridine (0.18 ml) was stirred overnight in methylene chloride. The mixture was added with triethylamine (0.2 ml), further stirred for 2 days, and diluted with methylene chloride. This mixture was washed with saturated aqueous sodium hydrogencarbonate and saturated brine, and dried over sodium sulfate, and the solvent was evaporated under reduced pressure. The residue was purified by silica gel column chromatography to obtain the title compound (98 mg). The starting material was also recovered (73 mg).

$^1$H-NMR (CDCl$_3$) δ: 1.29 (s, 3H), 1.31 (s, 3H), 3.09 (m, 1H), 3.37 (m, 2H), 3.49 (m, 2H), 6.79 (s, 1H), 7.31 (d, 1H), 7.65 (s, 1H), 8.58 (s, 1H), 9.09 (d, 1H) MS (ES+) m/z 325 (M$^+$+1), MS (ES−) m/z 323 (M$^+$−1)

(C) 3-{8-[2-(4-Isopropyl-1,3-thiazol-2-yl)ethyl]-4-oxo-4H-pyrido[1,2-a]pyrimidin-3yl}-4,5-dihydro-1,2,4-oxadiazol-5-one The 8-[2-(4-isopropyl-1,3-thiazol-2-yl)ethyl]-4-oxo-4H-pyrido[1,2-a]pyrimidine-3-carbonitrile (35 mg) obtained in (B), hydroxylamine (9 mg) and triethylamine (28 ml) were refluxed overnight by heating in ethanol. After the reaction mixture was cooled, the solvent was evaporated under reduced pressure, and the residue was purified by silica gel column chromatography to obtain an oxim compound (22 mg). This compound (11 mg), 1,1'-carbodiimidazole (5 mg) and pyridine (2 ml) were dissolved in tetrahydrofuran (0.5 ml), refluxed by heating for 45 minutes, and stirred overnight at room temperature. The reaction mixture was concentrated, and the residue was purified by silica gel column chromatography to obtain the title compound (1.6 mg).

$^1$H-NMR (CDCl$_3$) δ: 1.26 (s, 3H), 1.30 (s, 3H), 3.08 (m, 1H), 3.40 (m, 4H), 6.75 (s, 1H), 7.18 (brm, 1H), 7.70 (brs, 1H), 9.08 (brm, 1H) MS (ES+) m/z 384 (M$^+$+1), MS (ES−) m/z 382 (M$^+$−1)

Example 148

2-Hydroxy-8-[2-(4-isopropyl-1,3-thiazol-2-yl)ethyl]-3-(1H-1,2,3,4-tetrazol-5-yl)-4H-pyrido[1,2-a]pyrimidin-4-one 2-Hydroxy-8-[2-(4-isopropyl-1,3-thiazol-2-yl)ethyl]-3-[2-(4-methoxybenzyl)-2H-1,2,3,4-tetrazol-5-yl]-4H-pyrido[1,2-a]pyrimidin-4-one (30 mg) was added with anisole (0.15 ml) and trifluoroacetic acid (1 ml) and stirred at room temperature for 20 hours. After the solvent was evaporated under reduced pressure, the residue was added with methanol and toluene and the solvents were evaporated again under reduced pressure. The residue was added with methanol and methylene chloride, and the deposited crystals were collected by filtration to obtain the title compound (15 mg).

$^1$H-NMR (CD$_3$OD) δ: 1.25 (s, 3H), 1.28 (s, 3H), 3.04 (m, 1H), 3.35 (m, 2H), 3.46 (m, 2H), 7.04 (s, 1H), 7.31 (s, 1H), 7.45 (d, 1H), 9.11 (d, 1H) MS (ES+) m/z 384 (M$^+$+1)

Example 149

8-[2-(4-Isopropyl-1,3-thiazol-2-yl)ethyl]-2-methoxy-3-(1H-1,2,3,4-tetrazol-5-yl)-4H-pyrido[1,2-a]pyrimidin-4-one (A) 8-[2-(4-Isopropyl-1,3-thiazol-2-yl)ethyl]-2-methoxy-3-[2-(4-methoxybenzyl)-2H-1,2,3,4-tetrazol-5-yl]-4H-pyrido[1,2-a]pyrimidin-4-one 2-Hydroxy-8-[2-(4-isopropyl-1,3-thiazol-2-yl)ethyl]-3-[2-(4-methoxybenzyl)-2H-1,2,3,4-tetrazol-5-yl]-4H-pyrido[1,2-a]pyrimidin-4-one (24 mg) was dissolved in dimethylformamide (1.5 ml), added with triethylamine (1.6 ml) and dimethyl sulfate (22 mg) and stirred overnight at room temperature. The reaction mixture was further added with dimethyl sulfate (5 ml), stirred for 4 hours, and then added with water and extracted with ethyl acetate. After the organic layer was dried over sodium sulfate, the solvent was evaporated under reduced pressure, and the residue was purified by silica gel column chromatography to obtain the title compound (5 mg).

$^1$H-NMR (CDCl$_3$) δ: 1.28 (s, 3H), 1.33 (s, 3H), 3.09 (m, 1H), 3.29 (m, 2H), 3.44 (m, 2H), 3.79 (s, 3H), 4.03 (s, 3H), 5.79 (s, 2H), 6.79 (s, 1H), 6.88 (d, 2H), 7.02 (d, 1H), 7.41 (d, 2H), 9.02 (d, 1H) MS (ES+) m/z 518 (M$^+$+1), MS (ES−) m/z 516 (M$^+$−1)

(B) 8-[2-(4-Isopropyl-1,3-thiazol-2-yl)ethyl]-2-methoxy-3-(1H-1,2,3,4-tetrazol-5-yl)-4H-pyrido[1,2-a]pyrimidin-4-one The 8-[2-(4-isopropyl-1,3-thiazol-2-yl)ethyl]-2-methoxy-3-[2-(4-methoxy-benzyl)-2H-1,2,3,4-tetrazol-5-yl]-4H-pyrido[1,2-a]pyrimidin-4-one (5 mg) obtained in (A) was added with trifluoroacetic acid (0.3 ml) and anisole (0.1 ml) and stirred for 2 days. The solvent was evaporated under reduced pressure, and the residue was added with hexane and ethyl acetate. Insoluble solids were collected by filtration and dried to obtain the title compound (1.2 mg).

$^1$H-NMR (CDCl$_3$) δ: 1.30 (s, 3H), 1.32 (s, 3H), 3.12 (m, 1H), 3.37 (m, 2H), 3.49 (m, 2H), 4.29 (s, 3H), 6.79,(s, 1H), 7.53 (s, 1H), 9.10 (d, 1H) MS (ES+) m/z 398 (M$^+$+1), MS (ES−) m/z 396 (M$^+$−1)

Example 150

(E)-3-{2-Carboxymethylthio-8-[2-(4-isopropyl-1,3-thiazol-2-yl)ethyl]-4-oxo-4H-pyrido[1,2-a]pyrimidin-3-yl}-2-propenoic acid (A) tert-Butyl (E)-3-{2-[(diphenoxyphosphoryl)oxy]-8-[2-(4-isopropyl-1,3-thiazol-2-yl)-ethyl]-4-oxo-4H-pyrido[1,2-a]pyrimidin-3-yl}-2-propenoate tert-Butyl (E)-3-{8-[2-(4-isopropyl-1,3-thiazol-2-yl)ethyl]-2-hydroxy-4-oxo-4H-pyrido[1,2-a]pyrimidin-3-yl}-2-propenoate (80 mg) was suspended in methylene chloride (40 ml), added with triethylamine (0.13 ml) and diphenylphosphoryl chloride (0.15 ml), and then the mixture was stirred at room temperature for 16 hours. The reaction mixture was washed with saturated aqueous sodium hydrogencarbonate, 5% aqueous hydrochloric acid and saturated brine, and then dried over sodium sulfate and the solvent was evaporated under reduced pressure. The residue was purified by silica gel column chromatography to obtain the title compound (104 mg).

$^1$H-NMR (CDCl$_3$) δ: 1.26 (d, 6H), 1.51 (s, 9H), 3.05 (m, 1H), 3.2–3.4 (m, 4H), 6.73 (s, 1H), 7.1–7.5 (m, 13H), 7.75 (d, J=15.8 Hz, 1H), 8.96 (d, 1H)

(B) tert-Butyl (E)-3-{2-(tert-butoxycarbonylmethylthio)-8-[2-(4-isopropyl-1,3-thiazol-2-yl)ethyl]-4-oxo-4H-pyrido[1,2-a]pyrimidin-3-yl}-2-propenoate The tert-butyl (E)-3-{2-[(diphenoxyphosphoryl)oxy]-8-[2-(4-isopropyl-1,3-thiazol-2-yl)ethyl]-4-oxo-4H-pyrido[1,2-a]pyrimidin-3-yl}-2-propenoate (62 mg) obtained in (A) was dissolved in dimethylformamide (1 ml) and added dropwise with a solution of lithium sulfide in ethanol (0.1 g/ml) until the starting material disappeared. Separately, tert-butyl bromoacetate (0.04 ml) was dissolved in dimethylformamide (1 ml), added with sodium iodide (69 mg), and then stirred at room temperature for 40 minutes. These two of solutions were mixed and stirred at room temperature for 2 hours. The reaction mixture was distributed between ethyl acetate and water, and the organic layer was dried. The solvent was evaporated, and the residue was purified by silica gel column chromatography to obtain the title compound (19 mg).

$^1$H-NMR (CDCl$_3$) δ: 1.29 (d, 6H), 1.45 (s, 9H), 1.53 (s, 9H), 3.06 (m, 1H), 3.2–3.4 (m, 4H), 3.93 (s, 2H), 6.73 (s, 1H), 6.99 (d, 1H), 7.24 (d, J=15.6 Hz, overlapped with CHCl$_3$, 1H), 7.32 (s, 1H), 7.78 (d, J=15.6 Hz, 1H), 8.95 (d, 1H)

(C) (E)-3-{2-Carboxymethylthio-8-[2-(4-isopropyl-1,3-thiazol-2-yl)ethyl]-4-oxo-4H-pyrido[1,2-a]pyrimidin-3-yl}-2-propenoic acid The tert-butyl (E)-3-{2-(tert-butoxycarbonylmethylthio)-8-[2-(4-isopropyl-1,3-thiazol-2-yl)ethyl]-4-oxo-4H-pyrido[1,2-a]pyrimidin-3-yl}-2-propenoate (19 mg) obtained in (B) was dissolved in methylene chloride (2 ml), added with triethylsilane (0.5 ml) and trifluoroacetic acid (0.5 ml), and then the mixture was stirred at room temperature for 5 hours. After the solvent was evaporated under reduced pressure, the residue was purified by silica gel column chromatography to obtain the title compound (4 mg) as yellow powder.

$^1$H-NMR (CDCl$_3$) δ: 1.18 (d, 6H), 2.96 (m, 1H), 3.15 (m, 2H), 3.25 (m, 1H), 3.91 (d, 2H), 6.69 (s, 1H), 6.99 (d, 1H), 7.15 (d, J=15 Hz, 1H), 7.31 (s, 1H), 7.77 (d, J=15 Hz, 1H), 8.83 (d, J=7 Hz, 1H) MS (ES+) m/z 460 (M$^+$+1), MS (ES−) m/z 458 (M$^+$−1)

Example 151

(E)-3-{2-Methylthio-8-[2-(4-isopropyl-1,3-thiazol-2-yl)ethyl]-4-oxo-4H-pyrido[1,2-a]pyrimidin-3-yl}-2-propenoic acid $^1$H-NMR (CDCl$_3$) δ: 1.21 (d, 6H), 2.56 (s, 3H), 3.00 (m, 1H), 3.19 (m, 2H), 3.31 (m, 2H), 6.69 (s, 1H), 6.99 (d, 1H), 7.19 (d, J=15 Hz, 1H), 7.36 (s, 1H), 7.83 (d, J=15 Hz, 1H), 8.87 (d, J=7 Hz, 1H)

Example 152

(E)-3-{2-Aminocarbonylmethylthio-8-[2-(4-isopropyl-1,3-thiazol-2-yl)-ethyl]-4-oxo-4H-pyrido[1,2-a]pyrimidin-3-yl}-2-propenoic acid $^1$H-NMR (CDCl$_3$+CD$_3$OD) δ: 1.23 (d, 6H), 3.02 (m, 1H), 3.1-3.5 (m, with CD$_3$OD), 3.88 (d, 2H), 6.74 (s, 1H), 7.06 (d, 1H), 7.15 (d, J=16 Hz, 1H), 7.41 (s, 1H), 7.74 (d, J=16 Hz, 1H), 8.89 (d, J=8 Hz, 1H) MS (ES+) m/z 458 (M$^+$+1)

Example 153

(E)-3-{2-[2-(Aminoethylthiomethyl)-3-pyridylthio]-8-[2-(4-isopropyl-1,3-thiazol-2-yl)ethyl]-4-oxo-4H-pyrido[1,2-a]pyrimidin-3-yl}-2-propenoic acid $^1$H-NMR (CD$_3$OD) δ: 1.22 (d, 6H), 3.02 (m, 1H), 3.15–3.4 (m, with CHD$_2$OD), 6.95 (s, 1H), 7.02 (s, 1H), 7.28 (d, 1H), 7.32 (d, J=16 Hz, 1H), 7.52 (dd, 1H), 8.02 (d, J=16 Hz, 1H), 8.10 (d, 1H), 8.72 (m, 1H), 8.98 (d, 1H)

Example 154

1-Ethyl-7-[(E)-2-(4-isopropyl-1,3-thiazol-2-yl)-1-ethenyl]-4-oxo-1,4-dihydro[1,8]naphthylidine-3-carboxylic acid (A) Ethyl 1-ethyl-7-[(E)-2-(4-isopropyl-1,3-thiazol-2-yl)-1-ethenyl]-4-oxo-1,4-dihydro[1,8]naphthylidine-3-carboxylate

[(4-Isopropyl-1,3-thiazol-2-yl)methyl](triphenyl)phosphonium bromide (723 mg, Chem. Pharm. Bull., 1977, 25, 349–352) was suspended in tetrahydrofuran (20 ml), added dropwise with n-butyl lithium (1.6 M, 1.2 mmol) at −20° C. under nitrogen atmosphere, and stirred at the same temperature for 20 minutes. The reaction mixture was added with a solution of ethyl 1-ethyl-7-formyl-4-oxo-1,4-dihydro-[1,8]naphthylidine-3-carboxylate (316 mg) dissolved in tetrahydrofuran, and stirred for 2 hours. The reaction mixture was added with saturated aqueous ammonium chloride and extracted with ethyl acetate. After the organic layer was dried, the solvent was evaporated under reduced pressure. The residue was purified by silica gel column chromatography to obtain the title compound (456 mg).

$^1$H-NMR (300 MHz, CDCl$_3$) δ: 1.35 (d, 6H), 1.41 (t, 3H), 1.53 (t, 3H), 3.15 (m, 1H), 4.39 (q, 2H), 4.52 (q, 2H), 6.94 (s, 1H), 7.44 (d, J=15.8 Hz, 1H), 7.47 (d, 1H), 7.94 (d, J=15.8 Hz, 1H), 8.63 (s, 1H), 8.73 (d, 1H)

(B) 1-Ethyl-7-[(E)-2-(4-isopropyl-1,3-thiazol-2-yl)-1-ethenyl]-4-oxo-1,4-dihydro[1,8]-naphthylidine-3-carboxylic acid The ethyl 1-ethyl-7-[(E)-2-(4-isopropyl-1,3-thiazol-2-yl)-1-ethenyl]-4-oxo-1,4-dihydro[1,8]naphthylidine-3-carboxylate (120 mg) obtained in (A) and lithium hydroxide (26 mg) were added with methanol (10 ml) and water (5 ml), and then the mixture was stirred at room temperature for 16 hours. After the methanol was evaporated, pH of the residue was made 6 by using 5% hydrochloric acid, and insoluble substance was collected by filtration and dried to obtain the title compound (80 mg).

$^1$H-NMR (300 MHz, CDCl$_3$) δ: 1.39 (d, 6H), 1.61 (t, 3H), 3.25 (m, 1H), 4.69 (q, 2H), 7.05 (s, 1H), 7.62 (m, 2H), 8.13 (d, J=16 Hz, 1H), 8.80 (d, J=8 Hz, 1H), 8.94 (s, 1H) MS (ES+) m/z 370 (M$^+$+1), MS (ES−) m/z 368 (M$^+$−1)

Example 155

1-Ethyl-7-[(E)-2-(4-isopropyl-1,3-thiazol-2-yl)-1-ethenyl]-3-(1H-1,2,3,4-tetrazol-5-yl)-1,4-dihydro[1,8]naphthylidin-4-one (A) 1-Ethyl-7-[(E)-2-(4-isopropyl-1,3-thiazol-2-yl)-1-ethenyl]-4-oxo-1,4-dihydro[1,8]-naphthylidine-3-carboxamide Ethyl 1-ethyl-7-[(E)-2-(4-isopropyl-1,3-thiazol-2-yl)-1-ethenyl]-4-oxo-1,4-dihydro[1,8]naphthylidine-3-carboxylate (160 mg) was added with 25% aqueous ammonia (20 ml) and isopropanol (3ml) and heated at 100° C. for 16 hours in a Parr acid digestion bomb. After the reaction mixture was cooled, the solvent was evaporated to obtain the title compound (148 mg).

$^1$H-NMR (300 MHz, CDCl$_3$) δ: 1.36 (d, 6H), 1.56 (t, 3H), 3.18 (m, 1H), 4.61 (q, 2H), 5.75 (brs, 1H)6.97 (s, 1H), 7.47 (d, J=15.8 Hz, 1H), 7.51 (d, 1H), 7.98 (d, J=15.8 Hz, 1H), 8.75 (d, 1H), 8.95 (s, 1H), 9.56 (brs, 1H)

(B) 1-Ethyl-7-[(E)-2-(4-isopropyl-1,3-thiazol-2-yl)-1-ethenyl]-4-oxo-1,4-dihydro[1,8]-naphthylidine-3-carbonitrile The 1-ethyl-7-[(E)-2-(4-isopropyl-1,3-thiazol-2-yl)-1-ethenyl]-4-oxo-1,4-dihydro[1,8]naphthylidine-3-carboxamide (32 mg) obtained in (A) was dissolved in 1,2-dichloroethane, added with benzenesulfonyl chloride (0.12 ml), pyridine (0.18 ml) and dimethylaminopyridine (several pieces), and then the mixture was stirred at 40° C. for 24 hours. The reaction mixture was diluted with 1,2- dichloroethane, then washed with 5% hydrochloric acid, saturated aqueous sodium hydrogencarbonate and saturated brine, and then dried and the solvent was evaporated under reduced pressure. The residue was purified by silica gel column chromatography to obtain the title compound (19 mg).

$^1$H-NMR (300 MHz, CDCl$_3$) δ: 1.36 (d, 6H), 1.56 (t, 3H), 3.18 (m, 1H), 4.56 (q, 2H). 6.99 (s, 1H), 7.45 (d, J=15.8 Hz, 1H), 7.51 (d, 1H), 7.98 (d, J=15.8 Hz, 1H), 8.20 (s, 1H), 8.69 (d, 1H)

(C) 1-Ethyl-7-[(E)-2-(4-isopropyl-1,3-thiazol-2-yl)-1-ethenyl]-3-(1H-1,2,3,4-tetrazol-5-yl)-1,4-dihydro[1,8]naphthylidin-4-one The 1-ethyl-7-[(E)-2-(4-isopropyl-1,3-thiazol-2-yl)-1-ethenyl]-4-oxo-1,4-dihydro[1,8]naphthylidine-3-carbonitrile (32 mg) obtained in (B) was dissolved in tetrahydrofuran (20 ml), added with sodium azide (100 mg), ammonium chloride (200 mg) and stirred at 80° C. for 2 hours. The reaction mixture was added with water and adjusted to pH 8 with saturated aqueous sodium hydrogencarbonate, and the tetrahydrofuran was evaporated. The residue was added with five drops of 25% aqueous ammonia, and insoluble solids were removed by filtration. The filtrate was adjusted to pH 7 with 12% aqueous hydrochloric acid, loaded on a HP-20 reverse phase column, sufficiently washed with water, and then eluted with water/acetonitrile/aqueous ammonia (80:20:0.2, v/v). After the solvent was evaporated, the residue was added with tert-butyl methyl ketone, and insoluble substance was taken by filtration and dried to obtain the title compound (13 mg) as yellow powder.

$^1$H-NMR (300 MHz, CDCl$_3$+CD$_3$OD) δ: 1.24 (d, 6H), 1.50 (t, 3H), 3.02 (m, 1H), 4.61 (q, 2H), 6.92 (s, 1H), 7.40 (d, J=15.8 Hz, 1H), 7.51 (d, J=8 Hz, 1H), 7.91 (d, J=15.8 Hz, 1H), 8.66 (d, J=8 Hz, 1H), 9.04 (s, 1H) MS (ES+) m/z 394 (M$^+$+1), MS (ES−) m/z 392 (M$^+$−1)

Example 156

(E)-3-{7-Fluoro-2-(3-hydroxypiperidino)-8-[2-(4-isopropyl-1,3-thiazol-2-yl)ethyl]-4-oxo-4H-pyrido[1,2-a]pyrimidin-3-yl}-2-propenoic acid (A) N1-(4-Methyl-5-nitro-2-pyridyl)acetamide 4-Methyl-5-nitro-2-pyridinamine (3.69 g, 2.41 mmol) was added with acetic anhydride (10 ml) and stirred at 130° C. for 1.5 hours. The reaction mixture was left stand for cooling, and then added with distilled water (5.4 ml) at 0° C., heated to 130° C., and stirred for 45 minutes. The reaction mixture was left stand for cooling and concentrated, and the deposited crystals were collected by filtration and washed with distilled water to obtain the title compound (4.71 g, quantitative).

$^1$H-NMR (CDCl$_3$) δ: 2.26 (3H, s), 2.70 (3H, s), 8.19 (1H, br), 8.23 (1H, s), 8.95 (1H, s) MS; m/z: MH$^-$194

(B) N1-(5-Amino-4-methyl-2-pyridyl)acetamide

The N1-(4-methyl-5-nitro-2-pyridyl)acetamide (4.70 g, 24.1 mmol) obtained in (A) was dissolved in ethanol (150 ml), added with 10% palladium/carbon (0.95 g) and subjected to catalytic reduction overnight at 1 atm under hydrogen atmosphere. The catalyst was removed by filtration and washed with ethanol. The filtrate was concentrated and the resulting residue was purified by silica gel column chromatography (chloroform chloroform:methanol=100:5) to obtain the title compound (4.10 g, quantitative) as brown solid.

$^1$H-NMR (CD$_3$OD) δ: 2.11 (3H, s), 2.18 (3H, s), 7.61 (1H, s), 7.70 (1H, s)

(C) 6-(Acetylamino)-4-methyl-3-pyridinediazonium tetrafluoroborate

The N1-(5-amino-4-methyl-2-pyridyl)acetamide (8.00 g, 48.4 mmol) obtained in (B) was dissolved in tetrafluoroboric acid (160 ml) and slowly added dropwise with an aqueous solution (40 ml) of sodium nitrite (3.51 g, 50.8 mmol) at −20° C. under nitrogen atmosphere. The reaction mixture was further stirred at −10° C. for 1 hour and added with diethyl ether (800 ml), and the deposited white solid was collected by filtration and washed with diethyl ether to obtain the title compound (14.7 g, quantitative).

(D) N1-(5-Fluoro-4-methyl-2-pyridyl)acetamide

Toluene (280 ml) heated at 100° C. with stirring was added with the 6-(acetylamino)-4-methyl-3-pyridinediazonium tetrafluoroborate (12.8 g, 48.4 mmol) obtained in (C) and further refluxed by heating for 1 hour. After the reaction mixture was left stand for cooling and the solvent was evaporated, the residue was diluted with chloroform and washed with 1 N aqueous sodium hydroxide. The organic layer was dried over anhydrous magnesium sulfate, then the solvent was evaporated and the resulting residue was purified by silica gel column chromatography (chloroform: methanol=100:1) to obtain the title compound (3.48 g, 43%) as yellow solid.

$^1$H-NMR (CDCl$_3$) δ: 2.19 (3H, s), 2.32 (3H, s), 7.93 (1H, br), 7.98 (1H, s), 8.08 (1H, d, J=5.6 Hz) MS; m/z: (MH$^+$) 169

(E) 5-Fluoro-4-methyl-2-pyridinamine

The N1-(5-fluoro-4-methyl-2-pyridyl)acetamide (4.25 g, 25.3 mmol) obtained in (D) was dissolved in ethanol (3ml), added with 6 M aqueous hydrochloric acid (3ml) and refluxed by heating for 1 hour and 30 minutes. The reaction mixture was left stand for cooling and the solvent was concentrated. The resulting residue was dissolved in distilled water, and the system was made basic with 1 N aqueous sodium hydroxide and extracted twice with chloroform. The organic layer was dried over anhydrous magnesium sulfate and the solvent was evaporated to obtain the title compound (2.82 g, 88%) as solid.

$^1$H-NMR (CD$_3$OD) δ: 2.19 (3H, s), 6.45 (1H, m), 7.65 (1H, m) ES−MS; m/z: (MH$^+$) 127

(F) tert-Butyl N-(5-fluoro-4-methyl-2-pyridyl)carbamate

The 5-fluoro-4-methyl-2-pyridinamine (2.82 g, 22.4 mmol) obtained in (E) was dissolved in tert-butanol (100 ml), slowly added dropwise with a solution of di-tert-butyl dicarbonate (5.12 g, 23.5 mmol) in tetrahydrofuran (10 ml) over 1 hour, and then the mixture was stirred at room temperature. The deposited substance was removed by filtration, and the reaction mixture was concentrated. The resulting residue was purified by silica gel column chromatography (chloroform) to obtain the title compound (3.17 g, 66%) as white solid.

$^1$H-NMR (CDCl$_3$) δ: 1.53 (9H, s), 2.30 (3H, s), 7.74 (1H, br), 7.83 (1H, d, J=5.8 Hz), 7.99 (1H, d, J=1.2 Hz) MS; m/z: (MH$^+$) 227

(G) tert-Butyl N-{5-fluoro-4-[2-(4-isopropyl-1,3-thiazol-2-yl)ethyl]-2-pyridyl}carbamate The tert-butyl N-(5-fluoro-4-methyl-2-pyridyl)carbamate (75.6 mg, 0.334 mmol) obtained in (F) was dissolved in tetrahydrofuran (2 ml) and added dropwise with n-butyl lithium (1.5 M solution in hexane, 0.468 ml, 0.702 mmol) at −78° C. under argon atmosphere. The reaction mixture was warmed to room temperature, stirred for 1 hour, cooled to −78° C. again, added dropwise with a solution of 2-(bromomethyl)-4-isopropyl-1,3-thiazole (84.6 mg, 0.384 mmol) in tetrahydrofuran (2 ml), and then warmed to room temperature. The reaction mixture was added with water and extracted twice with ethyl acetate. The organic layer was dried over anhydrous magnesium sulfate, and the solvent was evaporated. The resulting residue was purified by silica gel column chromatography (chloroform:ethyl acetate=100:1) to obtain the title compound (40.0 mg, 33%).

$^1$H-NMR (CDCl$_3$) δ: 1.28 (6H, d, J=7.1 Hz), 1.54 (9H, s), 3.09 (1H, m), 3.15 (2H, m), 3.32 (2H, m), 6.71 (1H, s), 7.90 (1H, d, J=5.6 Hz), 8.05 (1H, d, J=1.5 Hz)8.23 (1H, br) MS; m/z: (MH$^+$) 366

(H) 5-Fluoro-4-[2-(4-isopropyl-1,3-thiazol-2-yl)ethyl]-2-pyridinamine

The tert-butyl N-{5-fluoro-4-[2-(4-isopropyl-1,3-thiazol-2-yl)ethyl]-2-pyridyl}-carbamate (393 mg, 1.08 mmol) obtained in (G) was dissolved in methylene chloride (10 ml), added with trifluoroacetic acid (10 ml) under ice cooling, and stirred overnight at room temperature. The reaction mixture was concentrated, and the resulting residue was dissolved in chloroform and washed with 1 N aqueous sodium hydroxide. The organic layer was dried over anhydrous magnesium sulfate and the solvent was evaporated. The resulting residue was purified by silica gel column chromatography (chloroform:methanol=100:2) to obtain the title compound (40.0 mg, 33%) as an oil.

$^1$H-NMR (CDCl$_3$) δ: 1.29 (6H, d, J=6.8 Hz), 3.05 (3H, m), 3.27 (2H, m), 6.32 (1H, m), 6.72 (1H, m), 7.84 (1H, m)

(I) 7-Fluoro-2-hydroxy-8-[2-(4-isopropyl-1,3-thiazol-2-yl)ethyl]-4-oxo-4H-pyrido[1,2-a]-pyrimidin-4-one The 5-fluoro-4-[2-(4-isopropyl-1,3-thiazol-2-yl)ethyl]-2-pyridinamine (310 mg, 1.15 mmol) obtained in (H) was dissolved in xylene (2.5 ml), added with di(2,4,6-trichlorophenyl)malonate (568 mg, 1.23 mmol), and refluxed by heating for 30 minutes. The reaction mixture was left stand for cooling and then concentrated, and the resulting residue was purified by silica gel column chromatography (chloroform:methanol=100:1) to obtain the title compound (325 mg, 84%) as yellow solid.

$^1$H-NMR (CDCl$_3$) δ: 1.27 (6H, d, J=6.8 Hz), 3.05 (1H, m), 3.40 (4H, m), 5.40 (1H, s), 6.75 (1H, s), 7.40 (1H, d, J=5.9 Hz), 9.00 (1H, d, J=4.6 Hz) MS; m/z: (MH$^+$) 334, (MH$^-$) 332

(J) 7-Fluoro-2-(3-hydroxypiperidino)-8-[2-(4-isopropyl-1,3-thiazol-2-yl)ethyl]-4-oxo-4H-pyrido[1,2-a]pyrimidin-4-one The 7-fluoro-2-hydroxy-8-[2-(4-isopropyl-1,3-thiazol-2-yl)ethyl]-4-oxo-4H-pyrido[1,2-a]pyrimidin-4-one (150 mg, 0.450 mmol) obtained in (I) was dissolved in a mixed solvent of tetrahydrofuran (3 ml) and dimethylformamide (1 ml), added with p-toluenesulfonyl chloride (129 mg, 0.675 mmol) and 4-dimethylaminopyridine (60.5 mg, 0.494 mmol), and then the mixture was stirred at room temperature for 2 hours. The reaction mixture was diluted with chloroform, washed with water and dried over anhydrous magnesium sulfate. The solvent was evaporated and the resulting residue was dissolved in dimethylformamide (3 ml), added with 3-hydroxypiperidine (310 mg, 2.25 mmol) and triethylamine (0.3 ml) and stirred at 80° C. for 2 hours. The reaction mixture was left stand for cooling, diluted with chloroform, washed with water and dried over anhydrous magnesium sulfate. Then, the solvent was evaporated and the resulting residue was purified by preparative TLC (chloroform:methanol=100:3) to obtain the title compound (147 mg, 79%) as yellow solid.

$^1$H-NMR (CDCl$_3$) δ: 1.29 (6H, d, J=6.8 Hz), 1.56 (1H, m), 1.64 (1H, m), 1.86 (1H, m), 1.99 (1H, m), 3.07 (1H, m), 3.21 (2H, m), 3.34 (1H, m), 3.36 (2H, m), 3.38 (1H, m), 3.82 (1H, m), 3.98 (1H, m), 5.66 (1H, s), 6.73 (1H, s), 7.11 (1H, d, J=6.6 Hz), 8.70 (1H, d, J=5.4 Hz)

(K) 1-{7-Fluoro-3-formyl-8-[2-(4-isopropyl-1,3-thiazol-2-yl)ethyl]-4-oxo-4H-pyrido-[1,2-a]pyrimidin-2-yl}-3-piperidyl formate Dimethylformamide (3ml) was added with phosphorus oxychloride (0.083 ml, 0.882 mmol) under ice cooling and stirred for 30 minutes. The mixture was added with a solution of the 7-fluoro-2-(3-hydroxypiperidino)-8-[2-(4-isopropyl-1,3-thiazol-2-yl)ethyl]-4-oxo-4H-pyrido[1,2-a]pyrimidin-4-one (147 mg, 0.353 mmol) obtained in (J) in dimethylformamide (2 ml), warmed to room temperature, and then stirred for 1 hour. The reaction mixture was further added with phosphorus oxychloride (0.083 ml, 0.882 mmol) and stirred for 30 minutes. The reaction mixture was added with saturated aqueous sodium hydrogencarbonate and extracted twice with ethyl acetate. The organic layer was dried over anhydrous magnesium sulfate, and the solvent was evaporated. The resulting residue was purified by silica gel column chromatography (chloroform→chloroform:methanol=400:1) and further purified by preparative TLC (chloroform:methanol=100:1) to obtain the title compound (145 mg, 87%) as yellow oil.

$^1$H-NMR (CDCl$_3$) δ: 1.28 (6H, d, J=6.8 Hz), 1.69 (1H, m), 1.85 (1H, m), 1.89 (1H, m), 2.02 (1H, m), 3.06 (1H, m), 3.25 (2H, m), 3.37 (2H, m), 3.63 (2H, m), 3.78 (1H, dd, J=13.7 and 6.6 Hz), 3.88 (1H, dd, J=13.7 and 3.2 Hz), 5.06 (1H, m), 6.74 (1H, s), 7.10 (1H, d, J=6.6 Hz), 7.98 (1H, s), 8.69 (1H, d, J=5.4 Hz), 10.1 (1H, s)

(L) tert-Butyl (E)-3-{7-fluoro-2-(3-formylpiperidino)-8-[2-(4-isopropyl-1,3-thiazol-2yl)-ethyl]-4-oxo-4H-pyrido[1,2-a]pyrimidin-3-yl}-2-propenoate The 1-{7-fluoro-3-formyl-8-[2-(4-isopropyl-1,3-thiazol-2-yl)ethyl]-4-oxo-4H-pyrido[1,2-a]pyrimidin-2-yl}-3-piperidyl formate (145 mg, 0.307 mmol) obtained in (K) was dissolved in tetrahydrofuran (5 ml), added with tert-butoxycarbonylmethylene-triphenylphosphorane (1.38 g, 3.68 mmol) and refluxed by heating for 2 days. The reaction mixture was concentrated, and the resulting residue was purified by preparative TLC (chloroform:methanol=100:4) to obtain the title compound (147 mg, 84%) as yellow solid.

$^1$H-NMR (CDCl$_3$) δ: 1.28 (6H, d, J=6.9 Hz), 1.51 (9H, s), 1.73 (1H, m), 1.85 (1H, m), 1.99 (2H, m), 3.06 (1H, m), 3.26

(2H, m), 3.38 (2H, m), 3.48 (1H, m), 3.52 (1H, m), 3.65 (1H, m), 3.74 (1H, m), 5.12 (1H, m), 6.73 (1H, s), 7.05 (1H, d, J=15.5 Hz), 7.21 (1H, d, J=6.9 Hz), 7.48 (1H, d, J=15.5 Hz), 8.07 (1H, s), 8.80 (1H, d, J=5.4 Hz)

(M) tert-Butyl (E)-3-{7-fluoro-2-(3-hydroxypiperidino)-8-[2-(4-isopropyl-1,3-thiazol-2-yl)ethyl]-4-oxo-4H-pyrido[1,2-a]pyrimidin-3-yl}-2-propenoate The tert-butyl (E)-3-{7-fluoro-2-(3-formylpiperidino)-8-[2-(4-isopropyl-1,3-thiazol-2-yl)ethyl]-4-oxo-4H-pyrido[1,2-a]pyrimidin-3-yl}-2-propenoate (147 mg, 0.258 mmol) obtained in (L) was dissolved in methanol (3ml), added with sodium methoxide (33.6 mg, 0.618 mmol), and then stirred at room temperature for 9 hours. The reaction mixture was added with distilled water and extracted with chloroform (twice). The organic layer was dried over anhydrous magnesium sulfate, and the solvent was evaporated. The resulting residue was purified by preparative TLC (chloroform:methanol=100:5) to obtain the title compound (91.6 mg, 65%).

$^1$H-NMR (CDCl$_3$) δ: 1.27 (6H, d, J=6.8 Hz), 1.51 (9H, s), 1.60 (2H, m), 1.83 (2H, m), 3.05 (1H, m), 3.26 (2H, m), 3.38 (2H, m), 3.53 (1H, m), 3.57 (2H, m), 3.73 (1H, m), 3.87 (1H, m), 4.01 (1H, m), 6.73 (1H, s), 7.03 (1H, d, J=15.6 Hz), 7.21 (1H, d, J=6.6 Hz), 7.48 (1H, d, J=15.6 Hz), 8.81 (1H, d, J=5.6 Hz)

(N) (E)-3-{7-Fluoro-2-(3-hydroxypiperidino)-8-[2-(4-isopropyl-1,3-thiazol-2-yl)ethyl]-4-oxo-4H-pyrido[1,2-a]pyrimidin-3-yl}-2-propenoic acid The tert-butyl (E)-3-{7-fluoro-2-(3-hydroxypiperidino)-8-[2-(4-isopropyl-1,3-thiazol-2-yl)ethyl]-4-oxo-4H-pyrido[1,2-a]pyrimidin-3-yl}-2-propenoate (43.6 mg, 0.0803 mmol) obtained in (M) was dissolved in 4 N hydrochloric acid/dioxane (3 ml) and stirred at room temperature for 2 hours. The reaction mixture was concentrated and the resulting residue was purified by preparative TLC (chloroform:methanol=10:1) to obtain the title compound (35.6 mg, 91%) as lyophilized product.

$^1$H-NMR (CDCl$_3$) δ: 1.27 (6H, d, J=6.8 Hz), 1.54 (1H, m), 1.71 (1H, m), 1.87 (2H, m), 3.06 (1H, m), 3.23 (2H, m), 3.37 (2H, m), 3.45 (1H, m), 3.62 (3H, m), 3.99 (1H, m), 6.73 (1H, s), 7.00 (1H, d, J=15.4 Hz), 7.18 (1H, d, J=6.6 Hz), 7.56 (1H, d, J=15.4 Hz), 8.73 (1H, d, J=4.9 Hz) MS; m/z: (MH$^+$) 487, (MH$^-$) 485

Example 157

(E)-3-{2-{3-[(Aminocarbonyl)oxy]piperidino}-7-fluoro-8-[2-(4-isopropyl-1,3-thiazol-2-yl)ethyl]-4-oxo-4H-pyrido[1,2-a]pyrimidin-3-yl}-2-propenoic acid (A) tert-Butyl (E)-3-{2-{3-[(aminocarbonyl)oxy]piperidino}-7-fluoro-8-[2-(4-isopropyl-1,3-thiazol-2-yl)ethyl]-4-oxo-4H-pyrido[1,2-a]pyrimidin-3-yl}-2-propenoate The tert-butyl (E)-3-{7-fluoro-2-(3-hydroxypiperidino)-8-[2-(4-isopropyl-1,3-thiazol-2-yl)ethyl]-4-oxo-4H-pyrido[1,2-a]pyrimidin-3-yl}-2-propenoate (48.0 mg, 0.0885 mmol) obtained in Example 156, (M) was dissolved in ethyl acetate (3 ml), added with trichloroacetyl isocyanate (0.052 ml, 0.442 mmol) and stirred at room temperature for 1 hour. The reaction mixture was added with methanol:chloroform (1:10, 10 ml) and concentrated, and the resulting residue was dissolved in a mixed solvent of methanol (3 ml) and distilled water (1 ml), added with sodium formate (12.0 mg, 0.177 mmol) and stirred overnight at room temperature. The solution was further added with sodium formate (12.0 mg, 0.177 mmol), stirred for 5 hours and then concentrated, and the resulting residue was purified by preparative TLC (chloroform:methanol=100:5) to obtain the title compound (71.3 mg, quantitative) as lyophilized product.

$^1$H-NMR (CDCl$_3$) δ: 1.27 (6H, d, J=6.8 Hz), 1.51 (9H, s), 1.78 (1H, m), 1.84–2.00 (3H, m), 3.06 (1H, m), 3.26 (2H, m), 3.27 (1H, m), 3.39 (2H, m), 3.52 (1H, m), 3.66 (2H, m), 4.81 (1H, m), 4.90 (1H,br), 6.70 (1H,br), 6.74 (1H, s), 7.08 (1H, d, J=15.6 Hz), 7.26 (1H, d, J=6.8 Hz), 7.68 (1H, d, J=15.6 Hz), 8.81 (1H, d, J=5.4 Hz) MS; m/z: (MH$^+$) 586, (MH$^-$) 584

(B) (E)-3-{2-{3-[(Aminocarbonyl)oxy]piperidino}-7-fluoro-8-[2-(4-isopropyl-1,3-thiaziol-2-yl)ethyl]-4-oxo-4H-pyrido[1,2-a]pyrimidin-3-yl}-2-propenoic acid The tert-butyl (E)-3-{2-{3-[(aminocarbonyl)oxy]piperidino}-7-fluoro-8-[2-(4-isopropyl-1,3-thiazol-2-yl)ethyl]-4-oxo-4H-pyrido[1,2-a]pyrimidin-3-yl}-2-propenoate (51.8 mg, 0.0884 mmol) obtained in (A) was dissolved in 4 N hydrochloric acid in dioxane (3 ml)and stirred at room temperature. The reaction mixture was concentrated and the resulting residue was purified by preparative TLC (chloroform:methanol=10:1) to obtain the title compound (26.8 mg, 57%) as lyophilized product.

$^1$H-NMR (CD$_3$OD) δ: 1.25 (6H, d, J=6.8 Hz), 1.68 (1H, m), 1.82 (1H, m), 1.97 (2H, m), 3.02 (1H, m), 3.25 (2H, m), 3.41 (2H, m), 3.48 (1H, m), 3.57 (1H, m), 3.66 (1H, m), 3.77 (1H, m), 4.73 (1H, m), 6.94 (1H, d, J=15.6 Hz), 6.97 (1H, s), 7.29 (1H, d, J=6.8 Hz), 7.55 (1H, d, J=15.6 Hz), 8.71 (1H, d, J=5.6 Hz) MS; m/z: (MH$^+$) 530, (MH$^-$) 528

Example 158

3-{2-(3-Formylpiperidino)-8-[2-(4-isopropyl-1,3-thiazol-2-yl)ethyl]-4-oxo-4H-pyrido[1,2-a]pyrimidin-3-yl}propanoic acid (A) Methyl (E)-3-{2-(3-formylpiperidino)-8-[2-(4-isopropyl-1,3-thiazol-2-yl)ethyl]-4-oxo-4H-pyrido[1,2-a]pyrimidin-3-yl}-2-propenoate 1-{3-Formyl-8-[2-(4-isopropyl-1,3-thiazol-2-yl)ethyl]-4-oxo-4H-pyrido[1,2-a]pyrimidin-2-yl}-3-piperidylformate (94.0 mg, 0.207 mmol) and bis(2,2,2-trifluoroethyl)-(methoxycarbonylmethyl)phosphonoate (0.131 ml, 0.620 mmol) were dissolved in tetrahydrofuran (2 ml), added with DBU (0.085 ml, 0.620 mmol) and lithium chloride (26.3 mg, 0.620 mmol), and then the mixture was stirred at room temperature for 1 hour.

The reaction mixture was concentrated and the obtained residue was purified by preparative TLC (chloroform:methanol=100:2) to obtain the title compound (80.9 mg, 76%).

$^1$H-NMR (CDCl$_3$) δ: 1.28 (6H, d, J=6.8 Hz), 1.74–2.00 (4H, m), 3.07 (1H, m), 3.20 (2H, t, J=7.8 Hz), 3.36 (2H, t,

J=7.8 Hz), 3.54 (2H, m), 3.67 (1H, m), 3.76 (1H, m), 3.77 (3H, s), 5.14 (1H, m), 6.73 (1H, s), 6.84 (1H, dd, J=7.3 and 1.7 Hz), 7.10 (1H, d, J=15.6 Hz), 7.20 (1H, s), 7.62 (1H, d, J=15.6 Hz), 8.09 (1H, s), 8.85 (1H, d, J=7.3 Hz)

(B) Methyl 3-{2-(3-formylpiperidino)-8-[2-(4-isopropyl-1,3-thiazol-2-yl)ethyl]-4-oxo-4H-pyrido[1,2-a]pyrimidin-3-yl}propanoate The methyl (E)-3-{2-(3-formylpiperidino)-8-[2-(4-isopropyl-1,3-thiazol-2-yl)-ethyl]-4-oxo-4H-pyrido[1,2-a]pyrimidin-3-yl}-2-propenoate (80.9 mg, 0.158 mmol) obtained in (A) was dissolved in ethanol (3 ml), added with 5% palladium/carbon (30 mg) and stirred at 1 atm for 2 days under hydrogen atmosphere. The catalyst was removed by filtration, and the filtrate was concentrated. The resulting residue was purified by preparative TLC (chloroform:methanol=100:2) to obtain the title compound (23.1 mg, 28%).

$^1$H-NMR (CDCl$_3$) δ: 1.29 (6H, d, J=6.8 Hz), 1.74–2.03 (4H, m), 3.07 (1H, m), 3.20 (2H, t, J=7.8 Hz), 2.73 (2H, m), 2.93 (2H, m), 3.15 (1H, m), 3.20 (2H, m), 3.30 (2H, m), 3.35 (2H, m), 3.37 (2H, m), 3.68 (3H, s), 5.12 (1H, m), 6.72 (1H, s), 6.81 (1H, d, J=7.20 (1H, s), 7.26 (1H, s), 8.07 (1H, s), 8.79 (1H, d, J=7.3 Hz) MS; m/z: 513 (MH$^+$), 511 (MH$^-$)

(C) 3-{2-(3-Formylpiperidino)-8-[2-(4-isopropyl-1,3-thiazol-2-yl)ethyl]-4-oxo-4H-pyrido-[1,2-a]pyrimidin-3-yl}propanoic acid The methyl 3-{2-(3-formylpiperidino)-8-[2-(4-isopropyl-1,3-thiazol-2-yl)ethyl]-4-oxo-4H-pyrido[1,2-a]pyrimidin-3-yl}propanoate (23.1 mg, 0.0451 mmol) obtained in (B) was dissolved in a mixed solution of methanol, tetrahydrofuran and water (1:1:1, 3 ml), added with lithium hydroxide monohydrate (3.8 mg, 0.0901 mmol), and stirred overnight at room temperature. The reaction mixture was added with 1 N hydrochloric acid (0.091 ml) to neutralize the system, and then the solvent was evaporated. The resulting residue was purified by preparative TLC (chloroform:methanol=10:1) to obtain the title compound (15.0 mg, 71%) as lyophilized product.

$^1$H-NMR (CD$_3$OD) δ: 1.26 (6H, d, J=6.8 Hz), 1.51 (1H, m), 1.67 (1H, m), 1.84 (1H, m), 1.99 (1H, m), 2.64 (2H, m), 2.90 (2H, m), 2.95–3.08 (3H, m), 3.20 (2H, t, J=7.3 Hz), 3.40 (2H, t, J=7.3 Hz), 3.57 (1H, m), 3.78 (2H, m), 6.96 (1H, s), 7.03 (1H, dd, J=7.3 and 2.0 Hz), 7.21 (1H, s), 8.74 (1H, d, J=7.3 Hz) MS; m/z: 471 (MH$^+$), 469 (MH$^-$)

Example 159

1-(2-Fluoroethyl)-7-[(E)-2-(4-isopropyl-1,3-thiazol-2-yl)-1-ethenyl]-3-(1H-1,2,3,4-tetrazol-5-yl)-1,4-dihydro-4-quinolinone (A) Ethyl 1-(2-fluoroethyl)-7-[(E)-2-(4-isopropyl-1,3-thiazol-2-yl)-1-ethenyl]-4-oxo-1,4-dihydro-3-quinolinecarboxylate Ethyl 7-[(E)-2-(4-isopropyl-1,3-thiazol-2-yl)-1-ethenyl]-4-oxo-1,4-dihydro-3-quinolinecarboxylate (368 mg, 1.00 mmol) was dissolved in dimethylformamide (6 ml), added with potassium carbonate (276 mg, 2.00 mmol) and 1-bromo-2-fluoroethane (0.223 ml, 3.00 mmol), and then the mixture was stirred overnight at 65° C. The reaction mixture was left stand for cooling and then diluted with ethyl acetate. The organic layer was washed with water and dried over anhydrous magnesium sulfate, and the solvent was evaporated. The resulting residue was purified by silica gel column chromatography (chloroform→chloroform:methanol=100:1) to obtain the title compound (254 mg, 61%) as colorless transparent oil.

$^1$H-NMR (CDCl$_3$) δ: 1.34 (6H, d, J=7.1 Hz), 1.39 (3H, t, J=7.1 Hz), 3.13 (1H, m), 4.36 (2H,q), 4.54 (2H, ddd, J=24.9, 4.6 and 4.4 Hz), 4.85 (2H, ddd, J=46.6, 4.6 and 4.4 Hz), 6.86 (1H, s), 7.40 (2H, s), 7.43 (1H, s), 7.57 (1H, dd, J=8.5 and 1.2 Hz), 8.43 (1H, s), 8.47 (1H, dd, J=8.5 and 2.0 Hz) MS; m/z: (MH$^+$) 415

(B) 1-(2-Fluoroethyl)-7-[(E)-2-(4-isopropyl-1,3-thiazol-2-yl)-1-ethenyl]-4-oxo-1,4-dihydro-3-quinolinecarboxylic acid The ethyl 1-(2-fluoroethyl)-7-[(E)-2-(4-isopropyl-1,3-thiazol-2-yl)-1-ethenyl]-4-oxo-1,4-dihydro-3-quinolinecarboxylate (254 mg, 0.613 mmol) obtained in (A) was dissolved in a mixed solution of methanol, tetrahydrofuran and water (1:1:1), added with 1 N aqueous sodium hydroxide (1.23 ml, 1.23 mmol), and then the mixture was stirred at room temperature for 8 hours. The reaction mixture was added with 1 N hydrochloric acid (1.23 ml, 1.23 mmol) to neutralize the system, and extracted with chloroform. The organic layer was dried over anhydrous magnesium sulfate, and the solvent was evaporated to obtain the title compound (174 mg, 73%) as yellow solid.

(C) 1-(2-Fluoroethyl)-7-[(E)-2-(4-isopropyl-1,3-thiazol-2-yl)-1-ethenyl]-4-oxo-1,4-dihydro-3-quinolinecarboxamide The 1-(2-fluoroethyl)-7-[(E)-2-(4-isopropyl-1,3-thiazol-2-yl)-1-ethenyl]-4-oxo-1,4-dihydro-3-quinolinecarboxylic acid (174 mg, 0.450 mmol) obtained in (B) was dissolved in dimethylformamide (3 ml), added with triethylamine (0.126 ml, 0.900 mmol) and ethyl chloroformate (0.086 ml, 0.900 mmol) under ice cooling, and then the mixture was stirred for 1 hour. The reaction mixture was warmed to room temperature, stirred for 30 minutes and further stirred at 0° C. for 1 hour. The reaction mixture was added with concentrated aqueous ammonia (0.15 ml) and stirred overnight at room temperature. The reaction mixture was diluted with ethyl acetate and washed successively with aqueous citric acid, saturated aqueous sodium hydrogencarbonate and saturated brine and dried over anhydrous magnesium sulfate. Then, the solvent was evaporated to obtain the title compound (164 mg, 94%) as pale yellow solid.

$^1$H-NMR (CDCl$_3$) δ: 1.36 (6H, d, J=6.8 Hz), 3.17 (1H, m), 4.59 (2H, ddd, J=23.9, 4.9 and 4.6 Hz), 4.87 (2H, ddd, J=46.4, 4.9 and 4.6 Hz), 5.75 (1H,br), 6.92 (1H, s), 7.28 (1H, m), 7.47 (2H, s), 7.69 (1H, d, J=8.6 Hz), 8.54 (1H, d, J=8.6 Hz), 8.79 (1H, s), 9.66 (1H, br) MS; m/z: (MH$^+$) 386

(D) 1-(2-Fluoroethyl)-7-[(E)-2-(4-isopropyl-1,3-thiazol-2-yl)-1-ethenyl]-4-oxo-1,4-dihydro-3-quinolinecarbonitrile A solution of dimethylformamide (0.109 ml, 1.40 mmol) in acetonitrile (2 ml) was added with oxalyl chloride (0.111 ml, 1.28 mmol) under ice cooling, stirred at the same temperature for 15 minutes, and then added with a solution of the 1-(2-fluoroethyl)-7-[(E)-2-(4-isopropyl-1,3-thiazol-2-yl)-1-ethenyl]-4-oxo-1,4dihydro-3-quinolinecarboxamide (164 mg, 0.425 mmol) obtained in (C) in acetonitrile (3 ml). The mixture was stirred at the same temperature for 10 minutes. This mixture was added with pyridine (0.206 ml, 2.55 mmol) and stirred at the same temperature for 10 minutes and further at room temperature for 2 hours. The reaction mixture was added with a solution of dimethylformamide (0.109 ml, 1.40 mmol) and oxalyl chloride (0.111 ml, 1.28 mmol) in acetonitrile (1 ml) prepared beforehand at 0° C., then added with pyridine (0.206 ml, 2.55 mmol), and stirred at room temperature for 1 hour. The reaction mixture was added with ethyl acetate and washed with aqueous citric acid, saturated aqueous sodium hydrogencarbonate and saturated brine. The organic layer was dried over anhydrous magnesium sulfate, and the solvent was evaporated. The resulting residue was purified by preparative TLC (chloroform:methanol=100:7) to obtain the title compound (179 mg, quantitative) as pale yellow as solid.

$^1$H-NMR (CDCl$_3$) δ: 1.36 (6H, d, J=7.1 Hz), 3.15 (1H, m), 4.52 (2H, ddd, J=24.6, 4.6 and 4.4 Hz), 4.85 (2H, ddd, J=46.6, 4.6 and 4.4 Hz), 6.93 (1H, s), 7.43 (1H, s), 7.46 (2H, s), 7.69 (1H, dd, J=8.5 and 1.2 Hz), 8.03 (1H, s), 8.49 (1H, d, J=8.6 Hz)

(E) 1-(2-Fluoroethyl)-7-[(E)-2-(4-isopropyl-1,3-thiazol-2-yl)-1-ethenyl]-3-(1H-1,2,3,4-tetrazol-5-yl)-1,4-dihydro-4-quinolinone A solution of aluminum chloride (55.7 mg, 0.418 mmol) in dimethylformamide (1 ml) was added with sodium azide (81.5 mg, 1.25 mmol) under ice cooling, and then stirred at room temperature for 15 minutes. Then, the reaction mixture was added with a solution of the 1-(2-fluoroethyl)-7-[(E)-2-(4-isopropyl-1,3-thiazol-2-yl)-1-ethenyl]-4-oxo-1,4-dihydro-3-quinolinecarbonitrile (51.2 mg, 0.139 mmol) obtained in (D) in dimethylformamide (1 ml) and stirred overnight at 85–90° C. The reaction mixture was poured into ice water/1 N hydrochloric acid (1 ml) and stirred at room temperature for 1.5 hours. The precipitates were collected by filtration and recrystallized from chloroform/methanol/hexane to obtain the title compound (15.1 mg, 26%) as colorless solid.

$^1$H-NMR (DMSO-d$_6$) δ: 1.29 (6H, d, J=7.1 Hz), 3.08 (1H, m), 4.82 (1H, m), 4.94 (2H, m), 4.95 (1H, m), 7.34 (1H, s), 7.64 (1H, d, J=16.2 Hz), 7.84 (1H, d, J=16.2 Hz), 7.96 (1H, d, J=8.6 Hz), 8.23 (1H, s), 8.37 (1H, d, J=8.6 Hz), 9.05 (1H, s) LCMS; m/z: 411 (MH$^+$)

Example 160

1-Cyclopropyl-6-fluoro-7-[(4-isopropyl-1,3-thiazol-2-yl)methyl]-2-morpholino-4-oxo-1,4-dihydro-3-quinolinecarboxylic acid (A) Ethyl 1-cyclopropyl-6,7-difluoro-2-(methylsulfonyl)-4-oxo-1,4-dihydro-3-quinoline-carboxylate Ethyl 1-cyclopropyl-6,7-difluoro-2-(methylsulfanyl)-4-oxo-1,4-dihydro-3-quinolinecarboxylate (300 mg, 0.976 mmol), which is a known compound [J. Heterocyclic Chem., 27, 839 (1990)], was dissolved in methylene chloride (6 ml), added with metachloroperformic acid (755 mg, 2.93 mmol) and stirred overnight. The reaction mixture was diluted with chloroform and washed successively with saturated aqueous sodium hydrogencarbonate and sodium hydrogensulfite. The organic layer was dried over anhydrous sodium sulfate, and the solvent was evaporated. The resulting residue was developed by silica gel column chromatography (hexane:ethyl acetate=2:1) to obtain the title compound (140 mg, 39%) as white solid. The resulting compound was further developed (chloroform:methanol=100:1) to obtain ethyl 1-cyclopropyl-6,7-difluoro-2-(methylsulfinyl)-4-oxo-1,4-dihydro-3-quinoline-carboxylate (101 mg, 29%) as colorless transparent oil.

Sulfone Compound (Title Compound)

$^1$H-NMR (CDCl$_3$) δ: 0.88 (2H, m), 1.39 (3H, t, J=7.1 Hz), 1.44 (2H, m), 3.56 (3H, s), 3.92 (1H, m), 4.43 (2H,q, J=7.1 Hz), 7.63 (1H, dd, J=11.5 and 6.4 Hz), 8.01 (1H, dd, J=9.8 and 8.6 Hz) ES–MS; m/z: 372 (MH$^+$)

Sulfoxide Compound $^1$H-NMR (CDCl$_3$) δ: 0.99 (2H, m), 1.39 (3H, t, J=6.9 Hz), 1.46 (2H, m), 3.16 (3H, s), 4.42 (3H, m), 7.66 (1H, dd, J=11.3 and 6.4 Hz), 8.13 (1H, t, J=9.3 Hz) ES–MS; m/z: 356 (MH$^+$)

(B) Ethyl 1-cyclopropyl-6,7-difluoro-2-morpholino-4-oxo-1,4-dihydro-3-quinoline-carboxylate The ethyl 1-cyclopropyl-6,7-difluoro-2-(methylsulfonyl)-4-oxo-1,4-dihydro-3-quinolinecarboxylate (140 mg, 0.377 mmol) obtained in (A) was dissolved in tetrahydrofuran (5 ml), added with morpholine (0.0395 ml, 0.452 mmol), N,N-diisopropylethylamine (0.131 ml, 0.754 mmol) and magnesium bromide diethyl etherate (389 mg, 1.51 mmol), and then the mixture was refluxed by heating for 2 hours. The reaction mixture was diluted with ethyl acetate and washed with water. The organic layer was dried over magnesium sulfate, and the solvent was evaporated under reduced pressure. The resulting residue was purified by preparative TLC (chloroform:methanol=100:5) to obtain the title compound (89.2 mg, 62%).

$^1$H-NMR (CDCl$_3$) δ: 0.80 (2H, m), 1.40 (3H, t, J=7.1 Hz), 1.41 (2H, m), 3.14 (1H, m), 3.36 (4H, t, J=4.4 Hz), 3.84 (4H, t, J=4.4 Hz), 4.38 (2H,q, J=7.1 Hz), 7.47 (1H, dd, J=11.7 and 6.4 Hz), 8.01 (1H, dd, J=10.0 and 9.0 Hz)

(C) Ethyl 1-cyclopropyl-6-fluoro-7-[(4-isopropyl-1, 3-thiazol-2-yl)methyl]-2-morpholino-4-oxo-1,4-dihydro-3-quinolinecarboxylate (4-Isopropyl-1,3-thiazol-2-yl)methanol (37.0 mg, 0.235 mmol) was dissolved in dimethylformamide (2 ml), added with 18-crown-6 (68.4 mg, 0.259 mmol) and sodium hydride (95%, 6.5 mg, 0.259 mmol), and stirred for 10 minutes under argon atmosphere. The reaction mixture was added with a solution of the ethyl 1-cyclopropyl-6,7-difluoro-2-morpholino-4-oxo-1,4-dihydro-3-quinolinecarboxylate (89.0 mg, 0.235 mmol) obtained in (B) in dimethylformamide (1 ml), and stirred at room temperature for 1 hour. Then, the reaction mixture was added with aqueous ammonium chloride and extracted with ethyl acetate. The organic layer was dried over magnesium sulfate, and the solvent was evaporated under reduced pressure. The resulting residue was purified by preparative TLC (chloroform:methanol=100:5, v/v) to obtain the title compound (102 mg, 84%).

$^1$H-NMR (CDCl$_3$) δ: 0.68 (2H, m), 1.29 (2H, m), 1.32 (6H, d, J=6.8 Hz), 1.39 (3H, t, J=7.1 Hz), 3.05 (1H, m), 3.11 (1H, m), 3.32 (4H, t, J=4.4 Hz), 3.82 (4H, t, J=4.4 Hz), 4.39 (2H,q, J=7.1 Hz), 5.52 (2H, s), 6.97 (1H, s), 7.27 (1H, d, J=7.3 Hz), 7.93 (1H, d, J=11.2 Hz) ES–MS; m/z: 516 (MH$^+$)

(D) 1-Cyclopropyl-6-fluoro-7-[(4-isopropyl-1,3-thiazol-2-yl)methyl]-2-morpholino-4-oxo-1,4-dihydro-3-quinolinecarboxylic acid A solution of aluminum chloride (266 mg, 2.00 mmol) in 1,2-dichloroethane (4 ml) was added with dimethyl sulfide (0.293 ml, 4.00 mmol) and stirred at 0° C. for 30 minutes. Then, the reaction mixture was added with ethyl 1-cyclopropyl-6-fluoro-7-[(4-isopropyl-1,3-thiazol-2-yl) methyl]-2-morpholino-4-oxo-1,4-dihydro-3-quinolinecarboxylate (51.5 mg, 0.0999 mmol) and refluxed overnight by heating. The reaction mixture was left stand for cooling, diluted with chloroform, washed with 1 N hydrochloric acid, and dried over anhydrous magnesium sulfate. The solvent was evaporated and the obtained residue was purified by preparative TLC (chloroform:methanol=10:1) to obtain the title compound (1.3 mg, 3%).

$^1$H-NMR (CDCl$_3$) δ: 0.58 (2H, m), 1.17 (2H, m), 1.33 (6H, d, J=6.8 Hz), 3.11 (1H, m), 3.29 (1H, m), 3.52 (4H, m), 4.00 (4H, m), 5.55 (2H, s), 6.97 (1H, s), 7.28 (1H, d, J=6.8 Hz), 7.90 (1H, d, J=10.7 Hz) LCMS; m/z: 487 (M)

Example 161

(Z)-3-(1-Cyclopropyl-6-fluoro-7-[(4-isopropyl-1,3-thiazol-2-yl)methyl]-4-oxo-1,4-dihydro-3-quinolyl)-2-propeonic acid (A) 1-Cyclopropyl-6,7-difluoro-4-oxo-1,4-dihydro-3-quinolinecarboxamide 1-Cyclopropyl-6,7-difluoro-4-oxo-1,4-dihydro-3-quinolinecarboxylic acid (1.00 g, 3.77 mmol) was dissolved in dimethylformamide (15 ml), added with triethylamine (0.788 ml, 5.66 mmol) and ethyl chloroformate (0.538 ml, 5.66 mmol) under ice cooling, and stirred for 1 hour. The reaction mixture was warmed to room temperature, stirred for 30 minutes, and further stirred at 0° C. for 1 hour. The reaction mixture was added with concentrated aqueous ammonia (0.75 ml) and stirred overnight at room temperature. The reaction mixture was diluted with ethyl acetate and washed successively with aqueous citric acid, saturated aqueous sodium hydrogencarbonate and saturated brine. The organic layer was dried over anhydrous magnesium sulfate, and the solvent was evaporated to obtain the title compound (1.23 g, quantitative) as white solid.

$^1$H-NMR (CD$_3$OD) δ: 1.21 (2H, m), 1.42 (2H, m), 3.56 (1H, m), 7.88 (1H, dd, J=11.2 and 6.4 Hz), 8.25 (1H, dd, J=10.5 and 8.5 Hz), 8.88 (1H, s)

(B) 1-Cyclopropyl-6,7-difluoro-4-oxo-1,4-dihydro-3-quinolinecarbonitrile

A solution of dimethylformamide (0.712 ml, 9.19 mmol) in acetonitrile (10 ml) was added with oxalyl chloride (0.729 ml, 8.36 mmol) under ice cooling, stirred at the same temperature for 15 minutes, added with a solution of the 1-cyclopropyl-6,7-difluoro-4-oxo-1,4-dihydro-3-quinolinecarboxamide (1.23 g, 4.18 mmol) obtained in (A) in acetonitrile (10 ml) and stirred at the same temperature for 10 minutes. This mixture was added with pyridine (1.35 ml, 16.7 mmol), stirred at the same temperature for 10 minutes, and then stirred overnight at room temperature. The reaction mixture was added with ethyl acetate, washed successively with aqueous citric acid, saturated aqueous sodium hydrogencarbonate and saturated brine, and dried over anhydrous magnesium sulfate to obtain the title compound (714 mg, 77%) as pale yellow solid.

$^1$H-NMR (CDCl$_3$) δ: 1.16 (2H, m), 1.42 (2H, m), 3.47 (1H, m), 7.78 (1H, dd, J=11.0 and 6.4 Hz), 8.16 (1H, s), 8.21 (1H, dd, J=10.0 and 8.6 Hz) MS; m/z: 247 (MH$^+$)

(C) 1-Cyclopropyl-6,7-difluoro-4-oxo-1,4-dihydro-3-quinolinecarbaldehyde

The 1-cyclopropyl-6,7-difluoro-4-oxo-1,4-dihydro-3-quinolinecarbonitrile (150 mg, 0.609 mmol) obtained in (B) was dissolved in a mixed solution of acetic acid, water and pyridine (1:1:2, 4 ml), added with Raney Nickel (catalytic amount) and sodium phosphinate monohydrate (258 mg, 2.44 mmol), and then the mixture was stirred overnight at 60° C. The reaction mixture was left stand for cooling and the catalyst was removed by filtration through a Celite layer and washed with hot ethanol. The reaction mixture was concentrated, then diluted with chloroform, and washed with aqueous copper sulfate. The organic layer was dried over anhydrous magnesium sulfate to obtain the title compound (97.0 mg, 64%) as pale yellow solid.

$^1$H-NMR (CDCl$_3$) δ: 1.18 (2H, m), 1.39 (2H, m), 3.47 (1H, m), 7.78 (1H, dd, J=11.2 and 6.3 Hz), 8.27 (1H, dd, J=10.2 and 8.8 Hz), 8.42 (1H, s), 10.37 (1H, s) LCMS; m/z: 250 (MH$^+$)

(D) tert-Butyl (E)- and (Z)-3-(1-cyclopropyl-6,7-difluoro-4-oxo-1,4-dihydro-3-quinolyl)-2-propenoate The 1-cyclopropyl-6,7-difluoro-4-oxo-1,4-dihydro-3-quinolinecarbaldehyde (97.0 mg, 0.389 mmol) obtained in (C) was dissolved in a mixed solvent of dimethylformamide and tetrahydrofuran (2:1, 3 ml), added with (tert-butoxycarbonyl-methylene)triphenylphosphorane (176 mg, 0.467 mmol), and stirred at 70° C. for 11 hours. The reaction mixture was concentrated, and the resulting residue was separated and purified by preparative TLC (chloroform:methanol=100:5) to obtain Z-isomer of the title compound (68.7 mg, 51%) and E-isomer of the title compound (32.9 mg, 29%) as pale yellow solids.

(Z-Isomer) Rf=Higher $^1$H-NMR (CDCl$_3$) δ: 1.23 (2H, m), 1.32 (2H, m), 1.50 (9H, s), 3.43 (1H, m), 5.86 (1H, d, J=13.2 Hz), 7.27 (1H, d, J=13.2 Hz), 7.71 (1H, dd, J=11.5 and 6.4 Hz), 8.22 (1H, dd, J=10.0 and 9.1 Hz), 9.36 (1H, s) MS; m/z: 348 (MH$^+$)

(E-Isomer) Rf=Lower $^1$H-NMR (CDCl$_3$) δ: 1.11 (2H, m), 1.33 (2H, m), 1.52 (9H, s), 3.43 (1H, m), 7.14 (1H, d, J=15.8 Hz), 7.39 (1H, d, J=15.8 Hz), 7.70 (1H, dd, J=11.5 and 6.3 Hz), 7.88 (1H, s), 8.24 (1H, dd, J=10.5 and 8.5 Hz) MS; m/z: 348 (MH$^+$)

(E) tert-Butyl (Z)-3-(1-cyclopropyl-6-fluoro-7-[(4-isopropyl-1,3-thiazol-2-yl)methyl]-4-oxo-1,4-dihydro-3-quinolyl)-2-propenoate (4-Isopropyl-1,3-thiazol-2-yl)methanol (31.1 mg, 0.198 mmol) was dissolved in dimethylformamide (1 ml), added with 18-crown-6 (57.5 mg, 0.218 mmol) and sodium hydride (95%, 5.5 mg, 0.218 mmol), and then the mixture was stirred for 15 minutes under argon atmosphere. The reaction mixture was added with a solution of the tert-butyl (Z)-3-(1-cyclopropyl-6,7-difluoro-4-oxo-1,4-dihydro-3-quinolyl)-2-propenoate (68.7 mg, 0.198 mmol) obtained in (D) in dimethylformamide (1 ml) and stirred at room temperature for 2 hours. Then, the reaction mixture was added with aqueous ammonium chloride and extracted with chloroform. The organic layer was dried over magnesium sulfate, and the solvent was evaporated under reduced pressure. The obtained residue was purified by preparative TLC (chloroform:methanol=100:1) to obtain the title compound (52.4 mg, 55%).

$^1$H-NMR (CDCl$_3$) δ: 1.15 (2H, m), 1.29 (2H, m), 1.33 (3H, d, J=6.8 Hz), 1.50 (9H, s), 3.11 (1H, m), 3.36 (1H, m), 5.58 (2H, s), 5.82 (1H, d, J=12.9 Hz), 6.97 (1H, s), 7.27 (1H, d, J=12.9 Hz), 7.55 (1H, d, J=6.8 Hz), 8.11 (1H, d, J=11.5 Hz), 9.32 (1H, s)

(F) (Z)-3-(1-Cyclopropyl-6-fluoro-7-[(4-isopropyl-1,3-thiazol-2-yl)methyl]-4-oxo-1,4-dihydro-3-quinolyl)-2-propeonic acid The (Z)-3-(1-cyclopropyl-6-fluoro-7-[(4-isopropyl-1,3-thiazol-2-yl)methyl]-4-oxo-1,4-dihydro-3-quinolyl)-2-propenoate (52.4 mg, 0.108 mmol) obtained in (E) was dissolved in 4 N hydrochloric acid in dioxane (2 ml) and stirred overnight. The reaction mixture was concentrated, and the deposited solid was collected by filtration using ether to obtain the title compound (54.3 mg, quantitative) as pale yellow solid.

$^1$H-NMR (CD$_3$OD/CDCl$_3$) δ: 1.36 (3H, d, J=7.10 Hz), 1.53 (2H, m), 1.73 (2H, m), 3.18 (1H, m), 4.38 (1H, m), 5.90 (2H, s), 6.77 (1H, d, J=9.6 Hz), 7.26 (1H, s), 8.25 (1H, d, J=9.6 Hz), 8.41 (2H, m), 9.79 (1H, s) ES–MS; m/z: 427 (MH$^-$)

Example 162

(E)-3-(1-Cyclopropyl-6-fluoro-7-[(4-isopropyl-1,3-thiazol-2-yl)methyl]-4-oxo-1,4-dihydro-3-quinolyl)-2-propeonic acid (A) tert-Butyl (E)-3-(1-Cyclopropyl-6-fluoro-7-[(4-isopropyl-1,3-thiazol-2-yl)methyl]-4-oxo-1,4-dihydro-3-quinolyl)-2-propenoate (4-Isopropyl-1,3-thiazol-2-yl)methanol (19.5 mg, 0.124 mmol) was dissolved in dimethylformamide (1 ml), added with 18-crown-6 (35.8 mg, 0.135 mmol) and sodium hydride (95%, 3.4 mg, 0.135 mmol), and stirred for 15 minutes under argon atmosphere. The reaction mixture was added with a solution of tert-butyl (E)-3-(1-cyclopropyl-6,7-difluoro-4-oxo-1,4-dihydro-3-quinolyl)-2-propenoate (39.2 mg, 0.124 mmol) in dimethylformamide (1 ml) and stirred at room temperature for 3 hours. Then, the reaction mixture was added with aqueous ammonium chloride and extracted with chloroform. The organic layer was dried over magnesium sulfate, and the solvent was evaporated under reduced pressure. The resulting residue was purified by preparative TLC (chloroform:methanol=100:1) to obtain the title compound (44.7 mg, 82%).

$^1$H-NMR (CDCl$_3$) δ: 1.03 (2H, m), 1.30 (2H, m), 1.31 (3H, d, J=6.8 Hz), 1.51 (9H, s), 3.11 (1H, m), 3.36 (1H, m), 5.57 (2H, s), 6.96 (1H, s), 7.12 (1H, d, J=15.8 Hz), 7.37 (1H, d, J=15.8 Hz), 7.53 (1H, d, J=6.8 Hz), 7.79 (1H, s), 8.10 (1H, d, J=11.2 Hz)

(B) (E)-3-(1-Cyclopropyl-6-fluoro-7-[(4-isopropyl-1,3-thiazol-2-yl)methyl]-4-oxo-1,4-dihydro-3-quinolyl)-2-propeonic acid The (E)-3-(1-cyclopropyl-6-fluoro-7-[(4-isopropyl-1,3-thiazol-2-yl)methyl]-4-oxo-1,4-dihydro-3-quinolyl)-2-propenoate (44.7 mg, 0.0992 mmol) obtained in (A) was dissolved in 4 N hydrochloric acid in dioxane (2 ml) and stirred overnight. The reaction mixture was concentrated, and the deposited solid was collected by filtration using ether to obtain the title compound (32.9 mg, 83%) as pale yellow solid.

$^1$H-NMR (CD$_3$OD/CDCl$_3$) δ: 1.14 (2H, m), 1.33 (3H, d, J=5.6 Hz), 1.38 (2H, m), 3.15 (1H, m), 3.56 (1H, m), 5.66 (2H, s), 7.13 (1H, d, J=15.6 Hz), 7.17 (1H, s), 7.60 (1H, d, J=15.6 Hz), 7.75 (1H, d, 6.9 Hz), 8.04 (1H, d, J=11.2 Hz), 8.25 (1H, s) ES–MS; m/z: 429 (MH$^+$)

Test Example 1

Effect of Combined Use with Antimicrobial Agent on Multidrug Resistant *Pseudomonas aeruginosa*

As multidrug resistant *Pseudomonas aeruginosa*, *Pseudomonas aeruginosa* PAM 1723 strain highly expressing the drug efflux pump was used. As antimicrobial drugs for the combinational uses, levofloxacin (LVFX) as a quinolone antibacterial agent and aztreonam (AZT) as a monobactam antibiotic were used. Each of the compounds shown in Table 1 with Example No., which falls within the compounds of the present invention, was subjected to the measurement of its minimum concentration (μg/ml) that was required to enhance the antibacterial activity of levofloxacin when the test compound was used in combination with levofloxacin applied at a concentration of 1/4, or 1/8 or less of the minimum inhibitory concentration against the PAM 1723 strain. As for aztreonam, a minimum concentration (μg/ml) of each text compound was measured that was required to enhance its antibacterial activity when the test compound was used in combination with azthreonam at a concentration of 1/8 or less of the MIC. Effects as combinational uses for 18 hours was indicated for each of the drugs. Effects were determined by visually observing the turbidity of the medium. The Müller-Hinton broth (MHB, Difco) was used as a medium, and the inoculum of the bacteria was 1×10$^6$ CFU/ml. As clearly shown in Table 1, the compounds of the present invention exhibited effect on the drug resistant *Pseudomonas aeruginosa* in the combinational uses mainly by inhibiting resistance due to the drug efflux pump, and accordingly, it can be concluded that the class of compounds are expected to be useful clinically.

TABLE 1

| Example No. | MPC4 LVFX | MPC8 LVFX | MPC8 AZT |
| --- | --- | --- | --- |
| 5 | 0.5 | 8 | 8 |
| 10 | 2 | 16 | 4 |
| 18 | ≦0.25 | 1 | 0.5 |
| 26 | 0.25 | 1 | 1 |
| 78 | 0.5 | 1 | 1 |
| 94 | 4 | 16 | 16 |
| 98 | 1 | 4 | 4 |
| 104 | 0.24 | 1 | 0.5 |
| 117 | 1 | 4 | 4 |
| 130 | 2 | 8 | 8 |
| 135 | 4 | 16 | 8 |
| 141 | 0.25 | 16 | 2 |
| 152 | 2 | 8 | 4 |
| 155 | 0.25 | 2 | 2 |

| Example No. | Chemical Formula |
| --- | --- |
| 5 | |
| 10 | |
| 18 | |
| 26 | |

TABLE 1-continued
78 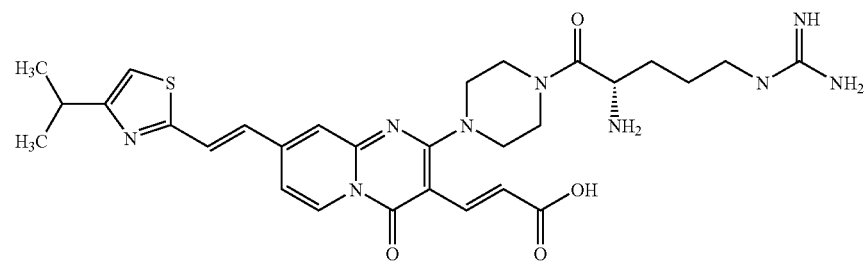
94 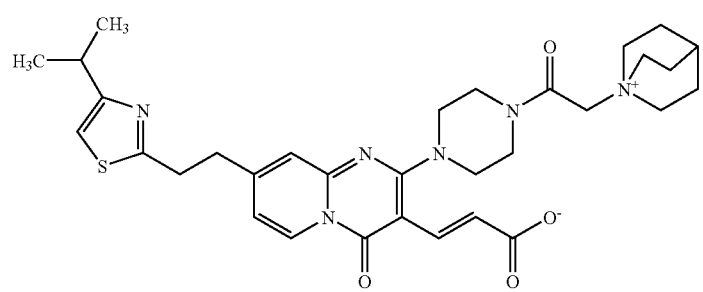
98 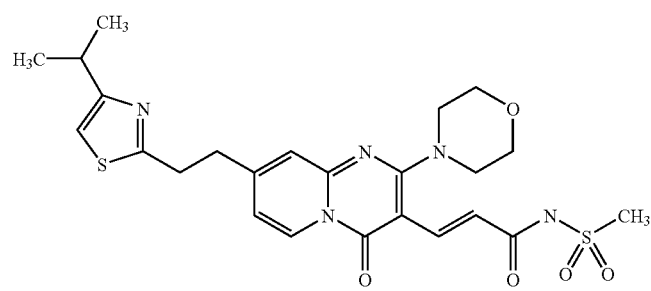
104 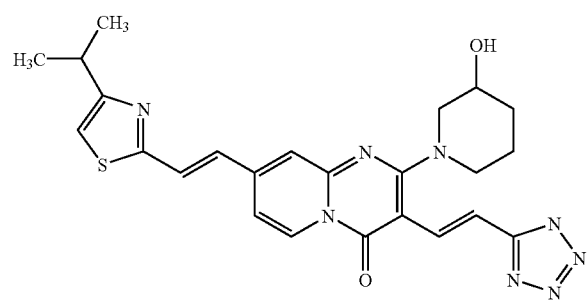
117 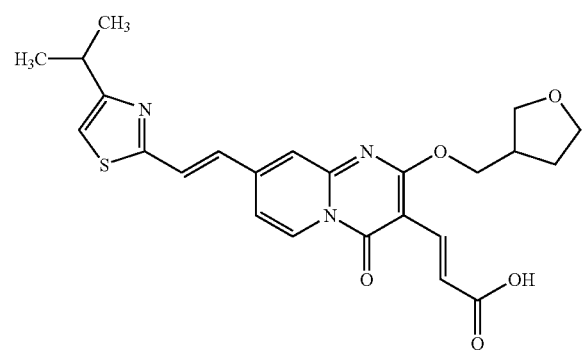

TABLE 1-continued
130 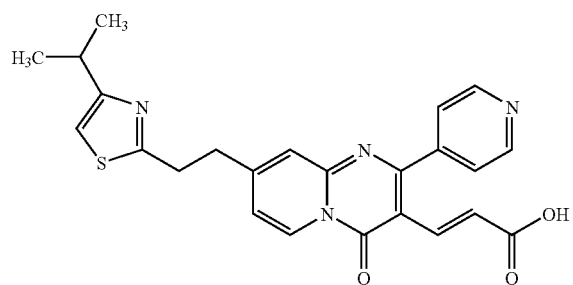
135 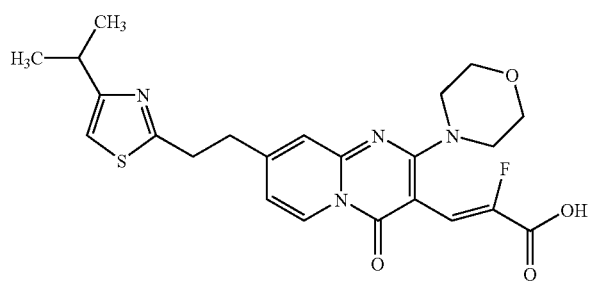
141 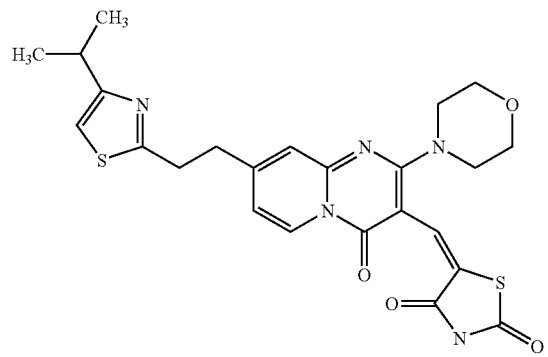
152 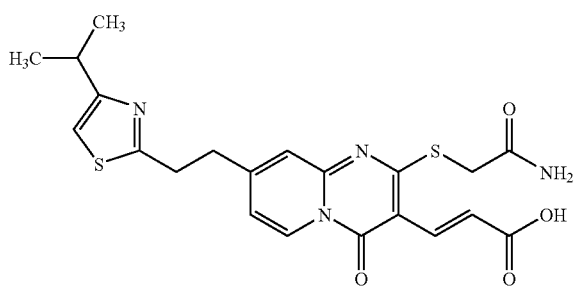
155 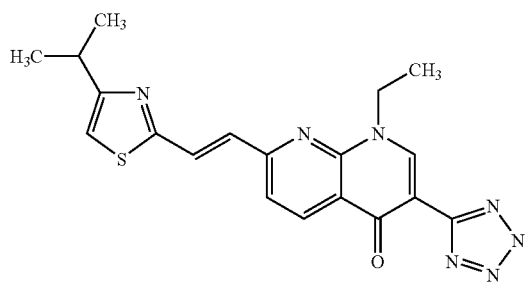

Test Example 2

Synergistic Effect of Combined Use of a Drug Efflux Pump Inhibitor and Plural Antibacterial Agents By using a drug efflux pump inhibitor in combination with two or more types of antibacterial agents that can be substrates of the drug efflux pump, strong synergistic effect can be obtained and thus an effective therapeutic method can be provided for treatment of infectious diseases caused by *Pseudomonas aeruginosa* Antibacterial agents for combination include antibacterial agents excreted by *Pseudomonas aeruginosa* Mex type drug efflux pump such as quinolones, β-lactams, tetracyclines, macrolides, chloramphenicol, sulfonamides, trimethoprim, β-lactamase inhibitors and so forth.

(1) Effect of Combined Used of a Pump Inhibitor, Levofloxacin (LVFX) and Meropenem (MEPM) Evaluated by the Three-Dimensional Checker Board Method The effect was measured by the three-dimensional checker board method by using *Pseudomonas aeruginosa* wild strain PAM 1020. The test strain was inoculated into Mueller-Hinton broth containing LVFX, MEPM (at 11 concentration levels and 0 μg/ml) and the compound of Example 26 (40-0.625 μg/ml and 0 μg/ml) at a concentration of $10^6$ CFU/ml and cultured at 37° C. for 18 hours. Then, MIC was measured for sole and combined use. Measurement was performed by the checker board method and FIC index was calculated according to the following equation.

FIC index=$a/a0+b/b0+c/c0$ wherein a0: MIC for Agent A used alone, a: MIC for Agent A when Agents A, B and C are used in combination, b0: MIC for Agent B used alone, b: MIC for Agent B when Agents A, B and C are used in combination, c0: MIC for Agent C used alone, c: MIC for Agent C when Agents A, B and C are used in combination.

It was determined that there was synergistic effect when FIC index was 0.75 or less, additive effect or weak synergistic effect when the index was more than 0.75 but not more than 1.125, no effect of combined use when the index was more than 1.125 but not more than 3.0, and antagonistic effect when the index was more than 3.0.

The results are shown in the following table. As for the effect of MEPM on the combined use of two types of drugs, LVFX and the compound of Example 26, effects of the addition of MEPM were clearly observed for all of effective concentrations of the compound of Example 26 (0.625-40 μg/ml). As for the effect of combined use of three types of drugs, apparent effects of the addition of MEPM were observed for all of effective concentrations of the compound of Example 26 (0.625-40 μg/ml).

MIC values of the used agents for the PAM 1020 strain were 0.25 μg/ml for LVFX, 80 μg/ml or more for the compound of Example 26, and 0.5 μg/ml for MEPM.

| | FIC index provided by combined use of 3 types of drugs | | | | | | | | | |
|---|---|---|---|---|---|---|---|---|---|---|
| | FIC index | | | | | | | | | |
| Compound of Example 26 | 0.016 (MEPM conc. μg/ml) | LVFX conc. (μg/ml) | 0.0313 (MEPM conc. μg/ml) | LVFX conc. (μg/ml) | 0.0625 (MEPM conc. μg/ml) | LVFX conc. (μg/ml) | 0.125 (MEPM conc. μg/ml) | LVFX conc. (μg/ml) | 0.25 (MEPM conc. μg/ml) | LVFX conc. (μg/ml) |
| 40 | 1.031 | 0.125 | 1.0625 | 0.125 | 0.750 | 0.0313 | — | — | — | — |
| 20 | 0.781 | 0.125 | 0.8125 | 0.125 | 0.500 | 0.0313 | — | — | — | — |
| 10 | 0.656 | 0.125 | 0.6875 | 0.125 | 0.500 | 0.0625 | 0.766 | 0.0039 | — | — |
| 5 | 0.594 | 0.125 | 0.625 | 0.125 | 0.438 | 0.0625 | 0.563 | 0.0156 | — | — |
| 2.5 | 1.063 | 0.25 | 0.59375 | 0.125 | 0.656 | 0.125 | 0.500 | 0.0313 | — | — |
| 1.25 | 1.047 | 0.25 | 1.07813 | 0.25 | 0.641 | 0.125 | 0.563 | 0.0625 | — | — |
| 0.625 | 1.039 | 0.25 | 1.07031 | 0.25 | 1.133 | 0.25 | 0.781 | 0.125 | 1.063 | 0.0078 |
| 0 | 1.031 | 0.25 | 1.0625 | 0.25 | 1.125 | 0.25 | 1.250 | 0.25 | 1.5 | 2 |

Example 3

Effect of Combined Use of Drug Efflux Pump Inhibitor and Disinfectant

By using a drug efflux pump inhibitor in combination with a disinfectant that can be a substrate of the drug efflux pump, effect of combined use can be achieved and an effective disinfection method can be provided.

Effects of a combined use of a drug efflux pump inhibitor and alkyldiaminoethylglycine hydrochloride (AEG, trade name: Tego 51) or chlorhexidine gluconate (CHG, trade name: Hibiten) on *Pseudomonas aeruginosa* PAM 1723 (a strain highly expressing MexAB-OprM drug efflux pump) was determined by the broth dilution method. The compound of Example 26 was added at a final concentration of 10 μg/ml to Mueller-Hinton broth (MHB) containing a disinfectant at a concentration after 2-fold serial dilution. The amount of the test bacteria inoculated was $1 \times 10^6$ CFU/ml, and after standing cultivation at 37° C. for 18 hours, the culture was observed by visual inspection. The minimum concentration that gave no turbidity as in the control of MHB was determined as MIC.

The results are shown in the following table. Evaluation of the effect of the combined use of the disinfectant and the compound of Example 26 revealed that the activities of AEG and CHG on PAM 1723 were enhanced by two times and four times, respectively, by the combined use with 10 μg/ml of the compound of Example 26.

| | MIC (µg/ml) | | | | | |
|---|---|---|---|---|---|---|
| | AEG | | | CHG | | |
| Strain | Single use | Combined use | Ratio* | Single use | Combined use | Ratio* |
| PAM 1723 | 64 | 32 | 2 | 16 | 4 | 4 |

*Ratio of MIC values for single use of the disinfectant and combined use with the compound of Example 26

What is claimed is:

1. A compound represented by the following formula (I) or a physiologically acceptable salt thereof, or a hydrate thereof:

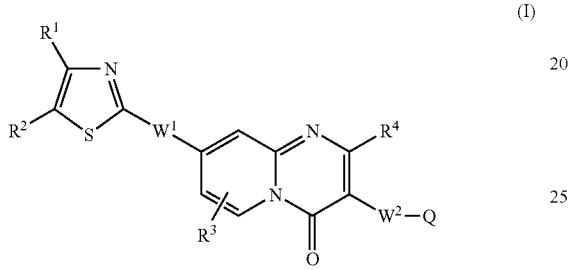

(I)

wherein, $R^1$ and $R^2$ each independently represent hydrogen atom, a halogen atom, hydroxyl group, a group of $OZ_{1-6}$ (the group of $OZ_{1-6}$ represents an alkyl group having 1–6 carbon atoms or a fluoroalkyl group having 1–6 carbon atoms, which bonds via the oxygen atom), a group of $S(O)_nZ_{1-4}$ ($Z_{1-4}$ represents an alkyl group having 1–4 carbon atoms or a fluoroalkyl group having 1–4 carbon atoms or an alkylene group derived therefrom), a group of $N(R^{12})(R^{13})$ ($R^{12}$ and $R^{13}$ each independently represent hydrogen atom, an alkyl group having 1–4 carbon atoms or a fluoroalkyl group having 1–4 carbon atoms), a group of $Z_{1-8}$ which may be substituted ($Z_{1-8}$ represents an alkyl group having 1–8 carbon atoms or a fluoroalkyl group having 1–8 carbon atoms), a 5- to 7-membered cyclic alkyl group, an aryl group, a heteroaryl group, or a 4- to 7-membered saturated or partially saturated heterocyclic group (the cyclic alkyl group, aryl group, heteroaryl group and heterocyclic group may have one to three substituents selected from the group consisting of a halogen atom, hydroxyl group, a group of $OZ_{1-4}$, a group of $S(O)_nZ^{1-4}$, a group of $N(R^{12})(R^{13})$, a group of $Z^{1-4}$, carboxyl group, a group of $CO_2Z_{1-4}$, group of $CONH_2$, a group of $CONH(Z_{1-4})$ and a group of $CON(Z_{1-4})(Z_{1-4})$);

$W^1$ represents a group selected from the group consisting of —CH=CH—, —N(R^{12})CO—, —CON(R^{12})—, —CH_2O— and —CH_2CH_2— (each of the aforementioned groups binds to the thiazole ring at the left end);

$R^3$ represents hydrogen atom, a halogen atom, hydroxyl group or an amino group;

$R^4$ represents a group selected from the group consisting of hydrogen atom, a group of —$OZ_{0-4}R^5$ ($Z_{0-4}$ represents an alkylene group having 1–4 carbon atoms, a fluorine-substituted alkylene group having 1–4 carbon atoms or a single bond, and $R^5$ represents a 5- to 7-membered cyclic alkyl group, an aryl group, a heteroaryl group or a 4- to 7-membered saturated or partially saturated heterocyclic group (the cyclic alkyl group, aryl group, heteroaryl group and heterocyclic group may have one to three substituents selected from the group consisting of a halogen atom, hydroxyl group, a group of $OZ_{1-4}$, a group of $S(O)_nZ_{1-4}$, a group of $N(R^{12})(R^{13})$, a group of $Z_{1-4}$, carboxyl group, a group of $CO_2Z_{1-4}$, group of $CONH_2$, a group of $CONH$ ($Z_{1-4}$) and a group of $CON(Z_{1-4})(Z_{1-4})$), a group of —$S(O)_nZ_{0-4}R^5$, a group of —$N(R^6)(R^7)$ {$R^6$ and $R^7$ each independently represent hydrogen atom or $Z_{1-4}$, or they may bind to each other to form a saturated or unsaturated 5- to 7-membered ring (the ring may contain one or two hetero atoms as ring constituting atoms), and $R^6$ and $R^7$ may have one to three substituents selected from the group consisting of a halogen atom, hydroxyl group, a group of $OCON(R^{12})(R^{13})$, a group of $CON(R^{12})(R^{13})$, a group of $N(R^{12})CON(R^{12})$ ($R^{13}$), a group of $Z_{1-4}$, a group of $OZ_{1-4}$, a group $S(O)_nZ_{1-4}$, group of $CH_2OH$, a group of $(CH_2)_mN(R^{12})$ ($R^{13}$), carboxyl group, cyano group, a group of $CO-Z_{1-4}(R^{10})-N(R^{12})(R^{13})$ ($R^{10}$ is a substituent corresponding to a side chain on an amino acid carbon or a group of —$Z_{1-4}-R^{11}$ ($R^{11}$ represents a substituent which forms a quaternary salt) and a group of

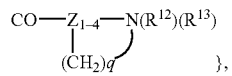

}, a 5- or 6-membered aryl group which may be substituted and a 5- or 6-membered unsaturated heterocyclic group which may be substituted;

$W^2$ represents a single bond or —$C(R^8)=C(R^9)$— ($R^8$ and $R^9$ each independently represent hydrogen atom, a halogen atom, a lower alkyl group, an alkoxy group, cyano group, carboxyl group, hydroxymethyl group, cyanomethyl group, vinyl group or a group of $N(R^{12})$ ($R^{13}$)), Q represents an acidic group, and $W^2$ and Q may bind together to form vinylidenethiazolidinedione in E- or Z-configuration or an equivalent heterocyclic ring; m and n each independently represent an integer of 0 to 2, and q represents an integer of 0 to 3.

2. A medicament composition for eliminating resistance of a microorganism with acquired drug resistance, which comprises a compound represented by formula (I) according to claim 1 or a physiologically acceptable salt thereof, or a hydrate thereof as an active ingredient.

3. A medicament composition for enhancing effect of an antimicrobial agent, which comprises a compound represented by formula (I) according to claim 1 or a physiologically acceptable salt thereof as an active ingredient.

4. A pharmaceutical composition for preventive and/or therapeutic treatment of a microbial infection, which comprises a compound represented by formula (I) according to claim 1 or a physiologically acceptable salt thereof, or a hydrate thereof, together with an antimicrobial agent.

5. A medicament composition which comprises a compound represented by the formula (I) according to claim 1 or a physiologically acceptable salt thereof, or a hydrate thereof as an active ingredient.

6. A method for therepecutic treatment of infection by *Pseudomonas aeruginosa* comprising administering to a mammal in need thereof a therapeutically effective amount of the composition according to claim 5.

7. The method according to claim 6, further comprising administering at least one antimicrobial agent.

8. The method according to claim 7, wherein the at least one antimicrobial agent is simultaneously administered with the composition.

9. The method according to claim 7, wherein the at least one antimicrobial agent is separately administered from the composition.

10. The method according to claim 7, wherein the at least one antimicrobial agent is successively administered with the composition.

11. The method according to claim 6 wherein the mammal is a human.

12. A method for inhibiting drug resistance acquisition due to a drug efflux pump comprising administering to a mammal in need thereof an effective amount to inhibit drug resistance acquisition due to a drug efflux pump of the composition according to claim 5.

13. The method according to claim 12 wherein the mammal is a human.

14. A compound represented by the following formula (I) or a physiologically acceptable salt thereof, or hydrate thereof:

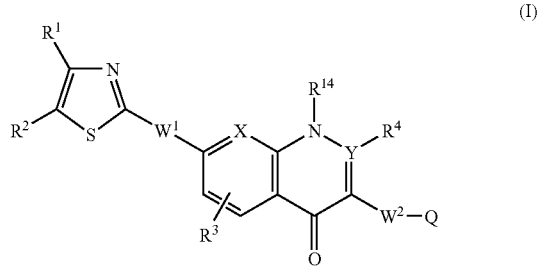

wherein, $R^1$ and $R^2$ each independently represent hydrogen atom, a halogen atom, hydroxyl group, a group of $OZ_{1-6}$ (the group of $OZ_{1-6}$ represents an alkyl group having 1–6 carbon atoms or a fluoroalkyl group having 1–6 carbon atoms, which bonds via the oxygen atom), a group of $S(O)_nZ_{1-4}$ ($Z_{1-4}$ represents an alkyl group having 1–4 carbon atoms or a fluoroalkyl group having 1–4 carbon atoms or an alkylene group derived therefrom), a group of $N(R^{12})(R^{13})$ ($R^{12}$ and $R^{13}$ each independently represent hydrogen atom, an alkyl group having 1–4 carbon atoms or a fluoroalkyl group having 1–4 carbon atoms), a group of $Z_{1-8}$ which may be substituted ($Z_{1-8}$ represents an alkyl group having 1–8 carbon atoms or a fluoroalkyl group having 1–8 carbon atoms), a 5- to 7-membered cyclic alkyl group, an aryl group, a heteroaryl group, or a 4- to 7-membered saturated or partially saturated heterocyclic group (the cyclic alkyl group, aryl group, heteroaryl group and heterocyclic group may have one to three substituents selected from the group consisting of a halogen atom, hydroxyl group, a group of $OZ_{1-4}$, a group of $S(O)_nZ_{1-4}$, a group of $N(R^{12})(R^{13})$, a group of $Z_{1-4}$, carboxyl group, a group of $CO_2Z_{1-4}$, a group of $CONH_2$, a group of $CONH(Z_{1-4})$ and a group of $CON(Z_{1-4})(Z_{1-4})$);

$W^1$ represents a group selected from the group consisting of —CH=CH—, —N($R^{12}$)CO—, —CON($R^{12}$)—, —CH$_2$O— and —CH$_2$C$_2$— (each of the aforementioned groups binds to the thiazole ring at the left end);

$R^3$ represents hydrogen atom, a halogen atom, hydroxyl group or an amino group;

R4 represents a group selected from the group consisting of hydrogen atom, a group of —OZ$_{0-4}$R$^5$ (Z$_{0-4}$ represents an alkylene group having 1–4 carbon atoms, a fluorine-substituted alkylene group having 1–4 carbon atoms or a single bond, and R$^5$ represents a 5- to 7-membered cyclic alkyl group, an aryl group, a heteroaryl group or a 4- to 7-membered saturated or partially saturated heterocyclic group (the cyclic alkyl group, aryl group, heteroaryl group and heterocyclic group may have one to three substituents selected from the group consisting of a halogen atom, hydroxyl group, a group of $OZ_{1-4}$, a group of $S(O)_nZ_{1-4}$, a group of $N(R^{12})(R^{13})$, a group of $Z_{1-4}$, carboxyl group, a group of $CO_2Z_{1-4}$, group of $CONH_2$, a group of $CONH(Z_{1-4})$ and a group of $CON(Z_{1-4})(Z_{1-4})$), a group of —S(O)$_n$Z$_{0-4}$R$^5$, a group of —N(R$^6$)(R$^7$) {R$^6$ and R$^7$ each independently represent hydrogen atom or $Z_{1-4}$, or they may bind to each other to form a saturated or unsaturated 5- to 7-membered ring (the ring may contain one or two hetero atoms as ring constituting atoms), and R$^6$ and R$^7$ may have one to three substituents selected from the group consisting of a halogen atom, hydroxyl group, a group of OCON(R$^{12}$)(R$^{13}$), a group of CON(R$^{12}$)(R$^{13}$), a group of N(R$^{12}$)CON(R$^{12}$)(R$^{13}$), a group of $Z_{1-4}$, a group of $OZ_{1-4}$, a group $S(O)_nZ_{1-4}$, group of CH$_2$OH, a group of (CH$_2$)$_m$N(R$^{12}$)(R$^{13}$), carboxyl group, cyano group, a group of CO—$Z_{1-4}$(R$^{10}$)—N(R$^{12}$)(R$^{13}$) (R$^{10}$ is a substituent corresponding to a side chain on an amino acid carbon or a group of —$Z_{1-4}$—R$^{11}$(R$^{11}$ represents a substituent which forms a quaternary salt) and a group of

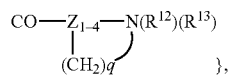

a 5- or 6-membered aryl group which may be substituted and a 5- or 6-membered unsaturated heterocyclic group which may be substituted;

$W^2$ represents a single bond or —C(R$^8$)=C(R$^9$)— (R$^8$ and R$^9$ each independently represent hydrogen atom, a halogen atom, a lower alkyl group, an alkoxy group, cyano group, carboxyl group, hydroxymethyl group, cyanomethyl group, vinyl group or a group of N(R$^{12}$)(R$^{13}$)), Q represents an acidic group, and W$^2$ and Q may bind together to form vinylidenethiazolidinedione in E- or Z-configuration or an equivalent heterocyclic ring; m and n each independently represent an integer of 0 to 2, and q represents an integer of 0 to 3; R$^{14}$ represents hydrogen atom, $Z_{1-4}$, $Z_{1-4}$R$^5$ or $Z_{1-4}$OR$^5$; and X represents C—H and Y represents C—H or nitrogen atom.

15. A medicament composition which comprises a compound represented by the formula (i) according to claim 14 or a physiologically acceptable salt thereof, or a hydrate thereof as an active ingredient.

16. A method for therapeutic treatment of infection by *Pseudomonas aeruginosa* comprising administering to a mammal in need thereof a therapeutically effective amount of the composition according to claim 15.

17. The method according to claim 15, further comprising administering at least one antimicrobial agent.

18. A method for inhibiting drug resistance acquisition due to a drug efflux pump comprising administering to a mammal in need thereof an effective amount to inhibit drug resistance acquisition due to a drug efflux pump of the composition according to claim 15.

19. The method according to claim 18 wherein the mammal is a human.

20. A method for therapeutic treatment of a microbial infection comprising administering to a mammal in need thereof a therapeutically effective amount of a composition comprising a compound represented by formula (I) or a physiologically acceptable salt thereof as an active ingredient and at least one antimicrobial agent:

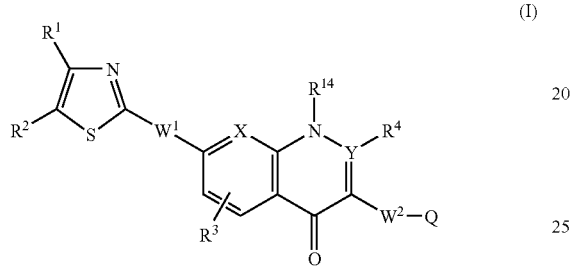

wherein, $R^1$ and $R^2$ each independently represent hydrogen atom, a halogen atom, hydroxyl group, a group of $OZ_{1-6}$ (the group of $OZ_{1-6}$ represents an alkyl group having 1–6 carbon atoms or a fluoroalkyl group having 1–6 carbon atoms, which bonds via the oxygen atom), a group of $S(O)_nZ_{1-4}$ ($Z_{1-4}$ represents an alkyl group having 1–4 carbon atoms or a fluoroalkyl group having 1–4 carbon atoms or an alkylene group derived therefrom), a group of $N(R^{12})(R^{13})$ ($R^{12}$ and $R^{13}$ each independently represent hydrogen atom, an alkyl group having 1–4 carbon atoms or a fluoroalkyl group having 1–4 carbon atoms), a group of $Z_{1-8}$ which may be substituted ($Z_{1-8}$ represents an alkyl group having 1–8 carbon atoms or a fluoroalkyl group having 1–8 carbon atoms), a 5- to 7-membered cyclic alkyl group, an aryl group, a heteroaryl group, or a 4- to 7-membered saturated or partially saturated heterocyclic group (the cyclic alkyl group, aryl group, heteroaryl group and heterocyclic group may have one to three substituents selected from the group consisting of a halogen atom, hydroxyl group, a group of $OZ_{1-4}$, a group of $S(O)_nZ_{1-4}$, a group of $N(R^{12})(R^{13})$, a group of $Z_{1-4}$, carboxyl group, a group of $CO_2Z_{1-4}$, group of $CONH_2$, a group of $CONH(Z_{1-4})$ and a group of $CON(Z_{1-4})(Z_{1-4})$);

$W^1$ represents a group selected from the group consisting of —CH=CH—, —N($R^{12}$)CO—, —CON($R^{12}$)—, —CH$_2$O— and —CH$_2$CH$_2$— (each of the aforementioned groups binds to the thiazole ring at the left end);

$R^3$ represents hydrogen atom, a halogen atom, hydroxyl group or an amino group;

$R^4$ represents a group selected from the group consisting of hydrogen atom, a group of —$OZ_{0-4}R^5$ ($Z_{0-4}$ represents an alkylene group having 1–4 carbon atoms, a fluorine-substituted alkylene group having 1–4 carbon atoms or a single bond, and $R^5$ represents a 5- to 7-membered cyclic alkyl group, an aryl group, a heteroaryl group or a 4- to 7-membered saturated or partially saturated heterocyclic group (the cyclic alkyl group, aryl group, heteroaryl group and heterocyclic group may have one to three substituents selected from the group consisting of a halogen atom, hydroxyl group, a group of $OZ_{1-4}$, a group of $S(O)_nZ_{1-4}$, a group of $N(R^{12})(R^{13})$, a group of $Z_{1-4}$, carboxyl group, a group of $CO_2Z_{1-4}$, group of $CONH_2$, a group of $CONH(Z_{1-4})$ and a group of $CONH(Z_{1-4})(Z_{1-4})$, a group of —$S(O)_nZ_{0-4}R^5$, a group of —$N(R^6)(R^7)$ {$R^6$ and $R^7$ each independently represent hydrogen atom or $Z_{1-4}$, or they may bind to each other to form a saturated or unsaturated 5- to 7-membered ring (the ring may contain one or two hetero atoms as ring constituting atoms), and $R^6$ $R^7$ may have one to three substituents selected from the group consisting of a halogen atom, hydroxyl group, a group of $OCON(R^{12})(R^{13})$, a group of $CON(R^{12})(R^{13})$, a group of $N(R^{12})CON(R^{12})(R^{13})$, a group of $Z_{1-4}$, a group of $OZ_{1-4}$, a group $S(O)_nZ_{1-4}$, group of $CH_2OH$, a group of $(CH_2)_mN(R^{12})(R^{13})$, carboxyl group, cyano group, a group of $CO$—$Z_{1-4}$ ($R^{10}$)—$N(R^{12})(R^{13})$ ($R^{10}$ is a substituent corresponding to a side chain on an amino acid carbon or a group of —$Z_{1-4}$—$R^{11}$ ($R^{11}$ represents a substituent which forms a quaternary salt) and a group of

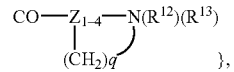

a 5- or 6-membered aryl group which may be substituted and a 5- or 6-membered unsaturated heterocyclic group which may be substituted;

$W^2$ represents a single bond or —C($R^8$)=C($R^9$)— ($R^8$ and $R^9$ each independently represent hydrogen atom, a halogen atom, a lower alkyl group, an alkoxy group, cyano group, carboxyl group, hydroxymethyl group, cyanomethyl group, vinyl group or a group of $N(R^{12})(R^{13})$), Q represents an acidic group, and $W^2$ and Q may bind together to form vinylidenethiazolidinedione in E- or Z-configuration or an equivalent heterocyclic ring; m and n each independently represent an integer of 0 to 2, and q represents an integer of 0 to 3; $R^{14}$ represents hydrogen atom, an alkyl group having 1, 3 or 4 carbon atoms or a fluoroalkyl group having 1–4 carbon atoms, $Z_{1-4}R^5$ or $Z_{1-4}OR^5$; and X and Y each independently represent C—H or nitrogen atom.

21. A method for inhibiting drug resistance acquisition due to a drug efflux pump comprising administering to a mammal an effective amount to inhibit drug resistance acquisition due to a drug efflux pump of a composition comprising a compound represented by formula (I) or a physiologically acceptable salt thereof, or a hydrate thereof as an active ingredient

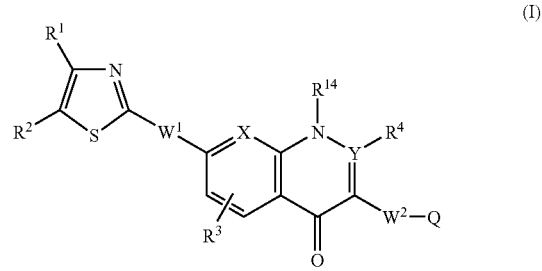

wherein, $R^1$ and $R^2$ each independently represent hydrogen atom, a halogen atom, hydroxyl group, a group of $OZ_{1-6}$ (the group of $OZ_{1-6}$ represents an alkyl group having 1–6 carbon atoms or a fluoroalkyl group having 1–6 carbon atoms, which bonds via the oxygen atom), a group of $S(O)_nZ_{1-4}$ ($Z_{1-4}$ represents an alkyl group having 1–4 carbon atoms or a fluoroalkyl group having 1–4 carbon atoms or an alkylene group derived therefrom), a group of $N(R^{12})(R^{13})$ ($R^{12}$ and $R^{13}$ each independently represent hydrogen atom, an alkyl group having 1–4 carbon atoms or a fluoroalkyl group having 1–4 carbon atoms), a group of $Z_{1-8}$ which may be substituted ($Z_{1-8}$ represents an alkyl group having 1–8 carbon atoms or a fluoroalkyl group having 1–8 carbon atoms), a 5- to 7-membered cyclic alkyl group, an aryl group, a heteroaryl group, or a 4- to 7-membered saturated or partially saturated heterocyclic group (the cyclic alkyl group, aryl group, heteroaryl group and heterocyclic group may have one to three substituents selected from the group consisting of a halogen atom, hydroxyl group, a group of $OZ_{1-4}$, a group of $S(O)_nZ_{1-4}$, a group of $N(R^{12})(R^{13})$, a group of $Z_{1-4}$, carboxyl group, a group of $CO_2Z_{1-4}$, group of $CONH_2$, a group of $CONH(Z_{1-4})$ and a group of $CON(Z_{1-4})(Z_{1-4})$);

$W^1$ represents a group selected from the group consisting of —CH=CH—, —N(R$^{12}$)CO—, —CON(R$^{12}$)—, —CH$_2$O— and —CH$_2$CH$_2$— (each of the aforementioned groups binds to the thiazole ring at the left end);

$R^3$ represents hydrogen atom, a halogen atom, hydroxyl group or an amino group;

$R^4$ represents a group selected from the group consisting of hydrogen atom, a group of —OZ$_{0-4}$R$^5$ (OZ$_{0-4}$ represents an alkylene group having 1–4 carbon atoms, a fluorine-substituted alkylene group having 1–4 carbon atoms or a single bond, and R$^5$ represents a 5- to 7-membered cyclic alkyl group, an aryl group, a heteroaryl group or a 4- to 7-membered saturated or partially saturated heterocyclic group (the cyclic alkyl group, aryl group, heteroaryl group and heterocyclic group may have one to three substituents selected from the group consisting of a halogen atom, hydroxyl group, a group of $OZ_{1-4}$, a group of $S(O)_nZ_{1-4}$, a group of $N(R^{12})(R^{13})$, a group of $Z_{1-4}$, carboxyl group, a group of $CO_2Z_{1-4}$, group of $CONH_2$, a group of $CONH(Z_{1-4})$ and a group of $CON(Z_{1-4})(Z_{1-4})$), a group of —S(O)$_n$R$^5$, a group of —N(R$^6$)(R$^7$) {R$^6$ and R$^7$ each independently represent hydrogen atom or $Z_{1-4}$, or they may bind to each other to form a saturated or unsaturated 5- to 7-membered ring (the ring may contain one or two hetero atoms as ring constituting atoms), and R$^6$ and R$^7$ may have one to three substituents selected from the group consisting of a halogen atom, hydroxyl group, a group of $OCON(R^{12})(R^{13})$, a group of $CON(R^{12})(R^{13})$, a group of $N(R^{12})CON(R^{12})(R^{13})$, a group of $Z_{1-4}$, a group of $OZ_{1-4}$, a group $S(O)_nZ_{1-4}$, group of $CH_2OH$, a group of $(CH_2)_mN(R^{12})(R^{13})$, carboxyl group, cyano group, a group of CO—$Z_{1-4}(R^{10})$—N$(R^{12})(R^{13})$ ($R^{10}$ is a substituent corresponding to a side chain on an amino acid carbon or a group of —$Z_{1-4}$—$R^{11}$ $R^{11}$ represents a substituent which forms a quaternary salt) and a group of

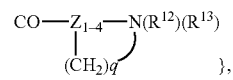

}, a 5- or 6-membered aryl group which may be substituted and a 5- or 6-membered unsaturated heterocyclic group which may be substituted;

$W^2$ represents a single bond or —C(R$^8$)=C(R$^9$)— (R$^8$ and R$^9$ each independently represent hydrogen atom, a halogen atom, a lower alkyl group, an alkoxy group, cyano group, carboxyl group, hydroxymethyl group, cyanomethyl group, vinyl group or a group of N(R$^{12}$)(R$^{13}$)), Q represents an acidic group, and W$^2$ and Q may bind together to form vinylidenethiazolidinedione in E- or Z-configuration or an equivalent heterocyclic ring; m and n each independently represent an integer of 0 to 2, and q represents an integer of 0 to 3; R$^{14}$ represents hydrogen atom, an alkyl group having 1, 3 or 4 carbon atoms or a fluoroalkyl group having 1–4 carbon atoms, $Z_{1-4}R^5$ or $Z_{1-4}OR^5$; and X and Y each independently represent C—H or nitrogen atom.

22. The method according to claim 21 wherein the mammal is a human.

* * * * *

UNITED STATES PATENT AND TRADEMARK OFFICE
CERTIFICATE OF CORRECTION

| | |
|---|---|
| PATENT NO. | : 7,056,917 B2 |
| APPLICATION NO. | : 09/842234 |
| DATED | : June 6, 2006 |
| INVENTOR(S) | : K. Nakayama et al. |

It is certified that error appears in the above-identified patent and that said Letters Patent is hereby corrected as shown below:

At column 138, line 62 (Claim 3, line 4) of the printed patent, after "thereof" should be --, or a hydrate thereof--.

At column 138, lines 63-63 (Claim 4, lines 1-2) of the printed patent, after "composition" delete "for preventive and/or therapeutic treatment of a microbial infection,".

Signed and Sealed this

Twentieth Day of November, 2007

JON W. DUDAS
*Director of the United States Patent and Trademark Office*